(12) United States Patent
Wakita et al.

(10) Patent No.: US 9,186,383 B2
(45) Date of Patent: Nov. 17, 2015

(54) MUTANT REPLICON DERIVED FROM GENOME OF HEPATITIS C VIRUS J6CF STRAIN

(75) Inventors: Takaji Wakita, Tokyo (JP); Asako Murayama, Tokyo (JP); Takanobu Kato, Yokohama (JP)

(73) Assignees: Japan As Represented by Director-General of National Institute of Infectious Diseases (JP); Toray Industries, Inc. (JP)

( * ) Notice: Subject to any disclaimer, the term of this patent is extended or adjusted under 35 U.S.C. 154(b) by 204 days.

(21) Appl. No.: 14/122,450

(22) PCT Filed: May 31, 2012

(86) PCT No.: PCT/JP2012/064070
§ 371 (c)(1),
(2), (4) Date: Nov. 26, 2013

(87) PCT Pub. No.: WO2012/165542
PCT Pub. Date: Dec. 6, 2012

(65) Prior Publication Data
US 2014/0302092 A1    Oct. 9, 2014

(30) Foreign Application Priority Data
May 31, 2011   (JP) ................. 2011-122795

(51) Int. Cl.
*A61K 35/76*    (2015.01)
*C12N 7/00*    (2006.01)
(Continued)

(52) U.S. Cl.
CPC ............... *A61K 35/76* (2013.01); *A61K 39/12* (2013.01); *C07K 14/005* (2013.01); *C12N 7/00* (2013.01); *C12N 2770/24222* (2013.01); *C12N 2770/24234* (2013.01); *G01N 2333/186* (2013.01); *G01N 2500/00* (2013.01)

(58) Field of Classification Search
None
See application file for complete search history.

(56) References Cited

U.S. PATENT DOCUMENTS

| 6,630,343 | B1 | 10/2003 | Bartenschlager |
| 2008/0220019 | A1 | 9/2008 | Wakita et al. |
| 2012/0003720 | A1 | 1/2012 | Wakita et al. |

(Continued)

FOREIGN PATENT DOCUMENTS

| JP | 2001-17187 | 1/2001 |
| JP | 2009-5589 | 1/2009 |

(Continued)

OTHER PUBLICATIONS

Leiyun Weng, et al., "Sphingomyelin Activates Hepatitis C Virus RNA Polymerase in a Genotype-Specific Manner," *Journal of Virology*, 2010, vol. 84, No. 22, pp. 11761-11770.

(Continued)

*Primary Examiner* — Michelle S Horning
(74) *Attorney, Agent, or Firm* — DLA Piper LLP (US)

(57) ABSTRACT

A nucleic acid includes the 5' untranslated region, a virus protein-coding region including the NS3 protein coding sequence, the NS4A protein coding sequence, the NS4B protein coding sequence, the NS5A protein coding sequence, and the NS5B protein coding sequence, and the 3' untranslated region of the HCV J6CF genome in that order from the 5' to 3' direction. The NS4A protein coding sequence has a mutation for substituting alanine at position 1680 with glutamic acid, as determined on the basis of the amino acid sequence of the precursor protein of the J6CF strain.

12 Claims, 14 Drawing Sheets

(51) Int. Cl.
*C07K 14/005* (2006.01)
*A61K 39/12* (2006.01)

(56) References Cited

U.S. PATENT DOCUMENTS

2013/0115592 A1 5/2013 Wakita et al.
2013/0183754 A1 7/2013 Wakita et al.

FOREIGN PATENT DOCUMENTS

| JP | 2011-122795 | 6/2011 |
| WO | 2004/104198 A1 | 12/2004 |
| WO | 2005/080575 A1 | 9/2005 |
| WO | 2006/022422 A1 | 3/2006 |
| WO | 2010/074249 A1 | 7/2010 |

OTHER PUBLICATIONS

Peter Simmonds, et al., "A Proposed System for the Nomenclature of Hepatitis C Viral Genotypes," *Hepatology*, 1994, vol. 19, pp. 1321-1324.
Qui-Lim Choo, et al., "Isolation of a cDNA Clone Derived from a Blood-Borne Non-A, Non-B Viral Hepatitis Genome," *Science*, Apr. 1989, vol. 24, pp. 359-362.
Takanobu Kato, et al., "Sequence Analysis of Hepatitis C Virus Isolated From a Fulminant Hepatitis Patient," *Journal of Medical Virology*, 2001, vol. 64, pp. 334-339.
Hiroaki Okamoto, et al., "Typing hepatitis C virus by polymerase chain reaction with type-specific primers: application to clinical surveys and tracing infectious sources," *Journal of General Virology*, 1992, vol. 73, pp. 673-679.
Kentaro Yoshioka, et al., "Detection of Hepatitis C Virus by Polymerase Chain Reaction and Response to Interferon-α Therapy: Relationship to Genotypes of Hepatitis C Virus," *Hepatology*, 1992, vol. 16, No. 2, pp. 293-299.
Shigehisa Mori, et al., "A New Type of Hepatitis C Virus in Patients in Thailand," *Biochemical and Biophysical Research Communications*, Feb. 28, 1992, vol. 183, No. 1, pp. 334-342.
V. Lohmann, et al., "Replication of Subgenomic Hepatitis C Virus RNAs in a Hepatoma Cell Line," *Science*, Jul. 2, 1999, vol. 285, pp. 110-113.
Keril J. Blight, et al., "Efficient Initiation of HCV RNA Replication in Cell Culture," *Science*, Dec. 8, 2000, vol. 290, pp. 1972-1974.
Peter Friebe, et al., "Sequences in the 5' Nontranslated Region of Hepatitis C Virus Required for RNA Replication," *Journal of Virology*, Dec. 2001, pp. 12047-12057.
Masanori Ikeda, et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *Journal of Virology*, Mar. 2002, pp. 2997-3006.
Takanobu Kato, et al., "Efficient Replication of the Genotype 2a Hepatitis C Virus Subgenomic Replicon," *Gastroenterology*, 2003, vol. 125, pages 1808-1817.
Takaji Wakita, et al., "Production of infectious hepatitis C virsu in tissue culture from a cloned viral genome," *Nature Medicine*, Jul. 2005, vol. 11, No. 7, pp. 791-796.
Asako Maurayama, et al., "The NS3 Helicase and NS5B-to3'X Regions are Important for Efficient Hepatitis C Virsu Strain JFH-1 Replication in Huh7 Cells," *Journal of Virology*, Aug. 2007, pp. 8030-8040.
Asako Murayama, et al., "RNA Polymerase Activity and Specific RNA Structure Are Required for Efficient HCV Replication in Cultured Cells," *PLoS Pathogens*, Apr. 2010, vol. 6, Issue 4, e1000885, pp. 1-11.
Lindenbach, B.D. et al., "Complete Replication of Hepatitis C Virus in Cell Culture," *Science*, Jul. 22, 2005, vol. 309, pp. 623-226.
Murayama, A. et al., "Identification of Virus Gene Mutation Necessary for Growth of Hepatitis C Virus J6CF Strain in Culture Cells," *The 58th Annual Meeting of the Japanese Society for Virology*, Oct. 15, 2010, pp. 197-198 and 2 sheets of English translation.
Pietschmann, T. et al., "Construction and Characterization of Infectious Intragenotypic and Intergenotypic Hepatitis C Virus Chimeras," *PNAS*, May 9, 2006, vol. 103, No. 19, pp. 7408-7413.
Wakita, T. et al., "Production of Infectious Hepatitis C Virus in Tissue Culture from a Cloned Viral Genome," *Nature Medicine*, Jul. 2005, vol. 11, No. 7, pp. 791-796 and Corrigenda, p. 905.
Yanagi, M. et al., "Hepatitis C Virus: An Infectious Molecular Clone of a Second Major Genotype (2a) and Lack of Viability of Intertypic 1a amd 2a Chimeras," *Virology*, 1999, vol. 262, pp. 250-263.

```
                         SEQUENCE LISTING

<160> NUMBER OF SEQ ID NOS: 33

<210> SEQ ID NO 1
<211> LENGTH: 8882
<212> TYPE: DNA
<213> ORGANISM: Artificial Sequence
<220> FEATURE:
<223> OTHER INFORMATION: Description of Artificial Sequence: Synthetic
      cDNA sequence of SGR-J6/5BSLX-JFH1+4Amut/Luc

<400> SEQUENCE: 1
acccgcccct aatagggggcg acactccgcc atgaatcact ccctgtgag  gaactactgt     60 cttcacgcag aaagcgtcta gccatggcgt tagtatgagt gtcgtacagc ctccaggccc    120 cccctcccg  ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacaa atcctaaacc    360
tcaaagaaaa accaaagaa  acaccaaccg acgcgtaatg gaagacgcca aaaacataaa    420
gaaaggcccg gcgccattct atcctctgga ggatggaacc gctggagagc aactgcataa    480
ggctatgaag agatacgccc tggttcctgg aacaattgct tttacagatg cacatatcga    540
ggtgaacatc acgtacgcgg aatacttcga atgtccgtt  cggttggcag aagctatgaa    600
acgatatggg ctgaatacaa atcacagaat cgtcgtatgc agtgaaaact ctcttcaatt    660
ctttatgccg gtgttgggcg cgttatttat cggagttgca gttgcgcccg cgaacgacat    720
ttataatgaa cgtgaattgc tcaacagtat gaacatttcg cagcctaccg tagtgtttgt    780
ttccaaaaag gggttgcaaa aaattttgaa cgtgcaaaaa aaattaccaa taatccagaa    840
aattattatc atggattcta aaacggatta ccagggattt cagtcgatgt acacgttcgt    900
cacatctcat ctacctcccg gttttaatga atacgatttt gtaccagagt cctttgatcg    960
tgacaaaaca attgcactga taatgaactc ctctggatct actgggttac ctaagggtgt   1020
ggcccttccg catagaactg cctgcgtcag attctcgcat gccagagatc ctatttttgg   1080
caatcaaatc attccggata ctgcgatttt aagtgttgtt ccattccatc acggttttgg   1140
aatgtttact acactcggat atttgatatg tggatttcga gtcgtcttaa tgtatagatt   1200
tgaagaagag ctgtttttac gatcccttca ggattacaaa attcaaagtg cgttgctagt   1260
accaacccta ttttcattct tcgccaaaag cactctgatt gacaaatacg atttatctaa   1320
tttacacgaa attgcttctg ggggcgcacc tctttcgaaa gaagtcgggg aagcggttgc   1380
aaaacgcttc catcttccag ggatacgaca aggatatggg ctcactgaga ctacatcagc   1440
tattctgatt acacccgagg gggatgataa accgggcgcg gtcggtaaag ttgttccatt   1500
ttttgaagcg aaggttgtgg atctggatac cgggaaaacg ctgggcgtta atcagagagg   1560
cgaattatgt gtcagaggac ctatgattat gtccggttat gtaaacaatc cggaagcgac   1620
caacgccttg attgacaagg atggatggct acattctgga gacatagctt actgggacga   1680
agacgaacac ttcttcatag ttgaccgctt gaagtcttta attaaataca aaggatatca   1740
ggtggccccc gctgaattgg aatcgatatt gttacaacac cccaacatct tcgacgcggg   1800
cgtggcaggt cttcccgacg atgacgccgg tgaacttccc gccgccgttg ttgttttgga   1860
gcacggaaag acgatgacgg aaaaagagat cgtggattac gtcgccagtc aagtaacaac   1920
```

```
cgcgaaaaag ttgcgcggag gagttgtgtt tgtggacgaa gtaccgaaag gtcttaccgg      1980
aaaactcgac gcaagaaaaa tcagagagat cctcataaag gccaagaagg gcggaaagtc      2040
caaattgtaa gtttaaaccc tctccctccc cccccccttaa cgttactggc cgaagccgct     2100
tggaataagg ccggtgtgcg tttgtctata tgttattttc caccatattg ccgtcttttg      2160
gcaatgtgag ggcccggaaa cctggccctg tcttcttgac gagcattcct aggggtcttt      2220
cccctctcgc caaaggaatg caaggtctgt tgaatgtcgt gaaggaagca gttcctctgg      2280
aagcttcttg aagacaaaca acgtctgtag cgacccttttg caggcagcgg aaccccccac     2340
ctggcgacag gtgcctctgc ggccaaaagc cacgtgtata agatacacct gcaaaggcgg      2400
cacaacccca gtgccacgtt gtgagttgga tagttgtgga aagagtcaaa tggctctcct      2460
caagcgtatt caacaagggg ctgaaggatg cccagaaggt acccccattgt atgggatctg     2520 atctggggcc tcggtgcaca tgctttacat gtgtttagtc gaggttaaaa aaacgtctag      2580 gcccccccgaa ccacggggac gtggtttttcc tttgaaaaac acgataatac catggctccc    2640
atcactgctt atgcccagca gacacgtggc cttttgggca ccatagtggt gagcatgacg      2700
gggcgcgaca agacagaaca ggctggggaa attcaggtcc tgtccacagt cactcagtcc      2760
ttcctcggaa catccatctc gggggttttg tggactgtct accatggagc tggcaacaag      2820
actctggccg gctcacgggg tccggtcacg cagatgtact ccagtgctga gggggactta     2880
gtagggtggc ccagcccccc tgggactaaa tctttggagc cgtgcacgtg tggagcggtc      2940
gacctgtacc tggtcacgcg gaacgctgat gtcatcccgg ctcgaagacg cggggacaaa      3000
cggggagcgc tactctcccc gagacctctt tccaccttga aggggtcctc aggaggcccg      3060
gtgctatgcc ccaggggcca cgctgtcgga gtcttccggg cagctgtgtg ctctcggggc      3120
gtggctaagt ccatagattt catcccccgtt gagacactcg acatcgtcac gcggtccccc     3180
acctttagtg acaacagcac accacctgct gtgccccaga cctatcaggt cgggtacttg      3240
catgccccga ctggcagtgg aaagagcacc aaagttcctg tcgcatatgc tgctcagggg      3300
tataaagtgc tagtgcttaa tccctcagtg gctgccaccc tggggtttgg ggcgtacttg      3360
tctaaggcac atggcatcaa tcccaacatt aggactggag tcaggactgt gacgaccggg      3420
gcgcccatca cgtactccac atatggcaaa ttcctcgccg atgggggctg tgcgggcggc      3480
gcctacgaca tcatcatatg tgatgaatgc catgccgtgg actctaccac catccttggc      3540
atcggaacag tccttgatca agcagagaca gctggggtca gactaactgt gctggctaca      3600
gctacgcccc ctgggtcagt gacaacccccc caccccaaca tagaggaggt ggcccttggg     3660
caggagggcg agatccccctt ctatgggagg gcgattcccc tgtcttacat caagggagga    3720
agacatctga tcttctgcca ttcaaagaaa aagtgtgacg agctcgcggc ggcccttcgg      3780
ggtatgggct tgaactcagt ggcatactac agagggttgg acgtctccgt aataccaact      3840
cagggagacg tagtggtcgt cgccaccgac gccctcatga cagggtatac tgggggacttt    3900 gactccgtga tcgactgcaa cgtagcggtc actcaagttg tagacttcag tttagaccccc    3960 acattcacca taaccacaca gattgtccct caagacgctg tctcacgtag ccagcgccgg      4020
ggtcgcacgg gtaggggaag actgggcatt tataggtatg tttccactgg tgagcgagcc      4080
tcaggaatgt ttgacagtgt agtgctctgt gagtgctacg acgcagggggc cgcatggtat    4140 gagctcacac catcggagac caccgtcagg ctcagggcgt atttcaacac gcccggtttg      4200
cctgtgtgcc aagaccatct tgagtttttgg gaggcagttt tcaccggcct cacacacata    4260
gatgcccact tccttttccca aacaaagcaa tcggggggaaa atttcgcata cttaacagcc    4320
```

```
taccaggcta cagtgtgcgc tagggccaaa gccccccccc cgtcctggga cgtcatgtgg    4380
aagtgtttga ctcgactcaa gcccacactc gtgggcccca cacctctcct gtaccgcttg    4440
ggctctgtta ccaacgaggt caccctcaca catcccgtga cgaaatacat cgccacctgc    4500
atgcaagccg accttgaggt catgaccagc acatgggtct tggcagggggg agtcttggcg    4560 gccgtcgccg cgtattgcct ggagaccggg tgtgtttgca tcatcggccg cttgcacatt    4620
aaccagcgag ccgtcgttgc gccggacaag gaggtcctct atgaggcttt tgatgagatg    4680
gaggaatgtg cctctagggc ggctctcatt gaagaggggc agcggatagc cgagatgctg    4740
aagtccaaga tccaaggctt attgcagcaa gcttccaaac aagctcaaga catacaaccc    4800
actgtgcagg cttcatggcc caaggtagaa caattctggg ccaaacacat gtggaacttc    4860
attagcggca tccaatacct cgcaggacta tcaacactgc cagggaaccc tgcagtagct    4920
tccatgatgg cgttcagtgc cgccctcacc agtccgctgt caacaagcac cactatcctt    4980
ctcaacattt tggggggctg gctagcatcc caaattgcac cacccgcggg ggccactggc    5040
ttcgttgtca gtggcctagt gggagctgcc gtaggcagta taggcttagg taaggtgcta    5100
gtggacatcc tggcagggta tggtgcgggc atttcggggg ctctcgtcgc attcaagatc    5160
atgtctggcg agaagccctc catggaggat gtcgtcaact tgctgcctgg aattctgtct    5220
ccgggtgcct tggtagtggg agtcatctgc gcggccattc tgcgccgaca cgtgggaccg    5280
ggggaaggcg ccgtccaatg gatgaataga ctcattgcct ttgcttccag aggaaatcac    5340
gtcgccccca cccactacgt gacggagtcg gatgcgtcgc agcgtgtgac ccaactactt    5400
ggctccctta ccataaccag cctgctcaga agactccaca actggattac tgaggactgc    5460
cccatcccat gctccggatc gtggctccgc gatgtgtggg actgggtttg caccatccta    5520
acagacttta aaaattggct gacctccaaa ttattcccaa agatgcccgg cctcccctttt    5580 gtctcctgtc aaaaggggta caagggcgtg tgggccggca ctggcatcat gaccacacgg    5640
tgtccttgcg gcgccaatat ctctggcaat gtccgcttgg gctccatgag aatcacgggg    5700
cctaagacct gcatgaatat ctggcagggg accttttccta tcaattgtta cacggagggc    5760
cagtgcgtgc cgaaacccgc gccaaacttt aaggtcgcca tctggagggt ggcggcctca    5820
gagtacgcgg aggtgacgca gcacgggtca taccactaca taacaggact caccactgat    5880
aacttgaaag tccccctgcca actaccctct cccgagttct tttcctgggt ggacggagtg    5940
cagatccata ggtttgcccc cacaccgaag ccgttttttcc gggatgaggt ctcgttctgc    6000
gttgggctta ttcatttgt cgtcgggtcc cagcttcctt gcgaccctga cccgacaca    6060 gacgtattga tgtccatgct aacagatcca tctcatatca cggcggagac tgcagcgcgg    6120
cgtttagcgc gggggtcacc cccatccgag gcaagctcct cggcgagcca gctatcggca    6180
ccatcgctgc gagccacctg caccacccac ggcaaagcct atgatgtgga catggtggat    6240
gctaacctgt tcatggggggg cgatgtgact cggatagagt ctgggtccaa agtggtcgtt    6300
ctggactctc tcgacccaat ggtcgaagaa aggagcgacc ttgagccttc gataccatca    6360
gaatacatgc tccccaagaa gaggttccca ccagctttac cggcctgggc acggcctgat    6420
tacaacccac cgcttgtgga atcgtggaaa aggccagatt accaaccggc cactgttgcg    6480
ggctgtgctc tccctcctcc taggaaaacc ccgacgcctc ccccaaggag gcgccggaca    6540
gtgggcctaa gtgaggactc cataggagat gcccttcaac agctggccat taagtccttt    6600
ggccagcccc ccccaagcgg cgattcaggc cttttccacgg gggcgggcgc tgccgattcc    6660
```

```
ggcagtcaga cgcctcctga tgagttggcc ctttcggaga caggttccat ctcttccatg    6720
cccccccctcg aggggggagct tggagatcca gacctggagc ctgagcaggt agagccccaa    6780
ccccccccc agggggggt ggcagctccc ggctcggact cggggtcctg gtctacttgc    6840
tccgaggagg acgactccgt cgtgtgctgc tccatgtcat actcctggac cggggctcta    6900
ataactcctt gtagtcccga agaggagaag ttaccgatta acccccttgag caactccctg    6960
ttgcgatatc acaacaaggt gtactgtacc acaacaaaga gcgcctcact aagggctaaa    7020
aaggtaactt ttgataggat gcaagtgctc gactcctact acgactcagt cttaaaggac    7080
attaagctag cggcctccaa ggtcaccgca aggctcctca ccatggagga ggcttgccag    7140
ttaaccccac cccattctgc aagatctaaa tatgggtttg ggctaagga ggtccgcagc    7200
ttgtccggga gggccgttaa ccacatcaag tccgtgtgga aggacctcct ggaggactca    7260
gaaacaccaa ttcccacaac cattatggcc aaaaatgagg tgttctgcgt ggaccccacc    7320
aagggggggca agaaagcagc tcgccttatc gtttaccctg acctcggcgt cagggtctgc    7380
gagaagatgg cccttttatga cattacacaa aaacttcctc aggcggtgat gggggcttct    7440
tatggattcc agtattcccc cgctcagcgg gtagagtttc tcttgaaagc atgggcggaa    7500
aagaaggacc ctatgggttt ttcgtatgat acccgatgct ttgactcaac cgtcactgag    7560
agagacatca ggactgagga gtccatatat cgggcctgct ccttgcccga ggaggcccac    7620
actgccatac actcgctaac tgagagactt tacgtgggag ggcctatgtt caacagcaag    7680
ggccaaacct gcgggtacag gcgttgccgc ccagcgggg tgctcaccac tagcatgggg    7740
aacaccatca catgctacgt gaaagcctta gcggcttgta aagctgcagg gataatcgcg    7800
cccacaatgc tggtatgcgg cgatgacttg gttgtcatct cagaaagcca ggggaccgag    7860
gaggacgagc ggaacctgag agccttcacg gaggctatga ccaggtattc tgccctcct    7920
ggtgaccccc ccagaccgga gtatgatctg gagctgataa catcttgctc ctcaaatgtg    7980
tctgtggcgc tgggcccaca aggccgccgc agatactacc tgaccagaga ccctaccact    8040
ccaatcgccc gggctgcctg ggaaacagtt agacactccc ctgtcaattc atggctggga    8100
aacatcatcc agtacgcccc gaccatatgg gctcgcatgg tcctgatgac acacttcttc    8160
tccattctca tggctcaaga cacgctggac cagaacctca actttgagat gtacggagcg    8220
gtgtactccg tgagtcccctt ggacctccca gctataattg aaaggttaca tgggcttgac    8280
gcttttttctc tgcacacata cactccccac gaactgacac gggtggcttc agccctcaga    8340
aaacttgggg cgccaccct cagagcgtgg aagagccggg cacgtgcagt cagggcgtcc    8400
ctcatctccc gtggagggaa agcggccgtt tgcggccgat atctcttcaa ttgggcggtg    8460
aagaccaagc tcaaactcac tccattgccg gaggcgcgcc tactggactt atccagttgg    8520
ttcaccgtcg gcgccggcgg gggcgacatt tttcacagcg tgtcgcgcgc ccgacccgc    8580
tcattactct tcggcctact cctactttttc gtaggggtag gcctcttcct actcccgct    8640
cggtagagcg gcacacacta ggtacactcc atagctaact gttcctttttt ttttttttt    8700
tttttttttt tttttttttt tttttttttct tttttttttt tttcccctctt tcttcccttc    8760
tcatcttatt ctactttcttt tcttggtggc tccatcttag ccctagtcac ggctagctgt    8820
gaaaggtccg tgagccgcat gactgcagag agtgccgtaa ctggtctctc tgcagatcat    8880
gt                                                                  8882
```

<210> SEQ ID NO 2
<211> LENGTH: 9678

<212> TYPE: DNA
<213> ORGANISM: Artificial Sequence
<220> FEATURE:
<223> OTHER INFORMATION: Description of Artificial Sequence: Synthetic cDNA sequence of FGR-J6/5BSLX-JFH1+4Amut
<220> FEATURE:
<221> NAME/KEY: CDS
<222> LOCATION: (341)..(9439)

<400> SEQUENCE: 2

```
acccgcccct aatagggggcg acactccgcc atgaatcact cccctgtgag gaactactgt    60
cttcacgcag aaagcgtcta gccatggcgt tagtatgagt gtcgtacagc ctccaggccc   120 cccctcccg ggagagccat agtggtctgc ggaaccggtg agtacaccgg aattgccggg   180
aagactgggt cctttcttgg ataaaccac tctatgcccg gccatttggg cgtgcccccg   240
caagactgct agccgagtag cgttgggttg cgaaaggcct tgtggtactg cctgatagggg   300 tgcttgcgag tgccccggga ggtctcgtag accgtgcacc atg agc aca aat cct   355
                                              Met Ser Thr Asn Pro
                                              1               5
```

| | | | | | | | | | | | | | | | | |
|---|---|---|---|---|---|---|---|---|---|---|---|---|---|---|---|---|
| aaa | cct | caa | aga | aaa | acc | aaa | aga | aac | acc | aac | cgt | cgc | cca | caa | gac | 403 |
| Lys | Pro | Gln | Arg | Lys | Thr | Lys | Arg | Asn | Thr | Asn | Arg | Arg | Pro | Gln | Asp | |
| | | | 10 | | | | 15 | | | | | 20 | | | | |
| gtt | aag | ttt | ccg | ggc | ggc | ggc | cag | atc | gtt | ggc | gga | gta | tac | ttg | ttg | 451 |
| Val | Lys | Phe | Pro | Gly | Gly | Gly | Gln | Ile | Val | Gly | Gly | Val | Tyr | Leu | Leu | |
| | | | 25 | | | | 30 | | | | 35 | | | | | |
| ccg | cgc | agg | ggc | ccc | agg | ttg | ggt | gtg | cgc | gcg | aca | agg | aag | act | tcg | 499 |
| Pro | Arg | Arg | Gly | Pro | Arg | Leu | Gly | Val | Arg | Ala | Thr | Arg | Lys | Thr | Ser | |
| | | 40 | | | | 45 | | | | 50 | | | | | | |
| gag | cgg | tcc | cag | cca | cgt | gga | agg | cgc | cag | ccc | atc | cct | aaa | gat | cgg | 547 |
| Glu | Arg | Ser | Gln | Pro | Arg | Gly | Arg | Arg | Gln | Pro | Ile | Pro | Lys | Asp | Arg | |
| | 55 | | | | 60 | | | | 65 | | | | | | | |
| cgc | tcc | act | ggc | aaa | tcc | tgg | gga | aaa | cca | gga | tac | ccc | tgg | ccc | cta | 595 |
| Arg | Ser | Thr | Gly | Lys | Ser | Trp | Gly | Lys | Pro | Gly | Tyr | Pro | Trp | Pro | Leu | |
| 70 | | | | 75 | | | | 80 | | | | 85 | | | | |
| tac | ggg | aat | gag | gga | ctc | ggc | tgg | gca | gga | tgg | ctc | ctg | tcc | ccc | cga | 643 |
| Tyr | Gly | Asn | Glu | Gly | Leu | Gly | Trp | Ala | Gly | Trp | Leu | Leu | Ser | Pro | Arg | |
| | | | 90 | | | | 95 | | | | 100 | | | | | |
| ggt | tcc | cgt | ccc | tct | tgg | ggc | ccc | aat | gac | ccc | cgg | cat | agg | tcg | cgc | 691 |
| Gly | Ser | Arg | Pro | Ser | Trp | Gly | Pro | Asn | Asp | Pro | Arg | His | Arg | Ser | Arg | |
| | | 105 | | | | 110 | | | | 115 | | | | | | |
| aac | gtg | ggt | aag | gtc | atc | gat | acc | cta | acg | tgc | ggc | ttt | gcc | gac | ctc | 739 |
| Asn | Val | Gly | Lys | Val | Ile | Asp | Thr | Leu | Thr | Cys | Gly | Phe | Ala | Asp | Leu | |
| | 120 | | | | 125 | | | | 130 | | | | | | | |
| atg | ggg | tac | atc | cct | gtc | gtg | ggc | gcc | ccg | ctc | ggc | ggc | gtc | gcc | aga | 787 |
| Met | Gly | Tyr | Ile | Pro | Val | Val | Gly | Ala | Pro | Leu | Gly | Gly | Val | Ala | Arg | |
| 135 | | | | 140 | | | | 145 | | | | | | | | |
| gct | ctc | gcg | cat | ggc | gtg | aga | gtc | ctg | gag | gac | ggg | gtt | aat | ttt | gca | 835 |
| Ala | Leu | Ala | His | Gly | Val | Arg | Val | Leu | Glu | Asp | Gly | Val | Asn | Phe | Ala | |
| 150 | | | 155 | | | | 160 | | | | 165 | | | | | |
| aca | ggg | aac | tta | ccc | ggt | tgc | tcc | ttt | tct | atc | ttc | ttg | ctg | gcc | ctg | 883 |
| Thr | Gly | Asn | Leu | Pro | Gly | Cys | Ser | Phe | Ser | Ile | Phe | Leu | Leu | Ala | Leu | |
| | | 170 | | | | 175 | | | | 180 | | | | | | |
| ctg | tcc | tgc | atc | acc | acc | ccg | gtc | tcc | gct | gcc | gaa | gtg | aag | aac | atc | 931 |
| Leu | Ser | Cys | Ile | Thr | Thr | Pro | Val | Ser | Ala | Ala | Glu | Val | Lys | Asn | Ile | |
| | 185 | | | | 190 | | | | 195 | | | | | | | |
| agt | acc | ggc | tac | atg | gtg | act | aac | gac | tgc | acc | aat | gac | agc | att | acc | 979 |
| Ser | Thr | Gly | Tyr | Met | Val | Thr | Asn | Asp | Cys | Thr | Asn | Asp | Ser | Ile | Thr | |
| 200 | | | | 205 | | | | 210 | | | | | | | | |
| tgg | cag | ctc | cag | gct | gct | gtc | ctc | cac | gtc | ccc | ggg | tgc | gtc | ccg | tgc | 1027 |
| Trp | Gln | Leu | Gln | Ala | Ala | Val | Leu | His | Val | Pro | Gly | Cys | Val | Pro | Cys | |

-continued

```
                215                 220                 225
gag aaa gtg ggg aat gca tct cag tgc tgg ata ccg gtc tca ccg aat     1075
Glu Lys Val Gly Asn Ala Ser Gln Cys Trp Ile Pro Val Ser Pro Asn
230                 235                 240                 245 gtg gcc gtg cag cgg ccc ggc gcc ctc acg cag ggc ttg cgg acg cac     1123
Val Ala Val Gln Arg Pro Gly Ala Leu Thr Gln Gly Leu Arg Thr His
                250                 255                 260 atc gac atg gtt gtg atg tcc gcc acg ctc tgc tct gcc ctc tac gtg     1171
Ile Asp Met Val Val Met Ser Ala Thr Leu Cys Ser Ala Leu Tyr Val
            265                 270                 275 ggg gac ctc tgc ggt ggg gtg atg ctc gca gcc caa atg ttc att gtc     1219
Gly Asp Leu Cys Gly Gly Val Met Leu Ala Ala Gln Met Phe Ile Val
        280                 285                 290 tcg ccg cag cac cac tgg ttt gtc caa gac tgc aat tgc tcc atc tac     1267
Ser Pro Gln His His Trp Phe Val Gln Asp Cys Asn Cys Ser Ile Tyr
    295                 300                 305 cct ggt acc atc act gga cac cgc atg gca tgg gac atg atg atg aac     1315
Pro Gly Thr Ile Thr Gly His Arg Met Ala Trp Asp Met Met Met Asn
310                 315                 320                 325 tgg tcg ccc acg gct acc atg atc ttg gcg tac gcg atg cgt gtc ccc     1363
Trp Ser Pro Thr Ala Thr Met Ile Leu Ala Tyr Ala Met Arg Val Pro
                330                 335                 340 gag gtc att ata gac atc att agc ggg gct cat tgg ggc gtc atg ttc     1411
Glu Val Ile Ile Asp Ile Ile Ser Gly Ala His Trp Gly Val Met Phe
            345                 350                 355 ggc ttg gcc tac ttc tct atg cag gga gcg tgg gcg aaa gtc gtt gtc     1459
Gly Leu Ala Tyr Phe Ser Met Gln Gly Ala Trp Ala Lys Val Val Val
        360                 365                 370 atc ctt ctg ttg gcc gcc ggg gtg gac gcg cgc acc cat act gtt ggg     1507
Ile Leu Leu Leu Ala Ala Gly Val Asp Ala Arg Thr His Thr Val Gly
    375                 380                 385 ggt tct gcc gcg cag acc acc ggg cgc ctc acc agc tta ttt gac atg     1555
Gly Ser Ala Ala Gln Thr Thr Gly Arg Leu Thr Ser Leu Phe Asp Met
390                 395                 400                 405 ggc ccc agg cag aaa atc cag ctc gtt aac acc aat ggc agc tgg cac     1603
Gly Pro Arg Gln Lys Ile Gln Leu Val Asn Thr Asn Gly Ser Trp His
                410                 415                 420 atc aac cgc acc gcc ctg aac tgc aat gac tcc ttg cac acc ggc ttt     1651
Ile Asn Arg Thr Ala Leu Asn Cys Asn Asp Ser Leu His Thr Gly Phe
            425                 430                 435 atc gcg tct ctg ttc tac acc cac agc ttc aac tcg tca gga tgt ccc     1699
Ile Ala Ser Leu Phe Tyr Thr His Ser Phe Asn Ser Ser Gly Cys Pro
        440                 445                 450 gaa cgc atg tcc gcc tgc cgc agt atc gag gcc ttc cgg gtg gga tgg     1747
Glu Arg Met Ser Ala Cys Arg Ser Ile Glu Ala Phe Arg Val Gly Trp
    455                 460                 465 ggc gcc ttg caa tat gag gat aat gtc acc aat cca gag gat atg aga     1795
Gly Ala Leu Gln Tyr Glu Asp Asn Val Thr Asn Pro Glu Asp Met Arg
470                 475                 480                 485 ccc tat tgc tgg cac tac cca cca agg cag tgt ggc gtg gtc tcc gcg     1843
Pro Tyr Cys Trp His Tyr Pro Pro Arg Gln Cys Gly Val Val Ser Ala
                490                 495                 500 aag act gtg tgt ggc cca gtg tac tgt ttc acc ccc agc cca gta gta     1891
Lys Thr Val Cys Gly Pro Val Tyr Cys Phe Thr Pro Ser Pro Val Val
            505                 510                 515 gtg ggc acg acc gac agg ctt gga gcg ccc act tac acg tgg ggg gag     1939
Val Gly Thr Thr Asp Arg Leu Gly Ala Pro Thr Tyr Thr Trp Gly Glu
        520                 525                 530 aat gag aca gat gtc ttc cta ttg aac agc act cga cca ccg ctg ggg     1987
```

```
                       -continued

Asn Glu Thr Asp Val Phe Leu Leu Asn Ser Thr Arg Pro Pro Leu Gly
    535                 540                 545 tca tgg ttc ggc tgc acg tgg atg aac tct tct ggc tac acc aag act    2035
Ser Trp Phe Gly Cys Thr Trp Met Asn Ser Ser Gly Tyr Thr Lys Thr
550                 555                 560                 565 tgc ggc gca cca ccc tgc cgt act aga gct gac ttc aac gcc agc acg    2083
Cys Gly Ala Pro Pro Cys Arg Thr Arg Ala Asp Phe Asn Ala Ser Thr
                570                 575                 580 gac ctg ttg tgc ccc acg gac tgt ttt agg aag cat cct gat acc act    2131
Asp Leu Leu Cys Pro Thr Asp Cys Phe Arg Lys His Pro Asp Thr Thr
            585                 590                 595 tac ctc aaa tgc ggc tct ggg ccc tgg ctc acg cca agg tgc ctg atc    2179
Tyr Leu Lys Cys Gly Ser Gly Pro Trp Leu Thr Pro Arg Cys Leu Ile
        600                 605                 610 gac tac ccc tac agg ctc tgg cat tac ccc tgc aca gtt aac tat acc    2227
Asp Tyr Pro Tyr Arg Leu Trp His Tyr Pro Cys Thr Val Asn Tyr Thr
    615                 620                 625 atc ttc aaa ata agg atg tat gtg gga ggg gtt gag cac agg ctc acg    2275
Ile Phe Lys Ile Arg Met Tyr Val Gly Gly Val Glu His Arg Leu Thr
630                 635                 640                 645 gct gca tgc aat ttc act cgt ggg gat cgt tgc aac ttg gag gac aga    2323
Ala Ala Cys Asn Phe Thr Arg Gly Asp Arg Cys Asn Leu Glu Asp Arg
                650                 655                 660 gac aga agt caa ctg tct cct ttg ttg cac tcc acc acg gaa tgg gcc    2371
Asp Arg Ser Gln Leu Ser Pro Leu Leu His Ser Thr Thr Glu Trp Ala
            665                 670                 675 att tta cct tgc tct tac tcg gac ctg ccc gcc ttg tcg act ggt ctt    2419
Ile Leu Pro Cys Ser Tyr Ser Asp Leu Pro Ala Leu Ser Thr Gly Leu
        680                 685                 690 ctc cac ctc cac caa aac atc gtg gac gta caa ttc atg tat ggc cta    2467
Leu His Leu His Gln Asn Ile Val Asp Val Gln Phe Met Tyr Gly Leu
    695                 700                 705 tca cct gcc ctc aca aaa tac atc gtc cga tgg gag tgg gta ata ctc    2515
Ser Pro Ala Leu Thr Lys Tyr Ile Val Arg Trp Glu Trp Val Ile Leu
710                 715                 720                 725 tta ttc ctg ctc tta gcg gac gcc agg gtt tgc gcc tgc tta tgg atg    2563
Leu Phe Leu Leu Leu Ala Asp Ala Arg Val Cys Ala Cys Leu Trp Met
                730                 735                 740 ctc atc ttg ttg ggc cag gcc gaa gca gca cta gag aag ctg gtc atc    2611
Leu Ile Leu Leu Gly Gln Ala Glu Ala Ala Leu Glu Lys Leu Val Ile
            745                 750                 755 ttg cac gct gcg agc gca gct agc tgc aat ggc ttc cta tat ttt gtc    2659
Leu His Ala Ala Ser Ala Ala Ser Cys Asn Gly Phe Leu Tyr Phe Val
        760                 765                 770 atc ttt ttc gtg gct gct tgg tac atc aag ggt cgg gta gtc ccc tta    2707
Ile Phe Phe Val Ala Ala Trp Tyr Ile Lys Gly Arg Val Val Pro Leu
    775                 780                 785 gct acc tat tcc ctc act ggc ctg tgg tcc ttt agc cta ctg cta cta    2755
Ala Thr Tyr Ser Leu Thr Gly Leu Trp Ser Phe Ser Leu Leu Leu Leu
790                 795                 800                 805 gca ttg ccc caa cag gct tat gct tat gac gca tct gtg cat ggc cag    2803
Ala Leu Pro Gln Gln Ala Tyr Ala Tyr Asp Ala Ser Val His Gly Gln
                810                 815                 820 ata gga gcg gct ctg ctg gta atg atc act ctc ttt act ctc acc ccc    2851
Ile Gly Ala Ala Leu Leu Val Met Ile Thr Leu Phe Thr Leu Thr Pro
            825                 830                 835 ggg tat aag acc ctt ctc agc cgg ttt ttg tgg tgg ttg tgc tat ctt    2899
Gly Tyr Lys Thr Leu Leu Ser Arg Phe Leu Trp Trp Leu Cys Tyr Leu
        840                 845                 850
```

| | | |
|---|---|---|
| ctg acc ctg ggg gaa gct atg gtc cag gag tgg gca cca cct atg cag<br>Leu Thr Leu Gly Glu Ala Met Val Gln Glu Trp Ala Pro Pro Met Gln<br>855                        860                        865 | | 2947 |
| gtg cgc ggt ggc cgt gat ggc atc ata tgg gcc gtc gcc ata ttc tac<br>Val Arg Gly Gly Arg Asp Gly Ile Ile Trp Ala Val Ala Ile Phe Tyr<br>870                        875                        880                        885 | | 2995 |
| cca ggt gtg gtg ttt gac ata acc aag tgg ctc ttg gcg gtg ctt ggg<br>Pro Gly Val Val Phe Asp Ile Thr Lys Trp Leu Leu Ala Val Leu Gly<br>                        890                        895                        900 | | 3043 |
| cct gct tac ctc cta aaa ggt gct ttg acg cgc gtg ccg tac ttc gtc<br>Pro Ala Tyr Leu Leu Lys Gly Ala Leu Thr Arg Val Pro Tyr Phe Val<br>905                        910                        915 | | 3091 |
| agg gct cac gct cta ctg agg atg tgc acc atg gca agg cat ctc gcg<br>Arg Ala His Ala Leu Leu Arg Met Cys Thr Met Ala Arg His Leu Ala<br>                        920                        925                        930 | | 3139 |
| ggg ggc agg tac gtc cag atg gcg cta cta gcc ctt ggc agg tgg act<br>Gly Gly Arg Tyr Val Gln Met Ala Leu Leu Ala Leu Gly Arg Trp Thr<br>935                        940                        945 | | 3187 |
| ggc act tac atc tat gac cac ctc acc cct atg tcg gat tgg gct gct<br>Gly Thr Tyr Ile Tyr Asp His Leu Thr Pro Met Ser Asp Trp Ala Ala<br>950                        955                        960                        965 | | 3235 |
| agt ggc ctg cgg gac ctg gcg gtc gcc gtt gag cct atc atc ttc agt<br>Ser Gly Leu Arg Asp Leu Ala Val Ala Val Glu Pro Ile Ile Phe Ser<br>                        970                        975                        980 | | 3283 |
| ccg atg gag aag aaa gtc att gtc tgg gga gcg gag aca gct gct tgt<br>Pro Met Glu Lys Lys Val Ile Val Trp Gly Ala Glu Thr Ala Ala Cys<br>985                        990                        995 | | 3331 |
| ggg gac att tta cac gga ctt ccc gtg tcc gcc cga ctt ggt cgg<br>Gly Asp Ile Leu His Gly Leu Pro Val Ser Ala Arg Leu Gly Arg<br>            1000                    1005                    1010 | | 3376 |
| gag gtc ctc ctt ggc cca gct gat ggc tat acc tcc aag ggg tgg<br>Glu Val Leu Leu Gly Pro Ala Asp Gly Tyr Thr Ser Lys Gly Trp<br>            1015                    1020                    1025 | | 3421 |
| agt ctt ctc gcc ccc atc act gct tac gcc cag cag aca cgt ggc<br>Ser Leu Leu Ala Pro Ile Thr Ala Tyr Ala Gln Gln Thr Arg Gly<br>            1030                    1035                    1040 | | 3466 |
| ctt ttg ggc acc ata gtg gtg agc atg acg ggg cgc gac aag aca<br>Leu Leu Gly Thr Ile Val Val Ser Met Thr Gly Arg Asp Lys Thr<br>            1045                    1050                    1055 | | 3511 |
| gaa cag gct ggg gaa att cag gtc ctg tcc aca gtc act cag tcc<br>Glu Gln Ala Gly Glu Ile Gln Val Leu Ser Thr Val Thr Gln Ser<br>            1060                    1065                    1070 | | 3556 |
| ttc ctc gga aca tcc atc tcg ggg gtt ttg tgg act gtc tac cat<br>Phe Leu Gly Thr Ser Ile Ser Gly Val Leu Trp Thr Val Tyr His<br>            1075                    1080                    1085 | | 3601 |
| gga gct ggc aac aag act ctg gcc ggc tca cgg ggt ccg gtc acg<br>Gly Ala Gly Asn Lys Thr Leu Ala Gly Ser Arg Gly Pro Val Thr<br>            1090                    1095                    1100 | | 3646 |
| cag atg tac tcc agt gct gag ggg gac tta gta ggg tgg ccc agc<br>Gln Met Tyr Ser Ser Ala Glu Gly Asp Leu Val Gly Trp Pro Ser<br>            1105                    1110                    1115 | | 3691 |
| ccc cct ggg act aaa tct ttg gag ccg tgc acg tgt gga gcg gtc<br>Pro Pro Gly Thr Lys Ser Leu Glu Pro Cys Thr Cys Gly Ala Val<br>            1120                    1125                    1130 | | 3736 |
| gac ctg tac ctg gtc acg cgg aac gct gat gtc atc ccg gct cga<br>Asp Leu Tyr Leu Val Thr Arg Asn Ala Asp Val Ile Pro Ala Arg<br>            1135                    1140                    1145 | | 3781 |
| aga cgc ggg gac aaa cgg gga gcg cta ctc tcc ccg aga cct ctt<br>Arg Arg Gly Asp Lys Arg Gly Ala Leu Leu Ser Pro Arg Pro Leu<br>            1150                    1155                    1160 | | 3826 |

-continued

| | | | | | | | | | | | | |
|---|---|---|---|---|---|---|---|---|---|---|---|---|
| tcc | acc | ttg | aag | ggg | tcc | tca | gga | ggc | ccg | gtg | cta | tgc | ccc | agg | 3871 |
| Ser | Thr | Leu | Lys | Gly | Ser | Ser | Gly | Gly | Pro | Val | Leu | Cys | Pro | Arg | |
| | | | 1165 | | | | 1170 | | | | | 1175 | | | |

```
tcc acc ttg aag ggg tcc tca gga ggc ccg gtg cta tgc ccc agg      3871
Ser Thr Leu Lys Gly Ser Ser Gly Gly Pro Val Leu Cys Pro Arg
            1165                1170                1175 ggc cac gct gtc gga gtc ttc cgg gca gct gtg tgc tct cgg ggc      3916
Gly His Ala Val Gly Val Phe Arg Ala Ala Val Cys Ser Arg Gly
        1180                1185                1190 gtg gct aag tcc ata gat ttc atc ccc gtt gag aca ctc gac atc      3961
Val Ala Lys Ser Ile Asp Phe Ile Pro Val Glu Thr Leu Asp Ile
    1195                1200                1205 gtc acg cgg tcc ccc acc ttt agt gac aac agc aca cca cct gct      4006
Val Thr Arg Ser Pro Thr Phe Ser Asp Asn Ser Thr Pro Pro Ala
        1210                1215                1220 gtg ccc cag acc tat cag gtc ggg tac ttg cat gcc ccg act ggc      4051
Val Pro Gln Thr Tyr Gln Val Gly Tyr Leu His Ala Pro Thr Gly
    1225                1230                1235 agt gga aag agc acc aaa gtt cct gtc gca tat gct gct cag ggg      4096
Ser Gly Lys Ser Thr Lys Val Pro Val Ala Tyr Ala Ala Gln Gly
        1240                1245                1250 tat aaa gtg cta gtg ctt aat ccc tca gtg gct gcc acc ctg ggg      4141
Tyr Lys Val Leu Val Leu Asn Pro Ser Val Ala Ala Thr Leu Gly
    1255                1260                1265 ttt ggg gcg tac ttg tct aag gca cat ggc atc aat ccc aac att      4186
Phe Gly Ala Tyr Leu Ser Lys Ala His Gly Ile Asn Pro Asn Ile
        1270                1275                1280 agg act gga gtc agg act gtg acg acc ggg gcg ccc atc acg tac      4231
Arg Thr Gly Val Arg Thr Val Thr Thr Gly Ala Pro Ile Thr Tyr
    1285                1290                1295 tcc aca tat ggc aaa ttc ctc gcc gat ggg ggc tgt gcg ggc ggc      4276
Ser Thr Tyr Gly Lys Phe Leu Ala Asp Gly Gly Cys Ala Gly Gly
        1300                1305                1310 gcc tac gac atc atc ata tgt gat gaa tgc cat gcc gtg gac tct      4321
Ala Tyr Asp Ile Ile Ile Cys Asp Glu Cys His Ala Val Asp Ser
    1315                1320                1325 acc acc atc ctt ggc atc gga aca gtc ctt gat caa gca gag aca      4366
Thr Thr Ile Leu Gly Ile Gly Thr Val Leu Asp Gln Ala Glu Thr
        1330                1335                1340 gct ggg gtc aga cta act gtg ctg gct aca gct acg ccc cct ggg      4411
Ala Gly Val Arg Leu Thr Val Leu Ala Thr Ala Thr Pro Pro Gly
    1345                1350                1355 tca gtg aca acc ccc cac ccc aac ata gag gag gtg gcc ctt ggg      4456
Ser Val Thr Thr Pro His Pro Asn Ile Glu Glu Val Ala Leu Gly
        1360                1365                1370 cag gag ggc gag atc ccc ttc tat ggg agg gcg att ccc ctg tct      4501
Gln Glu Gly Glu Ile Pro Phe Tyr Gly Arg Ala Ile Pro Leu Ser
    1375                1380                1385 tac atc aag gga gga aga cat ctg atc ttc tgc cat tca aag aaa      4546
Tyr Ile Lys Gly Gly Arg His Leu Ile Phe Cys His Ser Lys Lys
        1390                1395                1400 aag tgt gac gag ctc gcg gcg gcc ctt cgg ggt atg ggc ttg aac      4591
Lys Cys Asp Glu Leu Ala Ala Ala Leu Arg Gly Met Gly Leu Asn
    1405                1410                1415 tca gtg gca tac tac aga ggg ttg gac gtc tcc gta ata cca act      4636
Ser Val Ala Tyr Tyr Arg Gly Leu Asp Val Ser Val Ile Pro Thr
        1420                1425                1430 cag gga gac gta gtg gtc gtc gcc acc gac gcc ctc atg aca ggg      4681
Gln Gly Asp Val Val Val Val Ala Thr Asp Ala Leu Met Thr Gly
    1435                1440                1445 tat act ggg gac ttt gac tcc gtg atc gac tgc aac gta gcg gtc      4726
Tyr Thr Gly Asp Phe Asp Ser Val Ile Asp Cys Asn Val Ala Val
```

```
                    1450                 1455                 1460
act caa gtt gta gac ttc agt tta gac ccc aca ttc acc ata acc        4771
Thr Gln Val Val Asp Phe Ser Leu Asp Pro Thr Phe Thr Ile Thr
        1465                 1470                 1475 aca cag att gtc cct caa gac gct gtc tca cgt agc cag cgc cgg        4816
Thr Gln Ile Val Pro Gln Asp Ala Val Ser Arg Ser Gln Arg Arg
        1480                 1485                 1490 ggt cgc acg ggt agg gga aga ctg ggc att tat agg tat gtt tcc        4861
Gly Arg Thr Gly Arg Gly Arg Leu Gly Ile Tyr Arg Tyr Val Ser
        1495                 1500                 1505 act ggt gag cga gcc tca gga atg ttt gac agt gta gtg ctc tgt        4906
Thr Gly Glu Arg Ala Ser Gly Met Phe Asp Ser Val Val Leu Cys
        1510                 1515                 1520 gag tgc tac gac gca ggg gcc gca tgg tat gag ctc aca cca tcg        4951
Glu Cys Tyr Asp Ala Gly Ala Ala Trp Tyr Glu Leu Thr Pro Ser
        1525                 1530                 1535 gag acc acc gtc agg ctc agg gcg tat ttc aac acg ccc ggt ttg        4996
Glu Thr Thr Val Arg Leu Arg Ala Tyr Phe Asn Thr Pro Gly Leu
        1540                 1545                 1550 cct gtg tgc caa gac cat ctt gag ttt tgg gag gca gtt ttc acc        5041
Pro Val Cys Gln Asp His Leu Glu Phe Trp Glu Ala Val Phe Thr
        1555                 1560                 1565 ggc ctc aca cac ata gat gcc cac ttc ctt tcc caa aca aag caa        5086
Gly Leu Thr His Ile Asp Ala His Phe Leu Ser Gln Thr Lys Gln
        1570                 1575                 1580 tcg ggg gaa aat ttc gca tac tta aca gcc tac cag gct aca gtg        5131
Ser Gly Glu Asn Phe Ala Tyr Leu Thr Ala Tyr Gln Ala Thr Val
        1585                 1590                 1595 tgc gct agg gcc aaa gcc ccc ccg tcc tgg gac gtc atg tgg        5176
Cys Ala Arg Ala Lys Ala Pro Pro Pro Ser Trp Asp Val Met Trp
        1600                 1605                 1610 aag tgt ttg act cga ctc aag ccc aca ctc gtg ggc ccc aca cct        5221
Lys Cys Leu Thr Arg Leu Lys Pro Thr Leu Val Gly Pro Thr Pro
        1615                 1620                 1625 ctc ctg tac cgc ttg ggc tct gtt acc aac gag gtc acc ctc aca        5266
Leu Leu Tyr Arg Leu Gly Ser Val Thr Asn Glu Val Thr Leu Thr
        1630                 1635                 1640 cat ccc gtg acg aaa tac atc gcc acc tgc atg caa gcc gac ctt        5311
His Pro Val Thr Lys Tyr Ile Ala Thr Cys Met Gln Ala Asp Leu
        1645                 1650                 1655 gag gtc atg acc agc aca tgg gtc ttg gca ggg gga gtc ttg gcg        5356
Glu Val Met Thr Ser Thr Trp Val Leu Ala Gly Gly Val Leu Ala
        1660                 1665                 1670 gcc gtc gcc gcg tat tgc ctg gag acc ggg tgt gtt tgc atc atc        5401
Ala Val Ala Ala Tyr Cys Leu Glu Thr Gly Cys Val Cys Ile Ile
        1675                 1680                 1685 ggc cgc ttg cac att aac cag cga gcc gtc gtt gcg ccg gac aag        5446
Gly Arg Leu His Ile Asn Gln Arg Ala Val Val Ala Pro Asp Lys
        1690                 1695                 1700 gag gtc ctc tat gag gct ttt gat gag atg gag gaa tgt gcc tct        5491
Glu Val Leu Tyr Glu Ala Phe Asp Glu Met Glu Glu Cys Ala Ser
        1705                 1710                 1715 agg gcg gct ctc att gaa gag ggg cag cgg ata gcc gag atg ctg        5536
Arg Ala Ala Leu Ile Glu Glu Gly Gln Arg Ile Ala Glu Met Leu
        1720                 1725                 1730 aag tcc aag atc caa ggc tta ttg cag caa gct tcc aaa caa gct        5581
Lys Ser Lys Ile Gln Gly Leu Leu Gln Gln Ala Ser Lys Gln Ala
        1735                 1740                 1745 caa gac ata caa ccc act gtg cag gct tca tgg ccc aag gta gaa        5626
```

|         |         |         |         |         |         |         |         |         |         |         |         |         |         |         |      |
|---------|---------|---------|---------|---------|---------|---------|---------|---------|---------|---------|---------|---------|---------|---------|------|
| Gln     | Asp     | Ile     |         | Gln     | Pro     | Thr     | Val     | Gln     |         | Ala     | Ser     | Trp     | Pro     | Lys     | Val     | Glu |
|         |         | 1750    |         |         |         |         | 1755    |         |         |         |         |         | 1760    |         |         |     |

```
caa ttc tgg  gcc aaa cac  atg tgg aac  ttc att agc  ggc atc caa       5671
Gln Phe Trp  Ala Lys His  Met Trp Asn  Phe Ile Ser  Gly Ile Gln
            1765              1770              1775 tac ctc gca  gga cta tca  aca ctg cca  ggg aac cct  gca gta gct       5716
Tyr Leu Ala  Gly Leu Ser  Thr Leu Pro  Gly Asn Pro  Ala Val Ala
            1780              1785              1790 tcc atg atg  gcg ttc agt  gcc gcc ctc  acc agt ccg  ctg tca aca       5761
Ser Met Met  Ala Phe Ser  Ala Ala Leu  Thr Ser Pro  Leu Ser Thr
            1795              1800              1805 agc acc act  atc ctt ctc  aac att ttg  ggg ggc tgg  cta gca tcc       5806
Ser Thr Thr  Ile Leu Leu  Asn Ile Leu  Gly Gly Trp  Leu Ala Ser
            1810              1815              1820 caa att gca  cca ccc gcg  ggg gcc act  ggc ttc gtt  gtc agt ggc       5851
Gln Ile Ala  Pro Pro Ala  Gly Ala Thr  Gly Phe Val  Val Ser Gly
            1825              1830              1835 cta gtg gga  gct gcc gta  ggc agt ata  ggc tta ggt  aag gtg cta       5896
Leu Val Gly  Ala Ala Val  Gly Ser Ile  Gly Leu Gly  Lys Val Leu
            1840              1845              1850 gtg gac atc  ctg gca ggg  tat ggt gcg  ggc att tcg  ggg gct ctc       5941
Val Asp Ile  Leu Ala Gly  Tyr Gly Ala  Gly Ile Ser  Gly Ala Leu
            1855              1860              1865 gtc gca ttc  aag atc atg  tct ggc gag  aag ccc tcc  atg gag gat       5986
Val Ala Phe  Lys Ile Met  Ser Gly Glu  Lys Pro Ser  Met Glu Asp
            1870              1875              1880 gtc gtc aac  ttg ctg cct  gga att ctg  tct ccg ggt  gcc ttg gta       6031
Val Val Asn  Leu Leu Pro  Gly Ile Leu  Ser Pro Gly  Ala Leu Val
            1885              1890              1895 gtg gga gtc  atc tgc gcg  gcc att ctg  cgc cga cac  gtg gga ccg       6076
Val Gly Val  Ile Cys Ala  Ala Ile Leu  Arg Arg His  Val Gly Pro
            1900              1905              1910 ggg gaa ggc  gcc gtc caa  tgg atg aat  aga ctc att  gcc ttt gct       6121
Gly Glu Gly  Ala Val Gln  Trp Met Asn  Arg Leu Ile  Ala Phe Ala
            1915              1920              1925 tcc aga gga  aat cac gtc  gcc ccc acc  cac tac gtg  acg gag tcg       6166
Ser Arg Gly  Asn His Val  Ala Pro Thr  His Tyr Val  Thr Glu Ser
            1930              1935              1940 gat gcg tcg  cag cgt gtg  acc caa cta  ctt ggc tcc  ctt acc ata       6211
Asp Ala Ser  Gln Arg Val  Thr Gln Leu  Leu Gly Ser  Leu Thr Ile
            1945              1950              1955 acc agc ctg  ctc aga aga  ctc cac aac  tgg att act  gag gac tgc       6256
Thr Ser Leu  Leu Arg Arg  Leu His Asn  Trp Ile Thr  Glu Asp Cys
            1960              1965              1970 ccc atc cca  tgc tcc gga  tcg tgg ctc  cgc gat gtg  tgg gac tgg       6301
Pro Ile Pro  Cys Ser Gly  Ser Trp Leu  Arg Asp Val  Trp Asp Trp
            1975              1980              1985 gtt tgc acc  atc cta aca  gac ttt aaa  aat tgg ctg  acc tcc aaa       6346
Val Cys Thr  Ile Leu Thr  Asp Phe Lys  Asn Trp Leu  Thr Ser Lys
            1990              1995              2000 tta ttc cca  aag atg ccc  ggc ctc ccc  ttt gtc tcc  tgt caa aag       6391
Leu Phe Pro  Lys Met Pro  Gly Leu Pro  Phe Val Ser  Cys Gln Lys
            2005              2010              2015 ggg tac aag  ggc gtg tgg  gcc ggc act  ggc atc atg  acc aca cgg       6436
Gly Tyr Lys  Gly Val Trp  Ala Gly Thr  Gly Ile Met  Thr Thr Arg
            2020              2025              2030 tgt cct tgc  ggc gcc aat  atc tct ggc  aat gtc cgc  ttg ggc tcc       6481
Cys Pro Cys  Gly Ala Asn  Ile Ser Gly  Asn Val Arg  Leu Gly Ser
            2035              2040              2045
```

```
atg aga atc acg ggg cct aag acc tgc atg aat atc tgg cag ggg      6526
Met Arg Ile Thr Gly Pro Lys Thr Cys Met Asn Ile Trp Gln Gly
        2050                2055                2060 acc ttt cct atc aat tgt tac acg gag ggc cag tgc gtg ccg aaa      6571
Thr Phe Pro Ile Asn Cys Tyr Thr Glu Gly Gln Cys Val Pro Lys
        2065                2070                2075 ccc gcg cca aac ttt aag gtc gcc atc tgg agg gtg gcg gcc tca      6616
Pro Ala Pro Asn Phe Lys Val Ala Ile Trp Arg Val Ala Ala Ser
        2080                2085                2090 gag tac gcg gag gtg acg cag cac ggg tca tac cac tac ata aca      6661
Glu Tyr Ala Glu Val Thr Gln His Gly Ser Tyr His Tyr Ile Thr
        2095                2100                2105 gga ctc acc act gat aac ttg aaa gtc ccc tgc caa cta ccc tct      6706
Gly Leu Thr Thr Asp Asn Leu Lys Val Pro Cys Gln Leu Pro Ser
        2110                2115                2120 ccc gag ttc ttt tcc tgg gtg gac gga gtg cag atc cat agg ttt      6751
Pro Glu Phe Phe Ser Trp Val Asp Gly Val Gln Ile His Arg Phe
        2125                2130                2135 gcc ccc aca ccg aag ccg ttt ttc cgg gat gag gtc tcg ttc tgc      6796
Ala Pro Thr Pro Lys Pro Phe Phe Arg Asp Glu Val Ser Phe Cys
        2140                2145                2150 gtt ggg ctt aat tca ttt gtc gtc ggg tcc cag ctt cct tgc gac      6841
Val Gly Leu Asn Ser Phe Val Val Gly Ser Gln Leu Pro Cys Asp
        2155                2160                2165 cct gaa ccc gac aca gac gta ttg atg tcc atg cta aca gat cca      6886
Pro Glu Pro Asp Thr Asp Val Leu Met Ser Met Leu Thr Asp Pro
        2170                2175                2180 tct cat atc acg gcg gag act gca gcg cgg cgt tta gcg cgg ggg      6931
Ser His Ile Thr Ala Glu Thr Ala Ala Arg Arg Leu Ala Arg Gly
        2185                2190                2195 tca ccc cca tcc gag gca agc tcc tcg gcg agc cag cta tcg gca      6976
Ser Pro Pro Ser Glu Ala Ser Ser Ser Ala Ser Gln Leu Ser Ala
        2200                2205                2210 cca tcg ctg cga gcc acc tgc acc acc cac ggc aaa gcc tat gat      7021
Pro Ser Leu Arg Ala Thr Cys Thr Thr His Gly Lys Ala Tyr Asp
        2215                2220                2225 gtg gac atg gtg gat gct aac ctg ttc atg ggg ggc gat gtg act      7066
Val Asp Met Val Asp Ala Asn Leu Phe Met Gly Gly Asp Val Thr
        2230                2235                2240 cgg ata gag tct ggg tcc aaa gtg gtc gtt ctg gac tct ctc gac      7111
Arg Ile Glu Ser Gly Ser Lys Val Val Val Leu Asp Ser Leu Asp
        2245                2250                2255 cca atg gtc gaa gaa agg agc gac ctt gag cct tcg ata cca tca      7156
Pro Met Val Glu Glu Arg Ser Asp Leu Glu Pro Ser Ile Pro Ser
        2260                2265                2270 gaa tac atg ctc ccc aag aag agg ttc cca cca gct tta ccg gcc      7201
Glu Tyr Met Leu Pro Lys Lys Arg Phe Pro Pro Ala Leu Pro Ala
        2275                2280                2285 tgg gca cgg cct gat tac aac cca ccg ctt gtg gaa tcg tgg aaa      7246
Trp Ala Arg Pro Asp Tyr Asn Pro Pro Leu Val Glu Ser Trp Lys
        2290                2295                2300 agg cca gat tac caa ccg gcc act gtt gcg ggc tgt gct ctc cct      7291
Arg Pro Asp Tyr Gln Pro Ala Thr Val Ala Gly Cys Ala Leu Pro
        2305                2310                2315 cct cct agg aaa acc ccg acg cct ccc cca agg agg cgc cgg aca      7336
Pro Pro Arg Lys Thr Pro Thr Pro Pro Pro Arg Arg Arg Arg Thr
        2320                2325                2330 gtg ggc cta agt gag gac tcc ata gga gat gcc ctt caa cag ctg      7381
Val Gly Leu Ser Glu Asp Ser Ile Gly Asp Ala Leu Gln Gln Leu
        2335                2340                2345
```

```
gcc att aag tcc ttt ggc cag ccc ccc cca agc ggc gat tca ggc      7426
Ala Ile Lys Ser Phe Gly Gln Pro Pro Pro Ser Gly Asp Ser Gly
        2350                2355                2360 ctt tcc acg ggg gcg ggc gct gcc gat tcc ggc agt cag acg cct      7471
Leu Ser Thr Gly Ala Gly Ala Ala Asp Ser Gly Ser Gln Thr Pro
2365                2370                2375 cct gat gag ttg gcc ctt tcg gag aca ggt tcc atc tct tcc atg      7516
Pro Asp Glu Leu Ala Leu Ser Glu Thr Gly Ser Ile Ser Ser Met
    2380                2385                2390 ccc ccc ctc gag ggg gag ctt gga gat cca gac ctg gag cct gag      7561
Pro Pro Leu Glu Gly Glu Leu Gly Asp Pro Asp Leu Glu Pro Glu
        2395                2400                2405 cag gta gag ccc caa ccc ccc ccc cag ggg ggg gtg gca gct ccc      7606
Gln Val Glu Pro Gln Pro Pro Pro Gln Gly Gly Val Ala Ala Pro
2410                2415                2420 ggc tcg gac tcg ggg tcc tgg tct act tgc tcc gag gag gac gac      7651
Gly Ser Asp Ser Gly Ser Trp Ser Thr Cys Ser Glu Glu Asp Asp
    2425                2430                2435 tcc gtc gtg tgc tgc tcc atg tca tac tcc tgg acc ggg gct cta      7696
Ser Val Val Cys Cys Ser Met Ser Tyr Ser Trp Thr Gly Ala Leu
        2440                2445                2450 ata act cct tgt agt ccc gaa gag gag aag tta ccg att aac ccc      7741
Ile Thr Pro Cys Ser Pro Glu Glu Glu Lys Leu Pro Ile Asn Pro
2455                2460                2465 ttg agc aac tcc ctg ttg cga tat cac aac aag gtg tac tgt acc      7786
Leu Ser Asn Ser Leu Leu Arg Tyr His Asn Lys Val Tyr Cys Thr
    2470                2475                2480 aca aca aag agc gcc tca cta agg gct aaa aag gta act ttt gat      7831
Thr Thr Lys Ser Ala Ser Leu Arg Ala Lys Lys Val Thr Phe Asp
        2485                2490                2495 agg atg caa gtg ctc gac tcc tac tac gac tca gtc tta aag gac      7876
Arg Met Gln Val Leu Asp Ser Tyr Tyr Asp Ser Val Leu Lys Asp
2500                2505                2510 att aag cta gcg gcc tcc aag gtc acc gca agg ctc ctc acc atg      7921
Ile Lys Leu Ala Ala Ser Lys Val Thr Ala Arg Leu Leu Thr Met
    2515                2520                2525 gag gag gct tgc cag tta acc cca ccc cat tct gca aga tct aaa      7966
Glu Glu Ala Cys Gln Leu Thr Pro Pro His Ser Ala Arg Ser Lys
        2530                2535                2540 tat ggg ttt ggg gct aag gag gtc cgc agc ttg tcc ggg agg gcc      8011
Tyr Gly Phe Gly Ala Lys Glu Val Arg Ser Leu Ser Gly Arg Ala
2545                2550                2555 gtt aac cac atc aag tcc gtg tgg aag gac ctc ctg gag gac tca      8056
Val Asn His Ile Lys Ser Val Trp Lys Asp Leu Leu Glu Asp Ser
    2560                2565                2570 gaa aca cca att ccc aca acc att atg gcc aaa aat gag gtg ttc      8101
Glu Thr Pro Ile Pro Thr Thr Ile Met Ala Lys Asn Glu Val Phe
        2575                2580                2585 tgc gtg gac ccc acc aag ggg ggc aag aaa gca gct cgc ctt atc      8146
Cys Val Asp Pro Thr Lys Gly Gly Lys Lys Ala Ala Arg Leu Ile
2590                2595                2600 gtt tac cct gac ctc ggc gtc agg gtc tgc gag aag atg gcc ctt      8191
Val Tyr Pro Asp Leu Gly Val Arg Val Cys Glu Lys Met Ala Leu
    2605                2610                2615 tat gac att aca caa aaa ctt cct cag gcg gtg atg ggg gct tct      8236
Tyr Asp Ile Thr Gln Lys Leu Pro Gln Ala Val Met Gly Ala Ser
        2620                2625                2630 tat gga ttc cag tat tcc ccc gct cag cgg gta gag ttt ctc ttg      8281
Tyr Gly Phe Gln Tyr Ser Pro Ala Gln Arg Val Glu Phe Leu Leu
```

```
                    2635               2640                2645 aaa gca tgg gcg gaa aag aag gac cct atg ggt ttt tcg tat gat          8326
Lys Ala Trp Ala Glu Lys Lys Asp Pro Met Gly Phe Ser Tyr Asp
        2650                2655                2660 acc cga tgc ttt gac tca acc gtc act gag aga gac atc agg act          8371
Thr Arg Cys Phe Asp Ser Thr Val Thr Glu Arg Asp Ile Arg Thr
        2665                2670                2675 gag gag tcc ata tat cgg gcc tgc tcc ttg ccc gag gag gcc cac          8416
Glu Glu Ser Ile Tyr Arg Ala Cys Ser Leu Pro Glu Glu Ala His
        2680                2685                2690 act gcc ata cac tcg cta act gag aga ctt tac gtg gga ggg cct          8461
Thr Ala Ile His Ser Leu Thr Glu Arg Leu Tyr Val Gly Gly Pro
        2695                2700                2705 atg ttc aac agc aag ggc caa acc tgc ggg tac agg cgt tgc cgc          8506
Met Phe Asn Ser Lys Gly Gln Thr Cys Gly Tyr Arg Arg Cys Arg
        2710                2715                2720 gcc agc ggg gtg ctc acc act agc atg ggg aac acc atc aca tgc          8551
Ala Ser Gly Val Leu Thr Thr Ser Met Gly Asn Thr Ile Thr Cys
        2725                2730                2735 tac gtg aaa gcc tta gcg gct tgt aaa gct gca ggg ata atc gcg          8596
Tyr Val Lys Ala Leu Ala Ala Cys Lys Ala Ala Gly Ile Ile Ala
        2740                2745                2750 ccc aca atg ctg gta tgc ggc gat gac ttg gtt gtc atc tca gaa          8641
Pro Thr Met Leu Val Cys Gly Asp Asp Leu Val Val Ile Ser Glu
        2755                2760                2765 agc cag ggg acc gag gag gac gag cgg aac ctg aga gcc ttc acg          8686
Ser Gln Gly Thr Glu Glu Asp Glu Arg Asn Leu Arg Ala Phe Thr
        2770                2775                2780 gag gct atg acc agg tat tct gcc cct cct ggt gac ccc ccc aga          8731
Glu Ala Met Thr Arg Tyr Ser Ala Pro Pro Gly Asp Pro Pro Arg
        2785                2790                2795 ccg gag tat gat ctg gag ctg ata aca tct tgc tcc tca aat gtg          8776
Pro Glu Tyr Asp Leu Glu Leu Ile Thr Ser Cys Ser Ser Asn Val
        2800                2805                2810 tct gtg gcg ctg ggc cca caa ggc cgc cgc aga tac tac ctg acc          8821
Ser Val Ala Leu Gly Pro Gln Gly Arg Arg Arg Tyr Tyr Leu Thr
        2815                2820                2825 aga gac cct acc act cca atc gcc cgg gct gcc tgg gaa aca gtt          8866
Arg Asp Pro Thr Thr Pro Ile Ala Arg Ala Ala Trp Glu Thr Val
        2830                2835                2840 aga cac tcc cct gtc aat tca tgg ctg gga aac atc atc cag tac          8911
Arg His Ser Pro Val Asn Ser Trp Leu Gly Asn Ile Ile Gln Tyr
        2845                2850                2855 gcc ccg acc ata tgg gct cgc atg gtc ctg atg aca cac ttc ttc          8956
Ala Pro Thr Ile Trp Ala Arg Met Val Leu Met Thr His Phe Phe
        2860                2865                2870 tcc att ctc atg gct caa gac acg ctg gac cag aac ctc aac ttt          9001
Ser Ile Leu Met Ala Gln Asp Thr Leu Asp Gln Asn Leu Asn Phe
        2875                2880                2885 gag atg tac gga gcg gtg tac tcc gtg agt ccc ttg gac ctc cca          9046
Glu Met Tyr Gly Ala Val Tyr Ser Val Ser Pro Leu Asp Leu Pro
        2890                2895                2900 gct ata att gaa agg tta cat ggg ctt gac gct ttt tct ctg cac          9091
Ala Ile Ile Glu Arg Leu His Gly Leu Asp Ala Phe Ser Leu His
        2905                2910                2915 aca tac act ccc cac gaa ctg aca cgg gtg gct tca gcc ctc aga          9136
Thr Tyr Thr Pro His Glu Leu Thr Arg Val Ala Ser Ala Leu Arg
        2920                2925                2930 aaa ctt ggg gcg cca ccc ctc aga gcg tgg aag agc cgg gca cgt          9181
```

```
Lys Leu Gly Ala Pro Pro Leu Arg Ala Trp Lys Ser Arg Ala Arg
         2935                2940                2945 gca gtc agg gcg tcc ctc atc tcc cgt gga ggg aaa gcg gcc gtt      9226
Ala Val Arg Ala Ser Leu Ile Ser Arg Gly Gly Lys Ala Ala Val
        2950                2955                2960 tgc ggc cga tat ctc ttc aat tgg gcg gtg aag acc aag ctc aaa      9271
Cys Gly Arg Tyr Leu Phe Asn Trp Ala Val Lys Thr Lys Leu Lys
        2965                2970                2975 ctc act cca ttg ccg gag gcg cgc cta ctg gac tta tcc agt tgg      9316
Leu Thr Pro Leu Pro Glu Ala Arg Leu Leu Asp Leu Ser Ser Trp
        2980                2985                2990 ttc acc gtc ggc gcc ggc ggg ggc gac att ttt cac agc gtg tcg      9361
Phe Thr Val Gly Ala Gly Gly Gly Asp Ile Phe His Ser Val Ser
        2995                3000                3005 cgc gcc cga ccc cgc tca tta ctc ttc ggc cta ctc ctt ttc           9406
Arg Ala Arg Pro Arg Ser Leu Leu Phe Gly Leu Leu Leu Leu Phe
        3010                3015                3020 gta ggg gta ggc ctc ttc cta ctc ccc gct cgg tagagcggca            9449
Val Gly Val Gly Leu Phe Leu Leu Pro Ala Arg
        3025                3030 cacactaggt acactccata gctaactgtt cctttttttt tttttttttt           9509
tttttttttt ttttctttt tttttttttt ccctctttct tcccttctca tcttattcta 9569 ctttctttct tggtggctcc atcttagccc tagtcacggc tagctgtgaa aggtccgtga 9629 gccgcatgac tgcagagagt gccgtaactg gtctctctgc agatcatgt             9678

<210> SEQ ID NO 3
<211> LENGTH: 3033
<212> TYPE: PRT
<213> ORGANISM: Artificial Sequence
<220> FEATURE:
<223> OTHER INFORMATION: Description of Artificial Sequence: Synthetic
      precursor protein encoded by FGR-J6/5BSLX-JFH-1+4Amut

<400> SEQUENCE: 3

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175
```

```
Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
        210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
        290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
        355                 360                 365

Ala Lys Val Val Val Ile Leu Leu Leu Ala Ala Gly Val Asp Ala Arg
        370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
        435                 440                 445

Ser Ser Gly Cys Pro Glu Arg Met Ser Ala Cys Arg Ser Ile Glu Ala
        450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Lys Thr Val Cys Gly Pro Val Tyr Cys Phe Thr
            500                 505                 510

Pro Ser Pro Val Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
        530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
```

```
                595                 600                 605
        Pro Arg Cys Leu Ile Asp Tyr Pro Tyr Arg Leu Trp His Tyr Pro Cys
        610                 615                 620

Thr Val Asn Tyr Thr Ile Phe Lys Ile Arg Met Tyr Val Gly Gly Val
        625                 630                 635                 640

Glu His Arg Leu Thr Ala Ala Cys Asn Phe Thr Arg Gly Asp Arg Cys
                        645                 650                 655

Asn Leu Glu Asp Arg Asp Arg Ser Gln Leu Ser Pro Leu Leu His Ser
                        660                 665                 670

Thr Thr Glu Trp Ala Ile Leu Pro Cys Ser Tyr Ser Asp Leu Pro Ala
                        675                 680                 685

Leu Ser Thr Gly Leu Leu His Leu His Gln Asn Ile Val Asp Val Gln
        690                 695                 700

Phe Met Tyr Gly Leu Ser Pro Ala Leu Thr Lys Tyr Ile Val Arg Trp
        705                 710                 715                 720

Glu Trp Val Ile Leu Leu Phe Leu Leu Leu Ala Asp Ala Arg Val Cys
                        725                 730                 735

Ala Cys Leu Trp Met Leu Ile Leu Leu Gly Gln Ala Glu Ala Ala Leu
                        740                 745                 750

Glu Lys Leu Val Ile Leu His Ala Ala Ser Ala Ala Ser Cys Asn Gly
                        755                 760                 765

Phe Leu Tyr Phe Val Ile Phe Phe Val Ala Ala Trp Tyr Ile Lys Gly
        770                 775                 780

Arg Val Val Pro Leu Ala Thr Tyr Ser Leu Thr Gly Leu Trp Ser Phe
        785                 790                 795                 800

Ser Leu Leu Leu Ala Leu Pro Gln Gln Ala Tyr Ala Tyr Asp Ala
                        805                 810                 815

Ser Val His Gly Gln Ile Gly Ala Ala Leu Leu Val Met Ile Thr Leu
                        820                 825                 830

Phe Thr Leu Thr Pro Gly Tyr Lys Thr Leu Leu Ser Arg Phe Leu Trp
                        835                 840                 845

Trp Leu Cys Tyr Leu Leu Thr Leu Gly Glu Ala Met Val Gln Glu Trp
        850                 855                 860

Ala Pro Pro Met Gln Val Arg Gly Gly Arg Asp Gly Ile Ile Trp Ala
        865                 870                 875                 880

Val Ala Ile Phe Tyr Pro Gly Val Val Phe Asp Ile Thr Lys Trp Leu
                        885                 890                 895

Leu Ala Val Leu Gly Pro Ala Tyr Leu Leu Lys Gly Ala Leu Thr Arg
                        900                 905                 910

Val Pro Tyr Phe Val Arg Ala His Ala Leu Leu Arg Met Cys Thr Met
                        915                 920                 925

Ala Arg His Leu Ala Gly Gly Arg Tyr Val Gln Met Ala Leu Leu Ala
                        930                 935                 940

Leu Gly Arg Trp Thr Gly Thr Tyr Ile Tyr Asp His Leu Thr Pro Met
        945                 950                 955                 960

Ser Asp Trp Ala Ala Ser Gly Leu Arg Asp Leu Ala Val Ala Val Glu
                        965                 970                 975

Pro Ile Ile Phe Ser Pro Met Glu Lys Lys Val Ile Val Trp Gly Ala
                        980                 985                 990

Glu Thr Ala Ala Cys Gly Asp Ile Leu His Gly Leu Pro Val Ser Ala
                        995                 1000                1005

Arg Leu Gly Arg Glu Val Leu Leu Gly Pro Ala Asp Gly Tyr Thr
                1010                1015                1020
```

```
Ser Lys Gly Trp Ser Leu Leu Ala Pro Ile Thr Ala Tyr Ala Gln
    1025             1030            1035

Gln Thr Arg Gly Leu Leu Gly Thr Ile Val Val Ser Met Thr Gly
    1040             1045            1050

Arg Asp Lys Thr Glu Gln Ala Gly Glu Ile Gln Val Leu Ser Thr
    1055             1060            1065

Val Thr Gln Ser Phe Leu Gly Thr Ser Ile Ser Gly Val Leu Trp
    1070             1075            1080

Thr Val Tyr His Gly Ala Gly Asn Lys Thr Leu Ala Gly Ser Arg
    1085             1090            1095

Gly Pro Val Thr Gln Met Tyr Ser Ser Ala Glu Gly Asp Leu Val
    1100             1105            1110

Gly Trp Pro Ser Pro Pro Gly Thr Lys Ser Leu Glu Pro Cys Thr
    1115             1120            1125

Cys Gly Ala Val Asp Leu Tyr Leu Val Thr Arg Asn Ala Asp Val
    1130             1135            1140

Ile Pro Ala Arg Arg Arg Gly Asp Lys Arg Gly Ala Leu Leu Ser
    1145             1150            1155

Pro Arg Pro Leu Ser Thr Leu Lys Gly Ser Ser Gly Gly Pro Val
    1160             1165            1170

Leu Cys Pro Arg Gly His Ala Val Gly Val Phe Arg Ala Ala Val
    1175             1180            1185

Cys Ser Arg Gly Val Ala Lys Ser Ile Asp Phe Ile Pro Val Glu
    1190             1195            1200

Thr Leu Asp Ile Val Thr Arg Ser Pro Thr Phe Ser Asp Asn Ser
    1205             1210            1215

Thr Pro Pro Ala Val Pro Gln Thr Tyr Gln Val Gly Tyr Leu His
    1220             1225            1230

Ala Pro Thr Gly Ser Gly Lys Ser Thr Lys Val Pro Val Ala Tyr
    1235             1240            1245

Ala Ala Gln Gly Tyr Lys Val Leu Val Leu Asn Pro Ser Val Ala
    1250             1255            1260

Ala Thr Leu Gly Phe Gly Ala Tyr Leu Ser Lys Ala His Gly Ile
    1265             1270            1275

Asn Pro Asn Ile Arg Thr Gly Val Arg Thr Val Thr Thr Gly Ala
    1280             1285            1290

Pro Ile Thr Tyr Ser Thr Tyr Gly Lys Phe Leu Ala Asp Gly Gly
    1295             1300            1305

Cys Ala Gly Gly Ala Tyr Asp Ile Ile Ile Cys Asp Glu Cys His
    1310             1315            1320

Ala Val Asp Ser Thr Thr Ile Leu Gly Ile Gly Thr Val Leu Asp
    1325             1330            1335

Gln Ala Glu Thr Ala Gly Val Arg Leu Thr Val Leu Ala Thr Ala
    1340             1345            1350

Thr Pro Pro Gly Ser Val Thr Thr Pro His Pro Asn Ile Glu Glu
    1355             1360            1365

Val Ala Leu Gly Gln Glu Gly Glu Ile Pro Phe Tyr Gly Arg Ala
    1370             1375            1380

Ile Pro Leu Ser Tyr Ile Lys Gly Gly Arg His Leu Ile Phe Cys
    1385             1390            1395

His Ser Lys Lys Lys Cys Asp Glu Leu Ala Ala Ala Leu Arg Gly
    1400             1405            1410
```

```
Met Gly Leu Asn Ser Val Ala Tyr Tyr Arg Gly Leu Asp Val Ser
1415                1420                1425

Val Ile Pro Thr Gln Gly Asp Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Val Val Asp Phe Ser Leu Asp Pro Thr
1460                1465                1470

Phe Thr Ile Thr Thr Gln Ile Val Pro Gln Asp Ala Val Ser Arg
1475                1480                1485

Ser Gln Arg Arg Gly Arg Thr Gly Arg Gly Arg Leu Gly Ile Tyr
1490                1495                1500

Arg Tyr Val Ser Thr Gly Glu Arg Ala Ser Gly Met Phe Asp Ser
1505                1510                1515

Val Val Leu Cys Glu Cys Tyr Asp Ala Gly Ala Ala Trp Tyr Glu
1520                1525                1530

Leu Thr Pro Ser Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Ser Gly Glu Asn Phe Ala Tyr Leu Thr Ala Tyr
1580                1585                1590

Gln Ala Thr Val Cys Ala Arg Ala Lys Ala Pro Pro Pro Ser Trp
1595                1600                1605

Asp Val Met Trp Lys Cys Leu Thr Arg Leu Lys Pro Thr Leu Val
1610                1615                1620

Gly Pro Thr Pro Leu Leu Tyr Arg Leu Gly Ser Val Thr Asn Glu
1625                1630                1635

Val Thr Leu Thr His Pro Val Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Glu Thr Gly Cys
1670                1675                1680

Val Cys Ile Ile Gly Arg Leu His Ile Asn Gln Arg Ala Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Thr Val Gln Ala Ser Trp
1745                1750                1755

Pro Lys Val Glu Gln Phe Trp Ala Lys His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Leu Gly Gly
```

-continued

```
                1805                1810                1815

Trp Leu Ala Ser Gln Ile Ala Pro Pro Ala Gly Ala Thr Gly Phe
        1820                1825                1830

Val Val Ser Gly Leu Val Gly Ala Ala Val Gly Ser Ile Gly Leu
        1835                1840                1845

Gly Lys Val Leu Val Asp Ile Leu Ala Gly Tyr Gly Ala Gly Ile
        1850                1855                1860

Ser Gly Ala Leu Val Ala Phe Lys Ile Met Ser Gly Glu Lys Pro
        1865                1870                1875

Ser Met Glu Asp Val Val Asn Leu Leu Pro Gly Ile Leu Ser Pro
        1880                1885                1890

Gly Ala Leu Val Val Gly Val Ile Cys Ala Ala Ile Leu Arg Arg
        1895                1900                1905

His Val Gly Pro Gly Glu Gly Ala Val Gln Trp Met Asn Arg Leu
        1910                1915                1920

Ile Ala Phe Ala Ser Arg Gly Asn His Val Ala Pro Thr His Tyr
        1925                1930                1935

Val Thr Glu Ser Asp Ala Ser Gln Arg Val Thr Gln Leu Leu Gly
        1940                1945                1950

Ser Leu Thr Ile Thr Ser Leu Leu Arg Arg Leu His Asn Trp Ile
        1955                1960                1965

Thr Glu Asp Cys Pro Ile Pro Cys Ser Gly Ser Trp Leu Arg Asp
        1970                1975                1980

Val Trp Asp Trp Val Cys Thr Ile Leu Thr Asp Phe Lys Asn Trp
        1985                1990                1995

Leu Thr Ser Lys Leu Phe Pro Lys Met Pro Gly Leu Pro Phe Val
        2000                2005                2010

Ser Cys Gln Lys Gly Tyr Lys Gly Val Trp Ala Gly Thr Gly Ile
        2015                2020                2025

Met Thr Thr Arg Cys Pro Cys Gly Ala Asn Ile Ser Gly Asn Val
        2030                2035                2040

Arg Leu Gly Ser Met Arg Ile Thr Gly Pro Lys Thr Cys Met Asn
        2045                2050                2055

Ile Trp Gln Gly Thr Phe Pro Ile Asn Cys Tyr Thr Glu Gly Gln
        2060                2065                2070

Cys Val Pro Lys Pro Ala Pro Asn Phe Lys Val Ala Ile Trp Arg
        2075                2080                2085

Val Ala Ala Ser Glu Tyr Ala Glu Val Thr Gln His Gly Ser Tyr
        2090                2095                2100

His Tyr Ile Thr Gly Leu Thr Thr Asp Asn Leu Lys Val Pro Cys
        2105                2110                2115

Gln Leu Pro Ser Pro Glu Phe Phe Ser Trp Val Asp Gly Val Gln
        2120                2125                2130

Ile His Arg Phe Ala Pro Thr Pro Lys Pro Phe Phe Arg Asp Glu
        2135                2140                2145

Val Ser Phe Cys Val Gly Leu Asn Ser Phe Val Val Gly Ser Gln
        2150                2155                2160

Leu Pro Cys Asp Pro Glu Pro Asp Thr Asp Val Leu Met Ser Met
        2165                2170                2175

Leu Thr Asp Pro Ser His Ile Thr Ala Glu Thr Ala Ala Arg Arg
        2180                2185                2190

Leu Ala Arg Gly Ser Pro Pro Ser Glu Ala Ser Ser Ser Ala Ser
        2195                2200                2205
```

```
Gln Leu Ser Ala Pro Ser Leu Arg Ala Thr Cys Thr Thr His Gly
    2210            2215                2220
Lys Ala Tyr Asp Val Asp Met Val Asp Ala Asn Leu Phe Met Gly
    2225            2230                2235
Gly Asp Val Thr Arg Ile Glu Ser Gly Ser Lys Val Val Val Leu
    2240            2245                2250
Asp Ser Leu Asp Pro Met Val Glu Glu Arg Ser Asp Leu Glu Pro
    2255            2260                2265
Ser Ile Pro Ser Glu Tyr Met Leu Pro Lys Lys Arg Phe Pro Pro
    2270            2275                2280
Ala Leu Pro Ala Trp Ala Arg Pro Asp Tyr Asn Pro Pro Leu Val
    2285            2290                2295
Glu Ser Trp Lys Arg Pro Asp Tyr Gln Pro Ala Thr Val Ala Gly
    2300            2305                2310
Cys Ala Leu Pro Pro Pro Arg Lys Thr Pro Thr Pro Pro Pro Arg
    2315            2320                2325
Arg Arg Arg Thr Val Gly Leu Ser Glu Asp Ser Ile Gly Asp Ala
    2330            2335                2340
Leu Gln Gln Leu Ala Ile Lys Ser Phe Gly Gln Pro Pro Pro Ser
    2345            2350                2355
Gly Asp Ser Gly Leu Ser Thr Gly Ala Gly Ala Ala Asp Ser Gly
    2360            2365                2370
Ser Gln Thr Pro Pro Asp Glu Leu Ala Leu Ser Glu Thr Gly Ser
    2375            2380                2385
Ile Ser Ser Met Pro Pro Leu Glu Gly Glu Leu Gly Asp Pro Asp
    2390            2395                2400
Leu Glu Pro Glu Gln Val Glu Pro Gln Pro Pro Gln Gly Gly
    2405            2410                2415
Val Ala Ala Pro Gly Ser Asp Ser Gly Ser Trp Ser Thr Cys Ser
    2420            2425                2430
Glu Glu Asp Asp Ser Val Val Cys Cys Ser Met Ser Tyr Ser Trp
    2435            2440                2445
Thr Gly Ala Leu Ile Thr Pro Cys Ser Pro Glu Glu Glu Lys Leu
    2450            2455                2460
Pro Ile Asn Pro Leu Ser Asn Ser Leu Leu Arg Tyr His Asn Lys
    2465            2470                2475
Val Tyr Cys Thr Thr Thr Lys Ser Ala Ser Leu Arg Ala Lys Lys
    2480            2485                2490
Val Thr Phe Asp Arg Met Gln Val Leu Asp Ser Tyr Tyr Asp Ser
    2495            2500                2505
Val Leu Lys Asp Ile Lys Leu Ala Ala Ser Lys Val Thr Ala Arg
    2510            2515                2520
Leu Leu Thr Met Glu Glu Ala Cys Gln Leu Thr Pro Pro His Ser
    2525            2530                2535
Ala Arg Ser Lys Tyr Gly Phe Gly Ala Lys Glu Val Arg Ser Leu
    2540            2545                2550
Ser Gly Arg Ala Val Asn His Ile Lys Ser Val Trp Lys Asp Leu
    2555            2560                2565
Leu Glu Asp Ser Glu Thr Pro Ile Pro Thr Thr Ile Met Ala Lys
    2570            2575                2580
Asn Glu Val Phe Cys Val Asp Pro Thr Lys Gly Gly Lys Lys Ala
    2585            2590                2595
```

```
Ala Arg Leu Ile Val Tyr Pro Asp Leu Gly Val Arg Val Cys Glu
2600                 2605                 2610

Lys Met Ala Leu Tyr Asp Ile Thr Gln Lys Leu Pro Gln Ala Val
2615                 2620                 2625

Met Gly Ala Ser Tyr Gly Phe Gln Tyr Ser Pro Ala Gln Arg Val
2630                 2635                 2640

Glu Phe Leu Leu Lys Ala Trp Ala Glu Lys Lys Asp Pro Met Gly
2645                 2650                 2655

Phe Ser Tyr Asp Thr Arg Cys Phe Asp Ser Thr Val Thr Glu Arg
2660                 2665                 2670

Asp Ile Arg Thr Glu Glu Ser Ile Tyr Arg Ala Cys Ser Leu Pro
2675                 2680                 2685

Glu Glu Ala His Thr Ala Ile His Ser Leu Thr Glu Arg Leu Tyr
2690                 2695                 2700

Val Gly Gly Pro Met Phe Asn Ser Lys Gly Gln Thr Cys Gly Tyr
2705                 2710                 2715

Arg Arg Cys Arg Ala Ser Gly Val Leu Thr Thr Ser Met Gly Asn
2720                 2725                 2730

Thr Ile Thr Cys Tyr Val Lys Ala Leu Ala Ala Cys Lys Ala Ala
2735                 2740                 2745

Gly Ile Ile Ala Pro Thr Met Leu Val Cys Gly Asp Asp Leu Val
2750                 2755                 2760

Val Ile Ser Glu Ser Gln Gly Thr Glu Glu Asp Glu Arg Asn Leu
2765                 2770                 2775

Arg Ala Phe Thr Glu Ala Met Thr Arg Tyr Ser Ala Pro Pro Gly
2780                 2785                 2790

Asp Pro Pro Arg Pro Glu Tyr Asp Leu Glu Leu Ile Thr Ser Cys
2795                 2800                 2805

Ser Ser Asn Val Ser Val Ala Leu Gly Pro Gln Gly Arg Arg Arg
2810                 2815                 2820

Tyr Tyr Leu Thr Arg Asp Pro Thr Thr Pro Ile Ala Arg Ala Ala
2825                 2830                 2835

Trp Glu Thr Val Arg His Ser Pro Val Asn Ser Trp Leu Gly Asn
2840                 2845                 2850

Ile Ile Gln Tyr Ala Pro Thr Ile Trp Ala Arg Met Val Leu Met
2855                 2860                 2865

Thr His Phe Phe Ser Ile Leu Met Ala Gln Asp Thr Leu Asp Gln
2870                 2875                 2880

Asn Leu Asn Phe Glu Met Tyr Gly Ala Val Tyr Ser Val Ser Pro
2885                 2890                 2895

Leu Asp Leu Pro Ala Ile Ile Glu Arg Leu His Gly Leu Asp Ala
2900                 2905                 2910

Phe Ser Leu His Thr Tyr Thr Pro His Glu Leu Thr Arg Val Ala
2915                 2920                 2925

Ser Ala Leu Arg Lys Leu Gly Ala Pro Pro Leu Arg Ala Trp Lys
2930                 2935                 2940

Ser Arg Ala Arg Ala Val Arg Ala Ser Leu Ile Ser Arg Gly Gly
2945                 2950                 2955

Lys Ala Ala Val Cys Gly Arg Tyr Leu Phe Asn Trp Ala Val Lys
2960                 2965                 2970

Thr Lys Leu Lys Leu Thr Pro Leu Pro Glu Ala Arg Leu Leu Asp
2975                 2980                 2985

Leu Ser Ser Trp Phe Thr Val Gly Ala Gly Gly Gly Asp Ile Phe
```

-continued

```
    2990                2995                3000

His Ser  Val Ser Arg Ala Arg  Pro Arg Ser Leu Leu  Phe Gly Leu
    3005                3010                3015

Leu Leu  Leu Phe Val Gly Val  Gly Leu Phe Leu Leu  Pro Ala Arg
    3020                3025                3030
```

<210> SEQ ID NO 4
<211> LENGTH: 8915
<212> TYPE: DNA
<213> ORGANISM: Artificial Sequence
<220> FEATURE:
<223> OTHER INFORMATION: Description of Artificial Sequence: Synthetic cDNA sequence of SGR-J6/4Amut+SKF+VRm3/Luc

<400> SEQUENCE: 4

```
acccgcccct aataggggcg acactccgcc atgaatcact cccctgtgag gaactactgt     60
cttcacgcag aaagcgtcta gccatggcgt tagtatgagt gtcgtacagc ctccaggccc    120
cccctcccg ggagagccat agtggtctgc ggaaccggtg agtacaccgg aattgccggg     180
aagactgggt cctttcttgg ataaacccac tctatgcccg gccatttggg cgtgcccccg    240
caagactgct agccgagtag cgttgggttg cgaaaggcct tgtggtactg cctgataggg    300
tgcttgcgag tgccccggga ggtctcgtag accgtgcacc atgagcacaa atcctaaacc    360
tcaaagaaaa accaaaagaa acaccaaccg acgcgtaatg gaagacgcca aaaacataaa    420
gaaaggcccg gcgccattct atcctctgga ggatggaacc gctggagagc aactgcataa    480
ggctatgaag agatacgccc tggttcctgg aacaattgct tttacagatg cacatatcga    540
ggtgaacatc acgtacgcgg aatacttcga aatgtccgtt cggttggcag aagctatgaa    600
acgatatggg ctgaatacaa atcacagaat cgtcgtatgc agtgaaaact ctcttcaatt    660
ctttatgccg gtgttgggcg cgttatttat cggagttgca gttgcgcccg cgaacgacat    720
ttataatgaa cgtgaattgc tcaacagtat gaacatttcg cagcctaccg tagtgtttgt    780
ttccaaaaag gggttgcaaa aaattttgaa cgtgcaaaaa aaattaccaa taatccagaa    840
aattattatc atggattcta aaacggatta ccagggattt cagtcgatgt acacgttcgt    900
cacatctcat ctacctcccg gttttaatga atacgatttt gtaccagagt cctttgatcg    960
tgacaaaaca attgcactga taatgaactc ctctggatct actgggttac ctaagggtgt   1020
ggcccttccg catagaactg cctgcgtcag attctcgcat gccagagatc ctatttttgg   1080
caatcaaatc attccggata ctgcgatttt aagtgttgtt ccattccatc acggttttgg   1140
aatgtttact acactcggat atttgatatg tggatttcga gtcgtcttaa tgtatagatt   1200
tgaagaagag ctgtttttac gatcccttca ggattacaaa attcaaagtg cgttgctagt   1260
accaacccta ttttcattct tcgccaaaag cactctgatt gacaaatacg atttatctaa   1320
tttacacgaa attgcttctg gggcgcacc tctttcgaaa gaagtcgggg aagcggttgc    1380
aaaacgcttc catcttccag ggatacgaca aggatatggg ctcactgaga ctacatcagc   1440
tattctgatt acacccgagg gggatgataa accgggcgcg gtcggtaaag ttgttccatt   1500
ttttgaagcg aaggttgtgg atctggatac cgggaaaacg ctgggcgtta atcagagagg   1560
cgaattatgt gtcagaggac ctatgattat gtccggttat gtaaacaatc cggaagcgac   1620
caacgccttg attgacaagg atggatggct acattctgga gacatagctt actgggacga   1680
agacgaacac ttcttcatag ttgaccgctt gaagtcttta attaaataca aggatatca    1740
ggtggccccc gctgaattgg aatcgatatt gttacaacac cccaacatct tcgacgcggg   1800
```

```
cgtggcaggt cttcccgacg atgacgccgg tgaacttccc gccgccgttg ttgttttgga    1860
gcacggaaag acgatgacgg aaaaagagat cgtggattac gtcgccagtc aagtaacaac    1920
cgcgaaaaag ttgcgcggag gagttgtgtt tgtggacgaa gtaccgaaag gtcttaccgg    1980
aaaactcgac gcaagaaaaa tcagagagat cctcataaag gccaagaagg gcggaaagtc    2040
caaattgtaa gtttaaaccc tctccctccc cccccctaa cgttactggc cgaagccgct    2100
tggaataagg ccggtgtgcg tttgtctata tgttattttc caccatattg ccgtcttttg    2160
gcaatgtgag ggcccggaaa cctggccctg tcttcttgac gagcattcct aggggtcttt    2220
cccctctcgc caaggaatg caaggtctgt tgaatgtcgt gaaggaagca gttcctctgg    2280
aagcttcttg aagacaaaca acgtctgtag cgaccctttg caggcagcgg aaccccccac    2340
ctggcgacag gtgcctctgc ggccaaaagc cacgtgtata agatacacct gcaaaggcgg    2400
cacaacccca gtgccacgtt gtgagttgga tagttgtgga aagagtcaaa tggctctcct    2460
caagcgtatt caacaagggg ctgaaggatg cccagaaggt accccattgt atgggatctg    2520
atctggggcc tcggtgcaca tgctttacat gtgtttagtc gaggttaaaa aaacgtctag    2580
gccccccgaa ccacggggac gtggttttcc tttgaaaaac acgataatac catggctccc    2640
atcactgctt atgcccagca gacacgtggc cttttgggca ccatagtggt gagcatgacg    2700
gggcgcgaca agacagaaca ggctggggaa attcaggtcc tgtccacagt cactcagtcc    2760
ttcctcggaa catccatctc ggggttttg tggactgtct accatggagc tggcaacaag    2820
actctggccg gctcacgggg tccggtcacg cagatgtact ccagtgctga gggggactta    2880
gtagggtggc ccagccccc tgggactaaa tctttggagc cgtgcacgtg tggagcggtc    2940
gacctgtacc tggtcacgcg gaacgctgat gtcatcccgg ctcgaagacg cggggacaaa    3000
cggggagcgc tactctcccc gagacctctt tccaccttga aggggtcctc aggaggcccg    3060
gtgctatgcc ccaggggcca cgctgtcgga gtcttccggg cagctgtgtg ctctcggggc    3120
gtggctaagt ccatagattt catccccgtt gagacactcg acatcgtcac gcggtccccc    3180
acctttagtg acaacagcac accacctgct gtgccccaga cctatcaggt cgggtacttg    3240
catgccccga ctggcagtgg aaagagcacc aaagttcctg tcgcatatgc tgctcagggg    3300
tataaagtgc tagtgcttaa tccctcagtg gctgccaccc tggggtttgg ggcgtacttg    3360
tctaaggcac atggcatcaa tcccaacatt aggactggag tcaggactgt gacgaccggg    3420
gcgcccatca cgtactccac atatggcaaa ttcctcgccg atgggggctg tgcgggcggc    3480
gcctacgaca tcatcatatg tgatgaatgc catgccgtgg actctaccac catccttggc    3540
atcggaacag tccttgatca agcagagaca gctgggtca gactaactgt gctggctaca    3600
gctacgcccc ctgggtcagt gacaacccc caccccaaca tagaggaggt ggcccttggg    3660
caggagggcg agatccccct ctatgggagg gcgattcccc tgtcttacat caagggagga    3720
agacatctga tcttctgcca ttcaaagaaa aagtgtgacg agctcgcggc ggcccttcgg    3780
ggtatgggct tgaactcagt ggcatactac agagggttgg acgtctccgt aataccaact    3840
cagggagacg tagtggtcgt cgccaccgac gccctcatga cagggtatac tgggggacttt    3900
gactccgtga tcgactgcaa cgtagcggtc actcaagttg tagacttcag tttagacccc    3960
acattcacca taaccacaca gattgtccct caagacgctg tctcacgtag ccagcgccgg    4020
ggtcgcacgg gtaggggaag actgggcatt tataggtatg tttccactgg tgagcgagcc    4080
tcaggaatgt ttgacagtgt agtgctctgt gagtgctacg acgcagggc cgcatggtat    4140
gagctcacac catcggagac caccgtcagg ctcagggcgt atttcaacac gcccggtttg    4200
```

```
cctgtgtgcc aagaccatct tgagttttgg gaggcagttt tcaccggcct cacacacata   4260
gatgcccact tcctttccca aacaaagcaa tcgggggaaa atttcgcata cttaacagcc   4320
taccaggcta cagtgtgcgc tagggccaaa gccccccccc cgtcctggga cgtcatgtgg   4380
aagtgtttga ctcgactcaa gcccacactc gtgggcccca cactctcct gtaccgcttg    4440
ggctctgtta ccaacgaggt caccctcaca catcccgtga cgaaatacat cgccacctgc   4500
atgcaagccg accttgaggt catgaccagc acatgggtct tggcagggg agtcttggcg    4560
gccgtcgccg cgtattgcct ggagaccggg tgtgtttgca tcatcggccg cttgcacatt   4620
aaccagcgag ccgtcgttgc gccggacaag gaggtcctct atgaggcttt tgatgagatg   4680
gaggaatgtg cctctagggc ggctctcatt gaagaggggc agcggatagc cgagatgctg   4740
aagtccaaga tccaaggctt attgcagcaa gcttccaaac aagctcaaga catcaaccc    4800
actgtgcagg cttcatggcc caaggtagaa caattctggg ccaaacacat gtggaacttc   4860
attagcggca tccaatacct cgcaggacta tcaacactgc cagggaaccc tgcagtagct   4920
tccatgatgg cgttcagtgc cgccctcacc agtccgctgt caacaagcac cactatcctt   4980
ctcaacattt tggggggctg gctagcatcc caaattgcac cacccgcggg ggccactggc   5040
ttcgttgtca gtggcctagt gggagctgcc gtaggcagta taggcttagg taaggtgcta   5100
gtggacatcc tggcagggta tggtgcgggc atttcggggg ctctcgtcgc attcaagatc   5160
atgtctggcg agaagccctc catggaggat gtcgtcaact tgctgcctgg aattctgtct   5220
ccgggtgcct tggtagtggg agtcatctgc gcggccattc tgcgccgaca cgtgggaccg   5280
ggggaaggcg ccgtccaatg gatgaataga ctcattgcct ttgcttccag aggaaatcac   5340
gtcgccccca cccactacgt gacggagtcg gatgcgtcgc agcgtgtgac ccaactactt   5400
ggctccctta ccataaccag cctgctcaga agactccaca actggattac tgaggactgc   5460
cccatcccat gctccggatc gtggctccgc gatgtgtggg actgggtttg caccatccta   5520
acagacttta aaaattggct gacctccaaa ttattcccaa agatgcccgg cctcccctt    5580
gtctcctgtc aaaaggggta caagggcgtg tgggccggca ctggcatcat gaccacacgg   5640
tgtccttgcg gcgccaatat ctctggcaat gtccgcttgg gctccatgag aatcacgggg   5700
cctaagacct gcatgaatat ctggcagggg accttticcta tcaattgtta cacggagggc   5760
cagtgcgtgc cgaaacccgc gccaaacttt aaggtcgcca tctggagggt ggcggcctca   5820
gagtacgcgg aggtgacgca gcacgggtca taccactaca taacaggact caccactgat   5880
aacttgaaag tccccctgcca actaccctct cccgagttct tttcctgggt ggacggagtg   5940
cagatccata ggtttgcccc cacaccgaag ccgttttttcc gggatgaggt ctcgttctgc   6000
gttgggctta ttcatttgt cgtcgggtcc cagcttcctt gcgaccctga acccgacaca   6060
gacgtattga tgtccatgct aacagatcca tctcatatca cggcggagac tgcagcgcgg   6120
cgtttagcgc gggggtcacc cccatccgag gcaagctcct cggcgagcca gctatcggca   6180
ccatcgctgc gagccacctg caccacccac ggcaaagcct atgatgtgga catggtggat   6240
gctaacctgt tcatgggggg cgatgtgact cggatagagt ctgggtccaa agtggtcgtt   6300
ctggactctc tcgacccaat ggtcgaagaa aggagcgacc ttgagccttc gataccatca   6360
gaatacatgc tccccaagaa gaggttccca ccagctttac cggcctgggc acggcctgat   6420
tacaacccac cgcttgtgga atcgtggaaa aggccagatt accaaccggc cactgttgcg   6480
ggctgtgctc tccctcctcc taggaaaacc ccgacgcctc ccccaaggag gcgccggaca   6540
```

```
gtgggcctaa gtgaggactc cataggagat gcccttcaac agctggccat taagtccttt    6600
ggccagcccc ccccaagcgg cgattcaggc cttttccacgg gggcgggcgc tgccgattcc   6660
ggcagtcaga cgcctcctga tgagttggcc cttttcggaga caggttccat ctcttccatg   6720
ccccccctcg aggggggagct tggagatcca gacctggagc ctgagcaggt agagccccaa   6780
ccccccccc aggggggggt ggcagctccc ggctcggact cggggtcctg gtctacttgc     6840
tccgaggagg acgactccgt cgtgtgctgc tccatgtcat actcctggac cggggctcta    6900
ataactcctt gtagtcccga agaggagaag ttaccgatta accccttgag caactccctg    6960
ttgcgatatc acaacaaggt gtactgtacc acaacaaaga gcgcctcact aagggctaaa    7020
aaggtaactt ttgataggat gcaagtgctc gactcctact acgactcagt cttaaaggac    7080
attaagctag cggcctccaa ggtcaccgca aggctcctca ccatggagga ggcttgccag    7140
ttaaccccac cccattctgc aagatctaaa tatgggtttg ggctaagga ggtccgcagc     7200
ttgtccggga gggccgttaa ccacatcaag tccgtgtgga aggacctcct ggaggactca    7260
gaaacaccaa ttcccacaac cattatggcc aaaaatgagg tgttctgcgt ggaccccacc    7320
aaggggggca agaaagcagc tcgccttatc gtttaccctg acctcggcgt cagggtctgc    7380
gagaagatgg ccctttatga cattacacaa aaacttcctc aggcggtgat gggggcttct    7440
tatggattcc agtattcccc cgctcagcgg gtagagtttc tcttgaaagc atgggcggaa    7500
aagaaggacc ctatgggttt ttcgtatgat acccgatgct ttgactcaac cgtcactgag    7560
agagacatca ggactgagga gtccatatat cgggcctgct ccttgcccga ggaggcccac    7620
actgccatac actcgctaac tgagagactt tacgtgggag ggcctatgtt caacagcaag    7680
ggccaaacct gcgggtacag gcgttgccgc ccagcgggg tgctcaccac tagcatgggg    7740
aacaccatca catgctacgt gaaagcctta gcggcttgta aagctgcagg gataatcgcg    7800
cccacaatgc tggtatgcgg cgatgacttg gttgtcatct cagaaagcca ggggaccgag    7860
gaggacgagc ggaacctgag agccttcacg gaggctatga ccaggtattc tgcccctcct    7920
ggtgaccccc ccagaccgga gtatgatctg gagctgataa catcttgctc ctcaaatgtg    7980
tctgtggcgc tgggcccaca aggccgccgc agatactacc tgaccagaga ccctaccact    8040
ccaatcgccc gggctgcctg ggaaacagtt agacactccc ctgtcaattc atggctggga    8100
aacatcatcc agtacgcccc gaccatatgg gctcgcatgg tcctgatgac acacttcttc    8160
tccattctca tggctcaaga cacgctggac cagaacctca ctttgagat gtacggatca    8220
gtgtactccg tgagtccctt ggacctccca gctataattg aaaggttaca tgggcttgac   8280
gcttttttctc tgcacacata cactccccac gaactgacac gggtggcttc agccctcaga   8340
aaacttgggg cgccacccct cagagcgtgg aagagccggg cacgtgcagt cagggcgtcc    8400
ctcatctccc gtgggggaa agcggccgtt tgcggtcgat atctcttcaa ttgggcggtg    8460
aagaccaagc tcaaactcac tccattgccg gaagcgcgcc tcctggattt atccagctgg    8520
ttcaccgtcg gcgccggcgg gggcgacatt tttcacagcg tgtcgcgtgc ccgacccgc     8580
ttattgctct ttggcctact cctacttttt gtaggggtag gccttttcct actccccgct    8640
cggtagagcg gcacacatta ggtacactcc atagctaact gtcccttttt tttttttttt    8700
tttttttttt tttttttttt tttttttttt tttttttttt tttttttttt tttttttttt    8760
ttttttttc ttttttctc ttttccttct ttcttacctt attttacttt ctttcctggt      8820
ggctccatct tagccctagt cacgctagc tgtgaaaggt ccgtgagccg catgactgca     8880
gagagtgccg taactggtct ctctgcagat catgt                               8915
```

<210> SEQ ID NO 5
<211> LENGTH: 9711
<212> TYPE: DNA
<213> ORGANISM: Artificial Sequence
<220> FEATURE:
<223> OTHER INFORMATION: Description of Artificial Sequence: Synthetic
      cDNA sequence of FGR-J6/4Amut+SKF+VRm3
<220> FEATURE:
<221> NAME/KEY: CDS
<222> LOCATION: (341)..(9439)

<400> SEQUENCE: 5

```
acccgcccct aatagggggcg acactccgcc atgaatcact ccctgtgag gaactactgt      60 cttcacgcag aaagcgtcta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgccccggga ggtctcgtag accgtgcacc atg agc aca aat cct      355
                                               Met Ser Thr Asn Pro
                                               1               5 aaa cct caa aga aaa acc aaa aga aac acc aac cgt cgc cca caa gac      403
Lys Pro Gln Arg Lys Thr Lys Arg Asn Thr Asn Arg Arg Pro Gln Asp
                10                  15                  20 gtt aag ttt ccg ggc ggc ggc cag atc gtt ggc gga gta tac ttg ttg      451
Val Lys Phe Pro Gly Gly Gly Gln Ile Val Gly Gly Val Tyr Leu Leu
            25                  30                  35 ccg cgc agg ggc ccc agg ttg ggt gtg cgc gcg aca agg aag act tcg      499
Pro Arg Arg Gly Pro Arg Leu Gly Val Arg Ala Thr Arg Lys Thr Ser
        40                  45                  50 gag cgg tcc cag cca cgt gga agg cgc cag ccc atc cct aaa gat cgg      547
Glu Arg Ser Gln Pro Arg Gly Arg Arg Gln Pro Ile Pro Lys Asp Arg
    55                  60                  65 cgc tcc act ggc aaa tcc tgg gga aaa cca gga tac ccc tgg ccc cta      595
Arg Ser Thr Gly Lys Ser Trp Gly Lys Pro Gly Tyr Pro Trp Pro Leu
70                  75                  80                  85 tac ggg aat gag gga ctc ggc tgg gca gga tgg ctc ctg tcc ccc cga      643
Tyr Gly Asn Glu Gly Leu Gly Trp Ala Gly Trp Leu Leu Ser Pro Arg
                90                  95                 100 ggt tcc cgt ccc tct tgg ggc ccc aat gac ccc cgg cat agg tcg cgc      691
Gly Ser Arg Pro Ser Trp Gly Pro Asn Asp Pro Arg His Arg Ser Arg
            105                 110                 115 aac gtg ggt aag gtc atc gat acc cta acg tgc ggc ttt gcc gac ctc      739
Asn Val Gly Lys Val Ile Asp Thr Leu Thr Cys Gly Phe Ala Asp Leu
        120                 125                 130 atg ggg tac atc cct gtc gtg ggc gcc ccg ctc ggc ggc gtc gcc aga      787
Met Gly Tyr Ile Pro Val Val Gly Ala Pro Leu Gly Gly Val Ala Arg
    135                 140                 145 gct ctc gcg cat ggc gtg aga gtc ctg gag gac ggg gtt aat ttt gca      835
Ala Leu Ala His Gly Val Arg Val Leu Glu Asp Gly Val Asn Phe Ala
150                 155                 160                 165 aca ggg aac tta ccc ggt tgc tcc ttt tct atc ttc ttg ctg gcc ctg      883
Thr Gly Asn Leu Pro Gly Cys Ser Phe Ser Ile Phe Leu Leu Ala Leu
                170                 175                 180 ctg tcc tgc atc acc acc ccg gtc tcc gct gcc gaa gtg aag aac atc      931
Leu Ser Cys Ile Thr Thr Pro Val Ser Ala Ala Glu Val Lys Asn Ile
            185                 190                 195 agt acc ggc tac atg gtg act aac gac tgc acc aat gac agc att acc      979
Ser Thr Gly Tyr Met Val Thr Asn Asp Cys Thr Asn Asp Ser Ile Thr
```

-continued

```
                    200                 205                 210
tgg cag ctc cag gct gct gtc ctc cac gtc ccc ggg tgc gtc ccg tgc     1027
Trp Gln Leu Gln Ala Ala Val Leu His Val Pro Gly Cys Val Pro Cys
    215                 220                 225 gag aaa gtg ggg aat gca tct cag tgc tgg ata ccg tca ccg aat         1075
Glu Lys Val Gly Asn Ala Ser Gln Cys Trp Ile Pro Val Ser Pro Asn
230                 235                 240                 245 gtg gcc gtg cag cgg ccc ggc gcc ctc acg cag ggc ttg cgg acg cac     1123
Val Ala Val Gln Arg Pro Gly Ala Leu Thr Gln Gly Leu Arg Thr His
                250                 255                 260 atc gac atg gtt gtg atg tcc gcc acg ctc tgc tct gcc ctc tac gtg     1171
Ile Asp Met Val Val Met Ser Ala Thr Leu Cys Ser Ala Leu Tyr Val
            265                 270                 275 ggg gac ctc tgc ggt ggg gtg atg ctc gca gcc caa atg ttc att gtc     1219
Gly Asp Leu Cys Gly Gly Val Met Leu Ala Ala Gln Met Phe Ile Val
        280                 285                 290 tcg ccg cag cac cac tgg ttt gtc caa gac tgc aat tgc tcc atc tac     1267
Ser Pro Gln His His Trp Phe Val Gln Asp Cys Asn Cys Ser Ile Tyr
    295                 300                 305 cct ggt acc atc act gga cac cgc atg gca tgg gac atg atg atg aac     1315
Pro Gly Thr Ile Thr Gly His Arg Met Ala Trp Asp Met Met Met Asn
310                 315                 320                 325 tgg tcg ccc acg gct acc atg atc ttg gcg tac gcg atg cgt gtc ccc     1363
Trp Ser Pro Thr Ala Thr Met Ile Leu Ala Tyr Ala Met Arg Val Pro
                330                 335                 340 gag gtc att ata gac atc att agc ggg gct cat tgg ggc gtc atg ttc     1411
Glu Val Ile Ile Asp Ile Ile Ser Gly Ala His Trp Gly Val Met Phe
            345                 350                 355 ggc ttg gcc tac ttc tct atg cag gga gcg tgg gcg aaa gtc gtt gtc     1459
Gly Leu Ala Tyr Phe Ser Met Gln Gly Ala Trp Ala Lys Val Val Val
        360                 365                 370 atc ctt ctg ttg gcc gcc ggg gtg gac gcg cgc acc cat act gtt ggg     1507
Ile Leu Leu Leu Ala Ala Gly Val Asp Ala Arg Thr His Thr Val Gly
    375                 380                 385 ggt tct gcc gcg cag acc acc ggg cgc ctc acc agc tta ttt gac atg     1555
Gly Ser Ala Ala Gln Thr Thr Gly Arg Leu Thr Ser Leu Phe Asp Met
390                 395                 400                 405 ggc ccc agg cag aaa atc cag ctc gtt aac acc aat ggc agc tgg cac     1603
Gly Pro Arg Gln Lys Ile Gln Leu Val Asn Thr Asn Gly Ser Trp His
                410                 415                 420 atc aac cgc acc gcc ctg aac tgc aat gac tcc ttg cac acc ggc ttt     1651
Ile Asn Arg Thr Ala Leu Asn Cys Asn Asp Ser Leu His Thr Gly Phe
            425                 430                 435 atc gcg tct ctg ttc tac acc cac agc ttc aac tcg tca gga tgt ccc     1699
Ile Ala Ser Leu Phe Tyr Thr His Ser Phe Asn Ser Ser Gly Cys Pro
        440                 445                 450 gaa cgc atg tcc gcc tgc cgc agt atc gag gcc ttc cgg gtg gga tgg     1747
Glu Arg Met Ser Ala Cys Arg Ser Ile Glu Ala Phe Arg Val Gly Trp
    455                 460                 465 ggc gcc ttg caa tat gag gat aat gtc acc aat cca gag gat atg aga     1795
Gly Ala Leu Gln Tyr Glu Asp Asn Val Thr Asn Pro Glu Asp Met Arg
470                 475                 480                 485 ccc tat tgc tgg cac tac cca cca agg cag tgt ggc gtg gtc tcc gcg     1843
Pro Tyr Cys Trp His Tyr Pro Pro Arg Gln Cys Gly Val Val Ser Ala
                490                 495                 500 aag act gtg tgt ggc cca gtg tac tgt ttc acc ccc agc cca gta gta     1891
Lys Thr Val Cys Gly Pro Val Tyr Cys Phe Thr Pro Ser Pro Val Val
            505                 510                 515 gtg ggc acg acc gac agg ctt gga gcg ccc act tac acg tgg ggg gag     1939
```

```
                Val Gly Thr Thr Asp Arg Leu Gly Ala Pro Thr Tyr Thr Trp Gly Glu
                            520                 525                 530 aat gag aca gat gtc ttc cta ttg aac agc act cga cca ccg ctg ggg              1987
Asn Glu Thr Asp Val Phe Leu Leu Asn Ser Thr Arg Pro Pro Leu Gly
            535                 540                 545 tca tgg ttc ggc tgc acg tgg atg aac tct tct ggc tac acc aag act              2035
Ser Trp Phe Gly Cys Thr Trp Met Asn Ser Ser Gly Tyr Thr Lys Thr
550                 555                 560                 565 tgc ggc gca cca ccc tgc cgt act aga gct gac ttc aac gcc agc acg              2083
Cys Gly Ala Pro Pro Cys Arg Thr Arg Ala Asp Phe Asn Ala Ser Thr
                570                 575                 580 gac ctg ttg tgc ccc acg gac tgt ttt agg aag cat cct gat acc act              2131
Asp Leu Leu Cys Pro Thr Asp Cys Phe Arg Lys His Pro Asp Thr Thr
            585                 590                 595 tac ctc aaa tgc ggc tct ggg ccc tgg ctc acg cca agg tgc ctg atc              2179
Tyr Leu Lys Cys Gly Ser Gly Pro Trp Leu Thr Pro Arg Cys Leu Ile
        600                 605                 610 gac tac ccc tac agg ctc tgg cat tac ccc tgc aca gtt aac tat acc              2227
Asp Tyr Pro Tyr Arg Leu Trp His Tyr Pro Cys Thr Val Asn Tyr Thr
    615                 620                 625 atc ttc aaa ata agg atg tat gtg gga ggg gtt gag cac agg ctc acg              2275
Ile Phe Lys Ile Arg Met Tyr Val Gly Gly Val Glu His Arg Leu Thr
630                 635                 640                 645 gct gca tgc aat ttc act cgt ggg gat cgt tgc aac ttg gag gac aga              2323
Ala Ala Cys Asn Phe Thr Arg Gly Asp Arg Cys Asn Leu Glu Asp Arg
                650                 655                 660 gac aga agt caa ctg tct cct ttg ttg cac tcc acc acg gaa tgg gcc              2371
Asp Arg Ser Gln Leu Ser Pro Leu Leu His Ser Thr Thr Glu Trp Ala
            665                 670                 675 att tta cct tgc tct tac tcg gac ctg ccc gcc ttg tcg act ggt ctt              2419
Ile Leu Pro Cys Ser Tyr Ser Asp Leu Pro Ala Leu Ser Thr Gly Leu
        680                 685                 690 ctc cac ctc cac caa aac atc gtg gac gta caa ttc atg tat ggc cta              2467
Leu His Leu His Gln Asn Ile Val Asp Val Gln Phe Met Tyr Gly Leu
    695                 700                 705 tca cct gcc ctc aca aaa tac atc gtc cga tgg gag tgg gta ata ctc              2515
Ser Pro Ala Leu Thr Lys Tyr Ile Val Arg Trp Glu Trp Val Ile Leu
710                 715                 720                 725 tta ttc ctg ctc tta gcg gac gcc agg gtt tgc gcc tgc tta tgg atg              2563
Leu Phe Leu Leu Leu Ala Asp Ala Arg Val Cys Ala Cys Leu Trp Met
                730                 735                 740 ctc atc ttg ttg ggc cag gcc gaa gca gca cta gag aag ctg gtc atc              2611
Leu Ile Leu Leu Gly Gln Ala Glu Ala Ala Leu Glu Lys Leu Val Ile
            745                 750                 755 ttg cac gct gcg agc gca gct agc tgc aat ggc ttc cta tat ttt gtc              2659
Leu His Ala Ala Ser Ala Ala Ser Cys Asn Gly Phe Leu Tyr Phe Val
        760                 765                 770 atc ttt ttc gtg gct gct tgg tac atc aag ggt cgg gta gtc ccc tta              2707
Ile Phe Phe Val Ala Ala Trp Tyr Ile Lys Gly Arg Val Val Pro Leu
    775                 780                 785 gct acc tat tcc ctc act ggc ctg tgg tcc ttt agc cta ctg ctc cta              2755
Ala Thr Tyr Ser Leu Thr Gly Leu Trp Ser Phe Ser Leu Leu Leu Leu
790                 795                 800                 805 gca ttg ccc caa cag gct tat gct tat gac gca tct gtg cat ggc cag              2803
Ala Leu Pro Gln Gln Ala Tyr Ala Tyr Asp Ala Ser Val His Gly Gln
                810                 815                 820 ata gga gcg gct ctg ctg gta atg atc act ctc ttt act ctc acc ccc              2851
Ile Gly Ala Ala Leu Leu Val Met Ile Thr Leu Phe Thr Leu Thr Pro
            825                 830                 835
```

```
ggg tat aag acc ctt ctc agc cgg ttt ttg tgg tgg ttg tgc tat ctt    2899
Gly Tyr Lys Thr Leu Leu Ser Arg Phe Leu Trp Trp Leu Cys Tyr Leu
        840                 845                 850 ctg acc ctg ggg gaa gct atg gtc cag gag tgg gca cca cct atg cag    2947
Leu Thr Leu Gly Glu Ala Met Val Gln Glu Trp Ala Pro Pro Met Gln
855                 860                 865 gtg cgc ggt ggc cgt gat ggc atc ata tgg gcc gtc gcc ata ttc tac    2995
Val Arg Gly Gly Arg Asp Gly Ile Ile Trp Ala Val Ala Ile Phe Tyr
870                 875                 880                 885 cca ggt gtg gtg ttt gac ata acc aag tgg ctc ttg gcg gtg ctt ggg    3043
Pro Gly Val Val Phe Asp Ile Thr Lys Trp Leu Leu Ala Val Leu Gly
                890                 895                 900 cct gct tac ctc cta aaa ggt gct ttg acg cgc gtg ccg tac ttc gtc    3091
Pro Ala Tyr Leu Leu Lys Gly Ala Leu Thr Arg Val Pro Tyr Phe Val
            905                 910                 915 agg gct cac gct cta ctg agg atg tgc acc atg gca agg cat ctc gcg    3139
Arg Ala His Ala Leu Leu Arg Met Cys Thr Met Ala Arg His Leu Ala
        920                 925                 930 ggc ggc agg tac gtc cag atg gcg cta cta gcc ctt ggc agg tgg act    3187
Gly Gly Arg Tyr Val Gln Met Ala Leu Leu Ala Leu Gly Arg Trp Thr
935                 940                 945 ggc act tac atc tat gac cac ctc acc cct atg tcg gat tgg gct gca    3235
Gly Thr Tyr Ile Tyr Asp His Leu Thr Pro Met Ser Asp Trp Ala Ala
950                 955                 960                 965 agt ggc ctg cgg gac ctg gcg gtc gcc gtt gag cct atc atc ttc agt    3283
Ser Gly Leu Arg Asp Leu Ala Val Ala Val Glu Pro Ile Ile Phe Ser
                970                 975                 980 ccg atg gag aag aaa gtc att gtc tgg gga gcg gag aca gct gct tgt    3331
Pro Met Glu Lys Lys Val Ile Val Trp Gly Ala Glu Thr Ala Ala Cys
            985                 990                 995 ggg gac att tta cac gga ctt ccc gtg tcc gcc cga ctt ggt cgg        3376
Gly Asp Ile Leu His Gly Leu Pro Val Ser Ala Arg Leu Gly Arg
        1000                1005                1010 gag gtc ctc ctt ggc cca gct gat ggc tat acc tcc aag ggg tgg        3421
Glu Val Leu Leu Gly Pro Ala Asp Gly Tyr Thr Ser Lys Gly Trp
    1015                1020                1025 agt ctt ctc gcc ccc atc act gct tac gcc cag cag aca cgt ggc        3466
Ser Leu Leu Ala Pro Ile Thr Ala Tyr Ala Gln Gln Thr Arg Gly
1030                1035                1040 ctt ttg ggc acc ata gtg gtg agc atg acg ggg cgc gac aag aca        3511
Leu Leu Gly Thr Ile Val Val Ser Met Thr Gly Arg Asp Lys Thr
        1045                1050                1055 gaa cag gct ggg gaa att cag gtc ctg tcc aca gtc act cag tcc        3556
Glu Gln Ala Gly Glu Ile Gln Val Leu Ser Thr Val Thr Gln Ser
    1060                1065                1070 ttc ctc gga aca tcc atc tcg ggg gtt ttg tgg act gtc tac cat        3601
Phe Leu Gly Thr Ser Ile Ser Gly Val Leu Trp Thr Val Tyr His
1075                1080                1085 gga gct ggc aac aag act ctg gcc ggc tca cgg ggt ccg gtc acg        3646
Gly Ala Gly Asn Lys Thr Leu Ala Gly Ser Arg Gly Pro Val Thr
        1090                1095                1100 cag atg tac tcc agt gct gag ggg gac tta gta ggg tgg ccc agc        3691
Gln Met Tyr Ser Ser Ala Glu Gly Asp Leu Val Gly Trp Pro Ser
    1105                1110                1115 ccc cct ggg act aaa tct ttg gag ccg tgc acg tgt gga gcg gtc        3736
Pro Pro Gly Thr Lys Ser Leu Glu Pro Cys Thr Cys Gly Ala Val
1120                1125                1130 gac ctg tac ctg gtc acg cgg aac gct gat gtc atc ccg gct cga        3781
Asp Leu Tyr Leu Val Thr Arg Asn Ala Asp Val Ile Pro Ala Arg
        1135                1140                1145
```

```
aga cgc ggg gac aaa cgg gga gcg cta ctc tcc ccg aga cct ctt    3826
Arg Arg Gly Asp Lys Arg Gly Ala Leu Leu Ser Pro Arg Pro Leu
        1150                1155                1160 tcc acc ttg aag ggg tcc tca gga ggc ccg gtg cta tgc ccc agg    3871
Ser Thr Leu Lys Gly Ser Ser Gly Gly Pro Val Leu Cys Pro Arg
        1165                1170                1175 ggc cac gct gtc gga gtc ttc cgg gca gct gtg tgc tct cgg ggc    3916
Gly His Ala Val Gly Val Phe Arg Ala Ala Val Cys Ser Arg Gly
        1180                1185                1190 gtg gct aag tcc ata gat ttc atc ccc gtt gag aca ctc gac atc    3961
Val Ala Lys Ser Ile Asp Phe Ile Pro Val Glu Thr Leu Asp Ile
        1195                1200                1205 gtc acg cgg tcc ccc acc ttt agt gac aac agc aca cca cct gct    4006
Val Thr Arg Ser Pro Thr Phe Ser Asp Asn Ser Thr Pro Pro Ala
        1210                1215                1220 gtg ccc cag acc tat cag gtc ggg tac ttg cat gcc ccg act ggc    4051
Val Pro Gln Thr Tyr Gln Val Gly Tyr Leu His Ala Pro Thr Gly
        1225                1230                1235 agt gga aag agc acc aaa gtt cct gtc gca tat gct gct cag ggg    4096
Ser Gly Lys Ser Thr Lys Val Pro Val Ala Tyr Ala Ala Gln Gly
        1240                1245                1250 tat aaa gtg cta gtg ctt aat ccc tca gtg gct gcc acc ctg ggg    4141
Tyr Lys Val Leu Val Leu Asn Pro Ser Val Ala Ala Thr Leu Gly
        1255                1260                1265 ttt ggg gcg tac ttg tct aag gca cat ggc atc aat ccc aac att    4186
Phe Gly Ala Tyr Leu Ser Lys Ala His Gly Ile Asn Pro Asn Ile
        1270                1275                1280 agg act gga gtc agg act gtg acg acc ggg gcg ccc atc acg tac    4231
Arg Thr Gly Val Arg Thr Val Thr Thr Gly Ala Pro Ile Thr Tyr
        1285                1290                1295 tcc aca tat ggc aaa ttc ctc gcc gat ggg ggc tgt gcg ggc ggc    4276
Ser Thr Tyr Gly Lys Phe Leu Ala Asp Gly Gly Cys Ala Gly Gly
        1300                1305                1310 gcc tac gac atc atc ata tgt gat gaa tgc cat gcc gtg gac tct    4321
Ala Tyr Asp Ile Ile Ile Cys Asp Glu Cys His Ala Val Asp Ser
        1315                1320                1325 acc acc atc ctt ggc atc gga aca gtc ctt gat caa gca gag aca    4366
Thr Thr Ile Leu Gly Ile Gly Thr Val Leu Asp Gln Ala Glu Thr
        1330                1335                1340 gct ggg gtc aga cta act gtg ctg gct aca gct acg ccc cct ggg    4411
Ala Gly Val Arg Leu Thr Val Leu Ala Thr Ala Thr Pro Pro Gly
        1345                1350                1355 tca gtg aca acc ccc cac ccc aac ata gag gag gtg gcc ctt ggg    4456
Ser Val Thr Thr Pro His Pro Asn Ile Glu Glu Val Ala Leu Gly
        1360                1365                1370 cag gag ggc gag atc ccc ttc tat ggg agg gcg att ccc ctg tct    4501
Gln Glu Gly Glu Ile Pro Phe Tyr Gly Arg Ala Ile Pro Leu Ser
        1375                1380                1385 tac atc aag gga gga aga cat ctg atc ttc tgc cat tca aag aaa    4546
Tyr Ile Lys Gly Gly Arg His Leu Ile Phe Cys His Ser Lys Lys
        1390                1395                1400 aag tgt gac gag ctc gcg gcg gcc ctt cgg ggt atg ggc ttg aac    4591
Lys Cys Asp Glu Leu Ala Ala Ala Leu Arg Gly Met Gly Leu Asn
        1405                1410                1415 tca gtg gca tac tac aga ggg ttg gac gtc tcc gta ata cca act    4636
Ser Val Ala Tyr Tyr Arg Gly Leu Asp Val Ser Val Ile Pro Thr
        1420                1425                1430 cag gga gac gta gtg gtc gtc gcc acc gac gcc ctc atg aca ggg    4681
Gln Gly Asp Val Val Val Val Ala Thr Asp Ala Leu Met Thr Gly
```

-continued

|  | 1435 |  |  |  | 1440 |  |  |  | 1445 |  |  |  |
|---|---|---|---|---|---|---|---|---|---|---|---|---|
| tat | act | ggg | gac | ttt | gac | tcc | gtg | atc | gac | tgc | aac | gta | gcg | gtc | 4726 |
| Tyr | Thr | Gly | Asp | Phe | Asp | Ser | Val | Ile | Asp | Cys | Asn | Val | Ala | Val | |
|  | 1450 |  |  |  | 1455 |  |  |  | 1460 |  |  |  | act caa gtt gta gac ttc agt tta gac ccc aca ttc acc ata acc    4771
Thr Gln Val Val Asp Phe Ser Leu Asp Pro Thr Phe Thr Ile Thr
    1465                1470                1475 aca cag att gtc cct caa gac gct gtc tca cgt agc cag cgc cgg    4816
Thr Gln Ile Val Pro Gln Asp Ala Val Ser Arg Ser Gln Arg Arg
    1480                1485                1490 ggt cgc acg ggt agg gga aga ctg ggc att tat agg tat gtt tcc    4861
Gly Arg Thr Gly Arg Gly Arg Leu Gly Ile Tyr Arg Tyr Val Ser
    1495                1500                1505 act ggt gag cga gcc tca gga atg ttt gac agt gta gtg ctc tgt    4906
Thr Gly Glu Arg Ala Ser Gly Met Phe Asp Ser Val Val Leu Cys
    1510                1515                1520 gag tgc tac gac gca ggg gcc gca tgg tat gag ctc aca cca tcg    4951
Glu Cys Tyr Asp Ala Gly Ala Ala Trp Tyr Glu Leu Thr Pro Ser
    1525                1530                1535 gag acc acc gtc agg ctc agg gcg tat ttc aac acg ccc ggt ttg    4996
Glu Thr Thr Val Arg Leu Arg Ala Tyr Phe Asn Thr Pro Gly Leu
    1540                1545                1550 cct gtg tgc caa gac cat ctt gag ttt tgg gag gca gtt ttc acc    5041
Pro Val Cys Gln Asp His Leu Glu Phe Trp Glu Ala Val Phe Thr
    1555                1560                1565 ggc ctc aca cac ata gat gcc cac ttc ctt tcc caa aca aag caa    5086
Gly Leu Thr His Ile Asp Ala His Phe Leu Ser Gln Thr Lys Gln
    1570                1575                1580 tcg ggg gaa aat ttc gca tac tta aca gcc tac cag gct aca gtg    5131
Ser Gly Glu Asn Phe Ala Tyr Leu Thr Ala Tyr Gln Ala Thr Val
    1585                1590                1595 tgc gct agg gcc aaa gcc ccc ccg tcc tgg gac gtc atg tgg        5176
Cys Ala Arg Ala Lys Ala Pro Pro Pro Ser Trp Asp Val Met Trp
    1600                1605                1610 aag tgt ttg act cga ctc aag ccc aca ctc gtg ggc ccc aca cct    5221
Lys Cys Leu Thr Arg Leu Lys Pro Thr Leu Val Gly Pro Thr Pro
    1615                1620                1625 ctc ctg tac cgc ttg ggc tct gtt acc aac gag gtc acc ctc aca    5266
Leu Leu Tyr Arg Leu Gly Ser Val Thr Asn Glu Val Thr Leu Thr
    1630                1635                1640 cat ccc gtg acg aaa tac atc gcc acc tgc atg caa gcc gac ctt    5311
His Pro Val Thr Lys Tyr Ile Ala Thr Cys Met Gln Ala Asp Leu
    1645                1650                1655 gag gtc atg acc agc aca tgg gtc ttg gca ggg gga gtc ttg gcg    5356
Glu Val Met Thr Ser Thr Trp Val Leu Ala Gly Gly Val Leu Ala
    1660                1665                1670 gcc gtc gcc gcg tat tgc ctg gag acc ggg tgt gtt tgc atc atc    5401
Ala Val Ala Ala Tyr Cys Leu Glu Thr Gly Cys Val Cys Ile Ile
    1675                1680                1685 ggc cgc ttg cac att aac cag cga gcc gtc gtt gcg ccg gac aag    5446
Gly Arg Leu His Ile Asn Gln Arg Ala Val Val Ala Pro Asp Lys
    1690                1695                1700 gag gtc ctc tat gag gct ttt gat gag atg gag gaa tgt gcc tct    5491
Glu Val Leu Tyr Glu Ala Phe Asp Glu Met Glu Glu Cys Ala Ser
    1705                1710                1715 agg gcg gct ctc att gaa gag ggg cag cgg ata gcc gag atg ctg    5536
Arg Ala Ala Leu Ile Glu Glu Gly Gln Arg Ile Ala Glu Met Leu
    1720                1725                1730 aag tcc aag atc caa ggc tta ttg cag caa gct tcc aaa caa gct    5581

-continued

```
              Lys Ser Lys Ile Gln Gly Leu Leu Gln Gln Ala Ser Lys Gln Ala
                      1735            1740                1745 caa gac ata caa ccc act gtg cag gct tca tgg ccc aag gta gaa        5626
Gln Asp Ile Gln Pro Thr Val Gln Ala Ser Trp Pro Lys Val Glu
        1750            1755                1760 caa ttc tgg gcc aaa cac atg tgg aac ttc att agc ggc atc caa        5671
Gln Phe Trp Ala Lys His Met Trp Asn Phe Ile Ser Gly Ile Gln
        1765            1770                1775 tac ctc gca gga cta tca aca ctg cca ggg aac cct gca gta gct        5716
Tyr Leu Ala Gly Leu Ser Thr Leu Pro Gly Asn Pro Ala Val Ala
        1780            1785                1790 tcc atg atg gcg ttc agt gcc gcc ctc acc agt ccg ctg tca aca        5761
Ser Met Met Ala Phe Ser Ala Ala Leu Thr Ser Pro Leu Ser Thr
        1795            1800                1805 agc acc act atc ctt ctc aac att ttg ggg ggc tgg cta gca tcc        5806
Ser Thr Thr Ile Leu Leu Asn Ile Leu Gly Gly Trp Leu Ala Ser
        1810            1815                1820 caa att gca cca ccc gcg ggg gcc act ggc ttc gtt gtc agt ggc        5851
Gln Ile Ala Pro Pro Ala Gly Ala Thr Gly Phe Val Val Ser Gly
        1825            1830                1835 cta gtg gga gct gcc gta ggc agt ata ggc tta ggt aag gtg cta        5896
Leu Val Gly Ala Ala Val Gly Ser Ile Gly Leu Gly Lys Val Leu
        1840            1845                1850 gtg gac atc ctg gca ggg tat ggt gcg ggc att tcg ggg gct ctc        5941
Val Asp Ile Leu Ala Gly Tyr Gly Ala Gly Ile Ser Gly Ala Leu
        1855            1860                1865 gtc gca ttc aag atc atg tct ggc gag aag ccc tcc atg gag gat        5986
Val Ala Phe Lys Ile Met Ser Gly Glu Lys Pro Ser Met Glu Asp
        1870            1875                1880 gtc gtc aac ttg ctg cct gga att ctg tct ccg ggt gcc ttg gta        6031
Val Val Asn Leu Leu Pro Gly Ile Leu Ser Pro Gly Ala Leu Val
        1885            1890                1895 gtg gga gtc atc tgc gcg gcc att ctg cgc cga cac gtg gga ccg        6076
Val Gly Val Ile Cys Ala Ala Ile Leu Arg Arg His Val Gly Pro
        1900            1905                1910 ggg gaa ggc gcc gtc caa tgg atg aat aga ctc att gcc ttt gct        6121
Gly Glu Gly Ala Val Gln Trp Met Asn Arg Leu Ile Ala Phe Ala
        1915            1920                1925 tcc aga gga aat cac gtc gcc ccc acc cac tac gtg acg gag tcg        6166
Ser Arg Gly Asn His Val Ala Pro Thr His Tyr Val Thr Glu Ser
        1930            1935                1940 gat gcg tcg cag cgt gtg acc caa cta ctt ggc tcc ctt acc ata        6211
Asp Ala Ser Gln Arg Val Thr Gln Leu Leu Gly Ser Leu Thr Ile
        1945            1950                1955 acc agc ctg ctc aga aga ctc cac aac tgg att act gag gac tgc        6256
Thr Ser Leu Leu Arg Arg Leu His Asn Trp Ile Thr Glu Asp Cys
        1960            1965                1970 ccc atc cca tgc tcc gga tcg tgg ctc cgc gat gtg tgg gac tgg        6301
Pro Ile Pro Cys Ser Gly Ser Trp Leu Arg Asp Val Trp Asp Trp
        1975            1980                1985 gtt tgc acc atc cta aca gac ttt aaa aat tgg ctg acc tcc aaa        6346
Val Cys Thr Ile Leu Thr Asp Phe Lys Asn Trp Leu Thr Ser Lys
        1990            1995                2000 tta ttc cca aag atg ccc ggc ctc ccc ttt gtc tcc tgt caa aag        6391
Leu Phe Pro Lys Met Pro Gly Leu Pro Phe Val Ser Cys Gln Lys
        2005            2010                2015 ggg tac aag ggc gtg tgg gcc ggc act ggc atc atg acc aca cgg        6436
Gly Tyr Lys Gly Val Trp Ala Gly Thr Gly Ile Met Thr Thr Arg
        2020            2025                2030
```

| | | | | | | | | | | | | |
|---|---|---|---|---|---|---|---|---|---|---|---|---|
| tgt | cct | tgc | ggc | gcc | aat | atc | tct | ggc | aat | gtc | cgc | ttg | ggc | tcc | 6481 |
| Cys | Pro | Cys | Gly | Ala | Asn | Ile | Ser | Gly | Asn | Val | Arg | Leu | Gly | Ser | |
| | | 2035 | | | | | 2040 | | | | | 2045 | | | |

| atg | aga | atc | acg | ggg | cct | aag | acc | tgc | atg | aat | atc | tgg | cag | ggg | 6526 |
| Met | Arg | Ile | Thr | Gly | Pro | Lys | Thr | Cys | Met | Asn | Ile | Trp | Gln | Gly | |
| | | 2050 | | | | | 2055 | | | | | 2060 | | | | acc ttt cct atc aat tgt tac acg gag ggc cag tgc gtg ccg aaa   6571
Thr Phe Pro Ile Asn Cys Tyr Thr Glu Gly Gln Cys Val Pro Lys
        2065            2070            2075 ccc gcg cca aac ttt aag gtc gcc atc tgg agg gtg gcg gcc tca   6616
Pro Ala Pro Asn Phe Lys Val Ala Ile Trp Arg Val Ala Ala Ser
        2080            2085            2090 gag tac gcg gag gtg acg cag cac ggg tca tac cac tac ata aca   6661
Glu Tyr Ala Glu Val Thr Gln His Gly Ser Tyr His Tyr Ile Thr
        2095            2100            2105 gga ctc acc act gat aac ttg aaa gtc ccc tgc caa cta ccc tct   6706
Gly Leu Thr Thr Asp Asn Leu Lys Val Pro Cys Gln Leu Pro Ser
        2110            2115            2120 ccc gag ttc ttt tcc tgg gtg gac gga gtg cag atc cat agg ttt   6751
Pro Glu Phe Phe Ser Trp Val Asp Gly Val Gln Ile His Arg Phe
        2125            2130            2135 gcc ccc aca ccg aag ccg ttt ttc cgg gat gag gtc tcg ttc tgc   6796
Ala Pro Thr Pro Lys Pro Phe Phe Arg Asp Glu Val Ser Phe Cys
        2140            2145            2150 gtt ggg ctt aat tca ttt gtc gtc ggg tcc cag ctt cct tgc gac   6841
Val Gly Leu Asn Ser Phe Val Val Gly Ser Gln Leu Pro Cys Asp
        2155            2160            2165 cct gaa ccc gac aca gac gta ttg atg tcc atg cta aca gat cca   6886
Pro Glu Pro Asp Thr Asp Val Leu Met Ser Met Leu Thr Asp Pro
        2170            2175            2180 tct cat atc acg gcg gag act gca gcg cgg cgt tta gcg cgg ggg   6931
Ser His Ile Thr Ala Glu Thr Ala Ala Arg Arg Leu Ala Arg Gly
        2185            2190            2195 tca ccc cca tcc gag gca agc tcc tcg gcg agc cag cta tcg gca   6976
Ser Pro Pro Ser Glu Ala Ser Ser Ser Ala Ser Gln Leu Ser Ala
        2200            2205            2210 cca tcg ctg cga gcc acc tgc acc acc cac ggc aaa gcc tat gat   7021
Pro Ser Leu Arg Ala Thr Cys Thr Thr His Gly Lys Ala Tyr Asp
        2215            2220            2225 gtg gac atg gtg gat gct aac ctg ttc atg ggg ggc gat gtg act   7066
Val Asp Met Val Asp Ala Asn Leu Phe Met Gly Gly Asp Val Thr
        2230            2235            2240 cgg ata gag tct ggg tcc aaa gtg gtc gtt ctg gac tct ctc gac   7111
Arg Ile Glu Ser Gly Ser Lys Val Val Val Leu Asp Ser Leu Asp
        2245            2250            2255 cca atg gtc gaa gaa agg agc gac ctt gag cct tcg ata cca tca   7156
Pro Met Val Glu Glu Arg Ser Asp Leu Glu Pro Ser Ile Pro Ser
        2260            2265            2270 gaa tac atg ctc ccc aag aag agg ttc cca cca gct tta ccg gcc   7201
Glu Tyr Met Leu Pro Lys Lys Arg Phe Pro Pro Ala Leu Pro Ala
        2275            2280            2285 tgg gca cgg cct gat tac aac cca ccg ctt gtg gaa tcg tgg aaa   7246
Trp Ala Arg Pro Asp Tyr Asn Pro Pro Leu Val Glu Ser Trp Lys
        2290            2295            2300 agg cca gat tac caa ccg gcc act gtt gcg ggc tgt gct ctc cct   7291
Arg Pro Asp Tyr Gln Pro Ala Thr Val Ala Gly Cys Ala Leu Pro
        2305            2310            2315 cct cct agg aaa acc ccg acg cct ccc cca agg agg cgc cgg aca   7336
Pro Pro Arg Lys Thr Pro Thr Pro Pro Pro Arg Arg Arg Arg Thr
        2320            2325            2330

```
gtg ggc cta agt gag gac tcc ata gga gat gcc ctt caa cag ctg      7381
Val Gly Leu Ser Glu Asp Ser Ile Gly Asp Ala Leu Gln Gln Leu
            2335            2340            2345 gcc att aag tcc ttt ggc cag ccc ccc cca agc ggc gat tca ggc      7426
Ala Ile Lys Ser Phe Gly Gln Pro Pro Pro Ser Gly Asp Ser Gly
            2350            2355            2360 ctt tcc acg ggg gcg ggc gct gcc gat tcc ggc agt cag acg cct      7471
Leu Ser Thr Gly Ala Gly Ala Ala Asp Ser Gly Ser Gln Thr Pro
            2365            2370            2375 cct gat gag ttg gcc ctt tcg gag aca ggt tcc atc tct tcc atg      7516
Pro Asp Glu Leu Ala Leu Ser Glu Thr Gly Ser Ile Ser Ser Met
            2380            2385            2390 ccc ccc ctc gag ggg gag ctt gga gat cca gac ctg gag cct gag      7561
Pro Pro Leu Glu Gly Glu Leu Gly Asp Pro Asp Leu Glu Pro Glu
            2395            2400            2405 cag gta gag ccc caa ccc ccc ccc cag ggg ggg gtg gca gct ccc      7606
Gln Val Glu Pro Gln Pro Pro Pro Gln Gly Gly Val Ala Ala Pro
            2410            2415            2420 ggc tcg gac tcg ggg tcc tgg tct act tgc tcc gag gag gac gac      7651
Gly Ser Asp Ser Gly Ser Trp Ser Thr Cys Ser Glu Glu Asp Asp
            2425            2430            2435 tcc gtc gtg tgc tgc tcc atg tca tac tcc tgg acc ggg gct cta      7696
Ser Val Val Cys Cys Ser Met Ser Tyr Ser Trp Thr Gly Ala Leu
            2440            2445            2450 ata act cct tgt agt ccc gaa gag gag aag tta ccg att aac ccc      7741
Ile Thr Pro Cys Ser Pro Glu Glu Glu Lys Leu Pro Ile Asn Pro
            2455            2460            2465 ttg agc aac tcc ctg ttg cga tat cac aac aag gtg tac tgt acc      7786
Leu Ser Asn Ser Leu Leu Arg Tyr His Asn Lys Val Tyr Cys Thr
            2470            2475            2480 aca aca aag agc gcc tca cta agg gct aaa aag gta act ttt gat      7831
Thr Thr Lys Ser Ala Ser Leu Arg Ala Lys Lys Val Thr Phe Asp
            2485            2490            2495 agg atg caa gtg ctc gac tcc tac tac gac tca gtc tta aag gac      7876
Arg Met Gln Val Leu Asp Ser Tyr Tyr Asp Ser Val Leu Lys Asp
            2500            2505            2510 att aag cta gcg gcc tcc aag gtc acc gca agg ctc ctc acc atg      7921
Ile Lys Leu Ala Ala Ser Lys Val Thr Ala Arg Leu Leu Thr Met
            2515            2520            2525 gag gag gct tgc cag tta acc cca ccc cat tct gca aga tct aaa      7966
Glu Glu Ala Cys Gln Leu Thr Pro Pro His Ser Ala Arg Ser Lys
            2530            2535            2540 tat ggg ttt ggg gct aag gag gtc cgc agc ttg tcc ggg agg gcc      8011
Tyr Gly Phe Gly Ala Lys Glu Val Arg Ser Leu Ser Gly Arg Ala
            2545            2550            2555 gtt aac cac atc aag tcc gtg tgg aag gac ctc ctg gag gac tca      8056
Val Asn His Ile Lys Ser Val Trp Lys Asp Leu Leu Glu Asp Ser
            2560            2565            2570 gaa aca cca att ccc aca acc att atg gcc aaa aat gag gtg ttc      8101
Glu Thr Pro Ile Pro Thr Thr Ile Met Ala Lys Asn Glu Val Phe
            2575            2580            2585 tgc gtg gac ccc acc aag ggg ggc aag aaa gca gct cgc ctt atc      8146
Cys Val Asp Pro Thr Lys Gly Gly Lys Lys Ala Ala Arg Leu Ile
            2590            2595            2600 gtt tac cct gac ctc ggc gtc agg gtc tgc gag aag atg gcc ctt      8191
Val Tyr Pro Asp Leu Gly Val Arg Val Cys Glu Lys Met Ala Leu
            2605            2610            2615 tat gac att aca caa aaa ctt cct cag gcg gtg atg ggg gct tct      8236
Tyr Asp Ile Thr Gln Lys Leu Pro Gln Ala Val Met Gly Ala Ser
```

-continued

```
                 2620              2625                   2630 tat  gga  ttc  cag  tat  tcc  ccc  gct  cag  cgg  gta  gag  ttt  ctc  ttg       8281
Tyr  Gly  Phe  Gln  Tyr  Ser  Pro  Ala  Gln  Arg  Val  Glu  Phe  Leu  Leu
                 2635              2640                   2645 aaa  gca  tgg  gcg  gaa  aag  aag  gac  cct  atg  ggt  ttt  tcg  tat  gat       8326
Lys  Ala  Trp  Ala  Glu  Lys  Lys  Asp  Pro  Met  Gly  Phe  Ser  Tyr  Asp
                 2650              2655                   2660 acc  cga  tgc  ttt  gac  tca  acc  gtc  act  gag  aga  gac  atc  agg  act       8371
Thr  Arg  Cys  Phe  Asp  Ser  Thr  Val  Thr  Glu  Arg  Asp  Ile  Arg  Thr
                 2665              2670                   2675 gag  gag  tcc  ata  tat  cgg  gcc  tgc  tcc  ttg  ccc  gag  gag  gcc  cac       8416
Glu  Glu  Ser  Ile  Tyr  Arg  Ala  Cys  Ser  Leu  Pro  Glu  Glu  Ala  His
                 2680              2685                   2690 act  gcc  ata  cac  tcg  cta  act  gag  aga  ctt  tac  gtg  gga  ggg  cct       8461
Thr  Ala  Ile  His  Ser  Leu  Thr  Glu  Arg  Leu  Tyr  Val  Gly  Gly  Pro
                 2695              2700                   2705 atg  ttc  aac  agc  aag  ggc  caa  acc  tgc  ggg  tac  agg  cgt  tgc  cgc       8506
Met  Phe  Asn  Ser  Lys  Gly  Gln  Thr  Cys  Gly  Tyr  Arg  Arg  Cys  Arg
                 2710              2715                   2720 gcc  agc  ggg  gtg  ctc  acc  act  agc  atg  ggg  aac  acc  atc  aca  tgc       8551
Ala  Ser  Gly  Val  Leu  Thr  Thr  Ser  Met  Gly  Asn  Thr  Ile  Thr  Cys
                 2725              2730                   2735 tac  gtg  aaa  gcc  tta  gcg  gct  tgt  aaa  gct  gca  ggg  ata  atc  gcg       8596
Tyr  Val  Lys  Ala  Leu  Ala  Ala  Cys  Lys  Ala  Ala  Gly  Ile  Ile  Ala
                 2740              2745                   2750 ccc  aca  atg  ctg  gta  tgc  ggc  gat  gac  ttg  gtt  gtc  atc  tca  gaa       8641
Pro  Thr  Met  Leu  Val  Cys  Gly  Asp  Asp  Leu  Val  Val  Ile  Ser  Glu
                 2755              2760                   2765 agc  cag  ggg  acc  gag  gag  gac  gag  cgg  aac  ctg  aga  gcc  ttc  acg       8686
Ser  Gln  Gly  Thr  Glu  Glu  Asp  Glu  Arg  Asn  Leu  Arg  Ala  Phe  Thr
                 2770              2775                   2780 gag  gct  atg  acc  agg  tat  tct  gcc  cct  cct  ggt  gac  ccc  ccc  aga       8731
Glu  Ala  Met  Thr  Arg  Tyr  Ser  Ala  Pro  Pro  Gly  Asp  Pro  Pro  Arg
                 2785              2790                   2795 ccg  gag  tat  gat  ctg  gag  ctg  ata  aca  tct  tgc  tcc  tca  aat  gtg       8776
Pro  Glu  Tyr  Asp  Leu  Glu  Leu  Ile  Thr  Ser  Cys  Ser  Ser  Asn  Val
                 2800              2805                   2810 tct  gtg  gcg  ctg  ggc  cca  caa  ggc  cgc  cgc  aga  tac  tac  ctg  acc       8821
Ser  Val  Ala  Leu  Gly  Pro  Gln  Gly  Arg  Arg  Arg  Tyr  Tyr  Leu  Thr
                 2815              2820                   2825 aga  gac  cct  acc  act  cca  atc  gcc  cgg  gct  gcc  tgg  gaa  aca  gtt       8866
Arg  Asp  Pro  Thr  Thr  Pro  Ile  Ala  Arg  Ala  Ala  Trp  Glu  Thr  Val
                 2830              2835                   2840 aga  cac  tcc  cct  gtc  aat  tca  tgg  ctg  gga  aac  atc  atc  cag  tac       8911
Arg  His  Ser  Pro  Val  Asn  Ser  Trp  Leu  Gly  Asn  Ile  Ile  Gln  Tyr
                 2845              2850                   2855 gcc  ccg  acc  ata  tgg  gct  cgc  atg  gtc  ctg  atg  aca  cac  ttc  ttc       8956
Ala  Pro  Thr  Ile  Trp  Ala  Arg  Met  Val  Leu  Met  Thr  His  Phe  Phe
                 2860              2865                   2870 tcc  att  ctc  atg  gct  caa  gac  acg  ctg  gac  cag  aac  ctc  aac  ttt       9001
Ser  Ile  Leu  Met  Ala  Gln  Asp  Thr  Leu  Asp  Gln  Asn  Leu  Asn  Phe
                 2875              2880                   2885 gag  atg  tac  gga  tca  gtg  tac  tcc  gtg  agt  ccc  ttg  gac  ctc  cca       9046
Glu  Met  Tyr  Gly  Ser  Val  Tyr  Ser  Val  Ser  Pro  Leu  Asp  Leu  Pro
                 2890              2895                   2900 gct  ata  att  gaa  agg  tta  cat  ggg  ctt  gac  gct  ttt  tct  ctg  cac       9091
Ala  Ile  Ile  Glu  Arg  Leu  His  Gly  Leu  Asp  Ala  Phe  Ser  Leu  His
                 2905              2910                   2915 aca  tac  act  ccc  cac  gaa  ctg  aca  cgg  gtg  gct  tca  gcc  ctc  aga       9136
```

```
Thr Tyr Thr  Pro His Glu Leu Thr  Arg Val Ala Ser Ala  Leu Arg
        2920                 2925                 2930 aaa ctt ggg  gcg cca ccc ctc aga  gcg tgg aag agc cgg  gca cgt      9181
Lys Leu Gly  Ala Pro Pro Leu Arg  Ala Trp Lys Ser Arg  Ala Arg
        2935                 2940                 2945 gca gtc agg  gcg tcc ctc atc tcc  cgt ggg ggg aaa gcg  gcc gtt      9226
Ala Val Arg  Ala Ser Leu Ile Ser  Arg Gly Gly Lys Ala  Ala Val
        2950                 2955                 2960 tgc ggt cga  tat ctc ttc aat tgg  gcg gtg aag acc aag  ctc aaa      9271
Cys Gly Arg  Tyr Leu Phe Asn Trp  Ala Val Lys Thr Lys  Leu Lys
        2965                 2970                 2975 ctc act cca  ttg ccg gaa gcg cgc  ctc ctg gat tta tcc  agc tgg      9316
Leu Thr Pro  Leu Pro Glu Ala Arg  Leu Leu Asp Leu Ser  Ser Trp
        2980                 2985                 2990 ttc acc gtc  ggc gcc ggc ggg ggc  gac att ttt cac agc  gtg tcg      9361
Phe Thr Val  Gly Ala Gly Gly Gly  Asp Ile Phe His Ser  Val Ser
        2995                 3000                 3005 cgt gcc cga  ccc cgc tta ttg ctc  ttt ggc cta ctc cta  ctt ttt      9406
Arg Ala Arg  Pro Arg Leu Leu Leu  Phe Gly Leu Leu Leu  Leu Phe
        3010                 3015                 3020 gta ggg gta  ggc ctt ttc cta ctc  ccc gct cgg tagagcggca            9449
Val Gly Val  Gly Leu Phe Leu Leu  Pro Ala Arg
        3025                 3030 cacattaggt acactccata gctaactgtc ccttttttt ttttttttt ttttttttt   9509 ttttttttt ttttttttt ttttttttt ttttttttt ttttttttt ttttttcttt   9569 ttttctcttt tccttctttc ttaccttatt ttactttctt tcctggtggc tccatcttag   9629
ccctagtcac ggctagctgt gaaaggtccg tgagccgcat gactgcagag agtgccgtaa   9689
ctggtctctc tgcagatcat gt                                            9711

<210> SEQ ID NO 6
<211> LENGTH: 3033
<212> TYPE: PRT
<213> ORGANISM: Artificial Sequence
<220> FEATURE:
<223> OTHER INFORMATION: Description of Artificial Sequence: Synthetic
      precursor protein encoded by FGR-J6/4Amut+SKF+VRm3

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140
```

```
Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
            165                 170                 175

Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Val Met Leu Ala Ala
            275                 280                 285

Gln Met Phe Ile Val Ser Pro Gln His His Trp Phe Val Gln Asp Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
            355                 360                 365

Ala Lys Val Val Ile Leu Leu Leu Ala Ala Gly Val Asp Ala Arg
370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
            435                 440                 445

Ser Ser Gly Cys Pro Glu Arg Met Ser Ala Cys Arg Ser Ile Glu Ala
450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Lys Thr Val Cys Gly Pro Val Tyr Cys Phe Thr
            500                 505                 510

Pro Ser Pro Val Val Gly Thr Thr Asp Arg Leu Gly Ala Pro Thr
            515                 520                 525

Tyr Thr Trp Gly Glu Asn Glu Thr Asp Val Phe Leu Leu Asn Ser Thr
            530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
```

-continued

```
                565                 570                 575
Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
            595                 600                 605

Pro Arg Cys Leu Ile Asp Tyr Pro Tyr Arg Leu Trp His Tyr Pro Cys
            610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
                675                 680                 685

Leu Ser Thr Gly Leu Leu His Leu His Gln Asn Ile Val Asp Val Gln
                690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Ile Leu His Ala Ala Ser Ala Ala Ser Cys Asn Gly
                755                 760                 765

Phe Leu Tyr Phe Val Ile Phe Phe Val Ala Ala Trp Tyr Ile Lys Gly
                770                 775                 780

Arg Val Val Pro Leu Ala Thr Tyr Ser Leu Thr Gly Leu Trp Ser Phe
785                 790                 795                 800

Ser Leu Leu Leu Leu Ala Leu Pro Gln Gln Ala Tyr Ala Tyr Asp Ala
                805                 810                 815

Ser Val His Gly Gln Ile Gly Ala Ala Leu Leu Val Met Ile Thr Leu
                820                 825                 830

Phe Thr Leu Thr Pro Gly Tyr Lys Thr Leu Leu Ser Arg Phe Leu Trp
                835                 840                 845

Trp Leu Cys Tyr Leu Leu Thr Leu Gly Glu Ala Met Val Gln Glu Trp
                850                 855                 860

Ala Pro Pro Met Gln Val Arg Gly Gly Arg Asp Gly Ile Ile Trp Ala
865                 870                 875                 880

Val Ala Ile Phe Tyr Pro Gly Val Val Phe Asp Ile Thr Lys Trp Leu
                885                 890                 895

Leu Ala Val Leu Gly Pro Ala Tyr Leu Leu Lys Gly Ala Leu Thr Arg
                900                 905                 910

Val Pro Tyr Phe Val Arg Ala His Ala Leu Leu Arg Met Cys Thr Met
                915                 920                 925

Ala Arg His Leu Ala Gly Gly Arg Tyr Val Gln Met Ala Leu Leu Ala
                930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
                980                 985                 990
```

-continued

```
Glu Thr Ala Ala Cys Gly Asp Ile Leu His Gly Leu Pro Val Ser Ala
        995                 1000                1005

Arg Leu Gly Arg Glu Val Leu Leu Gly Pro Ala Asp Gly Tyr Thr
    1010                1015                1020

Ser Lys Gly Trp Ser Leu Leu Ala Pro Ile Thr Ala Tyr Ala Gln
    1025                1030                1035

Gln Thr Arg Gly Leu Leu Gly Thr Ile Val Val Ser Met Thr Gly
    1040                1045                1050

Arg Asp Lys Thr Glu Gln Ala Gly Glu Ile Gln Val Leu Ser Thr
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Ser Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Thr
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Val Phe Arg Ala Ala Val
    1175                1180                1185

Cys Ser Arg Gly Val Ala Lys Ser Ile Asp Phe Ile Pro Val Glu
    1190                1195                1200

Thr Leu Asp Ile Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Thr Thr Gly Ala
    1280                1285                1290

Pro Ile Thr Tyr Ser Thr Tyr Gly Lys Phe Leu Ala Asp Gly Gly
    1295                1300                1305

Cys Ala Gly Gly Ala Tyr Asp Ile Ile Ile Cys Asp Glu Cys His
    1310                1315                1320

Ala Val Asp Ser Thr Thr Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asn Ile Glu Glu
    1355                1360                1365

Val Ala Leu Gly Gln Glu Gly Glu Ile Pro Phe Tyr Gly Arg Ala
    1370                1375                1380
```

-continued

```
Ile Pro Leu Ser Tyr Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Leu Asn Ser Val Ala Tyr Tyr Arg Gly Leu Asp Val Ser
    1415                1420                1425

Val Ile Pro Thr Gln Gly Asp Val Val Val Ala Thr Asp Ala
    1430                1435                1440

Leu Met Thr Gly Tyr Thr Gly Asp Phe Asp Ser Val Ile Asp Cys
    1445                1450                1455

Asn Val Ala Val Thr Gln Val Val Asp Phe Ser Leu Asp Pro Thr
    1460                1465                1470

Phe Thr Ile Thr Thr Gln Ile Val Pro Gln Asp Ala Val Ser Arg
    1475                1480                1485

Ser Gln Arg Arg Gly Arg Thr Gly Arg Gly Arg Leu Gly Ile Tyr
    1490                1495                1500

Arg Tyr Val Ser Thr Gly Glu Arg Ala Ser Gly Met Phe Asp Ser
    1505                1510                1515

Val Val Leu Cys Glu Cys Tyr Asp Ala Gly Ala Ala Trp Tyr Glu
    1520                1525                1530

Leu Thr Pro Ser Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Ser Gly Glu Asn Phe Ala Tyr Leu Thr Ala Tyr
    1580                1585                1590

Gln Ala Thr Val Cys Ala Arg Ala Lys Ala Pro Pro Pro Ser Trp
    1595                1600                1605

Asp Val Met Trp Lys Cys Leu Thr Arg Leu Lys Pro Thr Leu Val
    1610                1615                1620

Gly Pro Thr Pro Leu Leu Tyr Arg Leu Gly Ser Val Thr Asn Glu
    1625                1630                1635

Val Thr Leu Thr His Pro Val Thr Lys Tyr Ile Ala Thr Cys Met
    1640                1645                1650

Gln Ala Asp Leu Glu Val Met Thr Ser Thr Trp Val Leu Ala Gly
    1655                1660                1665

Gly Val Leu Ala Ala Val Ala Ala Tyr Cys Leu Glu Thr Gly Cys
    1670                1675                1680

Val Cys Ile Ile Gly Arg Leu His Ile Asn Gln Arg Ala Val Val
    1685                1690                1695

Ala Pro Asp Lys Glu Val Leu Tyr Glu Ala Phe Asp Glu Met Glu
    1700                1705                1710

Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala
    1730                1735                1740

Ser Lys Gln Ala Gln Asp Ile Gln Pro Thr Val Gln Ala Ser Trp
    1745                1750                1755

Pro Lys Val Glu Gln Phe Trp Ala Lys His Met Trp Asn Phe Ile
    1760                1765                1770

Ser Gly Ile Gln Tyr Leu Ala Gly Leu Ser Thr Leu Pro Gly Asn
```

-continued

```
              1775                1780                1785
Pro Ala  Val Ala Ser Met  Met Ala Phe Ser  Ala Ala Leu Thr Ser
    1790             1795                1800
Pro Leu  Ser Thr Ser Thr  Thr Ile Leu Leu  Asn Ile Leu Gly Gly
    1805             1810                1815
Trp Leu  Ala Ser Gln Ile  Ala Pro Pro Ala  Gly Ala Thr Gly Phe
    1820             1825                1830
Val Val  Ser Gly Leu Val  Gly Ala Ala Val  Gly Ser Ile Gly Leu
    1835             1840                1845
Gly Lys  Val Leu Val Asp  Ile Leu Ala Gly  Tyr Gly Ala Gly Ile
    1850             1855                1860
Ser Gly  Ala Leu Val Ala  Phe Lys Ile Met  Ser Gly Glu Lys Pro
    1865             1870                1875
Ser Met  Glu Asp Val Val  Asn Leu Leu Pro  Gly Ile Leu Ser Pro
    1880             1885                1890
Gly Ala  Leu Val Val Gly  Val Ile Cys Ala  Ala Ile Leu Arg Arg
    1895             1900                1905
His Val  Gly Pro Gly Glu  Gly Ala Val Gln  Trp Met Asn Arg Leu
    1910             1915                1920
Ile Ala  Phe Ala Ser Arg  Gly Asn His Val  Ala Pro Thr His Tyr
    1925             1930                1935
Val Thr  Glu Ser Asp Ala  Ser Gln Arg Val  Thr Gln Leu Leu Gly
    1940             1945                1950
Ser Leu  Thr Ile Thr Ser  Leu Leu Arg Arg  Leu His Asn Trp Ile
    1955             1960                1965
Thr Glu  Asp Cys Pro Ile  Pro Cys Ser Gly  Ser Trp Leu Arg Asp
    1970             1975                1980
Val Trp  Asp Trp Val Cys  Thr Ile Leu Thr  Asp Phe Lys Asn Trp
    1985             1990                1995
Leu Thr  Ser Lys Leu Phe  Pro Lys Met Pro  Gly Leu Pro Phe Val
    2000             2005                2010
Ser Cys  Gln Lys Gly Tyr  Lys Gly Val Trp  Ala Gly Thr Gly Ile
    2015             2020                2025
Met Thr  Thr Arg Cys Pro  Cys Gly Ala Asn  Ile Ser Gly Asn Val
    2030             2035                2040
Arg Leu  Gly Ser Met Arg  Ile Thr Gly Pro  Lys Thr Cys Met Asn
    2045             2050                2055
Ile Trp  Gln Gly Thr Phe  Pro Ile Asn Cys  Tyr Thr Glu Gly Gln
    2060             2065                2070
Cys Val  Pro Lys Pro Ala  Pro Asn Phe Lys  Val Ala Ile Trp Arg
    2075             2080                2085
Val Ala  Ala Ser Glu Tyr  Ala Glu Val Thr  Gln His Gly Ser Tyr
    2090             2095                2100
His Tyr  Ile Thr Gly Leu  Thr Thr Asp Asn  Leu Lys Val Pro Cys
    2105             2110                2115
Gln Leu  Pro Ser Pro Glu  Phe Phe Ser Trp  Val Asp Gly Val Gln
    2120             2125                2130
Ile His  Arg Phe Ala Pro  Thr Pro Lys Pro  Phe Phe Arg Asp Glu
    2135             2140                2145
Val Ser  Phe Cys Val Gly  Leu Asn Ser Phe  Val Val Gly Ser Gln
    2150             2155                2160
Leu Pro  Cys Asp Pro Glu  Pro Asp Thr Asp  Val Leu Met Ser Met
    2165             2170                2175
```

```
Leu Thr Asp Pro Ser His Ile Thr Ala Glu Thr Ala Ala Arg Arg
    2180            2185                2190

Leu Ala Arg Gly Ser Pro Pro Ser Glu Ala Ser Ser Ser Ala Ser
    2195            2200                2205

Gln Leu Ser Ala Pro Ser Leu Arg Ala Thr Cys Thr Thr His Gly
    2210            2215                2220

Lys Ala Tyr Asp Val Asp Met Val Asp Ala Asn Leu Phe Met Gly
    2225            2230                2235

Gly Asp Val Thr Arg Ile Glu Ser Gly Ser Lys Val Val Val Leu
    2240            2245                2250

Asp Ser Leu Asp Pro Met Val Glu Glu Arg Ser Asp Leu Glu Pro
    2255            2260                2265

Ser Ile Pro Ser Glu Tyr Met Leu Pro Lys Lys Arg Phe Pro Pro
    2270            2275                2280

Ala Leu Pro Ala Trp Ala Arg Pro Asp Tyr Asn Pro Pro Leu Val
    2285            2290                2295

Glu Ser Trp Lys Arg Pro Asp Tyr Gln Pro Ala Thr Val Ala Gly
    2300            2305                2310

Cys Ala Leu Pro Pro Arg Lys Thr Pro Thr Pro Pro Pro Arg
    2315            2320                2325

Arg Arg Arg Thr Val Gly Leu Ser Glu Asp Ser Ile Gly Asp Ala
    2330            2335                2340

Leu Gln Gln Leu Ala Ile Lys Ser Phe Gly Gln Pro Pro Pro Ser
    2345            2350                2355

Gly Asp Ser Gly Leu Ser Thr Gly Ala Gly Ala Ala Asp Ser Gly
    2360            2365                2370

Ser Gln Thr Pro Pro Asp Glu Leu Ala Leu Ser Glu Thr Gly Ser
    2375            2380                2385

Ile Ser Ser Met Pro Pro Leu Glu Gly Glu Leu Gly Asp Pro Asp
    2390            2395                2400

Leu Glu Pro Glu Gln Val Glu Pro Gln Pro Pro Gln Gly Gly
    2405            2410                2415

Val Ala Ala Pro Gly Ser Asp Ser Gly Ser Trp Ser Thr Cys Ser
    2420            2425                2430

Glu Glu Asp Asp Ser Val Val Cys Cys Ser Met Ser Tyr Ser Trp
    2435            2440                2445

Thr Gly Ala Leu Ile Thr Pro Cys Ser Pro Glu Glu Glu Lys Leu
    2450            2455                2460

Pro Ile Asn Pro Leu Ser Asn Ser Leu Leu Arg Tyr His Asn Lys
    2465            2470                2475

Val Tyr Cys Thr Thr Thr Lys Ser Ala Ser Leu Arg Ala Lys Lys
    2480            2485                2490

Val Thr Phe Asp Arg Met Gln Val Leu Asp Ser Tyr Tyr Asp Ser
    2495            2500                2505

Val Leu Lys Asp Ile Lys Leu Ala Ala Ser Lys Val Thr Ala Arg
    2510            2515                2520

Leu Leu Thr Met Glu Glu Ala Cys Gln Leu Thr Pro Pro His Ser
    2525            2530                2535

Ala Arg Ser Lys Tyr Gly Phe Gly Ala Lys Glu Val Arg Ser Leu
    2540            2545                2550

Ser Gly Arg Ala Val Asn His Ile Lys Ser Val Trp Lys Asp Leu
    2555            2560                2565
```

```
Leu Glu Asp Ser Glu Thr Pro Ile Pro Thr Thr Ile Met Ala Lys
    2570                2575                2580
Asn Glu Val Phe Cys Val Asp Pro Thr Lys Gly Gly Lys Lys Ala
    2585                2590                2595
Ala Arg Leu Ile Val Tyr Pro Asp Leu Gly Val Arg Val Cys Glu
    2600                2605                2610
Lys Met Ala Leu Tyr Asp Ile Thr Gln Lys Leu Pro Gln Ala Val
    2615                2620                2625
Met Gly Ala Ser Tyr Gly Phe Gln Tyr Ser Pro Ala Gln Arg Val
    2630                2635                2640
Glu Phe Leu Leu Lys Ala Trp Ala Glu Lys Lys Asp Pro Met Gly
    2645                2650                2655
Phe Ser Tyr Asp Thr Arg Cys Phe Asp Ser Thr Val Thr Glu Arg
    2660                2665                2670
Asp Ile Arg Thr Glu Glu Ser Ile Tyr Arg Ala Cys Ser Leu Pro
    2675                2680                2685
Glu Glu Ala His Thr Ala Ile His Ser Leu Thr Glu Arg Leu Tyr
    2690                2695                2700
Val Gly Gly Pro Met Phe Asn Ser Lys Gly Gln Thr Cys Gly Tyr
    2705                2710                2715
Arg Arg Cys Arg Ala Ser Gly Val Leu Thr Thr Ser Met Gly Asn
    2720                2725                2730
Thr Ile Thr Cys Tyr Val Lys Ala Leu Ala Ala Cys Lys Ala Ala
    2735                2740                2745
Gly Ile Ile Ala Pro Thr Met Leu Val Cys Gly Asp Asp Leu Val
    2750                2755                2760
Val Ile Ser Glu Ser Gln Gly Thr Glu Glu Asp Glu Arg Asn Leu
    2765                2770                2775
Arg Ala Phe Thr Glu Ala Met Thr Arg Tyr Ser Ala Pro Pro Gly
    2780                2785                2790
Asp Pro Pro Arg Pro Glu Tyr Asp Leu Glu Leu Ile Thr Ser Cys
    2795                2800                2805
Ser Ser Asn Val Ser Val Ala Leu Gly Pro Gln Gly Arg Arg Arg
    2810                2815                2820
Tyr Tyr Leu Thr Arg Asp Pro Thr Thr Pro Ile Ala Arg Ala Ala
    2825                2830                2835
Trp Glu Thr Val Arg His Ser Pro Val Asn Ser Trp Leu Gly Asn
    2840                2845                2850
Ile Ile Gln Tyr Ala Pro Thr Ile Trp Ala Arg Met Val Leu Met
    2855                2860                2865
Thr His Phe Phe Ser Ile Leu Met Ala Gln Asp Thr Leu Asp Gln
    2870                2875                2880
Asn Leu Asn Phe Glu Met Tyr Gly Ser Val Tyr Ser Val Ser Pro
    2885                2890                2895
Leu Asp Leu Pro Ala Ile Ile Glu Arg Leu His Gly Leu Asp Ala
    2900                2905                2910
Phe Ser Leu His Thr Tyr Thr Pro His Glu Leu Thr Arg Val Ala
    2915                2920                2925
Ser Ala Leu Arg Lys Leu Gly Ala Pro Pro Leu Arg Ala Trp Lys
    2930                2935                2940
Ser Arg Ala Arg Ala Val Arg Ala Ser Leu Ile Ser Arg Gly Gly
    2945                2950                2955
Lys Ala Ala Val Cys Gly Arg Tyr Leu Phe Asn Trp Ala Val Lys
```

```
                2960                2965                2970
Thr Lys Leu Lys Leu Thr Pro Leu Pro Glu Ala Arg Leu Leu Asp
        2975                2980                2985

Leu Ser Ser Trp Phe Thr Val Gly Ala Gly Gly Asp Ile Phe
        2990                2995                3000

His Ser Val Ser Arg Ala Arg Pro Arg Leu Leu Leu Phe Gly Leu
        3005                3010                3015

Leu Leu Leu Phe Val Gly Val Gly Leu Phe Leu Leu Pro Ala Arg
        3020                3025                3030
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      sense primer 8680S-2a

<400> SEQUENCE: 7
ccttcacgga ggctatgacc a                                             21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer 9191R-2a

<400> SEQUENCE: 8
ccacgggaga tgagggacgc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer 9191S-2a

<400> SEQUENCE: 9
gcgtccctca tctcccgtgg                                               20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      antisense primer 9440R-IH

<400> SEQUENCE: 10
gtgtacctag tgtgtgccgc tcta                                          24

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      sense primer 3471S-2a

<400> SEQUENCE: 11
tgggcaccat agtggtgag                                                19

-continued

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      antisense primer A1680Eas

<400> SEQUENCE: 12
cacccggtct ccaggcaata cgcggcgacg                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      sense primer A1680Es

<400> SEQUENCE: 13
attgcctgga gaccgggtgt gtttgcatca                                    30

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      antisense primer 6542R-IH

<400> SEQUENCE: 14
cgcactggcc ctccgtgta                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer 7244S-RI

<400> SEQUENCE: 15
accgcttgtg gaatcgtgga                                               20

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      antisense primer J65BA450Sas

<400> SEQUENCE: 16
ggagtacact gatccgtaca tctcaaagtt gagg                               34

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      sense primer J65BA450Ss

<400> SEQUENCE: 17
tgtacggatc agtgtactcc gtgagtccct tg                                 32

```
<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      antisense primer 9454R-IH

<400> SEQUENCE: 18
gtgtgtgccg ctctaccgag cggggagtag                                          30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer J65BR517Kas

<400> SEQUENCE: 19
acggccgctt tcccccacg ggagatgag                                            29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer J65BR517Ks

<400> SEQUENCE: 20 gtgggggaa agcggccgtt tgcggtcga                                            29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer J65BY561Fas

<400> SEQUENCE: 21
cacgctgtga aaatgtcgc ccccgccgg                                            29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer J65BY561Fs

<400> SEQUENCE: 22
ggcgacattt ttcacagcgt gtcgcgtgc                                           29

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      sense primer 9254S-IH

<400> SEQUENCE: 23
gtgaagacca agctcaaact cactcc                                              26

<210> SEQ ID NO 24
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      antisense primer J6VRm3as

<400> SEQUENCE: 24
tatggagtgt acctaatgtg tgccgctcta c                                      31

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      sense primer J6VRm3s

<400> SEQUENCE: 25
cacacattag gtacactcca tagctaactg tc                                     32

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      antisense primer M13R

<400> SEQUENCE: 26
caggaaacag ctatgac                                                      17

<210> SEQ ID NO 27
<211> LENGTH: 591
<212> TYPE: PRT
<213> ORGANISM: Hepatitis C virus
<220> FEATURE:
<223> OTHER INFORMATION: NS5B protein of Hepatitis C virus strain J6CF

<400> SEQUENCE: 27
```

Ser Met Ser Tyr Ser Trp Thr Gly Ala Leu Ile Thr Pro Cys Ser Pro
1               5                   10                  15

Glu Glu Glu Lys Leu Pro Ile Asn Pro Leu Ser Asn Ser Leu Leu Arg
            20                  25                  30

Tyr His Asn Lys Val Tyr Cys Thr Thr Thr Lys Ser Ala Ser Leu Arg
        35                  40                  45

Ala Lys Lys Val Thr Phe Asp Arg Met Gln Val Leu Asp Ser Tyr Tyr
    50                  55                  60

Asp Ser Val Leu Lys Asp Ile Lys Leu Ala Ala Ser Lys Val Thr Ala
65                  70                  75                  80

Arg Leu Leu Thr Met Glu Glu Ala Cys Gln Leu Thr Pro Pro His Ser
                85                  90                  95

Ala Arg Ser Lys Tyr Gly Phe Gly Ala Lys Glu Val Arg Ser Leu Ser
            100                 105                 110

Gly Arg Ala Val Asn His Ile Lys Ser Val Trp Lys Asp Leu Leu Glu
        115                 120                 125

Asp Ser Glu Thr Pro Ile Pro Thr Thr Ile Met Ala Lys Asn Glu Val
    130                 135                 140

Phe Cys Val Asp Pro Thr Lys Gly Gly Lys Lys Ala Ala Arg Leu Ile
145                 150                 155                 160

Val Tyr Pro Asp Leu Gly Val Arg Val Cys Glu Lys Met Ala Leu Tyr
                165                 170                 175

```
Asp Ile Thr Gln Lys Leu Pro Gln Ala Val Met Gly Ala Ser Tyr Gly
            180                 185                 190
Phe Gln Tyr Ser Pro Ala Gln Arg Val Glu Phe Leu Leu Lys Ala Trp
            195                 200                 205
Ala Glu Lys Lys Asp Pro Met Gly Phe Ser Tyr Asp Thr Arg Cys Phe
210                 215                 220
Asp Ser Thr Val Thr Glu Arg Asp Ile Arg Thr Glu Glu Ser Ile Tyr
225                 230                 235                 240
Arg Ala Cys Ser Leu Pro Glu Glu Ala His Thr Ala Ile His Ser Leu
            245                 250                 255
Thr Glu Arg Leu Tyr Val Gly Gly Pro Met Phe Asn Ser Lys Gly Gln
            260                 265                 270
Thr Cys Gly Tyr Arg Arg Cys Arg Ala Ser Gly Val Leu Thr Thr Ser
            275                 280                 285
Met Gly Asn Thr Ile Thr Cys Tyr Val Lys Ala Leu Ala Ala Cys Lys
            290                 295                 300
Ala Ala Gly Ile Ile Ala Pro Thr Met Leu Val Cys Gly Asp Asp Leu
305                 310                 315                 320
Val Val Ile Ser Glu Ser Gln Gly Thr Glu Glu Asp Glu Arg Asn Leu
            325                 330                 335
Arg Ala Phe Thr Glu Ala Met Thr Arg Tyr Ser Ala Pro Pro Gly Asp
            340                 345                 350
Pro Pro Arg Pro Glu Tyr Asp Leu Glu Leu Ile Thr Ser Cys Ser Ser
            355                 360                 365
Asn Val Ser Val Ala Leu Gly Pro Gln Gly Arg Arg Arg Tyr Tyr Leu
            370                 375                 380
Thr Arg Asp Pro Thr Thr Pro Ile Ala Arg Ala Ala Trp Glu Thr Val
385                 390                 395                 400
Arg His Ser Pro Val Asn Ser Trp Leu Gly Asn Ile Ile Gln Tyr Ala
            405                 410                 415
Pro Thr Ile Trp Ala Arg Met Val Leu Met Thr His Phe Phe Ser Ile
            420                 425                 430
Leu Met Ala Gln Asp Thr Leu Asp Gln Asn Leu Asn Phe Glu Met Tyr
            435                 440                 445
Gly Ala Val Tyr Ser Val Ser Pro Leu Asp Leu Pro Ala Ile Ile Glu
            450                 455                 460
Arg Leu His Gly Leu Asp Ala Phe Ser Leu His Thr Tyr Thr Pro His
465                 470                 475                 480
Glu Leu Thr Arg Val Ala Ser Ala Leu Arg Lys Leu Gly Ala Pro Pro
            485                 490                 495
Leu Arg Ala Trp Lys Ser Arg Ala Arg Ala Val Arg Ala Ser Leu Ile
            500                 505                 510
Ser Arg Gly Gly Arg Ala Ala Val Cys Gly Arg Tyr Leu Phe Asn Trp
            515                 520                 525
Ala Val Lys Thr Lys Leu Lys Leu Thr Pro Leu Pro Glu Ala Arg Leu
            530                 535                 540
Leu Asp Leu Ser Ser Trp Phe Thr Val Gly Ala Gly Gly Gly Asp Ile
545                 550                 555                 560
Tyr His Ser Val Ser Arg Ala Arg Pro Arg Leu Leu Leu Phe Gly Leu
            565                 570                 575
Leu Leu Leu Phe Val Gly Val Gly Leu Phe Leu Leu Pro Ala Arg
            580                 585                 590
```

```
<210> SEQ ID NO 28
<211> LENGTH: 591
<212> TYPE: PRT
<213> ORGANISM: Hepatitis C virus
<220> FEATURE:
<223> OTHER INFORMATION: NS5B protein of Hepatitis C virus strain JFH-1

<400> SEQUENCE: 28

Ser Met Ser Tyr Ser Trp Thr Gly Ala Leu Ile Thr Pro Cys Ser Pro
1               5                   10                  15

Glu Glu Glu Lys Leu Pro Ile Asn Pro Leu Ser Asn Ser Leu Leu Arg
            20                  25                  30

Tyr His Asn Lys Val Tyr Cys Thr Thr Ser Lys Ser Ala Ser Gln Arg
        35                  40                  45

Ala Lys Lys Val Thr Phe Asp Arg Thr Gln Val Leu Asp Ala His Tyr
    50                  55                  60

Asp Ser Val Leu Lys Asp Ile Lys Leu Ala Ala Ser Lys Val Ser Ala
65                  70                  75                  80

Arg Leu Leu Thr Leu Glu Glu Ala Cys Gln Leu Thr Pro Pro His Ser
                85                  90                  95

Ala Arg Ser Lys Tyr Gly Phe Gly Ala Lys Glu Val Arg Ser Leu Ser
            100                 105                 110

Gly Arg Ala Val Asn His Ile Lys Ser Val Trp Lys Asp Leu Leu Glu
        115                 120                 125

Asp Pro Gln Thr Pro Ile Pro Thr Thr Ile Met Ala Lys Asn Glu Val
    130                 135                 140

Phe Cys Val Asp Pro Ala Lys Gly Gly Lys Lys Pro Ala Arg Leu Ile
145                 150                 155                 160

Val Tyr Pro Asp Leu Gly Val Arg Val Cys Glu Lys Met Ala Leu Tyr
                165                 170                 175

Asp Ile Thr Gln Lys Leu Pro Gln Ala Val Met Gly Ala Ser Tyr Gly
            180                 185                 190

Phe Gln Tyr Ser Pro Ala Gln Arg Val Glu Tyr Leu Leu Lys Ala Trp
        195                 200                 205

Ala Glu Lys Lys Asp Pro Met Gly Phe Ser Tyr Asp Thr Arg Cys Phe
    210                 215                 220

Asp Ser Thr Val Thr Glu Arg Asp Ile Arg Thr Glu Glu Ser Ile Tyr
225                 230                 235                 240

Gln Ala Cys Ser Leu Pro Glu Glu Ala Arg Thr Ala Ile His Ser Leu
                245                 250                 255

Thr Glu Arg Leu Tyr Val Gly Gly Pro Met Phe Asn Ser Lys Gly Gln
            260                 265                 270

Thr Cys Gly Tyr Arg Arg Cys Arg Ala Ser Gly Val Leu Thr Thr Ser
        275                 280                 285

Met Gly Asn Thr Ile Thr Cys Tyr Val Lys Ala Leu Ala Ala Cys Lys
    290                 295                 300

Ala Ala Gly Ile Val Ala Pro Thr Met Leu Val Cys Gly Asp Asp Leu
305                 310                 315                 320

Val Val Ile Ser Glu Ser Gln Gly Thr Glu Glu Asp Glu Arg Asn Leu
                325                 330                 335

Arg Ala Phe Thr Glu Ala Met Thr Arg Tyr Ser Ala Pro Pro Gly Asp
            340                 345                 350

Pro Pro Arg Pro Glu Tyr Asp Leu Glu Leu Ile Thr Ser Cys Ser Ser
        355                 360                 365
```

```
Asn Val Ser Val Ala Leu Gly Pro Arg Gly Arg Arg Tyr Tyr Leu
    370                 375                 380

Thr Arg Asp Pro Thr Thr Pro Leu Ala Arg Ala Ala Trp Glu Thr Val
385                 390                 395                 400

Arg His Ser Pro Ile Asn Ser Trp Leu Gly Asn Ile Ile Gln Tyr Ala
                405                 410                 415

Pro Thr Ile Trp Val Arg Met Val Leu Met Thr His Phe Phe Ser Ile
            420                 425                 430

Leu Met Val Gln Asp Thr Leu Asp Gln Asn Leu Asn Phe Glu Met Tyr
        435                 440                 445

Gly Ser Val Tyr Ser Val Asn Pro Leu Asp Leu Pro Ala Ile Ile Glu
450                 455                 460

Arg Leu His Gly Leu Asp Ala Phe Ser Met His Thr Tyr Ser His His
465                 470                 475                 480

Glu Leu Thr Arg Val Ala Ser Ala Leu Arg Lys Leu Gly Ala Pro Pro
                485                 490                 495

Leu Arg Val Trp Lys Ser Arg Ala Arg Ala Val Arg Ala Ser Leu Ile
            500                 505                 510

Ser Arg Gly Gly Lys Ala Ala Val Cys Gly Arg Tyr Leu Phe Asn Trp
        515                 520                 525

Ala Val Lys Thr Lys Leu Lys Leu Thr Pro Leu Pro Glu Ala Arg Leu
530                 535                 540

Leu Asp Leu Ser Ser Trp Phe Thr Val Gly Ala Gly Gly Gly Asp Ile
545                 550                 555                 560

Phe His Ser Val Ser Arg Ala Arg Pro Arg Ser Leu Leu Phe Gly Leu
                565                 570                 575

Leu Leu Leu Phe Val Gly Val Gly Leu Phe Leu Leu Pro Ala Arg
            580                 585                 590

<210> SEQ ID NO 29
<211> LENGTH: 9711
<212> TYPE: DNA
<213> ORGANISM: Hepatitis C virus
<220> FEATURE:
<223> OTHER INFORMATION: cDNA sequence of full-length genome RNA of
      Hepatitis C virus strain J6CF
<220> FEATURE:
<221> NAME/KEY: CDS
<222> LOCATION: (341)..(9439)

<400> SEQUENCE: 29
acccgcccct aatagggggcg acactccgcc atgaatcact cccctgtgag gaactactgt    60
cttcacgcag aaagcgtcta gccatggcgt tagtatgagt gtcgtacagc ctccaggccc   120 cccctcccg  ggagagccat agtggtctgc ggaaccggtg agtacaccgg aattgccggg   180
aagactgggt cctttcttgg ataaacccac tctatgcccg gccatttggg cgtgcccccg   240
caagactgct agccgagtag cgttgggttg cgaaaggcct tgtggtactg cctgataggg   300
tgcttgcgag tgccccggga ggtctcgtag accgtgcacc atg agc aca aat cct     355
                                            Met Ser Thr Asn Pro
                                            1               5 aaa cct caa aga aaa acc aaa aga aac acc aac cgt cgc cca caa gac    403
Lys Pro Gln Arg Lys Thr Lys Arg Asn Thr Asn Arg Arg Pro Gln Asp
            10                  15                  20 gtt aag ttt ccg ggc ggc ggc cag atc gtt ggc gga gta tac ttg ttg    451
Val Lys Phe Pro Gly Gly Gly Gln Ile Val Gly Gly Val Tyr Leu Leu
        25                  30                  35 ccg cgc agg ggc ccc agg ttg ggt gtg cgc gcg aca agg aag act tcg    499
```

```
                Pro Arg Arg Gly Pro Arg Leu Gly Val Arg Ala Thr Arg Lys Thr Ser
                         40                  45                  50 gag cgg tcc cag cca cgt gga agg cgc cag ccc atc cct aaa gat cgg         547
Glu Arg Ser Gln Pro Arg Gly Arg Arg Gln Pro Ile Pro Lys Asp Arg
 55                  60                  65 cgc tcc act ggc aaa tcc tgg gga aaa cca gga tac ccc tgg ccc cta         595
Arg Ser Thr Gly Lys Ser Trp Gly Lys Pro Gly Tyr Pro Trp Pro Leu
 70                  75                  80                  85 tac ggg aat gag gga ctc ggc tgg gca gga tgg ctc ctg tcc ccc cga         643
Tyr Gly Asn Glu Gly Leu Gly Trp Ala Gly Trp Leu Leu Ser Pro Arg
                 90                  95                 100 ggt tcc cgt ccc tct tgg ggc ccc aat gac ccc cgg cat agg tcg cgc         691
Gly Ser Arg Pro Ser Trp Gly Pro Asn Asp Pro Arg His Arg Ser Arg
                105                 110                 115 aac gtg ggt aag gtc atc gat acc cta acg tgc ggc ttt gcc gac ctc         739
Asn Val Gly Lys Val Ile Asp Thr Leu Thr Cys Gly Phe Ala Asp Leu
                120                 125                 130 atg ggg tac atc cct gtc gtg ggc gcc ccg ctc ggc ggc gtc gcc aga         787
Met Gly Tyr Ile Pro Val Val Gly Ala Pro Leu Gly Gly Val Ala Arg
135                 140                 145 gct ctc gcg cat ggc gtg aga gtc ctg gag gac ggg gtt aat ttt gca         835
Ala Leu Ala His Gly Val Arg Val Leu Glu Asp Gly Val Asn Phe Ala
150                 155                 160                 165 aca ggg aac tta ccc ggt tgc tcc ttt tct atc ttt ttg ctg gcc ctg         883
Thr Gly Asn Leu Pro Gly Cys Ser Phe Ser Ile Phe Leu Leu Ala Leu
                170                 175                 180 ctg tcc tgc atc acc acc ccg gtc tcc gct gcc gaa gtg aag aac atc         931
Leu Ser Cys Ile Thr Thr Pro Val Ser Ala Ala Glu Val Lys Asn Ile
                185                 190                 195 agt acc ggc tac atg gtg act aac gac tgc acc aat gac agc att acc         979
Ser Thr Gly Tyr Met Val Thr Asn Asp Cys Thr Asn Asp Ser Ile Thr
                200                 205                 210 tgg cag ctc cag gct gct gtc ctc cac gtc ccc ggg tgc gtc ccg tgc        1027
Trp Gln Leu Gln Ala Ala Val Leu His Val Pro Gly Cys Val Pro Cys
215                 220                 225 gag aaa gtg ggg aat gca tct cag tgc tgg ata ccg gtc tca ccg aat        1075
Glu Lys Val Gly Asn Ala Ser Gln Cys Trp Ile Pro Val Ser Pro Asn
230                 235                 240                 245 gtg gcc gtg cag cgg ccc ggc gcc ctc acg cag ggc ttg cgg acg cac        1123
Val Ala Val Gln Arg Pro Gly Ala Leu Thr Gln Gly Leu Arg Thr His
                250                 255                 260 atc gac atg gtt gtg atg tcc gcc acg ctc tgc tct gcc ctc tac gtg        1171
Ile Asp Met Val Val Met Ser Ala Thr Leu Cys Ser Ala Leu Tyr Val
                265                 270                 275 ggg gac ctc tgc ggt ggg gtg atg ctc gca gcc caa atg ttc att gtc        1219
Gly Asp Leu Cys Gly Gly Val Met Leu Ala Ala Gln Met Phe Ile Val
                280                 285                 290 tcg ccg cag cac cac tgg ttt gtc caa gac tgc aat tgc tcc atc tac        1267
Ser Pro Gln His His Trp Phe Val Gln Asp Cys Asn Cys Ser Ile Tyr
295                 300                 305 cct ggt acc atc act gga cac cgc atg gca tgg gac atg atg atg aac        1315
Pro Gly Thr Ile Thr Gly His Arg Met Ala Trp Asp Met Met Met Asn
310                 315                 320                 325 tgg tcg ccc acg gct acc atg atc ttg gcg tac gcg atg cgt gtc ccc        1363
Trp Ser Pro Thr Ala Thr Met Ile Leu Ala Tyr Ala Met Arg Val Pro
                330                 335                 340 gag gtc att ata gac atc att agc ggg gct cat tgg ggc gtc atg ttc        1411
Glu Val Ile Ile Asp Ile Ile Ser Gly Ala His Trp Gly Val Met Phe
                345                 350                 355
```

-continued

| | |
|---|---|
| ggc ttg gcc tac ttc tct atg cag gga gcg tgg gcg aaa gtc gtt gtc<br>Gly Leu Ala Tyr Phe Ser Met Gln Gly Ala Trp Ala Lys Val Val Val<br>360                            365                           370 | 1459 |
| atc ctt ctg ttg gcc gcc ggg gtg gac gcg cgc acc cat act gtt ggg<br>Ile Leu Leu Leu Ala Ala Gly Val Asp Ala Arg Thr His Thr Val Gly<br>375                            380                           385 | 1507 |
| ggt tct gcc gcg cag acc acc ggg cgc ctc acc agc tta ttt gac atg<br>Gly Ser Ala Ala Gln Thr Thr Gly Arg Leu Thr Ser Leu Phe Asp Met<br>390                            395                      400                       405 | 1555 |
| ggc ccc agg cag aaa atc cag ctc gtt aac acc aat ggc agc tgg cac<br>Gly Pro Arg Gln Lys Ile Gln Leu Val Asn Thr Asn Gly Ser Trp His<br>                        410                           415                       420 | 1603 |
| atc aac cgc acc gcc ctg aac tgc aat gac tcc ttg cac acc ggc ttt<br>Ile Asn Arg Thr Ala Leu Asn Cys Asn Asp Ser Leu His Thr Gly Phe<br>                     425                           430                       435 | 1651 |
| atc gcg tct ctg ttc tac acc cac agc ttc aac tcg tca gga tgt ccc<br>Ile Ala Ser Leu Phe Tyr Thr His Ser Phe Asn Ser Ser Gly Cys Pro<br>                    440                           445                       450 | 1699 |
| gaa cgc atg tcc gcc tgc cgc agt atc gag gcc ttc cgg gtg gga tgg<br>Glu Arg Met Ser Ala Cys Arg Ser Ile Glu Ala Phe Arg Val Gly Trp<br>455                            460                           465 | 1747 |
| ggc gcc ttg caa tat gag gat aat gtc acc aat cca gag gat atg aga<br>Gly Ala Leu Gln Tyr Glu Asp Asn Val Thr Asn Pro Glu Asp Met Arg<br>470                            475                      480                       485 | 1795 |
| ccc tat tgc tgg cac tac cca cca agg cag tgt ggc gtg gtc tcc gcg<br>Pro Tyr Cys Trp His Tyr Pro Pro Arg Gln Cys Gly Val Val Ser Ala<br>                          490                           495                       500 | 1843 |
| aag act gtg tgt ggc cca gtg tac tgt ttc acc ccc agc cca gtg gta<br>Lys Thr Val Cys Gly Pro Val Tyr Cys Phe Thr Pro Ser Pro Val Val<br>                    505                           510                       515 | 1891 |
| gtg ggc acg acc gac agg ctt gga gcg ccc act tac acg tgg ggg gag<br>Val Gly Thr Thr Asp Arg Leu Gly Ala Pro Thr Tyr Thr Trp Gly Glu<br>                  520                           525                       530 | 1939 |
| aat gag aca gat gtc ttc cta ttg aac agc act cga cca ccg ctg ggg<br>Asn Glu Thr Asp Val Phe Leu Leu Asn Ser Thr Arg Pro Pro Leu Gly<br>535                            540                      545 | 1987 |
| tca tgg ttc ggc tgc acg tgg atg aac tct tct ggc tac acc aag act<br>Ser Trp Phe Gly Cys Thr Trp Met Asn Ser Ser Gly Tyr Thr Lys Thr<br>550                            555                      560                       565 | 2035 |
| tgc ggc gca cca ccc tgc cgt act aga gct gac ttc aac gcc agc acg<br>Cys Gly Ala Pro Pro Cys Arg Thr Arg Ala Asp Phe Asn Ala Ser Thr<br>                    570                           575                       580 | 2083 |
| gac ctg ttg tgc ccc acg gac tgt ttt agg aag cat cct gat acc act<br>Asp Leu Leu Cys Pro Thr Asp Cys Phe Arg Lys His Pro Asp Thr Thr<br>                    585                           590                       595 | 2131 |
| tac ctc aaa tgc ggc tct ggg ccc tgg ctc acg cca agg tgc ctg atc<br>Tyr Leu Lys Cys Gly Ser Gly Pro Trp Leu Thr Pro Arg Cys Leu Ile<br>                  600                           605                       610 | 2179 |
| gac tac ccc tac agg ctc tgg cat tac ccc tgc aca gtt aac tat acc<br>Asp Tyr Pro Tyr Arg Leu Trp His Tyr Pro Cys Thr Val Asn Tyr Thr<br>615                            620                      625 | 2227 |
| atc ttc aaa ata agg atg tat gtg gga ggg gtt gag cac agg ctc acg<br>Ile Phe Lys Ile Arg Met Tyr Val Gly Gly Val Glu His Arg Leu Thr<br>630                            635                      640                       645 | 2275 |
| gct gca tgc aat ttc act cgt ggg gat cgt tgc aac ttg gag gac aga<br>Ala Ala Cys Asn Phe Thr Arg Gly Asp Arg Cys Asn Leu Glu Asp Arg<br>                    650                           655                       660 | 2323 |
| gac aga agt caa ctg tct cct ttg ttg cac tcc acc acg gaa tgg gcc<br>Asp Arg Ser Gln Leu Ser Pro Leu Leu His Ser Thr Thr Glu Trp Ala<br>                    665                           670                       675 | 2371 |

```
att tta cct tgc tct tac tcg gac ctg ccc gcc ttg tcg act ggt ctt    2419
Ile Leu Pro Cys Ser Tyr Ser Asp Leu Pro Ala Leu Ser Thr Gly Leu
        680             685             690 ctc cac ctc cac caa aac atc gtg gac gta caa ttc atg tat ggc cta    2467
Leu His Leu His Gln Asn Ile Val Asp Val Gln Phe Met Tyr Gly Leu
    695             700             705 tca cct gcc ctc aca aaa tac atc gtc cga tgg gag tgg gta ata ctc    2515
Ser Pro Ala Leu Thr Lys Tyr Ile Val Arg Trp Glu Trp Val Ile Leu
710             715             720             725 tta ttc ctg ctc tta gcg gac gcc agg gtt tgc gcc tgc tta tgg atg    2563
Leu Phe Leu Leu Leu Ala Asp Ala Arg Val Cys Ala Cys Leu Trp Met
                730             735             740 ctc atc ttg ttg ggc cag gcc gaa gca gca cta gag aag ctg gtc atc    2611
Leu Ile Leu Leu Gly Gln Ala Glu Ala Ala Leu Glu Lys Leu Val Ile
            745             750             755 ttg cac gct gcg agc gca gct agc tgc aat ggc ttc cta tat ttt gtc    2659
Leu His Ala Ala Ser Ala Ala Ser Cys Asn Gly Phe Leu Tyr Phe Val
        760             765             770 atc ttt ttc gtg gct gct tgg tac atc aag ggt cgg gta gtc ccc tta    2707
Ile Phe Phe Val Ala Ala Trp Tyr Ile Lys Gly Arg Val Val Pro Leu
    775             780             785 gct acc tat tcc ctc act ggc ctg tgg tcc ttt agc cta ctg ctc cta    2755
Ala Thr Tyr Ser Leu Thr Gly Leu Trp Ser Phe Ser Leu Leu Leu Leu
790             795             800             805 gca ttg ccc caa cag gct tat gct tat gac gca tct gtg cat ggc cag    2803
Ala Leu Pro Gln Gln Ala Tyr Ala Tyr Asp Ala Ser Val His Gly Gln
                810             815             820 ata gga gcg gct ctg ctg gta atg atc act ctc ttt act ctc acc ccc    2851
Ile Gly Ala Ala Leu Leu Val Met Ile Thr Leu Phe Thr Leu Thr Pro
            825             830             835 ggg tat aag acc ctt ctc agc cgg ttt ttg tgg tgg ttg tgc tat ctt    2899
Gly Tyr Lys Thr Leu Leu Ser Arg Phe Leu Trp Trp Leu Cys Tyr Leu
        840             845             850 ctg acc ctg ggg gaa gct atg gtc cag gag tgg gca cca cct atg cag    2947
Leu Thr Leu Gly Glu Ala Met Val Gln Glu Trp Ala Pro Pro Met Gln
    855             860             865 gtg cgc ggt ggc cgt gat ggc atc ata tgg gcc gtc gcc ata ttc tac    2995
Val Arg Gly Gly Arg Asp Gly Ile Ile Trp Ala Val Ala Ile Phe Tyr
870             875             880             885 cca ggt gtg gtg ttt gac ata acc aag tgg ctc ttg gcg gtg ctt ggg    3043
Pro Gly Val Val Phe Asp Ile Thr Lys Trp Leu Leu Ala Val Leu Gly
                890             895             900 cct gct tac ctc cta aaa ggt gct ttg acg cgc gtg ccg tac ttc gtc    3091
Pro Ala Tyr Leu Leu Lys Gly Ala Leu Thr Arg Val Pro Tyr Phe Val
            905             910             915 agg gct cac gct cta ctg agg atg tgc acc atg gca agg cat ctc gcg    3139
Arg Ala His Ala Leu Leu Arg Met Cys Thr Met Ala Arg His Leu Ala
        920             925             930 ggg ggc agg tac gtc cag atg gcg cta cta gcc ctt ggc agg tgg act    3187
Gly Gly Arg Tyr Val Gln Met Ala Leu Leu Ala Leu Gly Arg Trp Thr
    935             940             945 ggc act tac atc tat gac cac ctc acc cct atg tcg gat tgg gct gct    3235
Gly Thr Tyr Ile Tyr Asp His Leu Thr Pro Met Ser Asp Trp Ala Ala
950             955             960             965 agt ggc ctg cgg gac ctg gcg gtc gcc gtt gag cct atc atc ttc agt    3283
Ser Gly Leu Arg Asp Leu Ala Val Ala Val Glu Pro Ile Ile Phe Ser
                970             975             980 ccg atg gag aag aaa gtc att gtc tgg gga gcg gag aca gct gct tgt    3331
Pro Met Glu Lys Lys Val Ile Val Trp Gly Ala Glu Thr Ala Ala Cys
```

-continued

```
              985                 990                 995
ggg gac att tta cac gga ctt ccc gtg tcc gcc cga ctt ggt cgg        3376
Gly Asp Ile Leu His Gly Leu Pro Val Ser Ala Arg Leu Gly Arg
        1000                1005                1010 gag gtc ctc ctt ggc cca gct gat ggc tat acc tcc aag ggg tgg        3421
Glu Val Leu Leu Gly Pro Ala Asp Gly Tyr Thr Ser Lys Gly Trp
        1015                1020                1025 agt ctt ctc gcc ccc atc act gct tac gcc cag cag aca cgt ggc        3466
Ser Leu Leu Ala Pro Ile Thr Ala Tyr Ala Gln Gln Thr Arg Gly
        1030                1035                1040 ctt ttg ggc acc ata gtg gtg agc atg acg ggg cgc gac aag aca        3511
Leu Leu Gly Thr Ile Val Val Ser Met Thr Gly Arg Asp Lys Thr
        1045                1050                1055 gaa cag gct ggg gaa att cag gtc ctg tcc aca gtc act cag tcc        3556
Glu Gln Ala Gly Glu Ile Gln Val Leu Ser Thr Val Thr Gln Ser
        1060                1065                1070 ttc ctc gga aca tcc atc tcg ggg gtt ttg tgg act gtc tac cat        3601
Phe Leu Gly Thr Ser Ile Ser Gly Val Leu Trp Thr Val Tyr His
        1075                1080                1085 gga gct ggc aac aag act ctg gcc ggc tca cgg ggt ccg gtc acg        3646
Gly Ala Gly Asn Lys Thr Leu Ala Gly Ser Arg Gly Pro Val Thr
        1090                1095                1100 cag atg tac tcc agt gct gag ggg gac tta gta ggg tgg ccc agc        3691
Gln Met Tyr Ser Ser Ala Glu Gly Asp Leu Val Gly Trp Pro Ser
        1105                1110                1115 ccc cct ggg act aaa tct ttg gag ccg tgc acg tgt gga gcg gtc        3736
Pro Pro Gly Thr Lys Ser Leu Glu Pro Cys Thr Cys Gly Ala Val
        1120                1125                1130 gac ctg tac ctg gtc acg cgg aac gct gat gtc atc ccg gct cga        3781
Asp Leu Tyr Leu Val Thr Arg Asn Ala Asp Val Ile Pro Ala Arg
        1135                1140                1145 aga cgc ggg gac aaa cgg gga gcg cta ctc tcc ccg aga cct ctt        3826
Arg Arg Gly Asp Lys Arg Gly Ala Leu Leu Ser Pro Arg Pro Leu
        1150                1155                1160 tcc acc ttg aag ggg tcc tca gga ggc ccg gtg cta tgc ccc agg        3871
Ser Thr Leu Lys Gly Ser Ser Gly Gly Pro Val Leu Cys Pro Arg
        1165                1170                1175 ggc cac gct gtc gga gtc ttc cgg gca gct gtg tgc tct cgg ggc        3916
Gly His Ala Val Gly Val Phe Arg Ala Ala Val Cys Ser Arg Gly
        1180                1185                1190 gtg gct aag tcc ata gat ttc atc ccc gtt gag aca ctc gac atc        3961
Val Ala Lys Ser Ile Asp Phe Ile Pro Val Glu Thr Leu Asp Ile
        1195                1200                1205 gtc acg cgg tcc ccc acc ttt agt gac aac agc aca cca cct gct        4006
Val Thr Arg Ser Pro Thr Phe Ser Asp Asn Ser Thr Pro Pro Ala
        1210                1215                1220 gtg ccc cag acc tat cag gtc ggg tac ttg cat gcc ccg act ggc        4051
Val Pro Gln Thr Tyr Gln Val Gly Tyr Leu His Ala Pro Thr Gly
        1225                1230                1235 agt gga aag agc acc aaa gtt cct gtc gca tat gct gcc cag ggg        4096
Ser Gly Lys Ser Thr Lys Val Pro Val Ala Tyr Ala Ala Gln Gly
        1240                1245                1250 tat aaa gtg cta gtg ctt aat ccc tca gtg gct gcc acc ctg ggg        4141
Tyr Lys Val Leu Val Leu Asn Pro Ser Val Ala Ala Thr Leu Gly
        1255                1260                1265 ttt ggg gcg tac ttg tct aag gca cat ggc atc aat ccc aac att        4186
Phe Gly Ala Tyr Leu Ser Lys Ala His Gly Ile Asn Pro Asn Ile
        1270                1275                1280 agg act gga gtc agg act gtg acg acc ggg gcg ccc atc acg tac        4231
```

```
Arg Thr Gly Val Arg Thr Val Thr Gly Ala Pro Ile Thr Tyr
        1285                1290               1295 tcc aca tat ggc aaa ttc ctc gcc gat ggg ggc tgt gcg ggc ggc    4276
Ser Thr Tyr Gly Lys Phe Leu Ala Asp Gly Gly Cys Ala Gly Gly
        1300                1305               1310 gcc tac gac atc atc ata tgt gat gaa tgc cat gcc gtg gac tct    4321
Ala Tyr Asp Ile Ile Ile Cys Asp Glu Cys His Ala Val Asp Ser
        1315                1320               1325 acc acc atc ctt ggc atc gga aca gtc ctt gat caa gca gag aca    4366
Thr Thr Ile Leu Gly Ile Gly Thr Val Leu Asp Gln Ala Glu Thr
        1330                1335               1340 gct ggg gtc aga cta act gtg ctg gct aca gct acg ccc cct ggg    4411
Ala Gly Val Arg Leu Thr Val Leu Ala Thr Ala Thr Pro Pro Gly
        1345                1350               1355 tca gtg aca acc ccc cac ccc aac ata gag gag gtg gcc ctt ggg    4456
Ser Val Thr Thr Pro His Pro Asn Ile Glu Glu Val Ala Leu Gly
        1360                1365               1370 cag gag ggc gag atc ccc ttc tat ggg agg gcg att ccc ctg tct    4501
Gln Glu Gly Glu Ile Pro Phe Tyr Gly Arg Ala Ile Pro Leu Ser
        1375                1380               1385 tac atc aag gga gga aga cat ctg atc ttc tgc cat tca aag aaa    4546
Tyr Ile Lys Gly Gly Arg His Leu Ile Phe Cys His Ser Lys Lys
        1390                1395               1400 aag tgt gac gag ctc gcg gcg gcc ctt cgg ggt atg ggc ttg aac    4591
Lys Cys Asp Glu Leu Ala Ala Ala Leu Arg Gly Met Gly Leu Asn
        1405                1410               1415 tca gtg gca tac tac aga ggg ttg gac gtc tcc gta ata cca act    4636
Ser Val Ala Tyr Tyr Arg Gly Leu Asp Val Ser Val Ile Pro Thr
        1420                1425               1430 cag gga gac gta gtg gtc gtc gcc acc gac gcc ctc atg aca ggg    4681
Gln Gly Asp Val Val Val Val Ala Thr Asp Ala Leu Met Thr Gly
        1435                1440               1445 tat act ggg gac ttt gac tcc gtg atc gac tgc aac gta gcg gtc    4726
Tyr Thr Gly Asp Phe Asp Ser Val Ile Asp Cys Asn Val Ala Val
        1450                1455               1460 act caa gtt gta gac ttc agt tta gac ccc aca ttc acc ata acc    4771
Thr Gln Val Val Asp Phe Ser Leu Asp Pro Thr Phe Thr Ile Thr
        1465                1470               1475 aca cag att gtc cct caa gac gct gtc tca cgt agc cag cgc cgg    4816
Thr Gln Ile Val Pro Gln Asp Ala Val Ser Arg Ser Gln Arg Arg
        1480                1485               1490 ggt cgc acg ggt agg gga aga ctg ggc att tat agg tat gtt tcc    4861
Gly Arg Thr Gly Arg Gly Arg Leu Gly Ile Tyr Arg Tyr Val Ser
        1495                1500               1505 act ggt gag cga gcc tca gga atg ttt gac agt gta gtg ctc tgt    4906
Thr Gly Glu Arg Ala Ser Gly Met Phe Asp Ser Val Val Leu Cys
        1510                1515               1520 gag tgc tac gac gca ggg gcc gca tgg tat gag ctc aca cca tcg    4951
Glu Cys Tyr Asp Ala Gly Ala Ala Trp Tyr Glu Leu Thr Pro Ser
        1525                1530               1535 gag acc acc gtc agg ctc agg gcg tat ttc aac acg ccc ggt ttg    4996
Glu Thr Thr Val Arg Leu Arg Ala Tyr Phe Asn Thr Pro Gly Leu
        1540                1545               1550 cct gtg tgc caa gac cat ctt gag ttt tgg gag gca gtt ttc acc    5041
Pro Val Cys Gln Asp His Leu Glu Phe Trp Glu Ala Val Phe Thr
        1555                1560               1565 ggc ctc aca cac ata gat gcc cac ttc ctt tcc caa aca aag caa    5086
Gly Leu Thr His Ile Asp Ala His Phe Leu Ser Gln Thr Lys Gln
        1570                1575               1580
```

```
tcg ggg gaa aat ttc gca tac tta aca gcc tac cag gct aca gtg      5131
Ser Gly Glu Asn Phe Ala Tyr Leu Thr Ala Tyr Gln Ala Thr Val
        1585                1590                1595 tgc gct agg gcc aaa gcc ccc ccc ccg tcc tgg gac gtc atg tgg      5176
Cys Ala Arg Ala Lys Ala Pro Pro Pro Ser Trp Asp Val Met Trp
    1600                1605                1610 aag tgt ttg act cga ctc aag ccc aca ctc gtg ggc ccc aca cct      5221
Lys Cys Leu Thr Arg Leu Lys Pro Thr Leu Val Gly Pro Thr Pro
        1615                1620                1625 ctc ctg tac cgc ttg ggc tct gtt acc aac gag gtc acc ctc aca      5266
Leu Leu Tyr Arg Leu Gly Ser Val Thr Asn Glu Val Thr Leu Thr
        1630                1635                1640 cat ccc gtg acg aaa tac atc gcc acc tgc atg caa gcc gac ctt      5311
His Pro Val Thr Lys Tyr Ile Ala Thr Cys Met Gln Ala Asp Leu
        1645                1650                1655 gag gtc atg acc agc aca tgg gtc ttg gca ggg gga gtc ttg gcg      5356
Glu Val Met Thr Ser Thr Trp Val Leu Ala Gly Gly Val Leu Ala
        1660                1665                1670 gcc gtc gcc gcg tat tgc ctg gcg acc ggg tgt gtt tgc atc atc      5401
Ala Val Ala Ala Tyr Cys Leu Ala Thr Gly Cys Val Cys Ile Ile
        1675                1680                1685 ggc cgc ttg cac att aac cag cga gcc gtc gtt gcg ccg gac aag      5446
Gly Arg Leu His Ile Asn Gln Arg Ala Val Val Ala Pro Asp Lys
        1690                1695                1700 gag gtc ctc tat gag gct ttt gat gag atg gag gaa tgt gcc tct      5491
Glu Val Leu Tyr Glu Ala Phe Asp Glu Met Glu Glu Cys Ala Ser
        1705                1710                1715 agg gcg gct ctc att gaa gag ggg cag cgg ata gcc gag atg ctg      5536
Arg Ala Ala Leu Ile Glu Glu Gly Gln Arg Ile Ala Glu Met Leu
        1720                1725                1730 aag tcc aag atc caa ggc tta ttg cag caa gct tcc aaa caa gct      5581
Lys Ser Lys Ile Gln Gly Leu Leu Gln Gln Ala Ser Lys Gln Ala
        1735                1740                1745 caa gac ata caa ccc act gtg cag gct tca tgg ccc aag gta gaa      5626
Gln Asp Ile Gln Pro Thr Val Gln Ala Ser Trp Pro Lys Val Glu
        1750                1755                1760 caa ttc tgg gcc aaa cac atg tgg aac ttc att agc ggc atc caa      5671
Gln Phe Trp Ala Lys His Met Trp Asn Phe Ile Ser Gly Ile Gln
        1765                1770                1775 tac ctc gca gga cta tca aca ctg cca ggg aac cct gca gta gct      5716
Tyr Leu Ala Gly Leu Ser Thr Leu Pro Gly Asn Pro Ala Val Ala
        1780                1785                1790 tcc atg atg gcg ttc agt gcc gcc ctc acc agt ccg ctg tca aca      5761
Ser Met Met Ala Phe Ser Ala Ala Leu Thr Ser Pro Leu Ser Thr
        1795                1800                1805 agc acc act atc ctt ctc aac att ttg ggg ggc tgg cta gca tcc      5806
Ser Thr Thr Ile Leu Leu Asn Ile Leu Gly Gly Trp Leu Ala Ser
        1810                1815                1820 caa att gca cca ccc gcg ggg gcc act ggc ttc gtt gtc agt ggc      5851
Gln Ile Ala Pro Pro Ala Gly Ala Thr Gly Phe Val Val Ser Gly
        1825                1830                1835 cta gtg gga gct gcc gta ggc agt ata ggc tta ggt aag gtg cta      5896
Leu Val Gly Ala Ala Val Gly Ser Ile Gly Leu Gly Lys Val Leu
        1840                1845                1850 gtg gac atc ctg gca ggg tat ggt gcg ggc att tcg ggg gct ctc      5941
Val Asp Ile Leu Ala Gly Tyr Gly Ala Gly Ile Ser Gly Ala Leu
        1855                1860                1865 gtc gca ttc aag atc atg tct ggc gag aag ccc tcc atg gag gat      5986
Val Ala Phe Lys Ile Met Ser Gly Glu Lys Pro Ser Met Glu Asp
        1870                1875                1880
```

```
gtc gtc aac ttg ctg cct gga att ctg tct ccg ggt gcc ttg gta        6031
Val Val Asn Leu Leu Pro Gly Ile Leu Ser Pro Gly Ala Leu Val
        1885                1890                1895 gtg gga gtc atc tgc gcg gcc att ctg cgc cga cac gtg gga ccg        6076
Val Gly Val Ile Cys Ala Ala Ile Leu Arg Arg His Val Gly Pro
        1900                1905                1910 ggg gaa ggc gcc gtc caa tgg atg aat aga ctc att gcc ttt gct        6121
Gly Glu Gly Ala Val Gln Trp Met Asn Arg Leu Ile Ala Phe Ala
        1915                1920                1925 tcc aga gga aat cac gtc gcc ccc acc cac tac gtg acg gag tcg        6166
Ser Arg Gly Asn His Val Ala Pro Thr His Tyr Val Thr Glu Ser
        1930                1935                1940 gat gcg tcg cag cgt gtg acc caa cta ctt ggc tcc ctt acc ata        6211
Asp Ala Ser Gln Arg Val Thr Gln Leu Leu Gly Ser Leu Thr Ile
        1945                1950                1955 acc agc ctg ctc aga aga ctc cac aac tgg att act gag gac tgc        6256
Thr Ser Leu Leu Arg Arg Leu His Asn Trp Ile Thr Glu Asp Cys
        1960                1965                1970 ccc atc cca tgc ggc ggc tcg tgg ctc cgc gat gtg tgg gac tgg        6301
Pro Ile Pro Cys Gly Gly Ser Trp Leu Arg Asp Val Trp Asp Trp
        1975                1980                1985 gtt tgc acc atc cta aca gac ttt aaa aat tgg ctg acc tcc aaa        6346
Val Cys Thr Ile Leu Thr Asp Phe Lys Asn Trp Leu Thr Ser Lys
        1990                1995                2000 tta ttc cca aag atg ccc ggc ctc ccc ttt gtc tcc tgt caa aag        6391
Leu Phe Pro Lys Met Pro Gly Leu Pro Phe Val Ser Cys Gln Lys
        2005                2010                2015 ggg tac aag ggc gtg tgg gcc ggc act ggc atc atg acc aca cgg        6436
Gly Tyr Lys Gly Val Trp Ala Gly Thr Gly Ile Met Thr Thr Arg
        2020                2025                2030 tgt cct tgc ggc gcc aat atc tct ggc aat gtc cgc ttg ggc tcc        6481
Cys Pro Cys Gly Ala Asn Ile Ser Gly Asn Val Arg Leu Gly Ser
        2035                2040                2045 atg aga atc acg ggg cct aag acc tgc atg aat atc tgg cag ggg        6526
Met Arg Ile Thr Gly Pro Lys Thr Cys Met Asn Ile Trp Gln Gly
        2050                2055                2060 acc ttt cct atc aat tgt tac acg gag ggc cag tgc gtg ccg aaa        6571
Thr Phe Pro Ile Asn Cys Tyr Thr Glu Gly Gln Cys Val Pro Lys
        2065                2070                2075 ccc gcg cca aac ttt aag gtc gcc atc tgg agg gtg gcg gcc tca        6616
Pro Ala Pro Asn Phe Lys Val Ala Ile Trp Arg Val Ala Ala Ser
        2080                2085                2090 gag tac gcg gag gtg acg cag cac ggg tca tac cac tac ata aca        6661
Glu Tyr Ala Glu Val Thr Gln His Gly Ser Tyr His Tyr Ile Thr
        2095                2100                2105 gga ctc acc act gat aac ttg aaa gtc ccc tgc caa cta ccc tct        6706
Gly Leu Thr Thr Asp Asn Leu Lys Val Pro Cys Gln Leu Pro Ser
        2110                2115                2120 ccc gag ttc ttt tcc tgg gtg gac gga gtg cag atc cat agg ttt        6751
Pro Glu Phe Phe Ser Trp Val Asp Gly Val Gln Ile His Arg Phe
        2125                2130                2135 gcc ccc aca ccg aag ccg ttt ttc cgg gat gag gtc tcg ttc tgc        6796
Ala Pro Thr Pro Lys Pro Phe Phe Arg Asp Glu Val Ser Phe Cys
        2140                2145                2150 gtt ggg ctt aat tca ttt gtc gtc ggg tcc cag ctt cct tgc gac        6841
Val Gly Leu Asn Ser Phe Val Val Gly Ser Gln Leu Pro Cys Asp
        2155                2160                2165 cct gaa ccc gac aca gac gta ttg atg tcc atg cta aca gat cca        6886
Pro Glu Pro Asp Thr Asp Val Leu Met Ser Met Leu Thr Asp Pro
```

```
                  2170              2175              2180
tct cat atc acg gcg gag act gca gcg cgg cgt tta gcg cgg ggg      6931
Ser His Ile Thr Ala Glu Thr Ala Ala Arg Arg Leu Ala Arg Gly
        2185              2190              2195 tca ccc cca tcc gag gca agc tcc tcg gcg agc cag cta tcg gca      6976
Ser Pro Pro Ser Glu Ala Ser Ser Ser Ala Ser Gln Leu Ser Ala
    2200              2205              2210 cca tcg ctg cga gcc acc tgc acc acc cac ggc aaa gcc tat gat      7021
Pro Ser Leu Arg Ala Thr Cys Thr Thr His Gly Lys Ala Tyr Asp
        2215              2220              2225 gtg gac atg gtg gat gct aac ctg ttc atg ggg ggc gat gtg act      7066
Val Asp Met Val Asp Ala Asn Leu Phe Met Gly Gly Asp Val Thr
    2230              2235              2240 cgg ata gag tct ggg tcc aaa gtg gtc gtt ctg gac tct ctc gac      7111
Arg Ile Glu Ser Gly Ser Lys Val Val Val Leu Asp Ser Leu Asp
        2245              2250              2255 cca atg gtc gaa gaa agg agc gac ctt gag cct tcg ata cca tca      7156
Pro Met Val Glu Glu Arg Ser Asp Leu Glu Pro Ser Ile Pro Ser
    2260              2265              2270 gaa tac atg ctc ccc aag aag agg ttc cca cca gct tta ccg gcc      7201
Glu Tyr Met Leu Pro Lys Lys Arg Phe Pro Pro Ala Leu Pro Ala
        2275              2280              2285 tgg gca cgg cct gat tac aac ccg cct gtg gaa tcg tgg aaa          7246
Trp Ala Arg Pro Asp Tyr Asn Pro Pro Leu Val Glu Ser Trp Lys
    2290              2295              2300 agg cca gat tac caa ccg gcc act gtt gcg ggc tgt gct ctc cct      7291
Arg Pro Asp Tyr Gln Pro Ala Thr Val Ala Gly Cys Ala Leu Pro
        2305              2310              2315 cct cct agg aaa acc ccg acg cct ccc cca agg agg cgc cgg aca      7336
Pro Pro Arg Lys Thr Pro Thr Pro Pro Pro Arg Arg Arg Arg Thr
    2320              2325              2330 gtg ggc cta agt gag gac tcc ata gga gat gcc ctt caa cag ctg      7381
Val Gly Leu Ser Glu Asp Ser Ile Gly Asp Ala Leu Gln Gln Leu
        2335              2340              2345 gcc att aag tcc ttt ggc cag ccc ccc cca agc ggc gat tca ggc      7426
Ala Ile Lys Ser Phe Gly Gln Pro Pro Pro Ser Gly Asp Ser Gly
    2350              2355              2360 ctt tcc acg ggg gcg ggc gct gcc gat tcc ggc agt cag acg cct      7471
Leu Ser Thr Gly Ala Gly Ala Ala Asp Ser Gly Ser Gln Thr Pro
        2365              2370              2375 cct gat gag ttg gcc ctt tcg gag aca ggt tcc atc tct tcc atg      7516
Pro Asp Glu Leu Ala Leu Ser Glu Thr Gly Ser Ile Ser Ser Met
    2380              2385              2390 ccc ccc ctc gag ggg gag ctt gga gat cca gac ctg gag cct gag      7561
Pro Pro Leu Glu Gly Glu Leu Gly Asp Pro Asp Leu Glu Pro Glu
        2395              2400              2405 cag gta gag ccc caa ccc ccc cag ggg ggg gtg gca gct ccc          7606
Gln Val Glu Pro Gln Pro Pro Gln Gly Gly Val Ala Ala Pro
    2410              2415              2420 ggc tcg gac tcg ggg tcc tgg tct act tgc tcc gag gag gac gac      7651
Gly Ser Asp Ser Gly Ser Trp Ser Thr Cys Ser Glu Glu Asp Asp
        2425              2430              2435 tcc gtc gtg tgc tgc tcc atg tca tac tcc tgg acc ggg gct cta      7696
Ser Val Val Cys Cys Ser Met Ser Tyr Ser Trp Thr Gly Ala Leu
    2440              2445              2450 ata act cct tgt agt ccc gaa gag gag aag tta ccg att aac ccc      7741
Ile Thr Pro Cys Ser Pro Glu Glu Glu Lys Leu Pro Ile Asn Pro
        2455              2460              2465 ttg agc aac tcc ctg ttg cga tat cac aac aag gtg tac tgt acc      7786
```

-continued

| | | | | | | | | | | | | | | |
|---|---|---|---|---|---|---|---|---|---|---|---|---|---|---|
| Leu | Ser | Asn | Ser | Leu | Leu | Arg | Tyr | His | Asn | Lys | Val | Tyr | Cys | Thr |
| | | 2470 | | | | 2475 | | | | 2480 | | | | |

| aca | aca | aag | agc | gcc | tca | cta | agg | gct | aaa | aag | gta | act | ttt | gat | 7831 |
|---|---|---|---|---|---|---|---|---|---|---|---|---|---|---|---|
| Thr | Thr | Lys | Ser | Ala | Ser | Leu | Arg | Ala | Lys | Lys | Val | Thr | Phe | Asp | |
| | | 2485 | | | | 2490 | | | | 2495 | | | | | |

| agg | atg | caa | gtg | ctc | gac | tcc | tac | tac | gac | tca | gtc | tta | aag | gac | 7876 |
|---|---|---|---|---|---|---|---|---|---|---|---|---|---|---|---|
| Arg | Met | Gln | Val | Leu | Asp | Ser | Tyr | Tyr | Asp | Ser | Val | Leu | Lys | Asp | |
| | | 2500 | | | | 2505 | | | | 2510 | | | | | |

| att | aag | cta | gcg | gcc | tcc | aag | gtc | acc | gca | agg | ctc | ctc | acc | atg | 7921 |
|---|---|---|---|---|---|---|---|---|---|---|---|---|---|---|---|
| Ile | Lys | Leu | Ala | Ala | Ser | Lys | Val | Thr | Ala | Arg | Leu | Leu | Thr | Met | |
| | | 2515 | | | | 2520 | | | | 2525 | | | | | |

| gag | gag | gct | tgc | cag | tta | acc | cca | ccc | cat | tct | gca | aga | tct | aaa | 7966 |
|---|---|---|---|---|---|---|---|---|---|---|---|---|---|---|---|
| Glu | Glu | Ala | Cys | Gln | Leu | Thr | Pro | Pro | His | Ser | Ala | Arg | Ser | Lys | |
| | | 2530 | | | | 2535 | | | | 2540 | | | | | |

| tat | ggg | ttt | ggg | gct | aag | gag | gtc | cgc | agc | ttg | tcc | ggg | agg | gcc | 8011 |
|---|---|---|---|---|---|---|---|---|---|---|---|---|---|---|---|
| Tyr | Gly | Phe | Gly | Ala | Lys | Glu | Val | Arg | Ser | Leu | Ser | Gly | Arg | Ala | |
| | | 2545 | | | | 2550 | | | | 2555 | | | | | |

| gtt | aac | cac | atc | aag | tcc | gtg | tgg | aag | gac | ctc | ctg | gag | gac | tca | 8056 |
|---|---|---|---|---|---|---|---|---|---|---|---|---|---|---|---|
| Val | Asn | His | Ile | Lys | Ser | Val | Trp | Lys | Asp | Leu | Leu | Glu | Asp | Ser | |
| | | 2560 | | | | 2565 | | | | 2570 | | | | | |

| gaa | aca | cca | att | ccc | aca | acc | att | atg | gcc | aaa | aat | gag | gtg | ttc | 8101 |
|---|---|---|---|---|---|---|---|---|---|---|---|---|---|---|---|
| Glu | Thr | Pro | Ile | Pro | Thr | Thr | Ile | Met | Ala | Lys | Asn | Glu | Val | Phe | |
| | | 2575 | | | | 2580 | | | | 2585 | | | | | |

| tgc | gtg | gac | ccc | acc | aag | ggg | ggc | aag | aaa | gca | gct | cgc | ctt | atc | 8146 |
|---|---|---|---|---|---|---|---|---|---|---|---|---|---|---|---|
| Cys | Val | Asp | Pro | Thr | Lys | Gly | Gly | Lys | Lys | Ala | Ala | Arg | Leu | Ile | |
| | | 2590 | | | | 2595 | | | | 2600 | | | | | |

| gtt | tac | cct | gac | ctc | ggc | gtc | agg | gtc | tgc | gag | aag | atg | gcc | ctt | 8191 |
|---|---|---|---|---|---|---|---|---|---|---|---|---|---|---|---|
| Val | Tyr | Pro | Asp | Leu | Gly | Val | Arg | Val | Cys | Glu | Lys | Met | Ala | Leu | |
| | | 2605 | | | | 2610 | | | | 2615 | | | | | |

| tat | gac | att | aca | caa | aaa | ctt | cct | cag | gcg | gtg | atg | ggg | gct | tct | 8236 |
|---|---|---|---|---|---|---|---|---|---|---|---|---|---|---|---|
| Tyr | Asp | Ile | Thr | Gln | Lys | Leu | Pro | Gln | Ala | Val | Met | Gly | Ala | Ser | |
| | | 2620 | | | | 2625 | | | | 2630 | | | | | |

| tat | gga | ttc | cag | tat | tcc | ccc | gct | cag | cgg | gta | gag | ttt | ctc | ttg | 8281 |
|---|---|---|---|---|---|---|---|---|---|---|---|---|---|---|---|
| Tyr | Gly | Phe | Gln | Tyr | Ser | Pro | Ala | Gln | Arg | Val | Glu | Phe | Leu | Leu | |
| | | 2635 | | | | 2640 | | | | 2645 | | | | | |

| aaa | gca | tgg | gcg | gaa | aag | aag | gac | cct | atg | ggt | ttt | tcg | tat | gat | 8326 |
|---|---|---|---|---|---|---|---|---|---|---|---|---|---|---|---|
| Lys | Ala | Trp | Ala | Glu | Lys | Lys | Asp | Pro | Met | Gly | Phe | Ser | Tyr | Asp | |
| | | 2650 | | | | 2655 | | | | 2660 | | | | | |

| acc | cga | tgc | ttt | gac | tca | acc | gtc | act | gag | aga | gac | atc | agg | act | 8371 |
|---|---|---|---|---|---|---|---|---|---|---|---|---|---|---|---|
| Thr | Arg | Cys | Phe | Asp | Ser | Thr | Val | Thr | Glu | Arg | Asp | Ile | Arg | Thr | |
| | | 2665 | | | | 2670 | | | | 2675 | | | | | |

| gag | gag | tcc | ata | tat | cgg | gcc | tgc | tcc | ttg | ccc | gag | gag | gcc | cac | 8416 |
|---|---|---|---|---|---|---|---|---|---|---|---|---|---|---|---|
| Glu | Glu | Ser | Ile | Tyr | Arg | Ala | Cys | Ser | Leu | Pro | Glu | Glu | Ala | His | |
| | | 2680 | | | | 2685 | | | | 2690 | | | | | |

| act | gcc | ata | cac | tcg | cta | act | gag | aga | ctt | tac | gtg | gga | ggg | cct | 8461 |
|---|---|---|---|---|---|---|---|---|---|---|---|---|---|---|---|
| Thr | Ala | Ile | His | Ser | Leu | Thr | Glu | Arg | Leu | Tyr | Val | Gly | Gly | Pro | |
| | | 2695 | | | | 2700 | | | | 2705 | | | | | |

| atg | ttc | aac | agc | aag | ggc | caa | acc | tgc | ggg | tac | agg | cgt | tgc | cgc | 8506 |
|---|---|---|---|---|---|---|---|---|---|---|---|---|---|---|---|
| Met | Phe | Asn | Ser | Lys | Gly | Gln | Thr | Cys | Gly | Tyr | Arg | Arg | Cys | Arg | |
| | | 2710 | | | | 2715 | | | | 2720 | | | | | |

| gcc | agc | ggg | gtg | ctc | acc | act | agc | atg | ggg | aac | acc | atc | aca | tgc | 8551 |
|---|---|---|---|---|---|---|---|---|---|---|---|---|---|---|---|
| Ala | Ser | Gly | Val | Leu | Thr | Thr | Ser | Met | Gly | Asn | Thr | Ile | Thr | Cys | |
| | | 2725 | | | | 2730 | | | | 2735 | | | | | |

| tac | gtg | aaa | gcc | tta | gcg | gct | tgt | aaa | gct | gca | ggg | ata | atc | gcg | 8596 |
|---|---|---|---|---|---|---|---|---|---|---|---|---|---|---|---|
| Tyr | Val | Lys | Ala | Leu | Ala | Ala | Cys | Lys | Ala | Ala | Gly | Ile | Ile | Ala | |
| | | 2740 | | | | 2745 | | | | 2750 | | | | | |

| ccc | aca | atg | ctg | gta | tgc | ggc | gat | gac | ttg | gtt | gtc | atc | tca | gaa | 8641 |
|---|---|---|---|---|---|---|---|---|---|---|---|---|---|---|---|
| Pro | Thr | Met | Leu | Val | Cys | Gly | Asp | Asp | Leu | Val | Val | Ile | Ser | Glu | |
| | | 2755 | | | | 2760 | | | | 2765 | | | | | |

| | | | | | | | | | | | | |
|---|---|---|---|---|---|---|---|---|---|---|---|---|
| agc | cag | ggg | acc | gag | gag | gac | gag | cgg | aac | ctg | aga | gcc | ttc | acg | 8686 |
| Ser | Gln | Gly | Thr | Glu | Glu | Asp | Glu | Arg | Asn | Leu | Arg | Ala | Phe | Thr | |
| | | 2770 | | | | 2775 | | | | 2780 | | | | | |

| gag | gct | atg | acc | agg | tat | tct | gcc | cct | cct | ggt | gac | ccc | cca | aga | 8731 |
|---|---|---|---|---|---|---|---|---|---|---|---|---|---|---|---|
| Glu | Ala | Met | Thr | Arg | Tyr | Ser | Ala | Pro | Pro | Gly | Asp | Pro | Pro | Arg | |
| | | 2785 | | | | 2790 | | | | 2795 | | | | | |

| ccg | gag | tat | gat | ctg | gag | ctg | ata | aca | tct | tgc | tcc | tca | aat | gtg | 8776 |
|---|---|---|---|---|---|---|---|---|---|---|---|---|---|---|---|
| Pro | Glu | Tyr | Asp | Leu | Glu | Leu | Ile | Thr | Ser | Cys | Ser | Ser | Asn | Val | |
| | | 2800 | | | | 2805 | | | | 2810 | | | | | |

| tct | gtg | gcg | ctg | ggc | cca | caa | ggc | cgc | cgc | aga | tac | tac | ctg | acc | 8821 |
|---|---|---|---|---|---|---|---|---|---|---|---|---|---|---|---|
| Ser | Val | Ala | Leu | Gly | Pro | Gln | Gly | Arg | Arg | Arg | Tyr | Tyr | Leu | Thr | |
| | | 2815 | | | | 2820 | | | | 2825 | | | | | |

| aga | gac | cct | acc | act | cca | atc | gcc | cgg | gct | gcc | tgg | gaa | aca | gtt | 8866 |
|---|---|---|---|---|---|---|---|---|---|---|---|---|---|---|---|
| Arg | Asp | Pro | Thr | Thr | Pro | Ile | Ala | Arg | Ala | Ala | Trp | Glu | Thr | Val | |
| | | 2830 | | | | 2835 | | | | 2840 | | | | | |

| aga | cac | tcc | cct | gtc | aat | tca | tgg | ctg | gga | aac | atc | atc | cag | tac | 8911 |
|---|---|---|---|---|---|---|---|---|---|---|---|---|---|---|---|
| Arg | His | Ser | Pro | Val | Asn | Ser | Trp | Leu | Gly | Asn | Ile | Ile | Gln | Tyr | |
| | | 2845 | | | | 2850 | | | | 2855 | | | | | |

| gcc | ccg | acc | ata | tgg | gct | cgc | atg | gtc | ctg | atg | aca | cac | ttc | ttc | 8956 |
|---|---|---|---|---|---|---|---|---|---|---|---|---|---|---|---|
| Ala | Pro | Thr | Ile | Trp | Ala | Arg | Met | Val | Leu | Met | Thr | His | Phe | Phe | |
| | | 2860 | | | | 2865 | | | | 2870 | | | | | |

| tcc | att | ctc | atg | gct | caa | gac | acg | ctg | gac | cag | aac | ctc | aac | ttt | 9001 |
|---|---|---|---|---|---|---|---|---|---|---|---|---|---|---|---|
| Ser | Ile | Leu | Met | Ala | Gln | Asp | Thr | Leu | Asp | Gln | Asn | Leu | Asn | Phe | |
| | | 2875 | | | | 2880 | | | | 2885 | | | | | |

| gag | atg | tac | gga | gcg | gtg | tac | tcc | gtg | agt | ccc | ttg | gac | ctc | cca | 9046 |
|---|---|---|---|---|---|---|---|---|---|---|---|---|---|---|---|
| Glu | Met | Tyr | Gly | Ala | Val | Tyr | Ser | Val | Ser | Pro | Leu | Asp | Leu | Pro | |
| | | 2890 | | | | 2895 | | | | 2900 | | | | | |

| gct | ata | att | gaa | agg | tta | cat | ggg | ctt | gac | gct | ttt | tct | ctg | cac | 9091 |
|---|---|---|---|---|---|---|---|---|---|---|---|---|---|---|---|
| Ala | Ile | Ile | Glu | Arg | Leu | His | Gly | Leu | Asp | Ala | Phe | Ser | Leu | His | |
| | | 2905 | | | | 2910 | | | | 2915 | | | | | |

| aca | tac | act | ccc | cac | gaa | ctg | aca | cgg | gtg | gct | tca | gcc | ctc | aga | 9136 |
|---|---|---|---|---|---|---|---|---|---|---|---|---|---|---|---|
| Thr | Tyr | Thr | Pro | His | Glu | Leu | Thr | Arg | Val | Ala | Ser | Ala | Leu | Arg | |
| | | 2920 | | | | 2925 | | | | 2930 | | | | | |

| aaa | ctt | ggg | gcg | cca | ccc | ctc | aga | gcg | tgg | aag | agc | cgg | gca | cgt | 9181 |
|---|---|---|---|---|---|---|---|---|---|---|---|---|---|---|---|
| Lys | Leu | Gly | Ala | Pro | Pro | Leu | Arg | Ala | Trp | Lys | Ser | Arg | Ala | Arg | |
| | | 2935 | | | | 2940 | | | | 2945 | | | | | |

| gca | gtc | agg | gcg | tcc | ctc | atc | tcc | cgt | ggg | ggg | aga | gcg | gcc | gtt | 9226 |
|---|---|---|---|---|---|---|---|---|---|---|---|---|---|---|---|
| Ala | Val | Arg | Ala | Ser | Leu | Ile | Ser | Arg | Gly | Gly | Arg | Ala | Ala | Val | |
| | | 2950 | | | | 2955 | | | | 2960 | | | | | |

| tgc | ggt | cga | tat | ctc | ttc | aat | tgg | gcg | gtg | aag | acc | aag | ctc | aaa | 9271 |
|---|---|---|---|---|---|---|---|---|---|---|---|---|---|---|---|
| Cys | Gly | Arg | Tyr | Leu | Phe | Asn | Trp | Ala | Val | Lys | Thr | Lys | Leu | Lys | |
| | | 2965 | | | | 2970 | | | | 2975 | | | | | |

| ctc | act | cca | ttg | ccg | gaa | gcg | cgc | ctc | ctg | gat | tta | tcc | agc | tgg | 9316 |
|---|---|---|---|---|---|---|---|---|---|---|---|---|---|---|---|
| Leu | Thr | Pro | Leu | Pro | Glu | Ala | Arg | Leu | Leu | Asp | Leu | Ser | Ser | Trp | |
| | | 2980 | | | | 2985 | | | | 2990 | | | | | |

| ttc | acc | gtc | ggc | gcc | ggc | ggg | ggc | gac | att | tat | cac | agc | gtg | tcg | 9361 |
|---|---|---|---|---|---|---|---|---|---|---|---|---|---|---|---|
| Phe | Thr | Val | Gly | Ala | Gly | Gly | Gly | Asp | Ile | Tyr | His | Ser | Val | Ser | |
| | | 2995 | | | | 3000 | | | | 3005 | | | | | |

| cgt | gcc | cga | ccc | cgc | tta | ttg | ctc | ttt | ggc | cta | ctc | ctt | ttt | | 9406 |
|---|---|---|---|---|---|---|---|---|---|---|---|---|---|---|---|
| Arg | Ala | Arg | Pro | Arg | Leu | Leu | Leu | Phe | Gly | Leu | Leu | Leu | Phe | | |
| | | 3010 | | | | 3015 | | | | 3020 | | | | | |

| gta | ggg | gta | ggc | ctt | ttc | cta | ctc | ccc | gct | cgg | tagagcggca | 9449 |
|---|---|---|---|---|---|---|---|---|---|---|---|---|
| Val | Gly | Val | Gly | Leu | Phe | Leu | Leu | Pro | Ala | Arg | | |
| | | 3025 | | | | 3030 | | | | | | | cacattagct acactccata gctaactgtc ccttttttt ttttttttt ttttttttt 9509 ttttttttt ttttttttt ttttttttt ttttttttt ttttttttt tttttctttt 9569 ttttctcttt tccttctttc ttaccttatt ttacttctt tcctggtggc tccatcttag 9629 ccctagtcac ggctagctgt gaaaggtccg tgagccgcat gactgcagag agtgccgtaa 9689 ctggtctctc tgcagatcat gt                                                9711

<210> SEQ ID NO 30
<211> LENGTH: 3033
<212> TYPE: PRT
<213> ORGANISM: Hepatitis C virus
<220> FEATURE:
<223> OTHER INFORMATION: Precursor protein encoded by full-length genome
      RNA of Hepatitis C virus strain J6CF

<400> SEQUENCE: 30

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
    210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350
```

-continued

```
Trp Gly Val Met Phe Gly Leu Ala Tyr Phe Ser Met Gln Gly Ala Trp
        355                 360                 365

Ala Lys Val Val Ile Leu Leu Ala Ala Gly Val Asp Ala Arg
370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Phe Tyr Thr His Ser Phe Asn
                435                 440                 445

Ser Ser Gly Cys Pro Glu Arg Met Ser Ala Cys Arg Ser Ile Glu Ala
                450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Arg Gln Cys
                485                 490                 495

Gly Val Val Ser Ala Lys Thr Val Cys Gly Pro Val Tyr Cys Phe Thr
                500                 505                 510

Pro Ser Pro Val Val Gly Thr Thr Asp Arg Leu Gly Ala Pro Thr
                515                 520                 525

Tyr Thr Trp Gly Glu Asn Glu Thr Asp Val Phe Leu Leu Asn Ser Thr
530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Thr Thr Tyr Leu Lys Cys Gly Ser Gly Pro Trp Leu Thr
                595                 600                 605

Pro Arg Cys Leu Ile Asp Tyr Pro Tyr Arg Leu Trp His Tyr Pro Cys
                610                 615                 620

Thr Val Asn Tyr Thr Ile Phe Lys Ile Arg Met Tyr Val Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
                675                 680                 685

Leu Ser Thr Gly Leu Leu His Leu His Gln Asn Ile Val Asp Val Gln
                690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Ile Leu His Ala Ala Ser Ala Ala Ser Cys Asn Gly
                755                 760                 765
```

```
Phe Leu Tyr Phe Val Ile Phe Phe Val Ala Ala Trp Tyr Ile Lys Gly
    770                 775                 780

Arg Val Val Pro Leu Ala Thr Tyr Ser Leu Thr Gly Leu Trp Ser Phe
785                 790                 795                 800

Ser Leu Leu Leu Ala Leu Pro Gln Gln Ala Tyr Ala Tyr Asp Ala
                805                 810                 815

Ser Val His Gly Gln Ile Gly Ala Ala Leu Leu Val Met Ile Thr Leu
            820                 825                 830

Phe Thr Leu Thr Pro Gly Tyr Lys Thr Leu Leu Ser Arg Phe Leu Trp
                835                 840                 845

Trp Leu Cys Tyr Leu Leu Thr Leu Gly Glu Ala Met Val Gln Glu Trp
    850                 855                 860

Ala Pro Pro Met Gln Val Arg Gly Gly Arg Asp Gly Ile Ile Trp Ala
865                 870                 875                 880

Val Ala Ile Phe Tyr Pro Gly Val Val Phe Asp Ile Thr Lys Trp Leu
                885                 890                 895

Leu Ala Val Leu Gly Pro Ala Tyr Leu Leu Lys Gly Ala Leu Thr Arg
                900                 905                 910

Val Pro Tyr Phe Val Arg Ala His Ala Leu Leu Arg Met Cys Thr Met
            915                 920                 925

Ala Arg His Leu Ala Gly Gly Arg Tyr Val Gln Met Ala Leu Leu Ala
930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
            995                 1000                1005

Arg Leu Gly Arg Glu Val Leu Leu Gly Pro Ala Asp Gly Tyr Thr
    1010                1015                1020

Ser Lys Gly Trp Ser Leu Leu Ala Pro Ile Thr Ala Tyr Ala Gln
    1025                1030                1035

Gln Thr Arg Gly Leu Leu Gly Thr Ile Val Val Ser Met Thr Gly
    1040                1045                1050

Arg Asp Lys Thr Glu Gln Ala Gly Glu Ile Gln Val Leu Ser Thr
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Ser Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Thr
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Val Phe Arg Ala Ala Val
```

-continued

```
            1175                1180                1185

Cys Ser Arg Gly Val Ala Lys Ser Ile Asp Phe Ile Pro Val Glu
        1190                1195                1200

Thr Leu Asp Ile Val Thr Arg Ser Pro Thr Phe Ser Asp Asn Ser
        1205                1210                1215

Thr Pro Pro Ala Val Pro Gln Thr Tyr Gln Val Gly Tyr Leu His
        1220                1225                1230

Ala Pro Thr Gly Ser Gly Lys Ser Thr Lys Val Pro Val Ala Tyr
        1235                1240                1245

Ala Ala Gln Gly Tyr Lys Val Leu Val Leu Asn Pro Ser Val Ala
        1250                1255                1260

Ala Thr Leu Gly Phe Gly Ala Tyr Leu Ser Lys Ala His Gly Ile
        1265                1270                1275

Asn Pro Asn Ile Arg Thr Gly Val Arg Thr Val Thr Thr Gly Ala
        1280                1285                1290

Pro Ile Thr Tyr Ser Thr Tyr Gly Lys Phe Leu Ala Asp Gly Gly
        1295                1300                1305

Cys Ala Gly Gly Ala Tyr Asp Ile Ile Ile Cys Asp Glu Cys His
        1310                1315                1320

Ala Val Asp Ser Thr Thr Ile Leu Gly Ile Gly Thr Val Leu Asp
        1325                1330                1335

Gln Ala Glu Thr Ala Gly Val Arg Leu Thr Val Leu Ala Thr Ala
        1340                1345                1350

Thr Pro Pro Gly Ser Val Thr Thr Pro His Pro Asn Ile Glu Glu
        1355                1360                1365

Val Ala Leu Gly Gln Glu Gly Glu Ile Pro Phe Tyr Gly Arg Ala
        1370                1375                1380

Ile Pro Leu Ser Tyr Ile Lys Gly Gly Arg His Leu Ile Phe Cys
        1385                1390                1395

His Ser Lys Lys Lys Cys Asp Glu Leu Ala Ala Ala Leu Arg Gly
        1400                1405                1410

Met Gly Leu Asn Ser Val Ala Tyr Tyr Arg Gly Leu Asp Val Ser
        1415                1420                1425

Val Ile Pro Thr Gln Gly Asp Val Val Val Val Ala Thr Asp Ala
        1430                1435                1440

Leu Met Thr Gly Tyr Thr Gly Asp Phe Asp Ser Val Ile Asp Cys
        1445                1450                1455

Asn Val Ala Val Thr Gln Val Val Asp Phe Ser Leu Asp Pro Thr
        1460                1465                1470

Phe Thr Ile Thr Thr Gln Ile Val Pro Gln Asp Ala Val Ser Arg
        1475                1480                1485

Ser Gln Arg Arg Gly Arg Thr Gly Arg Gly Arg Leu Gly Ile Tyr
        1490                1495                1500

Arg Tyr Val Ser Thr Gly Glu Arg Ala Ser Gly Met Phe Asp Ser
        1505                1510                1515

Val Val Leu Cys Glu Cys Tyr Asp Ala Gly Ala Ala Trp Tyr Glu
        1520                1525                1530

Leu Thr Pro Ser Glu Thr Thr Val Arg Leu Arg Ala Tyr Phe Asn
        1535                1540                1545

Thr Pro Gly Leu Pro Val Cys Gln Asp His Leu Glu Phe Trp Glu
        1550                1555                1560

Ala Val Phe Thr Gly Leu Thr His Ile Asp Ala His Phe Leu Ser
        1565                1570                1575
```

-continued

```
Gln Thr Lys Gln Ser Gly Glu Asn Phe Ala Tyr Leu Thr Ala Tyr
            1580            1585                1590

Gln Ala Thr Val Cys Ala Arg Ala Lys Ala Pro Pro Pro Ser Trp
    1595            1600                1605

Asp Val Met Trp Lys Cys Leu Thr Arg Leu Lys Pro Thr Leu Val
1610            1615                1620

Gly Pro Thr Pro Leu Leu Tyr Arg Leu Gly Ser Val Thr Asn Glu
    1625            1630                1635

Val Thr Leu Thr His Pro Val Thr Lys Tyr Ile Ala Thr Cys Met
1640            1645                1650

Gln Ala Asp Leu Glu Val Met Thr Ser Thr Trp Val Leu Ala Gly
    1655            1660                1665

Gly Val Leu Ala Ala Val Ala Ala Tyr Cys Leu Ala Thr Gly Cys
    1670            1675                1680

Val Cys Ile Ile Gly Arg Leu His Ile Asn Gln Arg Ala Val Val
1685            1690                1695

Ala Pro Asp Lys Glu Val Leu Tyr Glu Ala Phe Asp Glu Met Glu
    1700            1705                1710

Glu Cys Ala Ser Arg Ala Ala Leu Ile Glu Glu Gly Gln Arg Ile
    1715            1720                1725

Ala Glu Met Leu Lys Ser Lys Ile Gln Gly Leu Leu Gln Gln Ala
    1730            1735                1740

Ser Lys Gln Ala Gln Asp Ile Gln Pro Thr Val Gln Ala Ser Trp
1745            1750                1755

Pro Lys Val Glu Gln Phe Trp Ala Lys His Met Trp Asn Phe Ile
    1760            1765                1770

Ser Gly Ile Gln Tyr Leu Ala Gly Leu Ser Thr Leu Pro Gly Asn
    1775            1780                1785

Pro Ala Val Ala Ser Met Met Ala Phe Ser Ala Ala Leu Thr Ser
    1790            1795                1800

Pro Leu Ser Thr Ser Thr Thr Ile Leu Leu Asn Ile Leu Gly Gly
    1805            1810                1815

Trp Leu Ala Ser Gln Ile Ala Pro Pro Ala Gly Ala Thr Gly Phe
    1820            1825                1830

Val Val Ser Gly Leu Val Gly Ala Ala Val Gly Ser Ile Gly Leu
    1835            1840                1845

Gly Lys Val Leu Val Asp Ile Leu Ala Gly Tyr Gly Ala Gly Ile
    1850            1855                1860

Ser Gly Ala Leu Val Ala Phe Lys Ile Met Ser Gly Glu Lys Pro
    1865            1870                1875

Ser Met Glu Asp Val Val Asn Leu Leu Pro Gly Ile Leu Ser Pro
    1880            1885                1890

Gly Ala Leu Val Val Gly Val Ile Cys Ala Ala Ile Leu Arg Arg
    1895            1900                1905

His Val Gly Pro Gly Glu Gly Ala Val Gln Trp Met Asn Arg Leu
    1910            1915                1920

Ile Ala Phe Ala Ser Arg Gly Asn His Val Ala Pro Thr His Tyr
    1925            1930                1935

Val Thr Glu Ser Asp Ala Ser Gln Arg Val Thr Gln Leu Leu Gly
    1940            1945                1950

Ser Leu Thr Ile Thr Ser Leu Leu Arg Arg Leu His Asn Trp Ile
    1955            1960                1965
```

```
Thr Glu Asp Cys Pro Ile Pro Cys Gly Gly Ser Trp Leu Arg Asp
    1970            1975                1980

Val Trp Asp Trp Val Cys Thr Ile Leu Thr Asp Phe Lys Asn Trp
    1985            1990                1995

Leu Thr Ser Lys Leu Phe Pro Lys Met Pro Gly Leu Pro Phe Val
    2000            2005                2010

Ser Cys Gln Lys Gly Tyr Lys Gly Val Trp Ala Gly Thr Gly Ile
    2015            2020                2025

Met Thr Thr Arg Cys Pro Cys Gly Ala Asn Ile Ser Gly Asn Val
    2030            2035                2040

Arg Leu Gly Ser Met Arg Ile Thr Gly Pro Lys Thr Cys Met Asn
    2045            2050                2055

Ile Trp Gln Gly Thr Phe Pro Ile Asn Cys Tyr Thr Glu Gly Gln
    2060            2065                2070

Cys Val Pro Lys Pro Ala Pro Asn Phe Lys Val Ala Ile Trp Arg
    2075            2080                2085

Val Ala Ala Ser Glu Tyr Ala Glu Val Thr Gln His Gly Ser Tyr
    2090            2095                2100

His Tyr Ile Thr Gly Leu Thr Thr Asp Asn Leu Lys Val Pro Cys
    2105            2110                2115

Gln Leu Pro Ser Pro Glu Phe Phe Ser Trp Val Asp Gly Val Gln
    2120            2125                2130

Ile His Arg Phe Ala Pro Thr Pro Lys Pro Phe Phe Arg Asp Glu
    2135            2140                2145

Val Ser Phe Cys Val Gly Leu Asn Ser Phe Val Val Gly Ser Gln
    2150            2155                2160

Leu Pro Cys Asp Pro Glu Pro Asp Thr Asp Val Leu Met Ser Met
    2165            2170                2175

Leu Thr Asp Pro Ser His Ile Thr Ala Glu Thr Ala Ala Arg Arg
    2180            2185                2190

Leu Ala Arg Gly Ser Pro Pro Ser Glu Ala Ser Ser Ser Ala Ser
    2195            2200                2205

Gln Leu Ser Ala Pro Ser Leu Arg Ala Thr Cys Thr Thr His Gly
    2210            2215                2220

Lys Ala Tyr Asp Val Asp Met Val Asp Ala Asn Leu Phe Met Gly
    2225            2230                2235

Gly Asp Val Thr Arg Ile Glu Ser Gly Ser Lys Val Val Val Leu
    2240            2245                2250

Asp Ser Leu Asp Pro Met Val Glu Glu Arg Ser Asp Leu Glu Pro
    2255            2260                2265

Ser Ile Pro Ser Glu Tyr Met Leu Pro Lys Lys Arg Phe Pro Pro
    2270            2275                2280

Ala Leu Pro Ala Trp Ala Arg Pro Asp Tyr Asn Pro Pro Leu Val
    2285            2290                2295

Glu Ser Trp Lys Arg Pro Asp Tyr Gln Pro Ala Thr Val Ala Gly
    2300            2305                2310

Cys Ala Leu Pro Pro Pro Arg Lys Thr Pro Thr Pro Pro Pro Arg
    2315            2320                2325

Arg Arg Arg Thr Val Gly Leu Ser Glu Asp Ser Ile Gly Asp Ala
    2330            2335                2340

Leu Gln Gln Leu Ala Ile Lys Ser Phe Gly Gln Pro Pro Pro Ser
    2345            2350                2355

Gly Asp Ser Gly Leu Ser Thr Gly Ala Gly Ala Ala Asp Ser Gly
```

```
                2360                2365                2370
Ser  Gln  Thr  Pro  Pro  Asp  Glu  Leu  Ala  Leu  Ser  Glu  Thr  Gly  Ser
                2375                2380                2385
Ile  Ser  Ser  Met  Pro  Pro  Leu  Glu  Gly  Glu  Leu  Gly  Asp  Pro  Asp
                2390                2395                2400
Leu  Glu  Pro  Glu  Gln  Val  Glu  Pro  Gln  Pro  Pro  Gln  Gly  Gly
                2405                2410                2415
Val  Ala  Ala  Pro  Gly  Ser  Asp  Ser  Gly  Ser  Trp  Ser  Thr  Cys  Ser
                2420                2425                2430
Glu  Glu  Asp  Asp  Ser  Val  Val  Cys  Cys  Ser  Met  Ser  Tyr  Ser  Trp
                2435                2440                2445
Thr  Gly  Ala  Leu  Ile  Thr  Pro  Cys  Ser  Pro  Glu  Glu  Glu  Lys  Leu
                2450                2455                2460
Pro  Ile  Asn  Pro  Leu  Ser  Asn  Ser  Leu  Leu  Arg  Tyr  His  Asn  Lys
                2465                2470                2475
Val  Tyr  Cys  Thr  Thr  Thr  Lys  Ser  Ala  Ser  Leu  Arg  Ala  Lys  Lys
                2480                2485                2490
Val  Thr  Phe  Asp  Arg  Met  Gln  Val  Leu  Asp  Ser  Tyr  Tyr  Asp  Ser
                2495                2500                2505
Val  Leu  Lys  Asp  Ile  Lys  Leu  Ala  Ala  Ser  Lys  Val  Thr  Ala  Arg
                2510                2515                2520
Leu  Leu  Thr  Met  Glu  Glu  Ala  Cys  Gln  Leu  Thr  Pro  Pro  His  Ser
                2525                2530                2535
Ala  Arg  Ser  Lys  Tyr  Gly  Phe  Gly  Ala  Lys  Glu  Val  Arg  Ser  Leu
                2540                2545                2550
Ser  Gly  Arg  Ala  Val  Asn  His  Ile  Lys  Ser  Val  Trp  Lys  Asp  Leu
                2555                2560                2565
Leu  Glu  Asp  Ser  Glu  Thr  Pro  Ile  Pro  Thr  Thr  Ile  Met  Ala  Lys
                2570                2575                2580
Asn  Glu  Val  Phe  Cys  Val  Asp  Pro  Thr  Lys  Gly  Gly  Lys  Lys  Ala
                2585                2590                2595
Ala  Arg  Leu  Ile  Val  Tyr  Pro  Asp  Leu  Gly  Val  Arg  Val  Cys  Glu
                2600                2605                2610
Lys  Met  Ala  Leu  Tyr  Asp  Ile  Thr  Gln  Lys  Leu  Pro  Gln  Ala  Val
                2615                2620                2625
Met  Gly  Ala  Ser  Tyr  Gly  Phe  Gln  Tyr  Ser  Pro  Ala  Gln  Arg  Val
                2630                2635                2640
Glu  Phe  Leu  Leu  Lys  Ala  Trp  Ala  Glu  Lys  Lys  Asp  Pro  Met  Gly
                2645                2650                2655
Phe  Ser  Tyr  Asp  Thr  Arg  Cys  Phe  Asp  Ser  Thr  Val  Thr  Glu  Arg
                2660                2665                2670
Asp  Ile  Arg  Thr  Glu  Glu  Ser  Ile  Tyr  Arg  Ala  Cys  Ser  Leu  Pro
                2675                2680                2685
Glu  Glu  Ala  His  Thr  Ala  Ile  His  Ser  Leu  Thr  Glu  Arg  Leu  Tyr
                2690                2695                2700
Val  Gly  Gly  Pro  Met  Phe  Asn  Ser  Lys  Gly  Gln  Thr  Cys  Gly  Tyr
                2705                2710                2715
Arg  Arg  Cys  Arg  Ala  Ser  Gly  Val  Leu  Thr  Thr  Ser  Met  Gly  Asn
                2720                2725                2730
Thr  Ile  Thr  Cys  Tyr  Val  Lys  Ala  Leu  Ala  Ala  Cys  Lys  Ala  Ala
                2735                2740                2745
Gly  Ile  Ile  Ala  Pro  Thr  Met  Leu  Val  Cys  Gly  Asp  Asp  Leu  Val
                2750                2755                2760
```

```
Val Ile Ser Glu Ser Gln Gly Thr Glu Asp Glu Arg Asn Leu
     2765             2770            2775

Arg Ala Phe Thr Glu Ala Met Thr Arg Tyr Ser Ala Pro Pro Gly
 2780             2785             2790

Asp Pro Pro Arg Pro Glu Tyr Asp Leu Glu Leu Ile Thr Ser Cys
 2795             2800             2805

Ser Ser Asn Val Ser Val Ala Leu Gly Pro Gln Gly Arg Arg Arg
 2810             2815             2820

Tyr Tyr Leu Thr Arg Asp Pro Thr Thr Pro Ile Ala Arg Ala Ala
 2825             2830             2835

Trp Glu Thr Val Arg His Ser Pro Val Asn Ser Trp Leu Gly Asn
 2840             2845             2850

Ile Ile Gln Tyr Ala Pro Thr Ile Trp Ala Arg Met Val Leu Met
 2855             2860             2865

Thr His Phe Phe Ser Ile Leu Met Ala Gln Asp Thr Leu Asp Gln
 2870             2875             2880

Asn Leu Asn Phe Glu Met Tyr Gly Ala Val Tyr Ser Val Ser Pro
 2885             2890             2895

Leu Asp Leu Pro Ala Ile Ile Glu Arg Leu His Gly Leu Asp Ala
 2900             2905             2910

Phe Ser Leu His Thr Tyr Thr Pro His Glu Leu Thr Arg Val Ala
 2915             2920             2925

Ser Ala Leu Arg Lys Leu Gly Ala Pro Pro Leu Arg Ala Trp Lys
 2930             2935             2940

Ser Arg Ala Arg Ala Val Arg Ala Ser Leu Ile Ser Arg Gly Gly
 2945             2950             2955

Arg Ala Ala Val Cys Gly Arg Tyr Leu Phe Asn Trp Ala Val Lys
 2960             2965             2970

Thr Lys Leu Lys Leu Thr Pro Leu Pro Glu Ala Arg Leu Leu Asp
 2975             2980             2985

Leu Ser Ser Trp Phe Thr Val Gly Ala Gly Gly Asp Ile Tyr
 2990             2995             3000

His Ser Val Ser Arg Ala Arg Pro Arg Leu Leu Leu Phe Gly Leu
 3005             3010             3015

Leu Leu Leu Phe Val Gly Val Gly Leu Phe Leu Leu Pro Ala Arg
 3020             3025             3030

<210> SEQ ID NO 31
<211> LENGTH: 236
<212> TYPE: DNA
<213> ORGANISM: Hepatitis C virus
<220> FEATURE:
<223> OTHER INFORMATION: cDNA sequence of 3' UTR of genome RNA of
      Hepatitis C virus strain JFH-1

<400> SEQUENCE: 31
agcggcacac actaggtaca ctccatagct aactgttcct tttttttttt tttttttttt       60
tttttttttt tttttttttt ttcttttttt ttttttttccc tctttcttcc cttctcatct     120
tattctactt tctttcttgg tggctccatc ttagccctag tcacggctag ctgtgaaagg      180
tccgtgagcc gcatgactgc agagagtgcc gtaactggtc tctctgcaga tcatgt         236

<210> SEQ ID NO 32
<211> LENGTH: 1776
<212> TYPE: DNA
<213> ORGANISM: Hepatitis C virus
```

<220> FEATURE:
<223> OTHER INFORMATION: DNA sequence encoding a chimeric NS5B protein composed of aa 1-515 of J6CF strain NS5B and aa 516-591 of JFH-1 strain NS5B

<400> SEQUENCE: 32

```
tccatgtcat actcctggac cggggctcta ataactcctt gtagtcccga agaggagaag      60
ttaccgatta acccttgag caactccctg ttgcgatatc acaacaaggt gtactgtacc     120
acaacaaaga gcgcctcact aagggctaaa aaggtaactt tgataggat gcaagtgctc     180
gactcctact acgactcagt cttaaaggac attaagctag cggcctccaa ggtcaccgca     240
aggctcctca ccatggagga ggcttgccag ttaaccccac ccattctgc aagatctaaa     300
tatgggtttg gggctaagga ggtccgcagc ttgtccggga gggccgttaa ccacatcaag     360
tccgtgtgga aggacctcct ggaggactca gaaacaccaa ttcccacaac cattatggcc     420
aaaaatgagg tgttctgcgt ggaccccacc aagggggca agaaagcagc tcgccttatc     480
gtttaccctg acctcggcgt cagggtctgc gagaagatgg cccttttatga cattacacaa     540
aaacttcctc aggcggtgat ggggcttct tatggattcc agtattcccc cgctcagcgg     600
gtagagtttc tcttgaaagc atgggcggaa aagaaggacc ctatgggttt ttcgtatgat     660
acccgatgct ttgactcaac cgtcactgag agagacatca ggactgagga gtccatatat     720
cgggcctgct ccttgcccga ggaggcccac actgccatac actcgctaac tgagagactt     780
tacgtgggag ggcctatgtt caacagcaag ggccaaacct gcgggtacag gcgttgccgc     840
gccagcgggg tgctcaccac tagcatgggg aacaccatca catgctacgt gaaagcctta     900
gcggcttgta agctgcagg gataatcgcg cccacaatgc tggtatgcgg cgatgacttg     960
gttgtcatct cagaaagcca ggggaccgag gaggacgagc ggaacctgag agccttcacg    1020
gaggctatga ccaggtattc tgcccctcct ggtgaccccc ccagaccgga gtatgatctg    1080
gagctgataa catcttgctc ctcaaatgtg tctgtggcgc tgggcccaca aggccgccgc    1140
agatactacc tgaccagaga ccctaccact ccaatcgccc gggctgcctg ggaaacagtt    1200
agacactccc ctgtcaattc atggctggga acatcatcc agtacgcccc gaccatatgg    1260
gctcgcatgg tcctgatgac acacttcttc tccattctca tggctcaaga cacgctggac    1320
cagaacctca ctttgagat gtacggagcg gtgtactccg tgagtccctt ggacctccca    1380
gctataattg aaaggttaca tgggcttgac gcttttttctc tgcacacata cactccccac    1440
gaactgacac gggtggcttc agccctcaga aaacttgggg cgccacccct cagagcgtgg    1500
aagagccggg cacgtgcagt cagggcgtcc ctcatctccc gtgggggaa agcggccgtt    1560
tgcggccgat atctcttcaa ttgggcggtg aagaccaagc tcaaactcac tccattgccg    1620
gaggcgcgcc tactgactt atccagttgg ttcaccgtcg gcgccggcgg gggcgacatt    1680
tttcacagcg tgtcgcgcgc ccgaccccgc tcattactct tcggcctact cctactttc    1740
gtagggtag gcctcttcct actccccgct cggtag                              1776
```

<210> SEQ ID NO 33
<211> LENGTH: 591
<212> TYPE: PRT
<213> ORGANISM: Artificial Sequence
<220> FEATURE:
<223> OTHER INFORMATION: Description of Artificial Sequence: Synthetic chimeric NS5B protein consisting of aa 1-515 of J6CF strain NS5B and aa 516-591 of JFH-1 strain NS5B

<400> SEQUENCE: 33

```
Ser Met Ser Tyr Ser Trp Thr Gly Ala Leu Ile Thr Pro Cys Ser Pro
 1               5                  10                  15

Glu Glu Glu Lys Leu Pro Ile Asn Pro Leu Ser Asn Ser Leu Leu Arg
            20                  25                  30

Tyr His Asn Lys Val Tyr Cys Thr Thr Lys Ser Ala Ser Leu Arg
            35                  40                  45

Ala Lys Lys Val Thr Phe Asp Arg Met Gln Val Leu Asp Ser Tyr Tyr
        50                  55                  60

Asp Ser Val Leu Lys Asp Ile Lys Leu Ala Ala Ser Lys Val Thr Ala
 65                  70                  75                  80

Arg Leu Leu Thr Met Glu Glu Ala Cys Gln Leu Thr Pro Pro His Ser
                85                  90                  95

Ala Arg Ser Lys Tyr Gly Phe Gly Ala Lys Glu Val Arg Ser Leu Ser
            100                 105                 110

Gly Arg Ala Val Asn His Ile Lys Ser Val Trp Lys Asp Leu Leu Glu
            115                 120                 125

Asp Ser Glu Thr Pro Ile Pro Thr Thr Ile Met Ala Lys Asn Glu Val
    130                 135                 140

Phe Cys Val Asp Pro Thr Lys Gly Gly Lys Lys Ala Ala Arg Leu Ile
145                 150                 155                 160

Val Tyr Pro Asp Leu Gly Val Arg Val Cys Glu Lys Met Ala Leu Tyr
                165                 170                 175

Asp Ile Thr Gln Lys Leu Pro Gln Ala Val Met Gly Ala Ser Tyr Gly
            180                 185                 190

Phe Gln Tyr Ser Pro Ala Gln Arg Val Glu Phe Leu Leu Lys Ala Trp
            195                 200                 205

Ala Glu Lys Lys Asp Pro Met Gly Phe Ser Tyr Asp Thr Arg Cys Phe
            210                 215                 220

Asp Ser Thr Val Thr Glu Arg Asp Ile Arg Thr Glu Glu Ser Ile Tyr
225                 230                 235                 240

Arg Ala Cys Ser Leu Pro Glu Glu Ala His Thr Ala Ile His Ser Leu
                245                 250                 255

Thr Glu Arg Leu Tyr Val Gly Gly Pro Met Phe Asn Ser Lys Gly Gln
            260                 265                 270

Thr Cys Gly Tyr Arg Arg Cys Arg Ala Ser Gly Val Leu Thr Thr Ser
            275                 280                 285

Met Gly Asn Thr Ile Thr Cys Tyr Val Lys Ala Leu Ala Ala Cys Lys
            290                 295                 300

Ala Ala Gly Ile Ile Ala Pro Thr Met Leu Val Cys Gly Asp Asp Leu
305                 310                 315                 320

Val Val Ile Ser Glu Ser Gln Gly Thr Glu Glu Asp Glu Arg Asn Leu
                325                 330                 335

Arg Ala Phe Thr Glu Ala Met Thr Arg Tyr Ser Ala Pro Pro Gly Asp
            340                 345                 350

Pro Pro Arg Pro Glu Tyr Asp Leu Glu Leu Ile Thr Ser Cys Ser Ser
            355                 360                 365

Asn Val Ser Val Ala Leu Gly Pro Gln Gly Arg Arg Tyr Tyr Leu
            370                 375                 380

Thr Arg Asp Pro Thr Thr Pro Ile Ala Arg Ala Ala Trp Glu Thr Val
385                 390                 395                 400

Arg His Ser Pro Val Asn Ser Trp Leu Gly Asn Ile Ile Gln Tyr Ala
                405                 410                 415
```

-continued

```
Pro Thr Ile Trp Ala Arg Met Val Leu Met Thr His Phe Phe Ser Ile
            420                 425                 430

Leu Met Ala Gln Asp Thr Leu Asp Gln Asn Leu Asn Phe Glu Met Tyr
        435                 440                 445

Gly Ala Val Tyr Ser Val Ser Pro Leu Asp Leu Pro Ala Ile Ile Glu
    450                 455                 460

Arg Leu His Gly Leu Asp Ala Phe Ser Leu His Thr Tyr Thr Pro His
465                 470                 475                 480

Glu Leu Thr Arg Val Ala Ser Ala Leu Arg Lys Leu Gly Ala Pro Pro
            485                 490                 495

Leu Arg Ala Trp Lys Ser Arg Ala Arg Ala Val Arg Ala Ser Leu Ile
                500                 505                 510

Ser Arg Gly Gly Lys Ala Ala Val Cys Gly Arg Tyr Leu Phe Asn Trp
        515                 520                 525

Ala Val Lys Thr Lys Leu Lys Leu Thr Pro Leu Pro Glu Ala Arg Leu
    530                 535                 540

Leu Asp Leu Ser Ser Trp Phe Thr Val Gly Ala Gly Gly Gly Asp Ile
545                 550                 555                 560

Phe His Ser Val Ser Arg Ala Arg Pro Arg Ser Leu Leu Phe Gly Leu
                565                 570                 575

Leu Leu Leu Phe Val Gly Val Gly Leu Phe Leu Leu Pro Ala Arg
                580                 585                 590
```

MUTANT REPLICON DERIVED FROM GENOME OF HEPATITIS C VIRUS J6CF STRAIN

The instant application contains a Sequence Listing which has been submitted electronically in ASCII format and is hereby incorporated by reference in its entirety. Said ASCII copy, created on Jun. 19, 2014, is named HIR-13-1599_SL.txt and is 268,313 bytes in size.

TECHNICAL FIELD

This disclosure relates to a mutant replicon derived from the genome of hepatitis C virus J6CF strain.

BACKGROUND

The hepatitis C virus (hereinafter, referred to as HCV) is a virus belonging to the flavivirus family the genome of which is a single-stranded (+) sense RNA and is known to cause hepatitis C. Based on recent studies, it has been revealed that HCV is classified into many types depending on genotype or serotype. According to phylogenetic analysis by Simmonds et al. using nucleotide sequences of HCV strains, HCV genotypes are classified into six types, and each type is further classified into several subtypes (Simmonds et al., Hepatology, (1994) Vol. 10, pp. 1321-1324). The full-length genomic nucleotide sequences of a plurality of HCV genotypes have also been determined to date (Choo et al., Science, (1989) Vol. 244, pp. 359-362, Kato et al., J. Med. Virol., (1992) Vol. 64, pp. 334-339, Okamoto et al., J. Gen. Virol., (1992) Vol. 73, pp. 673-679, Yoshioka et al., Hepatology, (1992) Vol. 16, pp. 293-299 and Mori et al., Biochem. Biophys. Res. Commun., (1992) Vol. 183, pp. 334-342).

Until recently, infection of cultured cells with HCV and replication of HCV genomes in cultured cells have been impossible. Accordingly, studies on mechanisms of HCV replication and infection have required in vivo experiments using chimpanzees as experimental animals. However, subgenomic replicon RNAs have been produced from the Con1 strain, the HCV-N strain, and the HCV-O strain belonging to the HCV genotype 1b, and the H77c strain belonging to the HCV genotype 1a, and this enabled studies on the HCV replication mechanism via in vitro experiments using cultured cells (JP 2001-17187 A, Lohmann et al., Science, (1999) Vol. 285, pp. 110-113, Blight et al., Science, (2000) Vol. 290, pp. 1972-1974, Friebe et al., J. Virol., (2001) Vol. 75, pp. 12047-12057 and Ikeda et al., J. Virol., (2002) Vol. 76, pp. 2997-3006). Herein, the subgenomic replicon RNA of HCV means an RNA which comprises a portion of HCV genome necessary for replication, and can autonomously replicate an RNA derived from the HCV genome when introduced into cultured cells, but does not have an ability to produce infectious HCV particles.

In addition, subgenomic replicon RNAs, and full-genomic replicon RNAs producing infectious HCV particles when introduced into Huh7 cells in vitro have been produced from the JFH-1 strain belonging to the HCV genotype 2a, and this enabled studies on the HCV infection mechanism via in vitro experiments using cultured cells (Kato et al., Gastroenterology, (2003) Vol. 125, pp. 1808-1817 and Wakita et al., Nature Medicine, (2005) Vol. 11, pp. 791-796). Herein, the full-genomic replicon RNA of HCV means an RNA which comprises a full-length HCV genome, i.e., a 5' untranslated region, structural genes, non-structural genes, and a 3' untranslated region, and can autonomously replicate an RNA derived from the HCV genome when introduced into cultured cells.

The J6CF strain is a HCV of genotype 2a, as is the JFH-1 strain. Homology between the J6CF strain and the JFH-1 strain is as high as about 90% at nucleic acid level and 91% at amino acid level. However, the J6CF strain lacks replication ability of its subgenomic replicon RNA, and it is not capable of virus particle production in a cell culture system using Huh7 cells.

Recently, substitution of an NS3 protein coding region, an NS5B protein coding region, and a 3' untranslated region of the J6CF genome with the sequences of the same regions of the JFH-1 strain was found to lead to autonomous replication in Huh7 cells (Murayama et al., J. Virol., (2007) Vol. 81, pp. 8030-8040). In addition, the subgenomic replicon RNA and full-genomic replicon RNA prepared by substituting an NS3 protein coding region and a 3' untranslated region of the J6CF genome with the sequences of the same regions of the JFH-1 strain and introducing three adaptive mutations in the NS5B protein coding region have been demonstrated to have autonomous replication ability and virus particle-producing ability (Murayama et al., PLoS Pathogens., (2010) Vol. 6, e1000885).

An experimental system that can efficiently amplify viruses is indispensable for studies on HCV and research and development of anti-HCV drugs. A system for amplifying HCV in cultured cells and a system for evaluating the propagation of HCV in cultured cells enable efficient screening of anti-HCV drugs. In addition, based on the systems, mechanisms of virus propagation will be understood, and new targets of anti-HCV drugs will be also found, and development of innovative anti-HCV drugs against such targets can be expected. Production of replicon RNA capable of autonomous replication in cultured cells or virus particle production is also desired for the J6CF strain.

Up to the present, however, it is believed that a full-genomic replicon RNA having infectious HCV particle-producing ability is required to comprise a sequence derived from the JFH-1 strain as a non-structural gene that is indispensable for virus replication. J6CF strain-derived full-genomic replicon RNAs autonomously replicating in cultured cells and producing HCV particles have been obtained, but they are limited to those composed of chimeric nucleic acids resulting from substitution of a considerable part of the non-structural genes in the J6CF genome with a sequence of the same region derived from the JFH-1 strain. Full-genomic replicon RNA having the J6CF genome as a backbone and having infectious HCV particle-producing ability is necessary for research of the J6CF strain, but has not yet been obtained.

As described above, subgenomic replicon RNA or full-genomic replicon RNA derived from HCV of genotype 2a corresponding to the replication mechanisms or replication efficiency of HCV strains other than the JFH-1 strain has not yet been obtained. Accordingly, it has been difficult to identify factors necessary for HCV replication serving as targets of new anti-HCV drugs or to screen for anti-HCV drugs capable of exerting drug efficacy independent of the replication mechanisms or replication efficiency. In addition, the types of artificially producible HCV particles serving as a raw material for HCV vaccine have been limited.

It could therefore be helpful to provide a replicon RNA having the genome of the hepatitis C virus J6CF strain as a backbone and having autonomous replication ability.

SUMMARY

We discovered that amino acid substitution of alanine with glutamic acid at position 1680 as determined on the basis of the amino acid sequence of the precursor protein of the J6CF strain would be critical to confer autonomous replication ability on the J6CF genome.

We thus provide:

[1] A nucleic acid comprising a 5' untranslated region, a virus protein-coding region which contains an NS3 protein coding sequence, an NS4A protein coding sequence, an NS4B protein coding sequence, an NS5A protein coding sequence, and an NS5B protein coding sequence, and a 3' untranslated region of the genome of the hepatitis C virus J6CF strain in that order from the 5' to 3' direction, wherein the NS4A protein coding sequence comprises a mutation substituting alanine at position 1680 with glutamic acid, as determined on the basis of the amino acid sequence as shown in SEQ ID NO: 30 of the precursor protein of the J6CF strain.

[2] The nucleic acid according to [1] above, wherein the NS5B protein coding sequence has mutations causing amino acid substitutions of the following (i) to (iii):

(i) amino acid substitution of alanine at position 2892 with serine;

(ii) amino acid substitution of arginine at position 2959 with lysine; and (iii) amino acid substitution of tyrosine at position 3003 with phenylalanine, as determined on the basis of the amino acid sequence as shown in SEQ ID NO: 30, and wherein the 3' untranslated region has a nucleotide substitution of cytosine at position 9458 with guanine, as determined on the basis of the nucleotide sequence as shown in SEQ ID NO: 29.

[3] The nucleic acid according to [1] above, wherein the NS5B protein coding sequence is substituted with a nucleotide sequence encoding a protein consisting of the amino acid sequence in which the sequence of amino acids 1 to 515 from the amino acid sequence as shown in SEQ ID NO: 27 and the sequence of amino acids 516 to 591 from the amino acid sequence as shown in SEQ ID NO: 28 are joined together in that order, and wherein the 3' untranslated region is substituted with the nucleotide sequence as shown in SEQ ID NO: 31.

[4] The nucleic acid according to [1] to [3] above, comprising a foreign gene and an IRES sequence.

[5] The nucleic acid according to [1] to [4] above, wherein the virus protein-coding region further comprises, on the 5' side of an NS3 protein coding sequence, a Core protein coding sequence, an E1 protein coding sequence, an E2 protein coding sequence, a p7 protein coding sequence, and an NS2 protein coding sequence of the hepatitis C virus genome in that order from the 5' to 3' direction.

[6] A subgenomic replicon RNA of hepatitis C virus comprising the nucleic acid according to any of [1] to [4] above.

[7] A full-genomic replicon RNA of hepatitis C virus comprising the nucleic acid according to [5] above.

[8] A hepatitis C virus particle containing the nucleic acid according to [5] above as a virus genome.

[9] An expression vector comprising the nucleic acid according to any of [1] to [5] above.

[10] A cell into which the nucleic acid according to any of [1] to [5] above had been introduced.

[11] A hepatitis C virus vaccine comprising the hepatitis C virus particle according to [8] above.

[12] A method for screening for an anti-hepatitis C virus substance comprising:

a step of culturing the cell according to [10] above or a mixture of the hepatitis C virus particle according to [8] above and a hepatitis C virus-sensitive cell in the presence and in the absence of a test substance;

a step of quantifying the amount of subgenomic replicon RNA, full-genomic replicon RNA, or hepatitis C virus particle in a culture obtained by the step of culturing; and a step of evaluating the result of the step of quantifying, wherein the test substance is determined as a substance having an anti-hepatitis C virus activity if the amount of the subgenomic replicon RNA, the full-genomic replicon RNA, or the hepatitis C virus particle quantified in the presence of the test substance is lower than the amount of the subgenomic replicon RNA, the full-genomic replicon RNA, or the hepatitis C virus particle quantified in the absence of the test substance.

This description includes the disclosure in Japanese Patent Application No. 2011-122795, the subject matter of which is incorporated by reference.

Thus, replicon RNA having autonomous replication ability in cultured cells can be produced using the genome of the hepatitis C virus J6CF strain as a backbone.

BRIEF DESCRIPTION OF THE DRAWINGS

FIG. 1 shows the structures of the JFH-1 strain-derived subgenomic replicon RNA expression vector, the J6CF strain-derived subgenomic replicon RNA expression vector, and the two J6CF/JFH-1 chimeric HCV subgenomic replicon RNA expression vectors.

FIG. 2 shows the structures of the JFH-1 strain-derived full-genomic replicon RNA expression vector, the J6CF strain-derived full-genomic replicon RNA expression vector, and three J6CF/JFH-1 chimeric HCV full-genomic replicon RNA expression vectors.

FIG. 3A shows relative luciferase activity indicating the amount of replication of HCV subgenomic replicon RNA in the Huh7.5.1 cell into which HCV subgenomic replicon RNA: SGR-JFH1/Luc, SGR-J6CF/Luc, SGR-J6/N3H+5BSLX-JFH1/Luc, or SGR-J6/5BSLX-JFH1/Luc, had been introduced. FIG. 3B shows the amount of the Core protein (indicating the virus producing ability) in a culture supernatant of the Huh7.5.1 cell into which J6CF/JFH-1 chimeric HCV full-genomic replicon RNA: FGR-J6/N3H+5BSLX-JFH1 or FGR-J6/5BSLX-JFH1, had been introduced.

FIG. 4 shows changes over time in the amounts of the Core protein in a culture supernatant (virus producing ability) when repeating subculture of the Huh7.5.1 cell into which J6CF/JFH-1 chimeric HCV full-genomic replicon RNA: FGR-J6/5BSLX-JFH1 or FGR-J6/5B-JFH1, had been introduced.

FIG. 5 shows the structures of A1680E mutation-containing J6CF/JFH-1 chimeric mutant HCV subgenomic replicon RNA and HCV full-genomic replicon RNA expression vectors. pJFH1 is a JFH-1 strain-derived HCV full-genomic replicon RNA expression vector in which the full-length genomic sequence of the JFH-1 strain is cloned downstream of the T7 promoter. pJ6CF is a J6CF strain-derived HCV full-genomic replicon RNA expression vector in which the full-length genomic sequence of the J6CF strain cloned into downstream of the T7 promoter.

FIG. 6 shows relative luciferase activity (indicating the replication level of the replicon RNA) in the Huh7.5.1 cell into which HCV subgenomic replicon RNA: SGR-J6/N3H+5BSLX-JFH1/Luc, SGR-J6/5BSLX-JFH1+4Amut/Luc, or SGR-J6/5BSLX-JFH1/Luc, had been introduced.

Figure 14:
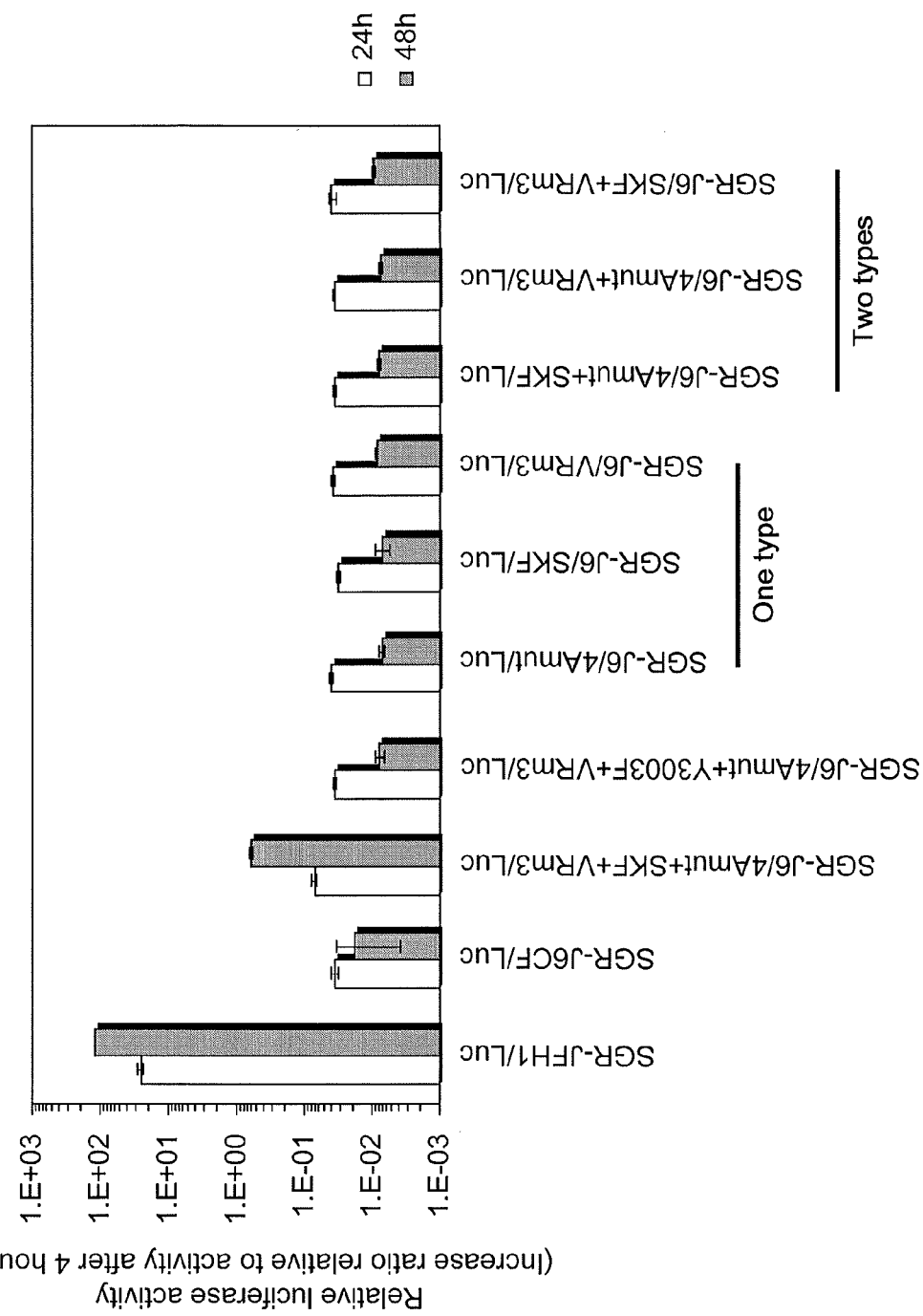

FIG. 14 shows relative luciferase activity (indicating the replication level of replicon RNA) in the Huh7.5.1 cell into which HCV subgenomic replicon RNA: SGR-JFH1/Luc or SGR-J6CF/Luc, or mutant HCV subgenomic replicon RNA: SGR-J6/4Amut+SKF+VRm3/Luc, SGR-J6/4Amut+Y3003F+VRm3/Luc, SGR-J6/4Amut/Luc, SGR-J6/SKF/Luc, SGR-J6/VRm3/Luc, SGR-J6/4Amut+SKF/Luc, SGR-J6/4Amut+VRm3/Luc, or SGR-J6/SKF+VRm3/Luc, had been introduced.

DETAILED DESCRIPTION

The scientific terms, technical terms, and nomenclature used throughout this description are intended to have the same meanings as those generally understood by those person skilled in the art unless otherwise specifically defined. The general technology and technical terms in the fields of molecular biology and immunology are based on the procedures and definitions described in Sambrook et al., Molecular Cloning: A Laboratory Manual (Third Edition, 2001) and Ed Harlow et al., Antibodies: A Laboratory Manual (1988). Furthermore, all documents, patents, and patent applications cited in the description are incorporated by reference herein in their entirety.

Hepatitis C virus (HCV) is a virus with a single-stranded (+) sense RNA as the genome. An HCV genome comprises a 5' untranslated region (5' UTR), a region comprising nucleotide sequences each encoding a Core protein, an E1 protein, an E2 protein, a p7 protein, an NS2 protein, an NS3 protein, an NS4A protein, an NS4B protein, an NS5A protein, and an NS5B protein (i.e., a virus protein-coding region), and a 3' untranslated region (3' UTR). The HCV genome (the full-length HCV genome) is an RNA composed of 5' UTR, nucleotide sequences each encoding a Core protein, an E1 protein, an E2 protein, a p7 protein, an NS2 protein, an NS3 protein, an NS4A protein, an NS4B protein, an NS5A protein, and an NS5B protein, and 3' UTR located in that order from the 5' to 3' direction. As an example of the full-length HCV genome, the full-length genomic cDNA sequence of the J6CF strain is shown in SEQ ID NO: 29. To differentiate the full-length of HCV genome from a nucleic acid of a part of the HCV genome, the full-length of HCV genome is also referred to as "the HCV full-length genome," "the full-length HCV genome," "the HCV full-length genomic RNA" "the full-length HCV genomic RNA" or "the full-length genomic RNA."

HCV is actually present as virus particles. The virus particles of HCV (HCV particles) contain HCV genomes inside virus capsids constituted by HCV structural proteins.

The Core protein, the E1 protein, the E2 protein, and the p7 protein of HCV are "structural proteins" constituting HCV particles. Nucleic acids encoding such structural proteins are referred to as "structural genes." The NS2 protein, the NS3 protein, the NS4A protein, the NS4B protein, the NS5A protein, and the NS5B protein of HCV are "non-structural proteins" that do not constitute HCV particles. Nucleic acids encoding such non-structural proteins are referred to as "non-structural genes." Non-structural proteins have functions associated with HCV genome replication, HCV protein processing, and other processes.

The 5' untranslated region (5' UTR) of HCV provides an internal ribosome entry site (hereinafter, referred to as IRES) for protein translation and an element necessary for replication. The 5' UTR of HCV is a region of about 340 nucleotides from the 5' end of the genome.

The 3' untranslated region (3' UTR) of HCV assists HCV replication. The 3'UTR of HCV contains a variable region, a poly-U region, and an additional region of approximately 100 nucleotides (X region).

HCV is translated into a single precursor protein (a polyprotein) in which ten viral proteins (Core protein, E1 protein, E2 protein, p7 protein, NS2 protein, NS3 protein, NS4A protein, NS4B protein, NS5A protein, and NS5B protein) are ligated in that order, and then, by intracellular and viral proteases, the precursor protein is cleaved into ten mature viral proteins (Core protein, E1 protein, E2 protein, p7 protein, NS2 protein, NS3 protein, NS4A protein, NS4B protein, NS5A protein, and NS5B protein). The amino acid sequence of the precursor protein of the J6CF strain is shown in SEQ ID NO: 30 as an example of an HCV precursor protein. This precursor protein is encoded by the full-length genomic sequence of the J6CF strain as shown in SEQ ID NO: 29.

While various HCV genotypes have been known, the HCV genomes of such various genotypes are known to have similar gene structures. The "genotype" of HCV refers to that in accordance with the international classification by Simmonds et al.

The J6CF strain is an HCV strain belonging to the genotype 2a, and the nucleotide sequence of the full-length HCV genome (SEQ ID NO: 29) and the amino acid sequence of the precursor protein (SEQ ID NO: 30) of the J6CF strain are disclosed under GenBank Accession No. AF177036. The sequence as shown in SEQ ID NO: 29 is a cDNA sequence of the full-length genomic RNA of the J6CF strain. In the corresponding RNA sequence, thymine (t) in the nucleotide sequence shall be replaced with uracil (u).

The 5' UTR of the J6CF strain consists of nucleotides 1 to 340 of the nucleotide sequence as shown in SEQ ID NO: 29, the Core protein coding sequence consists of nucleotides 341 to 913 of SEQ ID NO: 29, the E1 protein coding sequence consists of nucleotides 914 to 1489 of SEQ ID NO: 29, the E2 protein coding sequence consists of nucleotides 1490 to 2590 of SEQ ID NO: 29, the p7 protein coding sequence consists of nucleotides 2591 to 2779 of SEQ ID NO: 29, the NS2 protein coding sequence consists of nucleotides 2780 to 3430 of SEQ ID NO: 29, the NS3 protein coding sequence consists of nucleotides 3431 to 5323 of SEQ ID NO: 29, the NS4A protein coding sequence consists of nucleotides 5324 to 5485 of SEQ ID NO: 29, the NS4B protein coding sequence consists of nucleotides 5486 to 6268 of SEQ ID NO: 29, the NS5A protein coding sequence consists of nucleotides 6269 to 7666 of SEQ ID NO: 29, the NS5B protein coding sequence consists of nucleotides 7667 to 9442 (including the stop codon) of SEQ ID NO: 29, and 3' UTR consists of nucleotides 9443 to 9711 of SEQ ID NO: 29. The amino acid sequence of the NS5B protein of the J6CF strain is shown in SEQ ID NO: 27.

The JFH-1 strain is an HCV strain belonging to the genotype 2a, and the nucleotide sequence and the amino acid sequence of the full-length HCV genome of the JFH-1 strain are disclosed under GenBank Accession No. AB047639. The amino acid sequence of the NS5B protein of the JFH-1 strain is shown in SEQ ID NO: 28. The NS5B protein coding sequence of the JFH-1 strain consists of nucleotides 7667 to 9442 (including the stop codon) of the nucleotide sequence as disclosed under GenBank Accession No. AB047639 when the first nucleotide at the 5' terminus in the above-identified nucleotide sequence is defined as the first position. The 3' UTR of the JFH-1 strain consists of nucleotides 9443 to 9678 of the nucleotide sequence as disclosed under GenBank Accession No. AB047639. The nucleotide sequence of the 3' UTR of the JFH-1 strain is shown in SEQ ID NO: 31 of the Sequence Listing.

By using such HCV genomes, we provide nucleic acids such as replicon RNA capable of efficient autonomous replication or DNA encoding the same, that comprise a subgenomic or full-genomic sequence of an HCV strain of genotype 2a (preferably, the J6CF strain) into which a mutation conferring the autonomous replication ability had been introduced.

An adaptive mutation capable of conferring autonomous replication ability on subgenomic RNA or full-genomic RNA of an HCV strain of genotype 2a (preferably, the J6CF strain), which is to be introduced into replicon RNA, is amino acid substitution of alanine at position 1680 with glutamic acid (A1680E) in the amino acid sequence of the precursor protein of the J6CF strain.

HCV subgenomic replicon RNA or HCV full-genomic replicon RNA having high autonomous replication ability in cultured cells can be produced by introducing the A1680E mutation into a subgenomic RNA or full-genomic RNA of the J6CF strain alone or in combination with another adaptive mutation.

Examples of adaptive mutations to be introduced in combination with A1680E mutation include, but are not limited to, nucleotide mutations that cause amino acid substitution A2892S (substitution of alanine at position 2892 with serine), R2959K (substitution of arginine at position 2959 with lysine), and Y3003F (substitution of tyrosine at position 3003 with phenylalanine) in the amino acid sequence of the precursor protein of the J6CF strain and nucleotide mutation nt9458(c→g) (i.e., mutation of cytosine at position 9458 into guanine in the full-length genome of J6CF strain). Preferably, all of mutations A2892S, R2959K, Y3003F and nucleotide mutation nt9458(c→g) are introduced into a replicon RNA in combination with A1680E mutation.

HCV subgenomic replicon RNA or HCV full-genomic replicon RNA having high autonomous replication ability in cultured cells can be produced by introducing A1680E mutation as described above into a chimeric replicon RNA in which a part of the NS5B protein coding sequence of the genomic RNA of the J6CF strain (corresponding to amino acid positions 516 to 591 of the NS5B protein) and the 3' untranslated region are substituted with the sequences of the same regions of the JFH-1 strain (J6CF/JFH-1 chimeric replicon RNA).

HCV subgenomic replicon RNA or HCV full-genomic replicon RNA may comprise a mutation other than abovementioned mutations, i.e., A1680E, A2892S, R2959K, Y3003F, and nt9458(c→g)), provided that the RNA has autonomous replication ability equivalent to that of replicon RNA comprising only the above-mentioned mutations. An example of such other mutations is substitution of 1 or a plurality of nucleotides (e.g., 1 to 50, preferably 1 to 20, and more preferably 1 to 5 nucleotides). Replicon RNA comprising such other mutation have 92% or more, preferably 95% or more, more preferably 96% or more, further preferably 97% or more, and particularly preferably 99% or more (e.g., 99.5% or more) nucleotide sequence identity with the genomic sequence of the HCV J6CF strain. In an alternative example, it is also preferable that HCV subgenomic replicon RNA or HCV full-genomic replicon RNA comprise only the above mutations: A1680E, A2892S, R2959K, Y3003F, and nt9458 (c→g).

The term "replicon RNA" used herein refers to an RNA having an ability to autonomously replicate in cultured cells (typically HCV-sensitive cells). The replicon RNA introduced into cells autonomously replicates, and the resulting copies of the RNA are separated into daughter cells, following cell division. Thus, replicon RNA can be used to stably transfect cells.

The term "replicon RNA of HCV" or "HCV replicon RNA" refers to an autonomously replicable RNA that comprises a part or full-length of HCV genomic RNA. An autonomously replicable RNA that comprises a part of the HCV genomic RNA is referred to as "HCV subgenomic replicon RNA," and an autonomously replicable RNA that comprises the full-length HCV genomic RNA is referred to as "HCV full-genomic replicon RNA." The term "HCV replicon RNA" encompasses both HCV subgenomic replicon RNA and HCV full-genomic replicon RNA.

It is preferable that "HCV subgenomic replicon RNA" comprises the 5' untranslated region (5' UTR), nucleotide sequences each encoding an NS3 protein, an NS4A protein, an NS4B protein, an NS5A protein, and an NS5B protein, and the 3' untranslated region (3' UTR) of HCV in that order from the 5' to 3' direction. HCV subgenomic replicon RNA preferably comprises a foreign gene (a drug resistance gene or a reporter gene) and an IRES sequence for detection of the replicon RNA. In such a case, it is preferable to insert the foreign gene (the drug resistance gene or the reporter gene) and the IRES sequence on the 5' side of an NS3 protein coding sequence in the HCV subgenomic replicon RNA. A preferred HCV subgenomic replicon RNA, for example, comprises the 5' untranslated region (5' UTR), 36 nucleotide sequences at the 5' terminus of the Core protein coding region, a foreign gene (a drug resistance gene or a reporter gene), an IRES sequence, nucleotide sequences each encoding an NS3 protein, an NS4A protein, an NS4B protein, an NS5A protein, and an NS5B protein, and a 3' untranslated region (3' UTR) of HCV in that order from the 5' to 3' direction.

It is preferable that HCV full-genomic replicon RNA comprises the 5' untranslated region (5' UTR), nucleotide sequences each encoding a Core protein, an E1 protein, an E2 protein, a p7 protein, an NS2 protein, an NS3 protein, an NS4A protein, an NS4B protein, an NS5A protein, and an NS5B protein, and the 3' untranslated region (3' UTR) of HCV located in that order from the 5' to 3' direction.

If a full-length HCV genome has autonomous replication ability, such genome is replicon RNA. Replicon RNA containing the full-length HCV genome is referred to as HCV full-genomic replicon RNA. If an RNA comprising an HCV full-length genomic sequence (HCV full-length genomic RNA) has autonomous replication ability, it is HCV full-genomic replicon RNA.

The nucleic acid has basically the genomic sequence of an HCV strain of genotype 2a other than the JFH-1 strain (preferably the J6CF strain) as a backbone and comprises a mutation conferring autonomous replication ability in cultured cells. Typically, this nucleic acid is an HCV subgenomic replicon RNA, an HCV full-genomic replicon RNA, or a DNA encoding such RNA.

We provide a nucleic acid that may comprise a 5' untranslated region, a virus protein-coding region which contains an NS3 protein coding sequence, an NS4A protein coding sequence, an NS4B protein coding sequence, an NS5A protein coding sequence, and an NS5B protein coding sequence, and a 3' untranslated region of the genome of the hepatitis C virus J6CF strain in that order from the 5' to 3' direction, wherein the nucleic acid comprises a mutation substituting alanine at position 1680 with glutamic acid (i.e., a nucleotide mutation causing amino acid substitution of the alanine with glutamic acid), as determined on the basis of the amino acid sequence of the precursor protein of the J6CF strain as shown in SEQ ID NO: 30, in the NS4A protein coding sequence. When this nucleic acid comprises the full-length genomic sequence as a viral sequence (herein, the viral sequence referring to a nucleotide sequence from an HCV genome), the virus protein-coding region further comprises, on the 5' side of the NS3 protein coding sequence, a Core protein coding sequence, an E1 protein coding sequence, an E2 protein coding sequence, a p7 protein coding sequence, and an NS2 protein coding sequence in that order from the 5' to 3' direction.

Preferably, the nucleic acid comprises a 5' untranslated region, a virus protein-coding region which contains an NS3 protein coding sequence, an NS4A protein coding sequence, an NS4B protein coding sequence, an NS5A protein coding sequence, and an NS5B protein coding sequence, and a 3' untranslated region of the genome of the hepatitis C virus J6CF strain in that order from the 5' to 3' direction, wherein the NS4A protein coding sequence comprises a mutation substituting alanine at position 1680 with glutamic acid, as determined on the basis of the amino acid sequence of the precursor protein of the J6CF strain as shown in SEQ ID NO: 30, wherein the NS5B protein coding sequence comprises mutations causing (i) amino acid substitution of alanine at position 2892 with serine, (ii) amino acid substitution of arginine at position 2959 with lysine, and (iii) amino acid substitution of tyrosine at position 3003 with phenylalanine, as determined on the basis of the amino acid sequence as shown in SEQ ID NO: 30, and wherein the 3' untranslated region comprises nucleotide substitution of cytosine at position 9458 with guanine, as determined on the basis of the nucleotide sequence as shown in SEQ ID NO: 29.

The nucleic acid may comprise a subgenomic sequence (i.e., a sequence comprising a part of the HCV full-length genome) as a viral sequence (a nucleotide sequence from an HCV genome). The nucleic acid may be, for example, a subgenomic replicon RNA or a DNA encoding such RNA. When the nucleic acid comprises a foreign gene (a drug resistance gene or a reporter gene) and an IRES sequence, it may comprise a partial fragment from the 5' terminus of the Core protein coding region (e.g., a 36 nucleotide sequence of the 5' terminus) on the 5' side of the foreign gene. In this case, the nucleic acid comprises the 5' untranslated region (5' UTR), a 36 nucleotide sequence of the 5' terminus of the Core protein coding region, a foreign gene (a drug resistance gene or a reporter gene), an IRES sequence, nucleotide sequences each encoding an NS3 protein, an NS4A protein, an NS4B protein, an NS5A protein, and an NS5B protein, and the 3' untranslated region (3' UTR) of HCV in that order from the 5' to 3' direction. For example, the nucleic acid may be a subgenomic replicon RNA comprising the nucleotide sequence as shown in SEQ ID NO: 4 or a DNA encoding the same (when it is RNA, thymine (t) in the nucleotide sequence shall be replaced with uracil (u)).

Alternatively, the nucleic acid may comprise the full-genomic (full-length genomic) sequence as a viral sequence. For example, it may be a full-genomic replicon RNA or a DNA encoding such RNA. In the nucleic acid comprising the full-length genomic sequence as a viral sequence, the virus protein-coding region further comprises, on the 5' side of a NS3 protein coding sequence, a Core protein coding region, an E1 protein coding region, an E2 protein coding region, a p7 protein coding region, and an NS2 protein coding region in that order from the 5' to 3' direction. For example, the nucleic acid may be a full-genomic replicon RNA comprising the nucleotide sequence as shown in SEQ ID NO: 5 or a DNA encoding such RNA (when it is RNA, thymine (t) in the nucleotide sequence shall be replaced with uracil (u)).

The nucleic acid is a nucleic acid that comprises the 5' untranslated region, nucleotide sequences each encoding an NS3 protein, an NS4A protein, an NS4B protein, an NS5A protein, and an NS5B protein, and the 3' untranslated region of the genome of the HCV J6CF strain, wherein the nucleotide sequence of the nucleic acid comprises a mutation, wherein the nucleic acid comprises mutations causing substitution of alanine at position 1680 with glutamic acid, substitution of alanine at position 2892 with serine, substitution of arginine at position 2959 with lysine, and substitution of tyrosine at position 3003 with alanine, as determined on the basis of the amino acid sequence of the precursor protein of the HCV J6CF strain, and a mutation of cytosine at position 9458 into guanine as determined on the basis of the nucleotide sequence of the J6CF genome. This nucleic acid is preferably a mutant subgenomic replicon RNA derived from the J6CF strain resulting from introduction of the above-mentioned 5 mutations into a subgenomic replicon RNA of the J6CF strain, or a DNA encoding such RNA. The nucleic acid may comprise the nucleotide sequence as shown in SEQ ID NO: 4.

The nucleic acid may be a nucleic acid that comprises a nucleotide sequence that has a mutation in the nucleotide sequence of the full-length genome of the HCV J6CF strain, wherein the nucleic acid comprise mutations causing substitution of alanine at position 1680 with glutamic acid, substitution of alanine at position 2892 with serine, substitution of arginine at position 2959 with lysine, and substitution of tyrosine at position 3003 with phenylalanine, as determined on the basis of the amino acid sequence of the precursor protein of the HCV J6CF strain, and a mutation of cytosine at position 9458 into guanine as determined on the basis of the nucleotide sequence of the genome of the J6CF strain. Preferably, the nucleic acid is a mutant full-genomic replicon RNA derived from the J6CF strain resulting from introduction of the above-mentioned 5 mutations into a replicon RNA derived from the full-length genome of the J6CF strain, or a DNA encoding such RNA. The nucleic acid may comprise the nucleotide sequence as shown in SEQ ID NO: 5.

The term "mutant HCV subgenomic replicon RNA derived from the J6CF strain" or "mutant HCV full-genomic replicon RNA derived from the J6CF strain" used herein refers to a replicon RNA comprising a subgenomic sequence or full-genomic sequence of the J6CF strain, into which a mutation had been introduced. The genomic sequence of the J6CF strain into which no mutation had been introduced is referred to as "wild type" to differentiate such wild type sequence from the mutant.

The nucleic acid may be a nucleic acid that comprises a 5' untranslated region, a virus protein-coding region which contains an NS3 protein coding sequence, an NS4A protein coding sequence, an NS4B protein coding sequence, an NS5A protein coding sequence, and an NS5B protein coding sequence, and the 3' untranslated region of the genome of the hepatitis C virus J6CF strain in that order from the 5' to 3' direction, wherein the NS4A protein coding sequence comprises a mutation substituting alanine at position 1680 with glutamic acid (i.e., a nucleotide mutation causing an amino acid substitution of alanine with glutamic acid) as determined on the basis of the amino acid sequence of the precursor protein of the J6CF strain as shown in SEQ ID NO: 30, and wherein (a) the NS5B protein coding sequence is substituted with a nucleotide sequence encoding a protein consisting of the amino acid sequence in which the sequence of amino acids 1 to 515 of the amino acid sequence as shown in SEQ ID NO: 27 and the sequence of amino acids 516 to 591 of the amino acid sequence as shown in SEQ ID NO: 28 are joined together in that order, and (b) the 3' untranslated region is substituted with the nucleotide sequence as shown in SEQ ID NO: 31 (the 3' untranslated region derived from the JFH-1 strain).

Herein, the amino acid sequence of a protein consisting of the amino acid sequence in which the sequence of amino acids 1 to 515 of the amino acid sequence as shown in SEQ ID NO: 27 and the sequence of amino acids 516 to 591 of the amino acid sequence as shown in SEQ ID NO: 28 are joined together in that order, is shown in SEQ ID NO: 33. A nucleotide sequence encoding such protein may be, for example, the nucleotide sequence as shown in SEQ ID NO: 32.

The nucleic acid may comprise a subgenomic sequence as a viral sequence. For example, it may be a subgenomic replicon RNA or a DNA encoding such RNA. When the nucleic acid comprises a foreign gene (a drug resistance gene or a reporter gene) and an IRES sequence, it may comprise a partial fragment at the 5' terminus of the Core protein coding region (e.g., 5' terminal 36 nucleotide sequence) on the 5' side of the foreign gene. In such a case, the nucleic acid comprises a 5' untranslated region (5' UTR), a 5' terminal 36 nucleotide sequence of a Core protein coding region, a foreign gene (a drug resistance gene or a reporter gene), an IRES sequence, nucleotide sequences each encoding an NS3 protein, an NS4A protein, an NS4B protein, an NS5A protein, and an NS5B protein, and the 3' untranslated region (3' UTR) of HCV in that order from the 5' to 3' direction. For example, such nucleic acid may be a subgenomic replicon RNA comprising the nucleotide sequence as shown in SEQ ID NO: 1 or a DNA encoding such RNA (when it is RNA, thymine (t) in the nucleotide sequence shall be replaced with uracil (u)).

Alternatively, the nucleic acid may comprise a full-length genomic sequence as a viral sequence. For example, it may be a full-genomic replicon RNA or a DNA encoding such RNA. The virus protein-coding region in the nucleic acid comprising a full-length genomic sequence as a viral sequence further comprises, on the 5' side of the NS3 protein coding sequence, a Core protein coding sequence, a E1 protein coding sequence, a E2 protein coding sequence, a p7 protein coding sequence, and a NS2 protein coding sequence in that order from the 5' to 3' direction. For example, the nucleic acid may be a full-genomic replicon RNA comprising the nucleotide sequence as shown in SEQ ID NO: 2 or a DNA encoding such RNA (when it is RNA, thymine (t) in the nucleotide sequence shall be replaced with uracil (u)).

The nucleic acid may be a nucleic acid that comprises a mutation in a nucleotide sequence of a nucleic acid comprising: the 5' untranslated region of the genome of the HCV J6CF strain; nucleotide sequences each encoding an NS3 protein, an NS4A protein, an NS4B protein, and an NS5A protein; a nucleotide sequence encoding the sequence of amino acid residues 1 to 515 of the NS5B protein of the HCV J6CF strain; a nucleotide sequence encoding amino acid residues 516 to 591 of the NS5B protein of the HCV JFH-1 strain; and the 3' untranslated region of the HCV JFH-1 genome, and wherein the nucleic acid comprises a mutation causing substitution of alanine at position 1680 with glutamic acid.

The nucleic acid may be a chimera-typed nucleic acid comprising a mutation in a nucleotide sequence of a nucleic acid in which the 5' untranslated region of the genome of the HCV J6CF strain, nucleotide sequences each encoding a Core protein, an E1 protein, an E2 protein, a p7 protein, an NS2 protein, an NS3 protein, an NS4A protein, an NS4B protein, an NS5A protein, a nucleotide sequence encoding amino acid residues 1 to 515 of the NS5B protein (SEQ ID NO: 27) of the HCV J6CF strain, a nucleotide sequence encoding amino acid residues 516 to 591 of the NS5B protein (SEQ ID NO: 28) of the HCV JFH-1 strain, and the 3' untranslated region of the genome of the HCV JFH-1 strain are located in the order of the 5' untranslated region, nucleotide sequences each encoding a Core protein, an E1 protein, an E2 protein, a p7 protein, an NS2 protein, an NS3 protein, an NS4A protein, an NS4B protein, an NS5A protein, and an NS5B protein, and the 3' untranslated region from the 5' to 3' direction, and wherein the chimera-typed nucleic acid comprises a mutation causing substitution of alanine at position 1680 with glutamic acid. Such chimera-typed nucleic acid can be produced by substituting a part of the NS5B protein coding sequence and the 3' untranslated region of the HCV genomic sequence of the J6CF strain with the sequences of the corresponding regions derived from the genome of the JFH-1 strain and further introducing amino acid substitution A1680E thereinto. The NS5B protein in the J6CF/JFH-1 chimeric mutant nucleic acid is a chimeric NS5B protein derived from the J6CF strain and the JFH-1 strain. Preferably, such nucleic acid may comprise the nucleotide sequence as shown in SEQ ID NO: 2. The term "chimera-typed nucleic acid" (i.e., chimeric nucleic acid) or "chimera-typed HCV genome" (i.e., chimeric HCV genome) used herein refers to a nucleic acid or genome comprising genomic sequences of two or more different HCV strains.

The term "nucleic acid" includes RNA, DNA, and derivatives thereof. The terms "protein coding region," "nucleotide sequence encoding protein," "sequence encoding protein," and "protein coding sequence" used herein refer to a nucleotide sequence encoding the amino acid sequence of a given protein and may or may not contain a start codon and a stop codon.

Throughout the description, when a nucleic acid is RNA and a nucleotide sequence or a nucleotide of the RNA is identified by referring to a SEQ ID NO in the Sequence Listing, thymine (t) in the nucleotide sequence shown in the SEQ ID NO shall be replaced with uracil (u).

In the description, an amino acid at a particular position of an amino acid sequence as shown in SEQ ID NO is identified by the following expression: "(amino acid) at position 'Y' as determined on the basis of the amino acid sequence as shown in SEQ ID NO: 'X'." For example, the phrase "(amino acid) at position 'Y' as determined on the basis of the amino acid sequence of the precursor protein of the J6CF strain as shown in SEQ ID NO: 30" means that the amino acid is positioned at the "Y"th position in the amino acid sequence of the precursor protein of the HCV J6CF strain as shown in SEQ ID NO: 30 when the first amino acid (methionine) at its N-terminus is defined as the first position. When the expression "(amino acid) at position 'Y' as determined on the basis of the amino acid sequence as shown in SEQ ID NO: 'X'" is used, the amino acid identified by the expression may or may not be at the position "Y" of an amino acid sequence comprising the amino acid. Specifically, for example, the expression "a protein comprising the amino acid sequence of a precursor protein as shown in SEQ ID NO: 30 prepared by substituting alanine at 1680 with glutamic acid, as determined on the basis of the amino acid sequence of the precursor protein of the J6CF strain as shown in SEQ ID NO: 30 and inserting the reporter protein into the N terminus" means that alanine, which is present at the 1680th position of SEQ ID NO: 30 but is not at the 1680th position from the N terminus due to insertion of the reporter protein, has been substituted with glutamic acid in the protein.

The amino acid sequence of the precursor protein of the J6CF strain is shown in SEQ ID NO: 30. The amino acid sequence of the precursor protein of the J6CF strain as shown in SEQ ID NO: 30, which consists of 3033 amino acid residues starting from methionine at the translation start site to arginine (R) at position 3033, is encoded by a partial sequence consisting of nucleotides 341 to 9442 (including the stop codon) of the cDNA sequence of the full-length genomic RNA of the J6CF strain as shown in SEQ ID NO: 29.

The amino acid at position 1680 as determined on the basis of the amino acid sequence of the precursor protein of the J6CF strain as shown in SEQ ID NO: 30 is alanine (A) within the NS4A protein. Substitution of alanine (A) with glutamic acid (E) is denoted as A1680E, but it is also denoted as 1680AE, or 1680A→E. Other amino acid substitutions are denoted in a similar manner.

In the description, an amino acid is shown using a single character code that is generally used in the biology field (Sambrook et al., Molecular Cloning: A Laboratory Manual, Second Edition, 1989). In the description, an amino acid or an amino acid residue is expressed using a single character code or a three character code that is generally used in the biology field, which also includes an amino acid after post-translational modification such as hydration, glycosylation, and sulfation.

In the description, notations such as A1680E indicate substitutions of amino acid at a given position. However, such a notation also means a nucleotide mutation causing the amino acid substitution, depending on the context. When alanine (A) at position 1680 in the amino acid sequence encoded by the original nucleic acid is substituted with glutamic acid (E) due to mutation of a nucleotide of the nucleic acid, for example, such nucleotide mutation may be referred to as A1680E substitution (mutation). A nucleic acid encoding an amino acid sequence comprising such nucleotide mutation may be referred to as a nucleic acid comprising A1680E substitution (mutation) or a nucleic acid into which A1680E substitution (mutation) had been introduced. Alternatively, such mutation may be referred to as nucleotide mutation causing A1680E substitution (mutation) in the amino acid sequence. For example, an HCV replicon RNA into which A1680E substitution (mutation) had been introduced may be referred to as A1680E mutant HCV replicon RNA. When a plurality of mutations such as substitution of A1680E and amino acid substitutions of A2892S, R2959K, and Y3003F, are present simultaneously, such condition may be expressed as "comprising substitutions (mutations) of A1680E/A2892S/R2959K/Y3003F." The "amino acid substation" may be expressed as "amino acid mutation."

A nucleotide substitution causing a particular amino acid substitution can be selected based on the well known genetic code table. For example, a mutation causing A1680E substitution is a mutation of the codon encoding alanine; i.e., "GCT," "GCC," "GCA," or "GCG," into the codon encoding glutamic acid; i.e., "GAA" or "GAG." A nucleotide mutation causing A1680E substitution in the full-length genomic sequence (SEQ ID NO: 29) of the J6CF strain is a mutation of the codon "GCG" (position 5378 to 5380 in SEQ ID NO: 29) into the codon "GAA" or "GAG." Specifically, such mutation is a mutation of the nucleotide sequence of nucleotides 5379 to 5380 in SEQ ID NO: 29, i.e., 5'-cg-3', into 5'-aa-3' or a mutation of nucleotide 5379, cytosine (c), into adenine (a).

Similarly, amino acid substitution of alanine at position 2892 with serine, as determined on the basis of the amino acid sequence of the precursor protein of the J6CF strain as shown in SEQ ID NO: 30 in the Sequence Listing is denoted as A2892S. A nucleotide mutation causing A2892S substitution in the full-length genomic sequence (SEQ ID NO: 29) of the J6CF strain is a mutation of the codon encoding alanine "GCG" (positions 9014 to 9016 in SEQ ID NO: 29) into the codon encoding serine "TCT," "TCC," "TCA," "TCG," "AGT," or "AGC."

Similarly, amino acid substitution of arginine at position 2959 with lysine, as determined on the basis of the amino acid sequence of the precursor protein of the J6CF strain as shown in SEQ ID NO: 30 in the Sequence Listing is denoted as R2959K. A nucleotide mutation causing R2959K substitution in the full-length genomic sequence (SEQ ID NO: 29) of the J6CF strain is a mutation of the codon encoding arginine "AGA" (positions 9215 to 9217 in SEQ ID NO: 29) into the codon encoding lysine "AAA" or "AAG."

Similarly, amino acid substitution of tyrosine at position 3003 with phenylalanine, as determined on the basis of the amino acid sequence of the precursor protein of the J6CF strain as shown in SEQ ID NO: 30 in the Sequence Listing is denoted as Y3003F. A nucleotide mutation causing Y3003F substitution in the full-length genomic sequence (SEQ ID NO: 29) of the J6CF strain is a mutation of the codon encoding tyrosine "TAT" (positions 9347 to 9349 in SEQ ID NO: 29) into the codon encoding phenylalanine "TTT" or "TTC."

In the description, a nucleotide at a particular position of the nucleotide sequence as shown in SEQ ID NO is identified by the following expression: "(nucleotide) at position 'Y' as determined on the basis of the nucleotide sequence as shown in SEQ ID NO: 'X'." For example, the phrase "(nucleotide) at position 'Y' as determined on the basis of the nucleotide sequence as shown in SEQ ID NO: 29" means that the nucleotide is positioned at the "Y"th position in the full-length genomic nucleotide sequence of the HCV J6CF strain as shown in SEQ ID NO: 29 when the first nucleotide at its 5' terminus is defined as the first position. When the expression "(nucleotide) at position 'Y' as determined on the basis of the nucleotide sequence as shown in SEQ ID NO: 'X'" is used, the nucleotide identified by the expression may or may not be at the position "Y" of a nucleotide sequence comprising the nucleotide. Specifically, for example, the expression "replicon RNA comprising the full-length genomic sequence as shown in SEQ ID NO: 29 prepared by substituting cytosine (c) at position 9458 with guanine (g), as determined on the basis of the nucleotide sequence as shown in SEQ ID NO: 29 and inserting a reporter gene at the 5' end," for example, means that cytosine, which is present at the 9458th position of SEQ ID NO: 29 but is not at the 9458th position from the 5' end due to insertion of the reporter gene, has been substituted with guanine in the replicon RNA.

When a nucleotide substitution is to be denoted, "nt" can be additionally provided before the nucleotide number indicating the position of nucleotide mutation, to distinguish a nucleotide mutation from an amino acid substitution (or mutation). Also, a nucleotide mutation can be denoted with lower-case alphabetic letters (i.e., a: adenine; c: cytosine; g: guanine; u: uracil: and t: thymine). For example, the expression "nucleotide mutation nt9458 (c→g)" refers to substitution of a nucleotide at position 9458, cytosine (c), with guanine (g).

The nucleic acid such as the HCV subgenomic replicon RNA or HCV full-genomic replicon RNA, uses the genomic sequence of the J6CF strain as a backbone. A "nucleic acid using the J6CF genome as a backbone" refers to a nucleic acid that encodes an HCV precursor protein having 97% or more homology (preferably 99% or more, more preferably 99.5% or more, and further preferably 99.8% or more) with the amino acid sequence of the precursor protein of the J6CF strain (SEQ ID NO: 30). When the nucleic acid comprises a subgenomic sequence as a viral sequence, the degree of homology is determined in comparison with an amino acid sequence only of a region corresponding to the subgenomic sequence in the precursor protein of the J6CF strain. Homology analysis can be performed with the use of a genetic information processing software such as GENETYX®. When an amino acid sequence homology between the precursor protein of the JFH-1 strain and the precursor protein of the J6CF strain is analyzed using GENETYX® with the k-tuple value being 2, for example, the number of the identical amino acids is 2765 out of a total of 3033 amino acid residues, and the homology is 91%. A full-genomic replicon RNA derived from the J6CF strain, into which 5 mutations (i.e., A1680E, A2892S, R2959K, Y3003F, and nt9458 (c→g)) have been introduced, has 99.86% homology with the full-length genomic sequence of the wild-type J6CF strain in a precursor protein, and using the genomic sequence of the J6CF strain as a backbone. The nucleic acid using the genomic sequence of the J6CF strain as a backbone, is preferably a mutant HCV subgenomic replicon RNA derived from the J6CF strain, a mutant HCV full-genomic replicon RNA derived from the J6CF strain, or a DNA encoding such RNA.

The terms "mutant HCV subgenomic replicon RNA derived from the J6CF strain" and "mutant HCV full-genomic replicon RNA derived from the J6CF strain" refer to an HCV subgenomic replicon RNA and an HCV full-genomic replicon RNA each using the genomic sequence of the J6CF strain as a backbone and comprising one or more adaptive mutations (amino acid mutation and/or nucleotide mutation) that confer autonomous replication ability on the replicon RNA in cultured cells or improve replication efficiency, respectively.

A chimeric mutant HCV subgenomic replicon RNA or chimeric mutant HCV full-genomic replicon RNA, which is a chimera of the genomes of the J6CF strain and another HCV strain (e.g., the JFH-1 strain) and comprises one or more adaptive mutations (amino acid mutation and/or nucleotide mutation) conferring autonomous replication ability or improving replication efficiency is also within the scope of the mutant HCV subgenomic replicon RNA derived from the J6CF strain or the mutant HCV full-genomic replicon RNA derived from the J6CF strain, provided that such RNA uses the genomic sequence of the J6CF strain as a backbone as defined above.

The nucleic acid such as the mutant HCV subgenomic replicon RNA derived from the J6CF strain or the mutant HCV full-genomic replicon RNA derived from the J6CF strain, may further comprise a foreign gene such as a selectable marker gene or a reporter gene, and an IRES sequence.

For example, a mutant HCV subgenomic replicon RNA is, preferably, a nucleic acid comprising a 5' untranslated region (5' UTR), a foreign gene, an IRES sequence, sequences each encoding an NS3 protein, an NS4A protein, an NS4B protein, an NS5A protein, and an NS5B protein, and a 3' untranslated region (3' UTR) of HCV in that order from the 5' to 3' direction. A mutant HCV subgenomic replicon RNA may comprise a 5' terminal 36 nucleotide sequence of the Core protein coding region derived from the J6CF strain (the sequence of nucleotides 341 to 376 of SEQ ID NO: 29) between the 5' untranslated region and the foreign gene.

For example, the mutant HCV full-genomic replicon RNA preferably comprises a 5' untranslated region (5' UTR) of HCV, a foreign gene, an IRES sequence, sequences each encoding a Core protein, an E1 protein, an E2 protein, a p7 protein, an NS2 protein, an NS3 protein, an NS4A protein, an NS4B protein, an NS5A protein, and an NS5B protein of HCV, and a 3' untranslated region (3' UTR) of HCV in that order from the 5' to 3' direction.

A selectable marker gene is capable of conferring selectivity on a cell such that the cell in which the marker gene is expressed is exclusively selected, and an example thereof is a drug resistance gene. Examples of preferred selectable marker genes include, but are not limited to, neomycin resistance gene, hygromycin resistance gene, thymidine kinase gene, kanamycin resistance gene, pyrithiamine resistance gene, adenylyltransferase gene, zeocin resistance gene, and puromycin resistance gene. The neomycin resistance gene and the thymidine kinase gene are more preferred, and the neomycin resistance gene is further preferred.

The reporter gene encodes a gene product that serves as the indicator of gene expression. Examples of preferred reporter genes include structural genes of enzymes that catalyze luminescent reactions or color reactions. Examples of preferred reporter genes include, but are not limited to, chloramphenicol acetyl transferase gene derived from transposon Tn9, β-glucuronidase or β-galactosidase gene derived from E. coli, luciferase gene, green fluorescent protein gene, aequorin genes derived from jellyfish, and secretory placental alkaline phosphatase (SEAP) gene.

The HCV replicon RNA may contain either one or both of the drug resistance gene and the reporter gene. The HCV replicon RNA may contain one, or two or more marker genes such as the drug resistance gene or the reporter gene.

The term "IRES sequence" refers to an internal ribosome entry site that can allow a ribosome to bind an internal region of RNA and start translation. Preferred examples of the IRES sequence include EMCV IRES (internal ribosome entry site of encephalomyocarditis virus), FMDV IRES, and HCV IRES. The EMCV IRES and the HCV IRES are more preferred, and the EMCV IRES is the most preferred.

The drug resistance gene and/or the reporter gene are ligated to the 5' untranslated region, the virus protein-coding sequence, and the 3' untranslated region, to be translated in a proper reading frame (in-frame) from the HCV subgenomic replicon RNA or HCV full-genomic replicon RNA.

More preferably, the nucleic acid is a subgenomic replicon RNA or full-genomic replicon RNA having autonomous replication ability. Accordingly, we also provide a hepatitis C virus subgenomic replicon RNA or full-genomic replicon RNA comprising the nucleic acid.

The nucleic acid can be prepared using a DNA cloned from cDNA reverse-transcribed from the genomic RNA of the J6CF strain (GenBank Accession No. AF177036) and a DNA cloned from cDNA reverse-transcribed from the genome of the JFH-1 strain (GenBank Accession No. AB047639).

A nucleic acid construct comprising the subgenome derived from the J6CF strain can be prepared by, for example, excising with a restriction enzyme, or substituting via homologous recombination, a part of the DNA cloned from cDNA reverse-transcribed from the genomic RNA of the J6CF strain. For example, the region from the 37th position from the 5' terminus of the Core protein coding region to the NS2 protein coding region of the J6CF genomic clone (pJ6CF) may be substituted with a nucleotide sequence comprising a foreign gene and an IRES sequence (e.g., an EMCV IRES sequence) to prepare the nucleic acid construct comprising the subgenome derived from the J6CF strain.

A nucleic acid construct comprising the J6CF/JFH-1 chimeric HCV subgenome or full genome (chimeric HCV genome) without an A1680E mutation can be prepared by performing PCR using vectors cloned from cDNAs of the HCV genomic RNAs of the J6CF strain and the JFH-1 strain as a template, amplifying each of the HCV genomic regions to be ligated, and ligating the amplified regions to each other. For example, the region from the 5' untranslated region to the position 515 of the amino acid sequence of the NS5B protein of the J6CF strain may be amplified, the region from the position 516 to the 3' UTR of the amino acid sequence of the NS5B protein of the JFH-1 strain may be amplified, and these amplified products may be ligated to each other. Such technique is described in, for example, Wakita, T. et al., Nat. Med., (2005) Vol. 11, pp. 791-796; Lindenbach, B. D. et al., Science, (2005) Vol. 309, pp. 623-626; and Pietschmann, T. et al., Proc. Natl. Acad. Sci., U.S.A., (2007) Vol. 103, pp. 7408-7413.

Mutation can be introduced into the wild-type HCV genomic sequence or a chimeric HCV genomic sequence using PCR or a commercially available mutagenesis kit (e.g., KOD-Plus-Mutagenesis Kit manufactured by Toyobo Co., Ltd.). In a method using PCR, for example, a target sequence portion comprising a mutation can be amplified by PCR using a vector constructed by cloning cDNA of the wild-type HCV genomic RNA as a template and using forward and reverse primers designed from the cDNA sequence and comprising mutations of interest. Specifically, the target nucleic acid can be amplified by synthesizing a plurality of different PCR products having sequences overlapping with each other, mixing the PCR products, and performing PCR using the resulting mixture as a template, a forward primer containing the 5' terminus of the target nucleic acid, and a reverse primer containing the 5' terminus of the complementary strand of the nucleic acid. Each terminus of the synthesized nucleic acid is cleaved with a restriction enzyme and ligated to a vector constructed by cloning cDNA of the wild-type HCV genomic RNA and cleaved with the same enzyme. Thus, a mutation of interest can be introduced. Such techniques are also described in, for example, International Publication WO 04/104198 and WO 06/022422, Wakita, T. et al., (2005) Nat. Med., No. 11, pp. 791-796, and Lindenbach, B. D. et al., (2005) Science, No. 309, pp. 623-626.

When a mutation is to be introduced into the wild-type full-length HCV genomic sequence or the chimeric full-length HCV genomic sequence, a mutation may be introduced into the wild-type full-length HCV genomic sequence in the manner described above. Alternatively, a mutation may be first introduced into the wild-type HCV subgenomic sequence, and a missing sequence portion (e.g., a structural gene) compared with the wild-type HCV genomic sequence may then be ligated thereto to prepare a full-genomic sequence.

The mutant HCV subgenomic replicon RNA derived from the J6CF strain or the mutant HCV full-genomic replicon RNA derived from the J6CF strain can be prepared by preparing an expression vector in which a DNA encoding such RNA is cloned and introducing it into host cells to express the RNA.

The expression vector used in preparation of such mutant HCV replicon RNA can be prepared in accordance with a conventional technique. Preferably, the expression vector can be prepared using the technique described in International Publication WO 05/080575.

Specifically, for example, a DNA fragment (e.g., cDNA) corresponding to the mutant HCV subgenomic replicon RNA derived from the J6CF strain or the mutant HCV full-genomic replicon RNA derived from the J6CF strain is inserted downstream of a promoter in the expression vector using a conventional technique, to prepare a DNA clone. The expression vector refers to a vector comprising a promoter capable of inducing transcription of a gene or an RNA coding sequence under the control thereof. A plasmid vector is preferred as an expression vector. Examples of the promoters that can be used include T7 promoter, SP6 promoter, and T3 promoter, and the T7 promoter is preferred. Examples of the vectors that can be used include pUC19 (TaKaRa), pBR322 (TaKaRa), pGEM-T, pGEM-T Easy, pGEM-3Z, and pSP72 (Promega Corp.), pCRII (Invitrogen Corp.), and pT7Blue (Novagen, Inc.).

We also provide an expression vector comprising the nucleic acid as prepared in the manner described above. Such expression vector is capable of expressing (i.e., inducing transcription of) the mutant HCV subgenomic replicon RNA derived from the J6CF strain or the mutant HCV full-genomic replicon RNA derived from the J6CF strain. Such expression vector is referred to as the "replicon RNA expression vector."

The mutant HCV subgenomic replicon RNA or the mutant HCV full-genomic replicon RNA can be produced from a cloned expression vector by synthesizing RNA with an RNA polymerase using the produced DNA clone as described above as a template. When producing the RNA in vitro using a nucleic acid cloned from HCV cDNA under the control of the T7 promoter as a template, synthesis can be carried out with, for example, the MEGAscript T7 kit (Ambion, Inc.). The RNA synthesis can be started from the 5' UTR by a conventional method. When the DNA clone is a plasmid clone, RNA can also be synthesized using a DNA fragment cleaved out from the plasmid clone with a restriction enzyme as a template. It is preferred that the 3' terminus of the synthesized RNA coincide with the terminus of the 3' UTR of the HCV genomic RNA and that no other sequence be added or deleted.

The resulting mutant HCV subgenomic replicon RNA derived from the J6CF strain or mutant HCV full-genomic replicon RNA derived from the J6CF strain can be extracted and purified in accordance with an RNA extraction technique or purification technique well known for a skilled person in the art.

The mutant HCV subgenomic replicon RNA derived from the J6CF strain or the mutant HCV full-genomic replicon RNA derived from the J6CF strain prepared as described above can autonomously replicate in cultured cells with high efficiency. Cells in which replicon RNAs autonomously replicate can be obtained by introducing the mutant HCV subgenomic replicon RNA derived from the J6CF strain or the mutant HCV full-genomic replicon RNA derived from the J6CF strain into cells. We also provide cells into which such mutant HCV subgenomic replicon RNA derived from the J6CF strain or the mutant HCV full-genomic replicon RNA derived from the J6CF strain (or the nucleic acid comprising the HCV subgenomic sequence or full-genomic sequence) had been introduced.

An HCV replicon RNA can be introduced into cells with any known techniques. Examples of such techniques include calcium phosphate coprecipitation, a DEAE-dextran method, lipofection, microinjection, and electroporation. Lipofection and electroporation are preferred, and electroporation is further preferred.

In the cells into which the mutant HCV subgenomic replicon RNA derived from the J6CF strain or the mutant HCV full-genomic replicon RNA derived from the J6CF strain had been introduced, autonomous replication ability (replication ability) of the HCV replicon RNA can be evaluated based on, for example, functions of a foreign gene such as a selectable marker gene or reporter gene, contained in the HCV replicon RNA; i.e., activity of a gene product of the foreign gene resulting from expression.

When a foreign gene is a drug resistance gene, the replication ability of the HCV replicon RNA can be evaluated by, for example, culturing the cells in a selection medium containing a drug to which the gene is resistant, and counting the number of cells or the number of colonies of cells propagating therein. In that case, a larger number of cells or colonies of cells indicates higher replication ability.

When a foreign gene is an enzyme gene, typically, the replication ability of the HCV replicon RNA can be evaluated by culturing cells into which the HCV replicon RNA had been introduced, and assaying the enzyme activity therein. In that case, higher enzyme activity indicates higher replication ability. When the mutant HCV subgenomic replicon RNA derived from the J6CF strain or the mutant HCV full-genomic replicon RNA derived from the J6CF strain contains the luciferase gene, for example, luciferase activity in the cells can be assayed with a conventional technique.

Alternatively, the replication ability of the replicon RNA can be directly evaluated by quantifying the amount of the HCV replicon RNA in the cells into which the HCV replicon RNA had been introduced by quantitative RT-PCR.

If the amount of the mutant HCV subgenomic replicon RNA derived from the J6CF strain or the mutant HCV full-genomic replicon RNA derived from the J6CF strain tends to increase in cultured cells over time, the replicon RNA can be evaluated as having autonomous replication ability. Even if the replication level of the HCV replicon RNA is temporarily lowered to some extent (e.g., prior to approximately 24 hours after transfection into cells), the replicon RNA can be evaluated as having autonomous replication ability if the replication level continuously increases thereafter (e.g., from 30 hours after transfection). This is because a certain period of time is necessary until the amount of the replicated replicon RNA begins to increase after transfection.

The mutant HCV full-genomic replicon RNA derived from the J6CF strain has HCV particle producing ability in cultured cells. When the HCV full-genomic replicon RNA is introduced into cultured cells, it is continuously replicated therein, the replicated mutant HCV full-genomic replicon RNA derived from the J6CF strain (or the nucleic acid comprising the HCV full-genomic sequence) is packaged in a virus capsid composed of the HCV structural proteins (the Core protein, the E1 protein, the E2 protein, and the p7 protein) expressed in the cells, and the resulting HCV particles are released extracellularly.

The HCV particle producing ability of the mutant HCV full-genomic replicon RNA derived from the J6CF strain in cultured cells can be evaluated by introducing the RNA into the cells and culturing the cells, and measuring the HCV particles in the resulting culture supernatant. The HCV particles in the culture supernatant can be measured by detecting a structural protein constituting the HCV particles (e.g., the Core protein, the E1 protein, E2 protein, or p7 protein). The structural proteins in the culture supernatant can be detected using, for example, the antibodies against the Core protein, the E1 protein, or the E2 protein.

If the amount of the structural protein of the HCV particles detected in the culture supernatant tends to increase over time, the cells can be evaluated as producing HCV particles and releasing the HCV particles extracellularly. Whether or not the mutant HCV full-genomic replicon RNA derived from the J6CF strain can produce HCV particles in the cultured cells into which the replicon RNA is introduced is significantly influenced by the nucleotide sequence of the replicon RNA or the amino acid sequence of the protein encoded by the nucleotide sequence. If the production of HCV particles is observed, accordingly, the mutant HCV full-genomic replicon RNA derived from the J6CF strain that had been introduced into the cultured cells can be evaluated as having the virus particle producing ability in the cultured cells.

The virus particles produced and released by the cultured cells into which the mutant HCV full-genomic replicon RNA derived from the J6CF strain (or the nucleic acid comprising the HCV full-genomic sequence) had been introduced have an ability to infect another cultured cell. We provide such infectious HCV particles. The infectious HCV particles contains the mutant HCV full-genomic replicon RNA derived from the J6CF strain (or the nucleic acid comprising the HCV full-genomic sequence) as the virus genome.

The infectious ability of the HCV particles can be evaluated in the following manner. That is, the mutant HCV full-genomic replicon RNA derived from the J6CF strain is introduced into cells, the cells are cultured, the resulting culture supernatant is added to cultured cells (e.g., Huh7 cells or cells derived therefrom), the cells are subjected to immunostaining with an anti-Core antibody after a certain period of time (e.g., 48 hours later), and the number of the infected cells is then counted. Alternatively, the cell extract is subjected to SDS-polyacrylamide gel electrophoresis, the Core protein is detected via Western blotting, and the infected cells are then detected. Thus, the infectious ability can be evaluated.

Typically, the cells into which the mutant HCV subgenomic replicon RNA derived from the J6CF strain or the mutant HCV full-genomic replicon RNA derived from the J6CF strain are to be introduced or the cells that are to be infected with the infectious HCV particles produced in the cultured cells into which the HCV replicon RNA had been introduced are cultured cells. Particularly preferably, the cultured cells are cells permissive for autonomous replication of the HCV replicon RNA or formation and infection of HCV particles (such cells are referred to as HCV-sensitive cells).

Examples of the HCV-sensitive cells include hepatogenic cells such as Huh7 cells, HepG2 cells, and IMY-N9 cells; HeLa cells; 293 cells; and derivative cells thereof. Examples of derivative cells include cells derived from Huh7 cells such as Huh7.5 cells and Huh7.5.1 cells. Other examples of derivative cells include Huh7 cells, HepG2 cells, IMY-N9 cells, HeLa cells, and 293 cells engineered to express CD81 genes and/or Claudin1 genes (Lindenbach, B. D. et al., Science, (2005) vol. 309, pp. 623-626; Evans, M. J. et al., Nature, (2007) vol. 446, pp. 801-805; and Akazawa, D. et al., J. Virol., (2007) vol. 81, pp. 5036-5045). Huh7 cells and derivative cells thereof (e.g., Huh7.5 cells and Huh7.5.1 cells) are particularly preferred. The term "derivative cell" used with reference to a particular cell refers to a cell derived from such cell.

Use of the cells into which the mutant HCV full-genomic replicon RNA derived from the J6CF strain had been introduced and the cells infected with HCV particles comprising the mutant HCV full-genomic replicon RNA derived from the J6CF strain as the virus genome enables mass production of HCV particles via culture.

When the HCV particles produced and released extracellularly by the HCV-sensitive cells into which the mutant HCV full-genomic replicon RNA derived from the J6CF strain had been introduced are allowed to infect another HCV-sensitive cell, the HCV full-genomic replicon RNA (genome RNA) is replicated and packaged in the cell to produce HCV particles, and the cycle of the steps can be repeated. The cells can be infected with the produced HCV particles by, for example, adding the culture supernatant of the cells into which the HCV full-genomic replicon RNA had been introduced to the HCV-sensitive cells.

HCV particles that are obtained via introducing the mutant HCV full-genomic replicon RNA derived from the J6CF strain (or the nucleic acid comprising the HCV full-genomic sequence) into the HCV-sensitive cells can be used for HCV vaccines or antigens for preparation of anti-HCV antibodies.

Specifically, the HCV particles can be used for the production of vaccines. For vaccine use, specifically, intact HCV particles as described above, or a portion thereof, or a processed product thereof can be directly used as an antigen for vaccines. However, it is preferred that the HCV particles be attenuated or inactivated by a known method and the resulting processed HCV particles be used in preparation of vaccines. The virus can be inactivated by adding an inactivating agent such as formalin, β-propiolactone, or glutardialdehyde to, for example, a virus suspension, followed by mixing, to allow the agent to react with the virus (Appaiahgari, M. B. & Vrati, S., Vaccine, (2004) vol. 22, pp. 3669-3675). Alternatively, the HCV particles may be irradiated with ultraviolet rays to decompose HCV RNA, thereby destroying HCV infectivity (JP 2009-5589 A).

More preferably, the hepatitis C virus vaccine comprising the HCV particles is a vaccine comprising the intact HCV particles as described above or the attenuated or inactivated products thereof as antigens.

The vaccine can be prepared in an administrable form of solution or suspension. Alternatively, the vaccine can be prepared in a solid form (e.g., a lyophilized preparation) suitable for being dissolved or suspended in a liquid, so that the vaccine can be reconstituted immediately before use. Such a solid or preparation may be emulsified, or encapsulated in a liposome.

Active immunogenic ingredients such as HCV particles, can be often mixed with a pharmaceutically acceptable excipient that is compatible with the active ingredients. Examples of suitable excipient include water, physiological saline, dextrose, glycerol, ethanol, and mixtures thereof.

Furthermore, the vaccine can optionally contain a small amount of an auxiliary agent (e.g., a humidifier or emulsifier), a pH adjuster, and/or an adjuvant for enhancing vaccine efficacy.

The adjuvant is a non-specific stimulant to the immune system. It enhances the immune response of a host against the vaccine. Preferably, accordingly, the vaccine contains an adjuvant. Adjuvant efficacy can be determined by measuring the amount of antibodies resulting from administration of a vaccine composed of HCV particles.

Examples of an effective adjuvant include, but are not limited to, aluminum hydroxide, N-acetyl-muramyl-L-threonyl-D-isoglutamine (thr-MDP), N-acetyl-nor-muramyl-L-alanyl-D-isoglutamine (referred to as CGP11637 or nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (referred to as CGP19835A or MTP-PE), and RIBI. RIBI contains three components extracted from bacteria, i.e., monophosphoryl lipid A, trehalose dimycolate, and a cell wall skeleton (HPL+TDM+CWS), in 2% squalene/Tween® 80 emulsion.

Optionally, one or more compounds having adjuvant activity can be added to the vaccine as described above. Specific examples of known adjuvants include Freund's complete adjuvants, Freund's incomplete adjuvants, vitamin E, non-ionic block polymers, muramyl dipeptide, saponin, mineral oil, vegetable oil, and Carbopol. Examples of adjuvants that are particularly suitable for mucosal application include *Escherichia coli* (*E. coli*) thermolabile toxin (LT) and Cholera toxin (CT). Examples of other adequate adjuvants include aluminum hydroxide, aluminum phosphate, aluminum oxide, oil emulsion (e.g., Bayol® or Marcol 52®), saponin, and vitamin E solubilizates.

The HCV vaccine is generally administered parenterally, or by injection such as subcutaneous injection or intramuscular injection. Examples of other formulations that are suitable as other dosage forms include suppositories and, optionally, oral preparations.

In injections for subcutaneous, intracutaneous, intramuscular, or intravenous administration, specific examples of the pharmaceutically acceptable carrier or diluent for the HCV vaccine include stabilizers, carbohydrates (e.g., sorbitol, mannitol, starch, sucrose, glucose, and dextran), proteins such as albumin and casein, protein-containing substances such as bovine serum and skimmed milk, and buffers (e.g., phosphate buffer).

Examples of conventional binders and carriers that are to be used for the suppositories include polyalkylene glycol and triglyceride. The suppositories can be prepared from a mixture containing an active ingredient in an amount of 0.5% to 50%, and preferably 1% to 20%. The oral preparations contain excipients that are generally used. Examples of excipients include pharmaceutical-grade mannitol, lactose, starch, magnesium stearate, saccharine sodium, cellulose, and magnesium carbonate.

The HCV vaccine as described above is in the form of a solution, suspension, tablet, pill, capsule, sustained-release formulation, or powder, and it contains an active ingredient (HCV particles or a portion thereof) in an amount of 10% to 95%, and preferably 25% to 70%.

The HCV vaccine as described above is administered in a manner suitable for a dosage form and at a dose at which preventive and/or therapeutic effects can be achieved. The amount of an antigen to be administered is usually in a range of 0.01 μg to 100,000 μg per administration, and it depends on the patient to whom the vaccine is administered, the capacity of the patient for antibody synthesis in the immune system, and the desired degree of protection. The amount also depends on the administration route such as oral, subcutaneous, intracutaneous, intramuscular, or intravenous administration. The HCV vaccine may be administered according to a single-administration schedule or a multiple-administration schedule, and the multiple-administration schedule is preferred. In the multiple-administration schedule, one to ten separate administrations are performed at the time of initiation of inoculation, and another administration can be subsequently performed at a time interval that is necessary for maintaining and/or enhancing the immune response. For example, the second administration can be performed one to four months later. Administration may optionally be subsequently performed several months later. The administration regimens are determined depending on, at least partially, the necessity of an individual, and the regimens depend on the judgment made by a doctor.

The HCV vaccine may be administered to a healthy individual to induce an immune response to HCV in the healthy individual for the prevention of new HCV infection. Further, the vaccine may be used as a therapeutic vaccine that is intended to eliminate HCV by administering the same to a patient infected with HCV to induce a potent immune response against HCV in vivo.

We also provide the HCV vaccine described above. The HCV vaccine can be used for the prevention of HCV infection and for the treatment of hepatitis C.

The HCV particles described above are also useful as the antigens to produce anti-HCV antibodies. The antibodies can be produced by administering the HCV particles to mammals or birds. Examples of mammals include mice, rats, rabbits, goats, sheep, horses, cattle, guinea pigs, dromedaries, Bactrian camels, and lamas. Dromedaries, Bactrian camels, and lamas are suitable to produce an antibody consisting of the H chain. Examples of birds include chickens, geese, and ostriches. Sera are collected from the animals to which the HCV particles have been administered, and the antibody of interest can be obtained in accordance with a conventional technique.

We also provide the anti-HCV antibodies. Particularly preferred anti-HCV antibodies can be used as neutralizing antibodies that can inactivate HCV.

Cells of animals immunized via administration of the HCV particles can be used to produce hybridomas that generate monoclonal antibody-producing cells. Hybridomas can be produced by a method well known in the art such as the method described in Antibodies: A Laboratory Manual (Cold Spring Harbor Laboratory, 1988).

The monoclonal antibody-producing cells may be produced through cell fusion or other methods such as methods involving introduction of an oncogene DNA or immortalization of B lymphocytes by infection with Epstein-Barr virus.

Monoclonal or polyclonal antibodies obtained by such methods are useful for diagnosis of HCV, and therapy and prevention of hepatitis C.

The antibody produced by using the HCV particles as the antigens can be administered as a medicament together with a pharmaceutically acceptable solubilizer, additive, stabilizer, buffer, and/or the like. The administration may be made through any route, and subcutaneous, intracutaneous, or intramuscular administration is preferred, and intravenous administration is more preferred.

The cells into which the mutant HCV subgenomic replicon RNA derived from the J6CF strain or the mutant HCV full-genomic replicon RNA derived from the J6CF strain (or the nucleic acid comprising the HCV subgenomic sequence or the full-genomic sequence) had been introduced or the HCV particles comprising the mutant HCV full-genomic replicon RNA derived from the J6CF strain (or the nucleic acid comprising the HCV full-genomic sequence) as the virus genome can be preferably used in screening for substances such as neutralizing antibodies that inhibit HCV infection or compounds that inhibit HCV infection or replication. In an example of the method, in the presence or absence of a test substance, the cells into which the replicon RNA had been introduced and which replicate the replicon RNA are cultured, or the cells into which the full-genomic replicon RNA had been introduced and which produce HCV particles are cultured, or the HCV particles as described above are cultured with the HCV-sensitive cells, or the cells infected with the HCV particles as described above are cultured; and the HCV replicon RNA or HCV particles in the resulting culture are detected to evaluate the influence of the test substance. The term "culture" used herein includes a culture supernatant, a cell, and a cell lysate. Detection is preferably carried out via quantification of the amount of the HCV replicon RNA in a cell or a cell lysate or that of HCV particles in a culture supernatant. If HCV replicon RNA and HCV particles are not present in the culture in the presence of the test substance or the amount thereof is smaller than that in the absence of the test substance, the test substance used can be evaluated to be capable of inhibiting HCV infection or replication.

For example, anti-HCV substances can be screened for by culturing the HCV-sensitive cells together with the HCV particles in the presence and in the absence of the test substance, and detecting HCV particles or HCV replicon RNA in the culture, and determining whether or not the test substance inhibits HCV particle production (including infection, formation, and release) or replication of the HCV replicon RNA.

For example, we provide a method of screening for an anti-hepatitis C virus substance comprising: (i) a step of culturing the cell into which the replicon RNA had been introduced in the presence and in the absence of a test substance; (ii) a step of quantifying the amount of replicon RNA (or HCV particles) in the culture obtained in step (i); and (iii) a step of comparing the amount of replicon RNA (or HCV particles) quantified in the presence of the test substance with that of replicon RNA (or HCV particles) quantified in the absence of the test substance, to evaluate the replication-inhibiting activity of the test substance on the replicon RNA (or the HCV particle production-inhibiting activity).

In one example, the screening method is a method of screening for an anti-hepatitis C virus substance comprising:
  a step of culturing the cells into which the mutant HCV subgenomic replicon RNA derived from the J6CF strain or mutant HCV full-genomic replicon RNA derived from the J6CF strain (or the nucleic acid comprising the HCV subgenomic sequence or the full-genomic sequence) had been introduced, or a mixture of the HCV particles containing the mutant HCV full-genomic replicon RNA derived from the J6CF strain (or the nucleic acid comprising the HCV full-genomic sequence) as the virus genome with the HCV-sensitive cells, in the presence and in the absence of a test substance;
  a step of quantifying the amount of the subgenomic replicon RNA, the full-genomic replicon RNA, or the HCV particles generated in the culture via the step of culture; and
  a step of evaluating the test substance from the result of the above quantifying step in a manner such that if the amount of the subgenomic replicon RNA, the full-genomic replicon RNA, or the HCV particles quantified in the presence of a test substance is lower than that of the subgenomic replicon RNA, the full-genomic replicon RNA, or the HCV particles quantified in the absence of the test substance, the test substance is evaluated as having anti-hepatitis C virus activity.

HCV replicon RNA in a culture can be detected based on the functions of the foreign gene in the HCV replicon RNA; i.e., based on functions occurring as a result of expression of the foreign gene. When the foreign gene is an enzyme, for example, the enzyme activity can be assayed to detect the HCV replicon RNA. Alternatively, the HCV replicon RNA can be detected by quantifying the amount of RNA replicated in the culture via quantitative RT-PCR.

HCV particles in the culture can be detected using antibodies against proteins (e.g., the Core protein, E1 protein, or E2 protein) constituting the HCV particles released into the culture supernatant. Alternatively, HCV particles in the culture can be detected via immunostaining of non-structural proteins in the cells using antibodies against the non-structural proteins. The presence of the HCV particles can be indirectly detected by detecting the HCV replicon RNA contained in the HCV particles in the culture supernatant by amplifying the HCV replicon RNA via RT-PCR using specific primers.

The HCV full-genomic replicon RNA comprising the above-mentioned mutation(s) prepared by inserting a foreign gene and an IRES sequence into a genome of the J6CF mutant or the J6CF/JFH-1 chimeric mutant genome (consisting of an RNA in which the 5' UTR, the 5' terminal 36 nucleotides of the Core protein coding sequence, a luciferase gene, an EMCV IRES sequence, the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' UTR ligated in that order from the 5' to 3' direction can be advantageously used for screening for anti-HCV substances. When ligating regions to each other, an additional sequence such as a restriction enzyme site may be present at the site of ligation. The HCV full-genomic replicon RNA is introduced into Huh7 cells to obtain HCV particles, and HCV-sensitive cells are infected with the HCV particles with addition of the test substance, and the luciferase activity is measured 48 to 72 hours thereafter. A test material found to have an effect to inhibit the luciferase activity compared to the case of no addition of test substance (i.e., in the absence of the test substance) is determined to have activity of inhibiting infection with HCV.

Also, the mutant HCV subgenomic replicon RNA derived from the J6CF strain consisting of the nucleic acid as shown in SEQ ID NO: 1 or SEQ ID NO: 4 may be introduced into Huh7 cells. Subsequently the test substance may be added, and the luciferase activity may then be measured 48 to 72 hours thereafter. A test substance can be determined to have activity of inhibiting replication of HCV subgenomic replicon RNA if the test substance can inhibit the luciferase activity more effectively than in the case of no addition of test substance.

The anti-HCV substance obtainable as a result of the screening method described above is preferably capable of inhibiting virus infection or replication.

EXAMPLES

Our methods and materials are described in greater detail with reference to the following examples. It should be noted that these examples are provided for illustrative purposes and the technical scope of this disclosure is not limited to these examples.

At the outset, we prepared an HCV full-genomic replicon RNA, FGR-J6/5BSLX-JFH1, by substituting a part of the NS5B region derived from the J6CF strain and the 3' untranslated region in the HCV full-genomic replicon RNA, FGR-J6/N3H+5BSLX-JFH1, with the corresponding regions of the JFH-1 strain. Murayama et al., PLoS Pathogens., (2010) vol. 6, e1000885 discloses that the HCV full-genomic replicon RNA, FGR-J6/N3H+5BSLX-JFH1, was prepared by substituting the NS3 helicase region, a part of the NS5B protein region, and the 3' untranslated region of the J6CF strain with the corresponding regions of the JFH-1 strain. FGR-J6/5BSLX-JFH1 corresponds to an RNA having a structure in which the NS3 helicase region derived from the JFH-1 strain in FGR-J6/N3H+5BSLX-JFH1 has been restored to that derived from the JFH-1 strain. The prepared HCV full-genomic replicon RNA, FGR-J6/5BSLX-JFH1, was introduced into cultured cells. Although FGR-J6/5BSLX-JFH1 did not have autonomous replication ability, we had repeated subculture thereof, and a mutant that had acquired high autonomous replication ability was obtained as a consequence. We succeeded in finding a mutation which would remarkably enhance autonomous replication ability of replicon RNA, existing at a single site in the NS4A protein region. This mutation causes a substitution of alanine at position 1680 of the amino acid sequence (SEQ ID NO: 30) of the precursor protein of the J6CF strain (HCV precursor polyprotein) with glutamic acid. We also succeeded in the preparation of a full-genomic replicon RNA derived from the J6CF strain having high autonomous replication ability and infectious HCV particle-producing ability by introducing five mutations: the above-mentioned single mutation in the NS4A protein region, and four mutations in the NS5B protein region and the 3' untranslated region as described in Murayama et al., PLoS Pathogens., (2010) vol. 6, e1000885, into the genome of the wild-type J6CF strain. Hereafter, these are described in more detail.

Example 1

Construction of J6CF/JFH-1 Chimeric HCV Subgenomic Replicon RNA Expression Vector and HCV Full-Genomic Replicon RNA (Full-Length HCV Genomic RNAs) Expression Vector In this Example, expression vectors for synthesizing a chimera-typed (J6CF/JFH-1 chimeric) HCV subgenomic replicon RNA (J6CF/JFH-1 chimeric HCV subgenomic replicon RNA) and a chimera-typed (J6CF/JFH-1 chimeric) HCV full-genomic replicon RNA (J6CF/JFH-1 chimeric HCV full-genomic replicon RNA) derived from the genomic sequences of the J6CF strain and the JFH-1 strain to be used for the production of mutant replicons in the Examples below were constructed.

The nucleotide numbers below indicate the positions of nucleotides starting from the first nucleotide at the 5' terminus of the full-length genome of each HCV strain that is defined to be the first position. When the position of a DNA fragment resulting from digestion with restriction enzymes in the original DNA sequence is to be indicated by the nucleotide number, it is indicated by the nucleotide number at the start position of the recognition sequence of the restriction enzyme. For example, when the full-length genome of the JFH-1 strain is digested with ClaI and EcoT22I, the ClaI recognition sequence starts at nucleotide 3929 in the full-length genome of the JFH-1 strain, and such sequence is cleaved at a site between nucleotide 3930 and nucleotide 3931 by ClaI; and the EcoT22I recognition sequence starts at nucleotide 5293 in the full-length genome of the JFH-1 strain, and such sequence is cleaved at a site between nucleotide 5297 and nucleotide 5298 by EcoT22I. In this case, a DNA fragment resulting from the digestion with ClaI and EcoT22I is denoted as "being (or equivalent to) the nucleotide sequence of nucleotides 3929 to 5293 of the full-length genome of the JFH-1 strain."

pJFH1 is a plasmid DNA disclosed in Wakita, T. et al., Nat. Med., (2005) vol. 11, pp. 791-796. pJFH1 was prepared by cloning the genomic cDNA obtained via reverse transcription of the full-length genomic RNA of the HCV JFH-1 strain (GenBank Accession No. AB047639) into downstream of the T7 RNA promoter sequence inserted into the pUC19 plasmid.

pJ6CF is a plasmid DNA prepared from the plasmid disclosed in Yanagi, M. et al., Virology, (1999) vol. 262, pp. 250-263. pJ6CF was prepared by cloning the genomic cDNA obtained via reverse transcription of the full-length genomic RNA of the HCV J6CF strain (GenBank Accession No. AF177036) into downstream of the T7 RNA promoter sequence inserted into the pUC19 plasmid.

An HCV subgenomic replicon RNA expression vector, pSGR-J6/N3H+5BSLX-JFH1/Luc, (FIG. 1C) is a plasmid DNA also described in Murayama, A. et al., PLoS Pathogens., (2010) vol. 6, e1000885. To prepare pSGR-J6/N3H+5BSLX-JFH1/Luc, a DNA fragment obtained by digestion of pJFH1 with ClaI and EcoT22I (equivalent to the nucleotide sequence of nucleotides 3929 to 5293 of the full-length genome of the JFH-1 strain; i.e., a part of the NS3 protein) was used to substitute for a sequence of the corresponding region in the plasmid pSGR-J6CF/Luc (comprising 5' terminal 36 nucleotides of the Core protein, the luciferase gene, and the EMCV IRES, and encoding a subgenomic replicon RNA of the J6CF strain; FIG. 1B) described in Murayama, A. et al., J. Virology, (2007) vol. 81, pp. 8030-8040, and the nucleotide sequence in the plasmid corresponding to nucleotides 9212 to 9711 (i.e., to the 3' terminus of the genome of the J6CF strain) of the full-length genome of the J6CF strain (SEQ ID NO: 29) was substituted with the nucleotide sequence of nucleotides 9212 to 9678 (i.e., to the 3' terminus of the genome of the JFH-1 strain) of the full-length genome of the JFH-1 strain (GenBank Accession No. AB047639).

A specific method of preparing pSGR-J6/N3H+5BSLX-JFH1/Luc (FIG. 1C) is as follows. First, the ClaI restriction enzyme site (the recognition sequence starts at nucleotide 3929 of the full-length genome of the J6CF strain and it is cleaved between nucleotide 3930 and nucleotide 3931 by ClaI) and the EcoT22I restriction enzyme site (the recognition sequence starts at nucleotide 5293 of the full-length genome of the J6CF strain and it is cleaved between nucleotide 5297 and nucleotide 5298 by EcoT22I) were introduced into pSGR-J6CF/Luc via PCR, and the resultant was cleaved by ClaI and EcoT22I. Into the resulting pSGR-J6CF/Luc cleavage fragment, a DNA fragment obtained by digestion of pJFH1 with ClaI and EcoT22I (i.e., the nucleotide sequence of nucleotides 3929 to 5293 of the full-length genome of the JFH-1 strain) was inserted for substitution of the region from ClaI to EcoT22I sites. As a result, the NS3 helicase region of the J6CF strain (from nucleotides 3929 to 5293 of the full-length genome of the J6CF strain) was substituted with a sequence of the corresponding region of the JFH-1 strain (the "N3H" region in FIG. 1C). The resulting plasmid DNA is referred to as "pSGR-J6/N3H-JFH1/Luc."

Subsequently, as 1st PCR-1, PCR was carried out using pJ6CF as a template, 8680S-2a sense primer (5'-CCT-TCACGGAGGCTATGACCA-3'; SEQ ID NO: 7), and 9191R-2a antisense primer (5'-CCACGGGAGATGAGG-GACGC-3'; SEQ ID NO: 8). In addition, as 1st PCR-2, PCR was carried out using pJFH1 as a template, 9191S-2a sense primer (5'-GCGTCCCTCATCTCCCGTGG-3'; SEQ ID NO: 9), and 9440R-IH antisense primer (5'-GTGTACCTAGTGT-GTGCCGCTCTA-3'; SEQ ID NO: 10). Further, as 2nd PCR, PCR was carried out using a mixture of two types of the amplified fragments obtained by the 1st PCR-1 and the 1st PCR-2 as a template, 8680S-2a sense primer (SEQ ID NO: 7), and 9440R-IH antisense primer (SEQ ID NO: 10). The resulting chimeric amplified product from the J6CF strain and the JFH-1 strain was digested with SfiI and AscI to produce a DNA fragment (corresponding to the region of nucleotides 8794 to 9211 of the full-length genome of the J6CF strain and the region of nucleotides 9212 to 9291 of the full-length genome of the JFH-1 strain), and the produced DNA fragment and an AscI/XbaI-digested DNA fragment of pJFH1 (corresponding to the region from nucleotide 9289 to the 3' terminus of the full-length genome of the JFH-1 strain) were inserted into the SfiI-XbaI sites (corresponding to the region from nucleotide 8789 to the 3' terminus of the full-length genome of the J6CF strain) of pSGR-J6/N3H-JFH1/Luc. Thus, the region encoding the amino acid sequence of amino acids 516 to 591 of the NS5B protein and the 3' untranslated region (3' UTR) of the J6CF strain in the plasmid were substituted with the sequence derived from the JFH-1 strain (the "5BSLX" region in FIG. 1C). The plasmid DNA thus obtained is pSGR-J6/N3H+5BSLX-JFH1/Luc (FIG. 1C). That is, pSGR-J6/N3H+5BSLX-JFH1/Luc is a plasmid in which the NS3 helicase region (the region of nucleotides 3929 to 5293 of the full-length genome of the J6CF strain) and the 5BSLX region composed of a region encoding the amino acid sequence of amino acids 516 to 591 of the NS5B protein and the 3' untranslated region in pSGR-J6CF/Luc have been substituted with the nucleotide sequences derived from the JFH-1 strain (nucleotides 3931 to 5297 and nucleotides 9212 to 9678 of the full-length genome of the JFH-1 strain).

Also, the pSGR-J6/5BSLX-JFH1/Luc plasmid (FIG. 1D) was prepared. pSGR-J6/5BSLX-JFH1/Luc is a plasmid in which the nucleotide sequence corresponding to nucleotides 9212 to 9711 (the 3' terminus of the J6CF strain) of the full-length genome of the J6CF strain in pSGR-J6CF/Luc is substituted with the nucleotide sequence of nucleotides 9212 to 9678 (the 3' terminus of the JFH-1 strain) of the full-length genome of the JFH-1 strain.

A specific method of preparing pSGR-J6/5BSLX-JFH1/Luc (FIG. 1D) is as follows. The SfiI-AscI fragment (corresponding to the region of nucleotides 8789 to 9211 of the full-length genome of the J6CF strain and the region of nucleotides 9212 to 9289 of the full-length genome of the JFH-1 strain) of the amplified product of 2nd PCR which was prepared during the process of preparing pSGR-J6/N3H+5BSLX-JFH1/Luc using pSGR-J6CF/Luc and a DNA fragment obtained by digestion of pJFH1 with AscI and XbaI (the region from nucleotide 9289 to the 3' terminus of the full-length genome of the JFH-1 strain) were inserted into the SfiI-XbaI sites of pSGR-J6CF/Luc (corresponding to the region from nucleotide 8789 to the 3' terminus of the full-length genome of the J6CF strain). Thus, a region encoding the amino acid sequence of amino acids 516 to 591 of the NS5B protein and the untranslated region (3' UTR) of the J6CF strain in the plasmid were substituted with the sequence of the corresponding region derived from the JFH-1 strain (the "5BSLX" region in FIG. 1D). The plasmid DNA thus obtained is pSGR-J6/5BSLX-JFH1/Luc (FIG. 1D). That is, pSGR-J6/5BSLX-JFH1/Luc is a plasmid in which the 5BSLX region composed of a region encoding the amino acid sequence of amino acids 516 to 591 of the NS5B protein and the 3' untranslated region of pSGR-J6CF/Luc is substituted with the nucleotide sequence derived from the JFH-1 strain (nucleotides 9212 to 9678 of the full-length genome of the JFH-1 strain).

Figure 1:
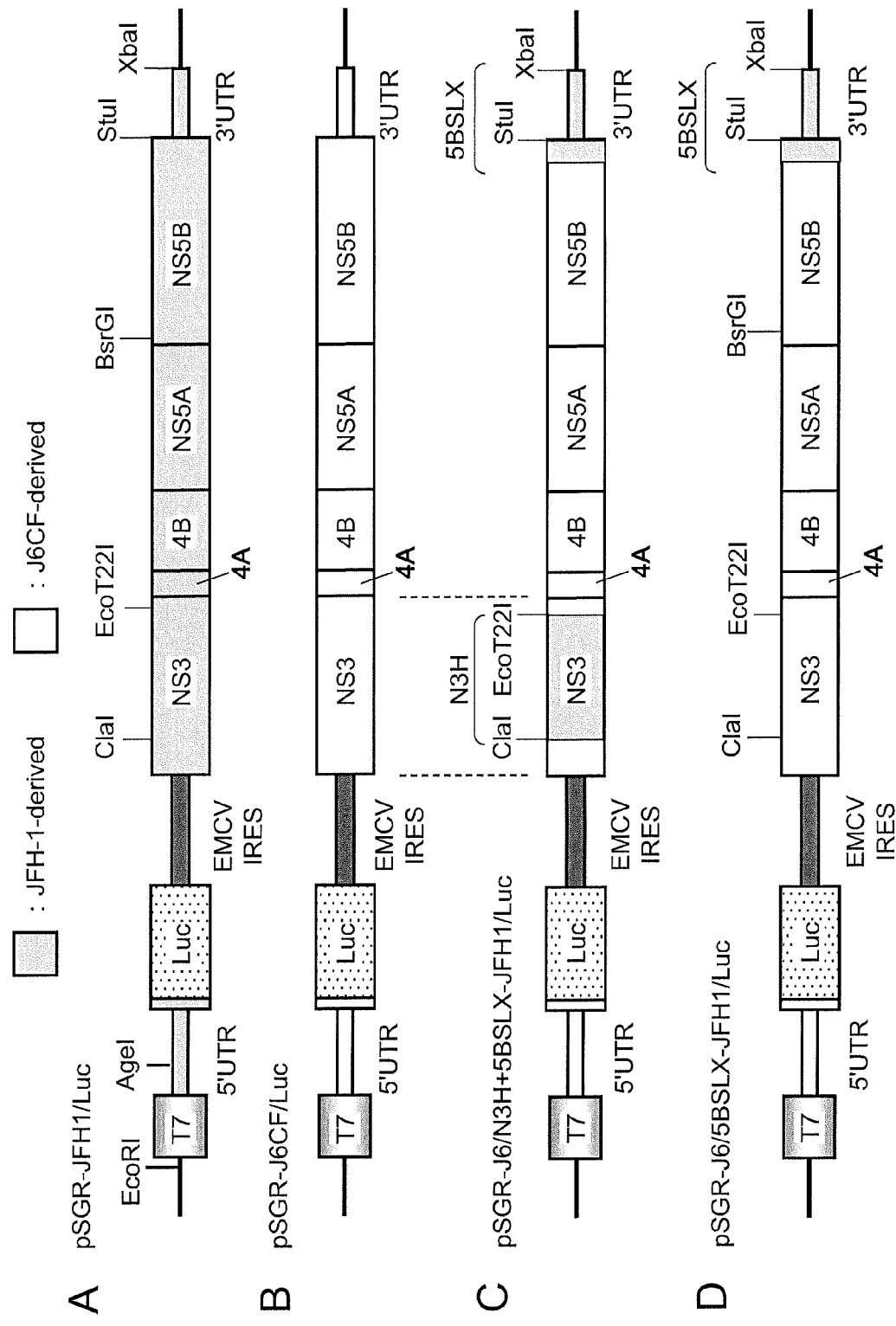

FIG. 1 summarizes the structures of J6CF/JFH-1 chimeric HCV subgenomic replicon RNA expression vectors. In FIG. 1, "T7" denotes the T7 promoter. The T7 promoter is a sequence element necessary for transcribing the HCV subgenomic replicon RNAs from the respective expression vectors using T7 RNA polymerase. "Luc" denotes luciferase gene, and "EMCV IRES" denotes internal ribosome entry site of encephalomyocarditis virus. "NS3" denotes an NS3 protein coding region, "4A" denotes an NS4A protein coding region, "4B" denotes an NS4B protein coding region, "NS5A" denotes an NS5A protein coding region, and "NS5B" denotes an NS5B protein coding region. In FIG. 1, "EcoRI," "AgeI," "ClaI," "EcoT22I," "BsrGI," "StuI," and "XbaI" indicate their restriction enzyme sites.

The NS5B protein coding regions of the J6CF strain and the JFH-1 strain each correspond to the nucleotide sequence of nucleotides 7667 to 9442 (including a stop codon) of the full-length genomes of the J6CF and JFH-1 strains and encode an NS5B protein of 591 amino acid residues. The region of nucleotides 7667 to 9211 of the full-length genome of the J6CF strain encodes the amino acid sequence of amino acids 1 to 515 of the NS5B protein of the J6CF strain. The region of nucleotides 9212 to 9442 (including a stop codon) of the full-length genome of the JFH-1 strain encodes the amino acid sequence of amino acids 516 to 591 of the NS5B protein of the JFH-1 strain. The entire amino acid sequence of the NS5B protein of the J6CF strain is shown in SEQ ID NO: 27, and the entire amino acid sequence of the NS5B protein of the JFH-1 strain is shown in SEQ ID NO: 28.

Figure 2:
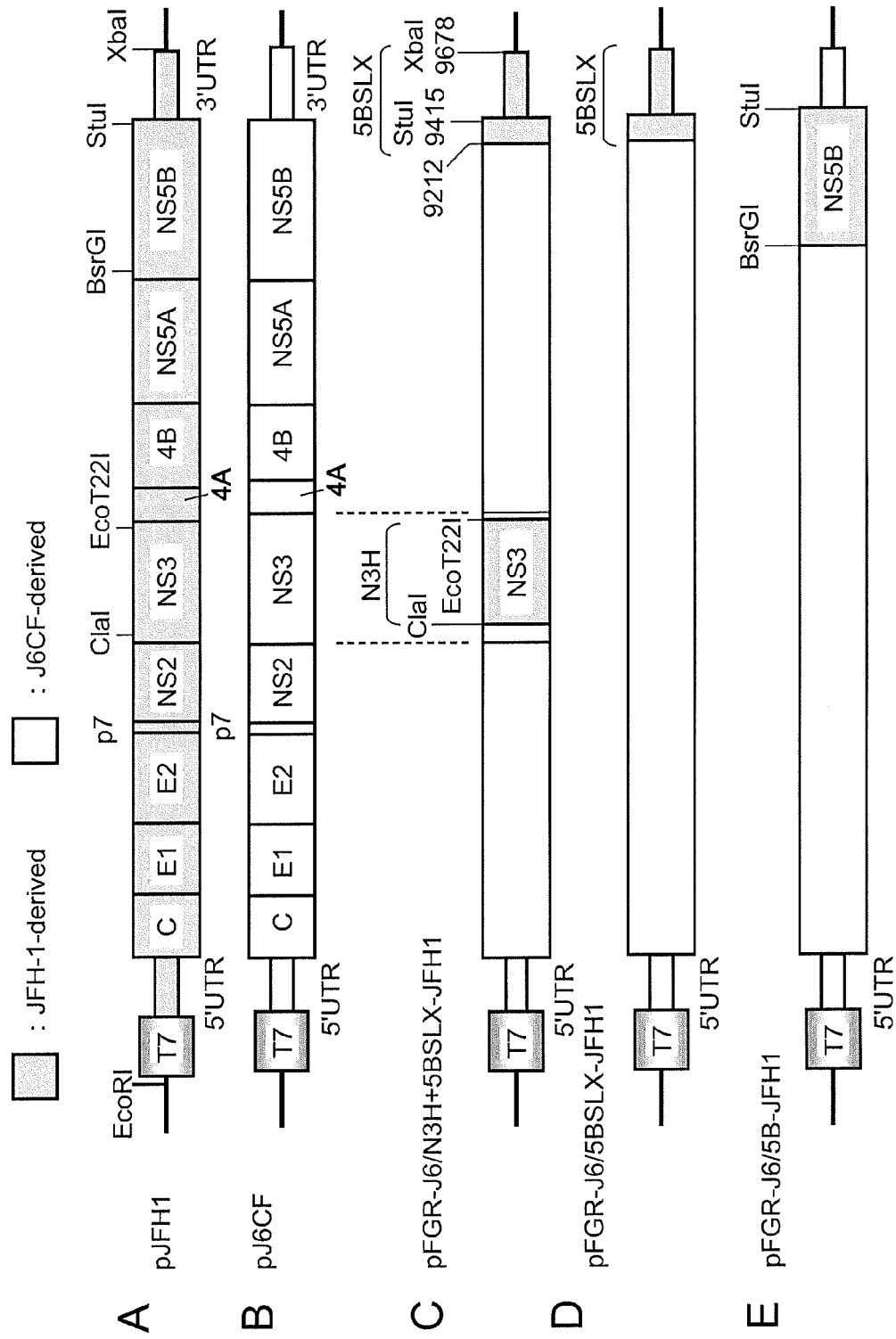

Subsequently, an HCV full-genomic replicon RNA expression vector, pFGR-J6/N3H+5BSLX-JFH1, was prepared as described above, but using pJ6CF instead of pSGR-J6CF/Luc, by substituting the NS3 helicase region (the "N3H" region in FIG. 2C; the region of nucleotides 3929 to 5293 of the full-length genome of the J6CF strain) and the 5BSLX region (the "5BSLX" region in FIG. 2) with a sequence of the corresponding region of the JFH-1 strain (i.e., the region of nucleotides 9212 to 9678 of the full-length genome of the JFH-1 strain), (FIG. 2C).

pFGR-J6/5BSLX-JFH1 was prepared as described above, but using pJ6CF (FIG. 2B) instead of pSGR-J6CF/Luc, by substituting the 5BSLX region (the region of nucleotides 9212 to 9678 of the full-length genome of the JFH-1 strain) with a sequence of the corresponding region of the JFH-1 strain (FIG. 2D).

Further, a sequence of the region from the BsrGI site (the recognition sequence starts at nucleotide 7781 of the full-length genome of the J6CF strain and it is cleaved between nucleotide 7781 and nucleotide 7782 by BsrGI) to the StuI site (the recognition sequence starts at nucleotide 9415 of the full-length genome of the J6CF strain and it is cleaved between nucleotide 9417 and nucleotide 9418 by StuI) of pJ6CF was substituted with the sequence of the corresponding region of pJFH1 to prepare a pFGR-J6/5B-JFH1 plasmid vector (FIG. 2E).

A specific method of preparing pFGR-J6/5B-JFH1 is as follows. First, the BsrGI restriction enzyme site was inserted into pJFH1 at a site starting at nucleotide 7781 of the full-length genome of the J6CF strain via PCR. Subsequently, pJ6CF into which the BsrGI restriction enzyme site had been introduced was digested with BsrGI and StuI. The BsrGI-StuI cleavage fragment of pJ6CF (corresponding to the region from nucleotide 7782 to 9417 of the full-length genome of the J6CF strain) was substituted with a DNA fragment (an NS5B fragment corresponding to the region of nucleotides 7782 to 9417 of the full-length genome of the JFH-1 strain) obtained by digestion of pJFH1 at the BsrGI site (the recognition sequence starts at nucleotide 7781 of the full-length genome of the JFH-1 strain and it is cleaved between nucleotide 7781 and nucleotide 7782 by BsrGI) and the StuI site (the recognition sequence starts at nucleotide 9415 of the full-length genome of the JFH-1 strain and it is cleaved between nucleotide 9417 and nucleotide 9418 by StuI). The plasmid DNA thus obtained is pFGR-J6/5B-JFH1.

FIG. 2 summarizes the J6CF/JFH-1 chimeric HCV full-genomic replicon RNA expression vectors. In FIG. 2, "T7" denotes the T7 promoter. "C" denotes a Core protein coding region, "E1" denotes an E1 protein coding region, "E2" denotes an E2 protein coding region, "p7" denotes a p7 protein coding region, "NS3" denotes an NS3 protein coding region, "4A" denotes an NS4A protein coding region, "4B" denotes an NS4B protein coding region, "NS5A" denotes an NS5A protein coding region, and "NS5B" denotes an NS5B protein coding region. In the figure, "EcoRI," "ClaI," "EcoT22I," "BsrGI," "StuI," and "XbaI" indicate their restriction enzyme sites.

Example 2

Preparation of HCV Subgenomic Replicon RNA and HCV Full-Genomic Replicon RNA (Full-Length HCV Genomic RNA)

The expression vector pSGR-JFH1/Luc (comprising the luciferase gene and EMCV IRES and encoding subgenomic replicon RNA of the JFH-1 strain; FIG. 1A) described in Kato, T. et al., JCM November, (2005) vol. 43, pp. 5679-5684 and the expression vectors pSGR-J6CF/Luc, pSGR-J6/N3H+5BSLX-JFH1/Luc, and pSGR-J6/5BSLX-JFH1/Luc disclosed in Example 1 were each digested with the restriction enzyme XbaI.

Subsequently, 20 U of Mung Bean Nuclease was added to 10 to 20 µg of the XbaI-cleaved DNA fragment (the total amount of the reaction solution: 50 µl), followed by incubation at 30° C. for 30 minutes. Mung Bean Nuclease is an enzyme that catalyzes a reaction of blunt-ending by selectively degrading the single-stranded portion of the double-stranded DNA. When RNA transcription is carried out with RNA polymerase by directly using as a template DNA the above XbaI-cleaved DNA fragment, in general, a replicon RNA in which extra CUAG (4 nucleotides) corresponding to a portion of the XbaI recognition sequence has been added at the 3' terminus is synthesized. In this Example, accordingly, the XbaI-cleaved DNA fragment was treated with Mung Bean Nuclease to remove the four nucleotides CTAG from the XbaI-cleaved DNA fragment.

Thereafter, the Mung Bean Nuclease-treated solution containing the XbaI-cleaved DNA fragments was subjected to a common protein removal treatment to purify XbaI-cleaved DNA fragments from each of which four nucleotides CTAG have been removed, and the resultants were used as template DNAs in the subsequent reaction. 20 µl of an RNA transcription solution containing 0.5 to 1.0 µg of the template DNAs was prepared from the template DNAs using an RNA transcription kit (MEGAscript®, Ambion, Inc.) in accordance with the manufacturer's instruction, followed by the reaction at 37° C. for 3 to 16 hours.

After completion of the RNA synthesis, DNaseI (2 U) was added to the reaction solution at 37° C. for 15 minutes for reaction, and RNA extraction was performed with acidic phenol to remove the template DNA. HCV subgenomic replicon RNA was thus synthesized. Herein, HCV subgenomic replicon RNAs synthesized from the expression vectors pSGR-JFH1/Luc, pSGR-J6CF/Luc, pSGR-J6/N3H+5BSLX-JFH1/Luc, and pSGR-J6/5BSLX-JFH1/Luc are referred to as SGR-JFH1/Luc, SGR-J6CF/Luc, SGR-J6/N3H+5BSLX-JFH1/Luc, and SGR-J6/5BSLX-JFH1/Luc, respectively.

HCV full-genomic replicon RNA was synthesized in the same manner as with the above-mentioned synthesis of HCV subgenomic replicon RNA, using the expression vectors prepared in Example 1 (pFGR-J6/N3H+5BSLX-JFH1, pFGR-J6/5BSLX-JFH1, and pFGR-J6/5B-JFH1). Herein, HCV full-genomic replicon RNAs synthesized from the expression vectors pFGR-J6/N3H+5BSLX-JFH1, pFGR-J6/5BSLX-JFH1, and pFGR-J6/5B-JFH1 are referred to as FGR-J6/N3H+5BSLX-JFH1, FGR-J6/5BSLX-JFH1, and FGR-J6/5B-JFH1, respectively.

Example 3

Introduction of HCV Subgenomic Replicon RNA and HCV Full-Genomic Replicon RNA (Full-Length HCV Genomic RNA) into Cells The HCV subgenomic replicon RNA or HCV full-genomic replicon RNA (HCV replicon RNA) prepared in Example 2 was introduced (transfected) into the Huh7.5.1 cell (Zhong, J. et al., Proc. Natl. Acad. Sci., U.S.A., (2005) vol. 102, pp. 9294-9299) via electroporation (van den Hoff M. J. et al., Nucleic Acids Res., (1992) vol. 20, p. 2902) in the manner specifically described below.

The trypsin-treated Huh7.5.1 cells were washed several times with Opti-MEM I medium (Invitrogen), and then suspended in 400 μl of a Cytomix solution (120 mM KCl, 0.15 mM $CaCl_2$, 10 mM $K_2HPO_4/KH_2PO_4$, 25 mM Hepes, 2 mM EGTA, 5 mM $MgCl_2$, 20 mM ATP, and 50 mM glutathione) to prepare a suspension of $3\times10^6$ cells/ml. After the cell suspension was transferred to a 4-mm cuvette, 5 μg of the HCV subgenomic replicon RNA or HCV full-genomic replicon RNA was added thereto, and pulsed at 260 V and 950 μF using Gene Pulser II (Bio-Rad) for electroporation (transfection) of HCV replicon RNA into the Huh7.5.1 cells. The cells into which the HCV replicon RNA had been introduced were suspended in a DMEM medium, and seeded in 12-well plate.

Example 4

RNA Replication in Cells into which HCV Subgenomic Replicon RNA Had been Introduced The Huh7.5.1 cells into which the HCV subgenomic replicon RNA had been introduced in Example 3 were seeded in 12-well plate, and the cells were collected 4, 24, and 48 hours after transfection. The collected cells were lysed in 250 μl of a lysis buffer (Passive Lysis reagent, Promega), centrifuged and the resulting culture supernatant was used as a sample. Luciferase activity of the sample was assayed using a luciferase assay system (Promega) and a luminometer (LB9507; EG&G Berthold).

Figure 3:
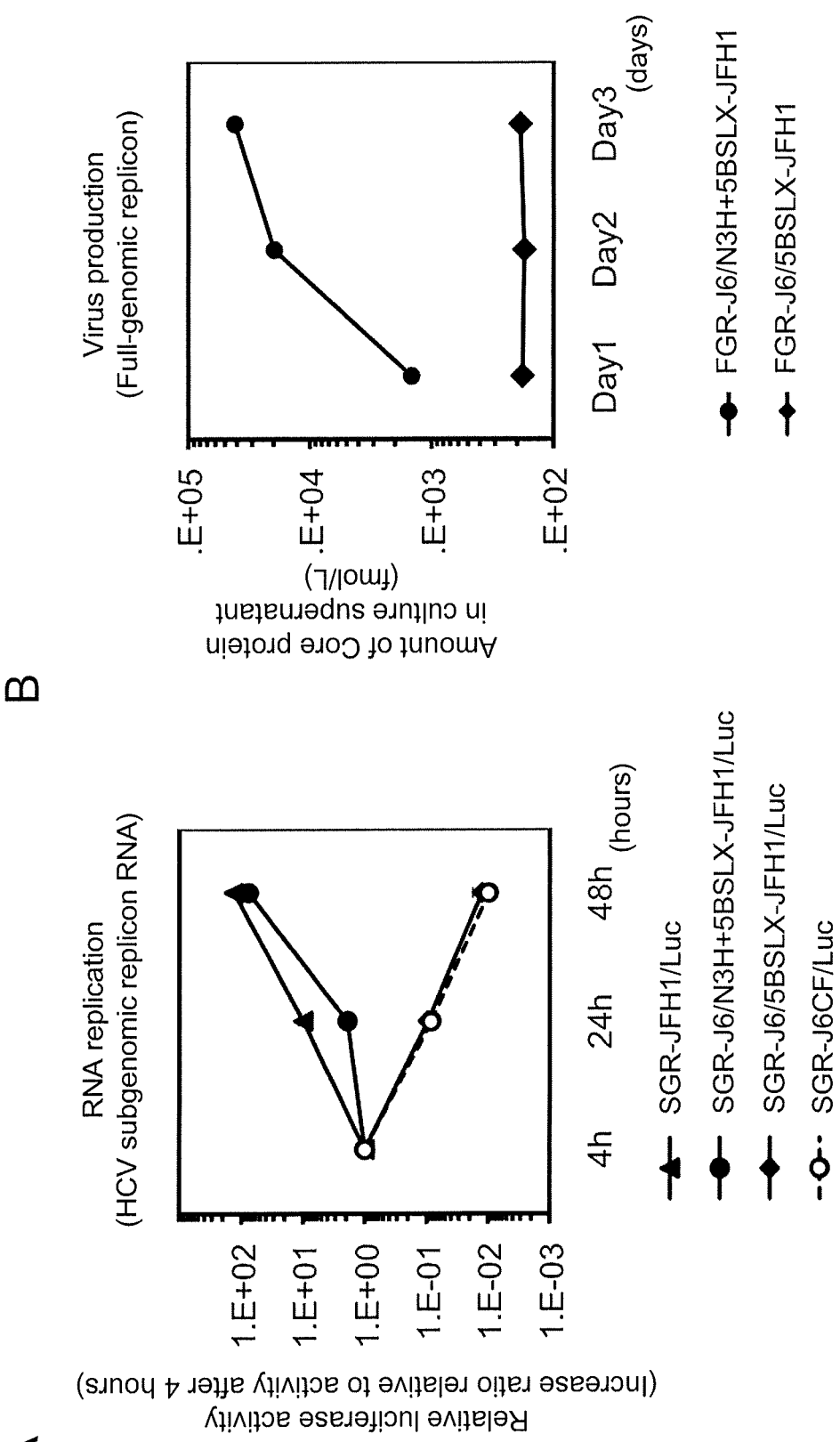

FIG. 3A shows the assay results. In FIG. 3A, the horizontal axis indicates hours after transfection, and the vertical axis indicates luciferase activity levels at each time point relative to the luciferase activity assayed 4 hours after transfection as a reference. FIG. 3A shows changes over time in replication levels of HCV subgenomic replicon RNA. As shown in FIG. 3A, luciferase activity levels were increased over time in the cells into which the HCV subgenomic replicon RNAs, SGR-JFH1/Luc or SGR-J6/N3H+5BSLX-JFH1/Luc, had been introduced. This indicates that SGR-JFH1/Luc and SGR-J6/N3H+5BSLX-JFH1/Luc are autonomously replicable. The N3H sequence derived from the JFH-1 strain, which had been introduced into SGR-J6/N3H+5BSLX-JFH1/Luc, was considered to have conferred autonomous replication ability on the subgenomic replicon RNA derived from the J6CF strain.

Example 5

Production of Viruses (Virus Particles) from Cells into which HCV Full-Genomic Replicon RNA (Full-Length HCV Genomic RNA) Had been Introduced The Huh7.5.1 cells into which HCV full-genomic replicon RNA had been introduced in Example 3 were seeded in 12-well plate and cultured, and the culture supernatant was collected 1, 2, and 3 days after transfection. The collected culture supernatant was applied to a 0.45-μm filter (Millipore) to remove contaminants, and the resultant was used as a sample for HCV Core protein assays. HCV Core proteins were measured using the HCV antigen ELISA test kit (Ortho-Clinical Diagnostics K. K.).

FIG. 3B shows the results thereof. In FIG. 3B, the horizontal axis indicates days after transfection (1, 2, and 3 days after transfection), and the vertical axis indicates the amount of Core protein in the culture supernatant (fmol/l). FIG. 3B indicates the virus level in the culture supernatant produced by the cultured cells into which the HCV full-genomic replicon RNA had been introduced. As shown in FIG. 3B, the amount of Core proteins in the culture supernatant of the cells into which FGR-J6/N3H+5BSLX-JFH1 had been introduced was increased over time, while the amount of Core proteins in the culture supernatant of the cells into which FGR-J6/5BSLX-JFH1 had been introduced was not increased. Thus, the cells into which FGR-J6/N3H+5BSLX-JFH1 had been introduced were found to produce viruses. The N3H sequence derived from the JFH-1 strain, which had been introduced into FGR-J6/N3H+5BSLX-JFH1, was considered to have conferred virus producing ability on the full-genomic replicon RNA derived from the J6CF strain.

Example 6

Obtaining Mutants Via Subculture of Cells into which J6CF/JFH-1 Chimeric HCV Full-Genomic Replicon RNA (Full-Length HCV Genomic RNA) Had been Introduced J6CF/JFH-1 chimeric HCV full-genomic replicon RNAs (FGR-J6/5BSLX-JFH1 and FGR-J6/5B-JFH1) were each introduced (transfected) into the Huh7.5.1 cells as described in Example 3. The cells into which the HCV full-genomic replicon RNA had been introduced were cultured with passaging at the intervals of 3 to 5 days, and the amount of HCV Core proteins in the culture supernatant was monitored during the culture. HCV Core proteins were measured as described in Example 5.

Figure 4:
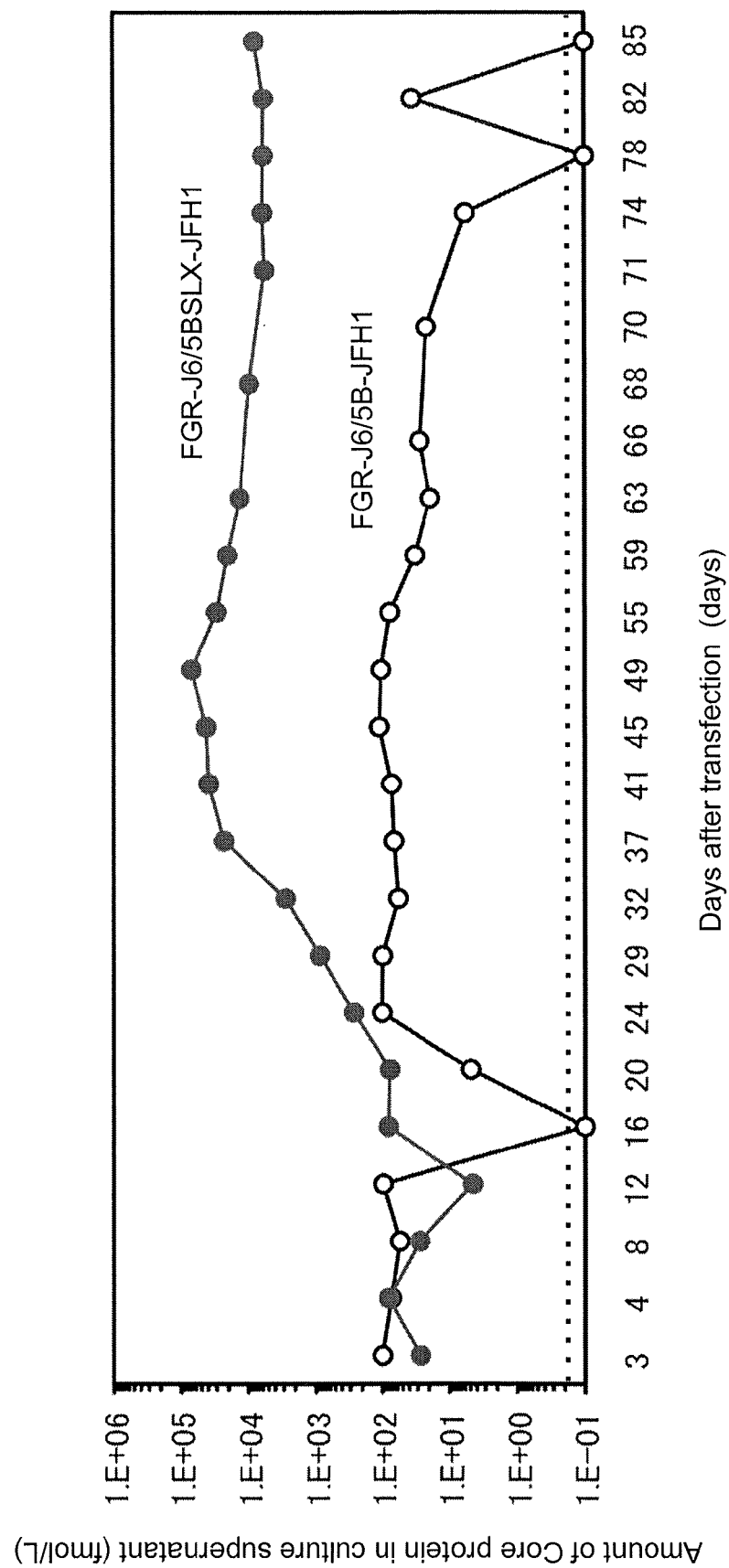

FIG. 4 shows the results thereof. In FIG. 4, the horizontal axis indicates days after transfection, and the vertical axis indicates the amount of Core proteins in the culture supernatant (fmol/l). As shown in FIG. 4, the amount of Core proteins in the culture supernatant began to increase and virus production was observed from about 1 month after transfection for the cells into which FGR-J6/5BSLX-JFH1 had been introduced; while virus production was not observed for the cells into which FGR-J6/5B-JFH1 had been introduced.

Subsequently, virus genomic RNA was extracted from the culture supernatant of the cells into which FGR-J6/5BSLX-JFH1 had been introduced at 49 days after transfection when the amount of Core proteins reached its maximal level therein (FIG. 4) using ISOGEN-LS (Nippon Gene). The virus genomic RNA was used as a template to synthesize cDNA using a reverse transcriptase (Super script III Reverse Transcriptase, Invitrogen), followed by sequencing.

As a result, a mutant virus genome comprising a nucleotide mutation (substitution of the second nucleotide, cytosine, of the codon "GCG" encoding alanine with adenine) causing substitution of amino acid at position 1680 of the precursor protein (polyprotein) of the J6CF strain, alanine (A), with glutamic acid (E) (A1680E) was successfully identified.

Example 7

Preparation of J6CF/JFH-1 Chimeric Mutant HCV Subgenomic Replicon RNA and J6CF/JFH-1 Chimeric Mutant HCV Full-Genomic Replicon RNA (Full-Length HCV Genomic RNA)

As a J6CF/JFH-1 chimeric mutant HCV replicon RNA expression vector, a nucleic acid construct was prepared by introducing the amino acid substitution (mutation) A1680E in the NS4A protein region identified in Example 6 into the expression vectors, pSGR-J6/5BSLX-JFH1/Luc and pFGR-J6/5BSLX-JFH1. The expression vector prepared by introducing a nucleotide mutation causing A1680E substitution into pSGR-J6/5BSLX-JFH1/Luc is referred to as "pSGR-J6/5BSLX-JFH1+4Amut/Luc," and the expression vector prepared by introducing a nucleotide mutation causing A1680E substitution into pFGR-J6/5BSLX-JFH1 is referred to as "pFGR-J6/5BSLX-JFH1+4Amut." The term "4Amut" used herein refers to a mutation causing amino acid substitution A1680E.

Specifically, 4Amut was introduced into each expression vector as follows. At the outset, as 1st PCR-1, PCR was carried out using pJ6CF as a template, 3471S-2a sense primer (5'-TGGGCACCATAGTGGTGAG-3'; SEQ ID NO: 11), and A1680Eas antisense primer (5'-CACCCGGTCtCCAGGCAATACGCGGCGACG-3'; SEQ ID NO: 12) (a nucleotide indicated by a lower-case alphabetic letter in the primer sequence represents a nucleotide mutation to be introduced). Subsequently, as 1st PCR-2, PCR was carried out using pJ6CF as a template, A1680Es sense primer (5'-ATTGCCTGGaGACCGGGTGTGTTTGCATCA-3'; SEQ ID NO: 13) (a nucleotide indicated by a lower-case alphabetic letter in the primer sequence represents a nucleotide mutation to be introduced), and 6542R-IH antisense primer (5'-CGCACTGGCCCTCCGTGTA-3'; SEQ ID NO: 14). Further, as 2nd PCR, PCR was carried out using a mixture of two types of the amplified fragments obtained by the 1st PCR-1 and 1st PCR-2 above as a template, 3471S-2a sense primer (SEQ ID NO: 11), and 6542R-IH antisense primer (SEQ ID NO: 14). The resulting amplified product was digested with BbvCI and EcoRI restriction enzymes to produce a DNA fragment (corresponding to the region of nucleotides 3662 to 6006 of the full-length genome of the J6CF strain), and the produced DNA fragment was used to substitute for the region from BbvCI to EcoRI in pSGR-J6/5BSLX-JFH1/Luc and of pFGR-J6/5BSLX-JFH1 (the region of nucleotides 3662 to 6006 of the full-length genome of the J6CF strain) to produce pSGR-J6/5BSLX-JFH1+4Amut/Luc and pFGR-J6/5BSLX-JFH1+4Amut, respectively.

Figure 5:
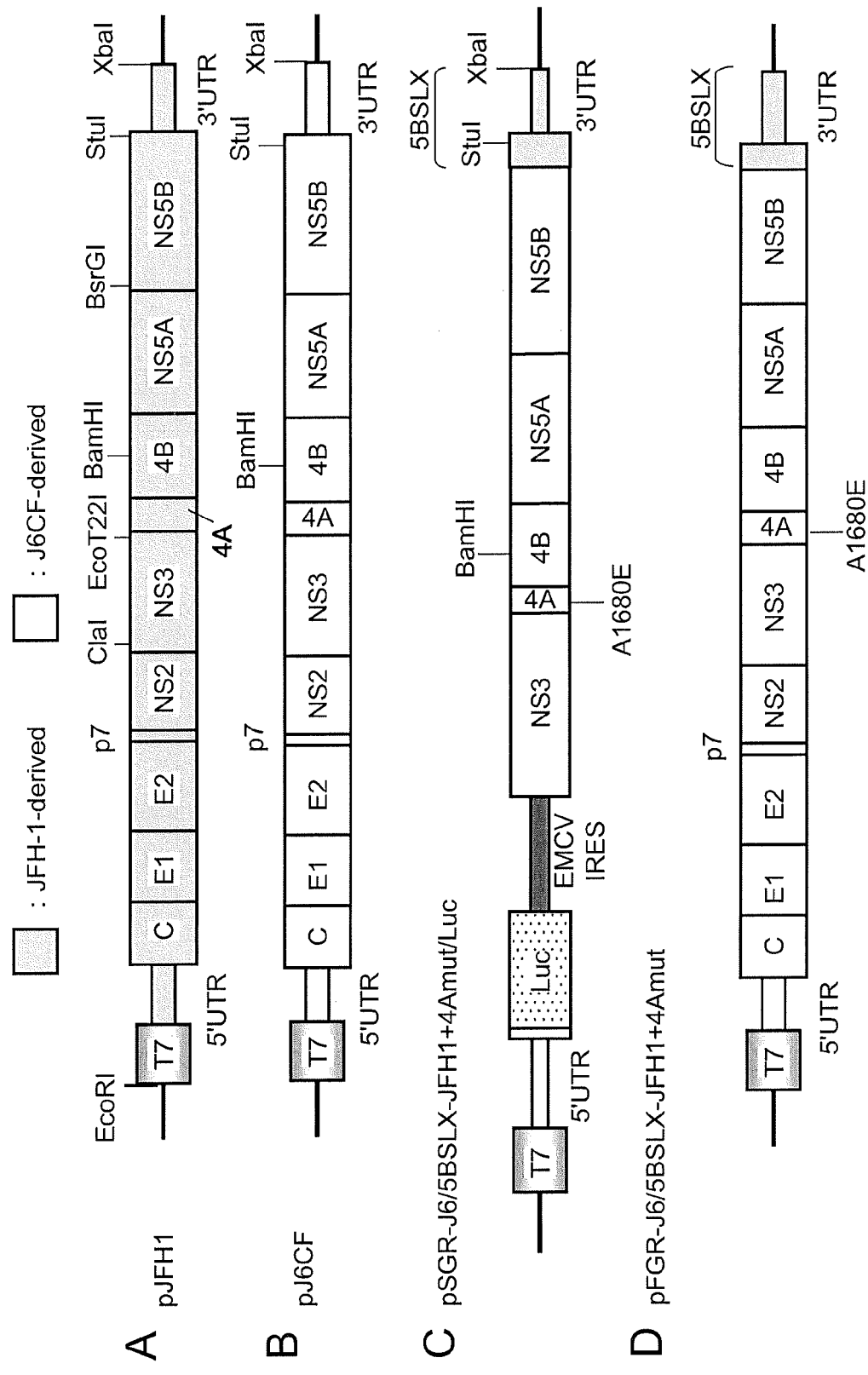

FIG. 5C and FIG. 5D show the structures of the mutant replicon expression vectors prepared above. In FIGS. 5C and 5D, "A1680E" schematically indicates the position at which a mutation (4Amut) causing substitution of alanine (A) at position 1680 in the J6CF precursor protein (polyprotein) with glutamic acid (E) (A1680E) is introduced. In the figures, other notations indicate the same objects as in FIGS. 1 and 2.

HCV replicon RNAs were synthesized from the J6CF/JFH-1 chimeric mutant HCV subgenomic replicon RNA expression vector (pSGR-J6/5BSLX-JFH1+4Amut/Luc) and the J6CF/JFH-1 chimeric mutant HCV full-genomic replicon RNA expression vector (pFGR-J6/5BSLX-JFH1+4Amut) as described in Example 2.

HCV replicon RNAs synthesized from the expression vectors pSGR-J6/5BSLX-JFH1+4Amut/Luc and pFGR-J6/5BSLX-JFH1+4Amut are referred to as SGR-J6/5BSLX-JFH1+4Amut/Luc and FGR-J6/5BSLX-JFH1+4Amut, respectively. These RNAs are chimeric mutant replicon RNAs which are chimeric genomes derived from the genomes of the J6CF strain and the JFH-1 strain and comprise an A1680E mutation.

SEQ ID NO: 1 shows the nucleotide sequence of SGR-J6/5BSLX-JFH1+4Amut/Luc, which is a J6CF/JFH-1 chimeric mutant HCV subgenomic replicon RNA. SEQ ID NO: 2 shows the nucleotide sequence of FGR-J6/5BSLX-JFH1+4Amut, which is a J6CF/JFH-1 chimeric mutant HCV full-genomic replicon RNA, and SEQ ID NO: 3 shows the amino acid sequence of the full-length HCV precursor protein encoded by the nucleotide sequence. Although the nucleotide sequences of SEQ ID NOs: 1 and 2 are indicated as DNA sequences, sequences generated by replacement of thymine (t) in the nucleotide sequences with uracil (u) are their corresponding RNA sequences. Accordingly, the replicon RNA sequences can be specified with reference to SEQ ID NOs: 4 and 5.

Example 8

RNA Replication in Cells into which J6CF/JFH-1 Chimeric Mutant HCV Subgenomic Replicon RNA Had been Introduced 5 μg of the HCV subgenomic replicon RNA prepared in Example 2 or Example 7 was introduced (transfected) into the Huh7.5.1 cells as described in Example 3. The cells into which the HCV subgenomic replicon RNA had been introduced were seeded in 12-well plate and cultured, and the cells were collected 4, 24, and 48 hours after transfection. The collected cells were lysed in 250 μl of a lysis buffer (Passive Lysis reagent, Promega), centrifuged and the resulting culture supernatant was used as a sample. Luciferase activity of the sample was assayed using the luciferase assay system (Promega) and a luminometer (LB9507; EG&G Berthold).

Figure 6:
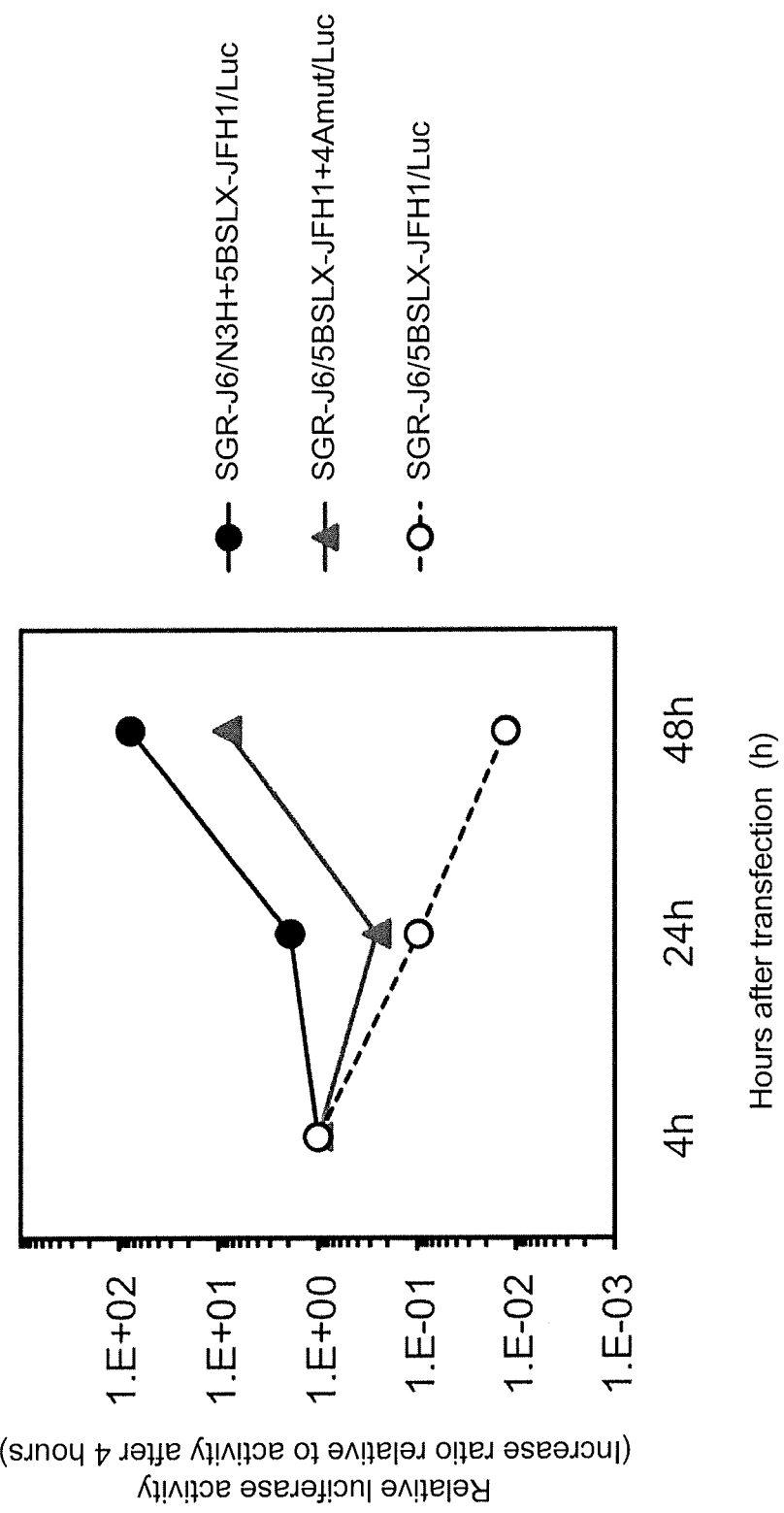
Figure 7:
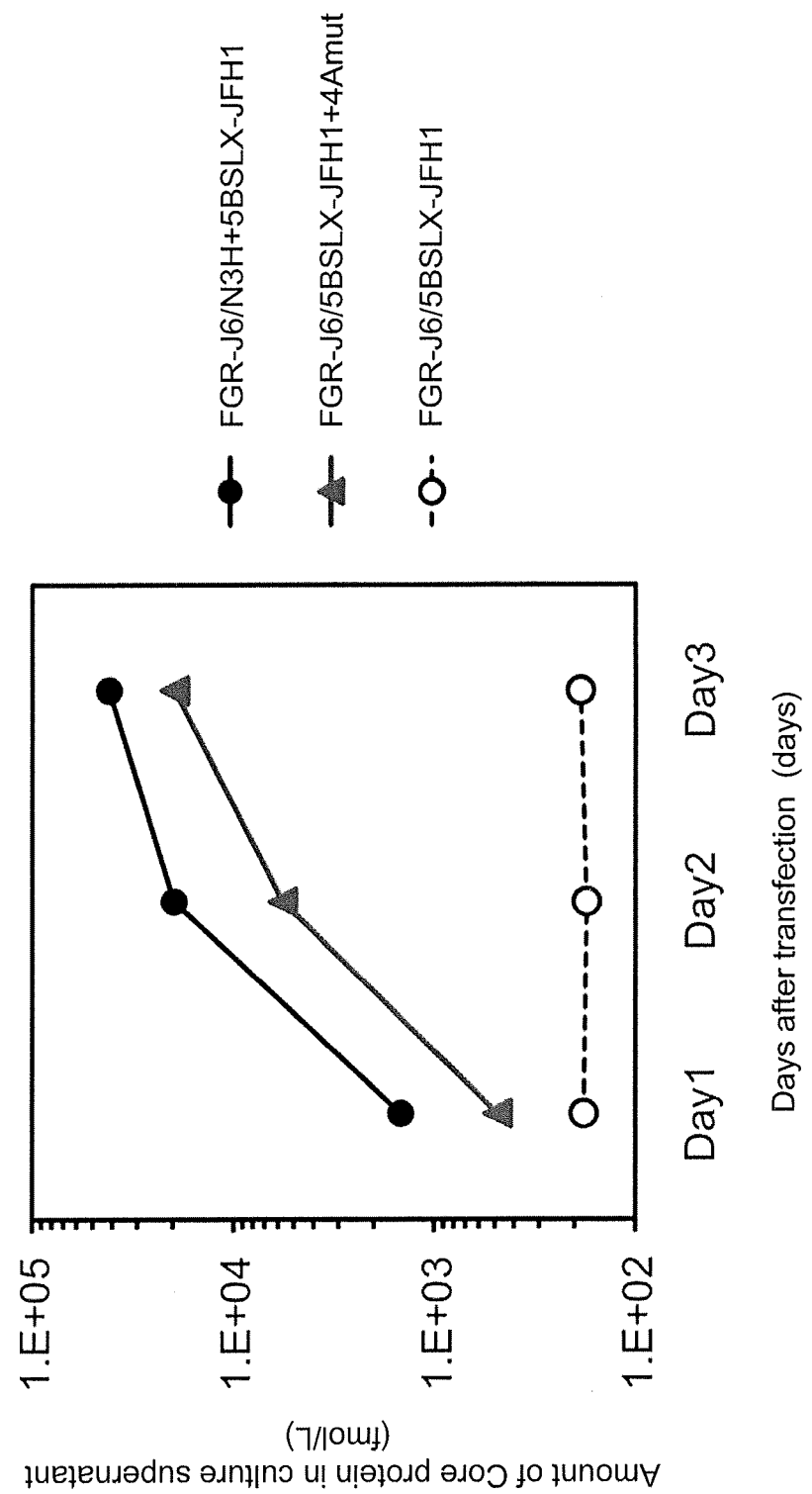
FIG. 7 shows the amount of the Core protein (the virus producing ability) in a culture supernatant of the Huh7.5.1 cell into which HCV full-genomic replicon RNA: FGR-J6/N3H+5BSLX-JFH1, FGR-J6/5BSLX-JFH1+4Amut, or FGR-J6/5BSLX-JFH1, had been introduced.

FIG. 6 shows the assay results. In FIG. 6, the horizontal axis indicates hours after transfection, and the vertical axis indicates luciferase activity levels at each time point relative to the luciferase activity assayed 4 hours after transfection as a reference. As shown in FIG. 6, luciferase activity levels were increased over time in the cells into which SGR-J6/5BSLX-JFH1+4Amut/Luc that is a J6CF/JFH-1 chimeric mutant HCV subgenomic replicon RNA, had been introduced. This indicates that SGR-J6/5BSLX-JFH1+4Amut/Luc is autonomously replicable. It was found that A1680E mutation in the NS4A protein region is critical in efficiently replicating the J6CF genome in cells.

The increase of the luciferase activity levels observed for SGR-J6/5BSLX-JFH1+4Amut/Luc was very similar to the result observed for SGR-J6/N3H+5BSLX-JFH1/Luc, which is a J6CF/JFH-1 chimeric HCV subgenomic replicon RNA into which the N3H sequence derived from the JFH-1 strain had been introduced (FIG. 6). Therefore, it can be said that A1680E mutation has an effect to confer autonomous replication ability on a replicon RNA derived from the J6CF strain, as with the N3H sequence derived from the JFH-1 strain.

Example 9

Virus Production from Cells into which J6CF/JFH-1 Chimeric Mutant HCV Full-Genomic Replicon RNA (Full-Length HCV Genomic RNA) Had been Introduced 5 μg of HCV full-genomic replicon RNA prepared in Example 2 or Example 7 was introduced (transfected) into the Huh7.5.1 cells as described in Example 3. The cells into which the HCV full-genomic replicon RNA had been introduced were seeded in 12-well plate and cultured, and the culture supernatant was collected 1, 2, and 3 days after transfection. The collected culture supernatant was applied to a 0.45-μm filter (Millipore) to remove contaminants, and the resultant was used as a sample for HCV Core protein assays. HCV Core proteins were measured using the HCV antigen ELISA test kit (Ortho-Clinical Diagnostics K. K.).

FIG. 7 shows the results thereof. In FIG. 7, the horizontal axis indicates days after transfection, and the vertical axis indicates the amount of Core protein in the culture supernatant (fmol/l). As shown in FIG. 7, the amount of Core protein in the culture supernatant of the cells into which FGR-J6/5BSLX-JFH1+4Amut had been introduced was increased over time. Thus, the cells into which FGR-J6/5BSLX-JFH1+4Amut had been introduced were found to produce viruses.

Example 10

Production of Mutant (Five-Site Mutagenized) HCV Subgenomic Replicon RNA and HCV Full-Genomic Replicon RNA (Full-Length HCV Genomic RNA) Derived from the J6CF Strain An expression vector to synthesize a mutant (five-site mutagenized) HCV subgenomic replicon RNA derived from the J6CF strain; introduction of the substitutions (mutations): A1680E/A2892S/R2959K/Y3003F/nt9458(c→g)) was prepared. Specifically, a nucleic acid construct was produced by introducing nucleotide mutations causing amino acid substitutions: A2892S (substitution of alanine at position 2892 of the precursor protein of the J6CF strain with serine), R2959K (substitution of arginine at position 2959 of the precursor protein of the J6CF strain with lysine), and Y3003F (substitution of tyrosine at position 3003 of the precursor protein of the J6CF strain with phenylalanine) in the NS5B protein region, and the nucleotide mutation nt9458(c→g) in a variable region (VR) in the 3' terminal untranslated region of the HCV genome (the mutation of cytosine at position 9458 of the full-length genomic sequence of the J6CF strain with guanine), as well as a nucleotide mutation causing amino acid substitution A1680E (substitution of alanine at position 1680 of the precursor protein of the J6CF strain with glutamic acid) in the NS4A protein region found in Example 6, into pSGR-J6CF/Luc. The mutations A2892S, R2959K, Y3003F, and nt9458(c→g) are described in Murayama et al., PLoS Pathogens., (2010) vol. 6, e1000885.

The resulting J6CF strain-derived mutant HCV subgenomic replicon RNA expression vector is referred to as pSGR-J6/4Amut+SKF+VRm3/Luc, and a mutant HCV subgenomic replicon RNA prepared from the vector as described in Example 2 is referred to as SGR-J6/4Amut+SKF+VRm3/Luc. "SKF" refers to the amino acid substitutions (mutations) A2892S, R2959K, and Y3003F, and "VRm3" refers to the nucleotide mutation nt9458(c→g) in a variable region in the 3' terminal untranslated region of the genome.

In a similar way, an expression vector to synthesize a mutant (five-site mutagenized) HCV full-genomic replicon RNA derived from the J6CF strain was prepared. Specifically, a nucleic acid construct was produced by introducing nucleotide substitutions causing the amino acid substitution A1680E in the NS4A protein region, and the amino acid substitutions A2892S, R2959K, and Y3003F in the NS5B protein region; and the nucleotide mutation nt9458(c→g) in a variable region in the 3' terminal untranslated region of the HCV genome into J6CF. The resulting J6CF strain-derived mutant HCV full-genomic replicon RNA expression vector is referred to as pFGR-J6/4Amut+SKF+VRm3, and a mutant HCV full-genomic replicon RNA prepared from the vector as described in Example 2 is referred to as FGR-J6/4Amut+SKF+VRm3.

The A1680E mutation was introduced into pSGR-J6CF/Luc and pJ6CF as described in Example 7. Further, for the introduction of nucleotide mutations causing 3 mutations in the NS5B protein (amino acid substitutions: A2892S, R2959K, and Y3003F; SKF) and the nucleotide mutation (nucleotide mutation nt9458(c→g)) in a 3' terminal variable region of the HCV genome into the resulting expression vectors comprising the A1680E mutation introduced, a BamHI/StuI-digested DNA fragment (comprising a part of the NS4B coding region to approximately the entire NS5B coding region) of pSGR-J6/N3H+3'UTR-JFH1/SKF that is an HCV subgenomic replicon RNA expression vector comprising amino acid substitutions SKF as described in Murayama et al., PLoS Pathogens., (2010) vol. 6, e1000885, and a StuI/XbaI-digested DNA fragment (comprising a 3' terminal partial region of the NS5B coding region and the 3' untranslated region) of pSGR-J6/N3H+5BSLX-JFH1/VR-J6 m3 that is an HCV subgenomic replicon RNA expression vector comprising VRm3 as described in Murayama et al., PLoS Pathogens., (2010) vol. 6, e1000885 were used to substitute for the sequences of the corresponding regions of such expression vector comprising the A1680E mutation.

FIG. 8 shows the structures of the expression vectors, pSGR-J6/4Amut+SKF+VRm3/Luc and pFGR-J6/4Amut+SKF+VRm3. In FIG. 8, "A1680E," "A2892S," "R2959K," "Y3003F," and "nt9458(c→g)" schematically indicate the positions at which such mutations are introduced. In the figures, other notations indicate the same objects as in FIGS. 1 and 2.

pSGR-J6/N3H+3'UTR-JFH1/SKF was prepared by the method described in Murayama et al., PLoS Pathogens., (2010) vol. 6, e1000885.

As examples of methods of introducing mutations A2892S, R2959K, and Y3003F, the procedures employed when producing vectors via introduction of mutations A2892S, R2959K, and Y3003F into pSGR-J6CF/Luc are described below.

First, for the introduction of A2892S ("S" of SKF), as 1st PCR-1, PCR was carried out using pJ6CF as a template, 7244S-RI sense primer (5'-ACCGCTTGTG-GAATCGTGGA-3'; SEQ ID NO: 15), and J65BA450Sas antisense primer (5'-GGAGTACACtGaTCCGTACATCT-CAAAGTTGAGG-3'; SEQ ID NO: 16). Subsequently, as 1st PCR-2, PCR was carried out using pJ6CF as a template, J65BA450Ss sense primer (5'-TGTACGGAtCaGTG-TACTCCGTGAGTCCCTTG-3'; SEQ ID NO: 17), and 9454R-IH antisense primer (5'-GTGTGTGCCGCTCTAC-CGAGCGGGGAGTAG-3'; SEQ ID NO: 18). A nucleotide indicated by a lower-case alphabetic letter in the primer sequence represents a nucleotide mutation to be introduced.

Further, as 2nd PCR, PCR was carried out using a mixture of two types of the amplified fragments obtained by the 1st PCR-1 and 1st PCR-2 above as a template, 7244S-RI sense primer (SEQ ID NO: 15), and the 9454R-IH antisense primer (SEQ ID NO: 18). The resulting amplified product was digested with XhoI and StuI restriction enzymes to produce a DNA fragment (corresponding to the region of nucleotides 7523 to 9415 of the full-length genome of the J6CF strain), and the produced DNA fragment and a StuI/XbaI-digested DNA fragment of pJFH1 (corresponding to the region from nucleotides 9415 to the 3' terminus of the full-length genome of the JFH-1 strain) were used to substitute for the XhoI-XbaI region of pSGR-J6CF/Luc (nucleotide 7523 to the 3' terminus of the full-length genome of the J6CF strain). For the introduction of R2959K ("K" of SKF), as 1st PCR-1, PCR was carried out using pJ6CF as a template, 7244S-RI sense primer (5'-ACCGCTTGTGGAATCGTGGA-3'; SEQ ID NO: 15), and J65BR517Kas antisense primer (5'-ACGGCCGCTtTC-CCCCCACGGGAGATGAG-3'; SEQ ID NO: 19). Subsequently, as 1st PCR-2, PCR was carried out using pJ6CF as a template, J65BR517Ks sense primer (5'-GTGGGGG-GAaAGCGGCCGTTTGCGGTCGA-3'; SEQ ID NO: 20), and 9454R-IH antisense primer (5'-GTGTGTGCCGCTC-TACCGAGCGGGGAGTAG-3'; SEQ ID NO: 18). A nucleotide indicated by a lower-case alphabetic letter in the primer sequence represents a nucleotide mutation to be introduced. Further, as 2nd PCR, PCR was carried out using a mixture of two types of the amplified fragments obtained by the 1st PCR-1 and 1st PCR-2 above as a template, 7244S-RI sense primer (SEQ ID NO: 15), and 9454R-IH antisense primer (SEQ ID NO: 18). The resulting amplified product was digested with XhoI and StuI restriction enzymes to produce a DNA fragment (nucleotides 7523 to 9415 of the full-length genome of the J6CF strain), and the produced DNA fragment and a StuI/XbaI-digested DNA fragment of pJFH1 (nucleotide 9415 to the 3' terminus of the full-length genome of the JFH-1 strain) were used to substitute for the XhoI-XbaI region of pSGR-J6CF/Luc (nucleotide 7523 to the 3' terminus of the full-length genome of the J6CF strain). For the introduction of Y3003F ("F" of SKF), as 1st PCR-1, PCR was carried out using pJ6CF as a template, 7244S-RI sense primer (5'-ACCGCTTGTGGAATCGTGGA-3'; SEQ ID NO: 15), and J65BY561Fas antisense primer (5'-CACGCTGT-GAaAAATGTCGCCCCCGCCGG-3'; SEQ ID NO: 21). Subsequently, as 1st PCR-2, PCR was carried out using pJ6CF as a template, J65BY561Fs sense primer (5'-GGCGA-CATTTtTCACAGCGTGTCGCGTGC-3'; SEQ ID NO: 22), and 9454R-IH antisense primer (5'-GTGTGTGCCGCTC-TACCGAGCGGGGAGTAG-3'; SEQ ID NO: 18). A nucleotide indicated by a lower-case alphabetic letter in the primer sequence represents a nucleotide mutation to be introduced. Further, as 2nd PCR, PCR was carried out using a mixture of two types of the amplified fragments obtained by the 1st PCR-1 and 1st PCR-2 above as a template, 7244S-RI sense primer (SEQ ID NO: 15), and 9454R-IH antisense primer (SEQ ID NO: 18). The resulting amplified product was digested with XhoI and StuI restriction enzymes to produce a DNA fragment (nucleotides 7523 to 9415 of the full-length genome of the J6CF strain), and the produced DNA fragment and a StuI/XbaI-digested DNA fragment of pJFH1 (nucleotide 9415 to the 3' terminus of the full-length genome of the JFH-1 strain) were used to substitute for the XhoI-XbaI region of pSGR-J6CF/Luc (nucleotide 7523 to the 3' terminus of the full-length genome of the J6CF strain).

pSGR-J6/N3H+5BSLX-JFH1/VR-J6 m3 was prepared by the method described in Murayama et al., PLoS Pathogens., (2010) vol. 6, e1000885. As an example of a method of introducing the mutation nt9458(c→g) into a variable region in the 3' untranslated region, a method employed when preparing a vector by introducing the mutation nt9458(c→g) into pSGR-J6CF/Luc is described. As 1st PCR-1, PCR was carried out using pJ6CF as a template, 9254S-IH sense primer (5'-GTGAAGACCAAGCTCAAACTCACTCC-3'; SEQ ID NO: 23), and J6VRm3 as antisense primer (5'-TATGGAGT-GTAcCTAATGTGTGCCGCTCTAC-3'; SEQ ID NO: 24). Subsequently, as 1st PCR-2, PCR was carried out using pJ6CF as a template, J6VRm3s sense primer (5'-CACA-CATTAGgTACACTCCATAGCTAACTGTC-3'; SEQ ID NO: 25), and M13R antisense primer (5'-CAGGAAACAGC-TATGAC-3'; SEQ ID NO: 26). A nucleotide indicated by a lower-case alphabetic letter in the primer sequence represents a nucleotide mutation to be introduced. Further, as 2nd PCR, PCR was carried out using a mixture of two types of the amplified fragments obtained by the 1st PCR-1 and 1st PCR-2 above as a template, 92545-IH sense primer (SEQ ID NO: 23), and M13R antisense primer (SEQ ID NO: 26). The resulting amplified fragment was digested with SgrAI and XbaI restriction enzymes to produce a DNA fragment (nucleotide 9328 to the 3' terminus of the full-length genome of the J6CF strain), and the produced DNA fragment was used to substitute for the SgrAI-XbaI region of pSGR-J6CF/Luc (nucleotide 9328 to the 3' terminus of the full-length genome of the J6CF strain). As a result, a J6CF mutant HCV subgenomic replicon RNA expression vector comprising the mutation nt9458 (c→g) was prepared.

Subsequently, J6CF mutant HCV subgenomic replicon RNA and J6CF mutant HCV full-genomic replicon RNA were synthesized from the J6CF mutant HCV replicon RNA expression vector prepared above, as described in Example 2.

SEQ ID NO: 4 shows the nucleotide sequence of SGR-J6+4Amut+SKF+VRm3/Luc, which is a mutant (five-site mutagenized) HCV subgenomic replicon RNA derived from the J6CF strain. SEQ ID NO: 5 shows the nucleotide sequence of FGR-J6+4Amut+SKF+VRm3, which is a mutant (five-site mutagenized) HCV full-genomic replicon RNA derived from the J6CF strain, and SEQ ID NO: 6 shows the amino acid sequence of the full-length mutant (five-site mutagenized) HCV precursor protein encoded by the nucleotide sequence. Although the nucleotide sequences of SEQ ID NOs: 4 and 5 are indicated as DNA sequences, sequences generated by replacement of thymine (t) in the nucleotide sequences with uracil (u) are their corresponding RNA sequences. Accordingly, the replicon RNA sequences can be specified with reference to SEQ ID NOs: 4 and 5.

Example 11

RNA Replication in Cells into which Mutant (Five-Site Mutagenized) HCV Subgenomic Replicon RNA Derived from the J6CF Strain Had been Introduced 5 µg of the mutant (five-site mutagenized) HCV subgenomic replicon RNA derived from the J6CF strain prepared in Example 10 was introduced (transfected) into the Huh7.5.1 cells as described in Example 3. The cells into which the HCV subgenomic replicon RNA had been introduced were seeded in 12-well plate and cultured, and the cells were collected 4, 24, and 48 hours after transfection. The collected cells were lysed in 250 µl of a lysis buffer (Passive Lysis reagent, Promega), centrifuged and the resulting culture supernatant was used as a sample. Luciferase activity of the sample was assayed using the luciferase assay system (Promega) and a luminometer (LB9507; EG&G Berthold).

Figure 9:
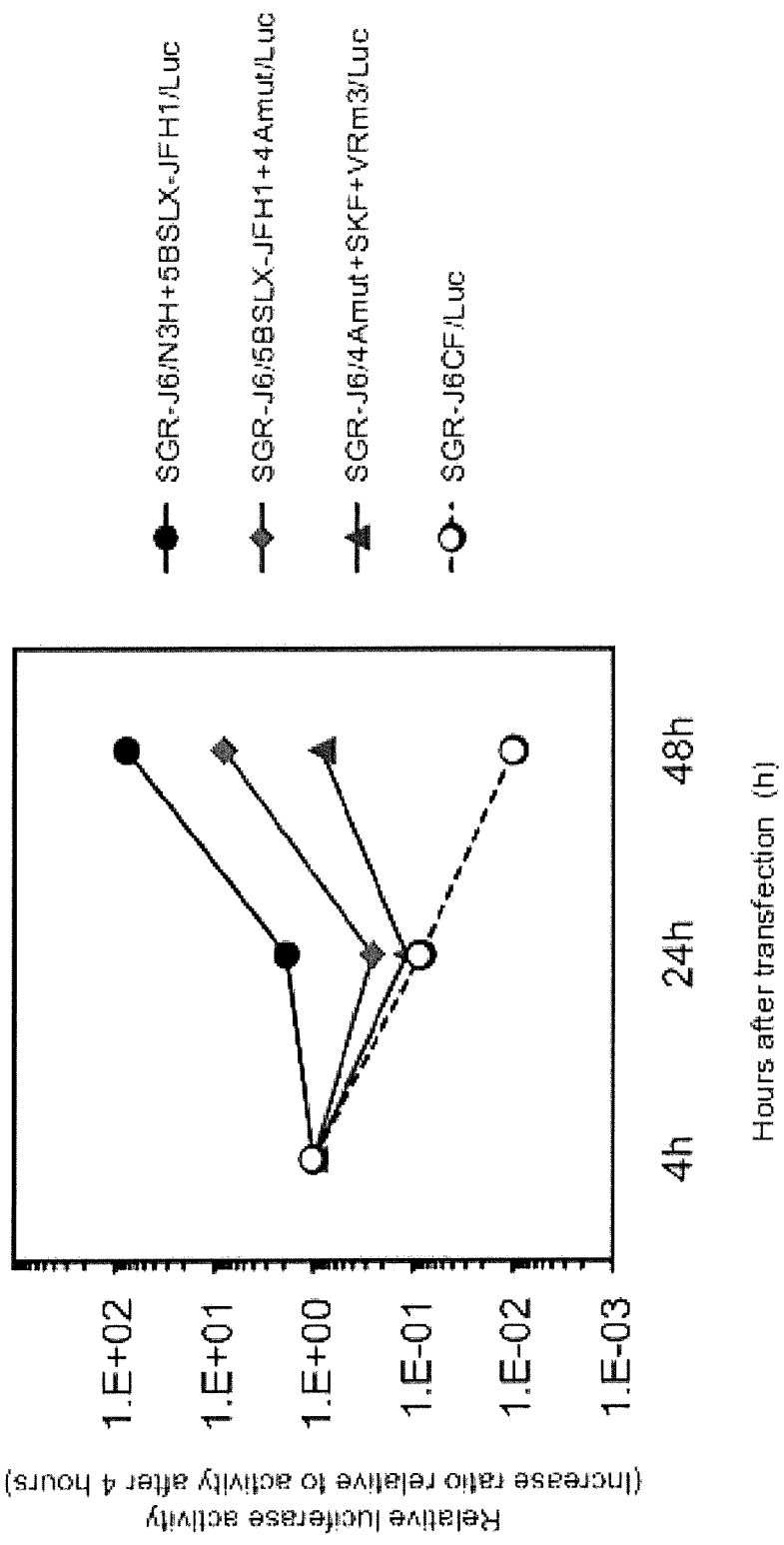
FIG. 9 shows relative luciferase activity (indicating the replication level of the replicon RNA) in the Huh7.5.1 cell into which HCV subgenomic replicon RNA: SGR-J6/N3H+5BSLX-JFH1/Luc, SGR-J6/5BSLX-JFH1+4Amut/Luc, SGR-J6/4Amut+SKF+VRm3/Luc, or SGR-J6CF/Luc, had been introduced.

FIG. 9 shows the assay results. In FIG. 9, the horizontal axis indicates hours after transfection, and the vertical axis indicates luciferase activity levels at each time point relative to the luciferase activity assayed 4 hours after transfection as a reference. As shown in FIG. 9, luciferase activity levels were increased over time in the cells into which SGR-J6/4Amut+SKF+VRm3/Luc that is a mutant (five-site mutagenized) HCV subgenomic replicon RNA derived from the J6CF strain had been introduced. This indicates that SGR-J6/4Amut+SKF+VRm3/Luc is autonomously replicable. Accordingly, five mutations: A1680E, A2892S, R2959K, Y3003F, and nt9458(c→g) were found to be critical in replicating a non-chimeric J6CF genome in cells.

Example 12

Virus Production from Cells into which Mutant (Five-Site Mutagenized) HCV Full-Genomic Replicon RNA Derived from the J6CF Strain (Full-Length HCV Genomic RNA) Had been Introduced 5 μg of the HCV full-genomic replicon RNA prepared in Example 2, Example 7, or Example 10 was introduced (transfected) into the Huh7.5.1 cells as described in Example 3. The cells into which the HCV full-genomic replicon RNA had been introduced were seeded in 12-well plate and cultured, and the culture medium was collected 1, 2, and 3 days after transfection. The collected culture supernatant was applied to a 0.45-μm filter (Millipore) to remove contaminants, and the resultant was used as a sample for HCV Core protein assays. HCV Core proteins were measured using the HCV antigen ELISA test kit (Ortho-Clinical Diagnostics K. K.).

Figure 10:
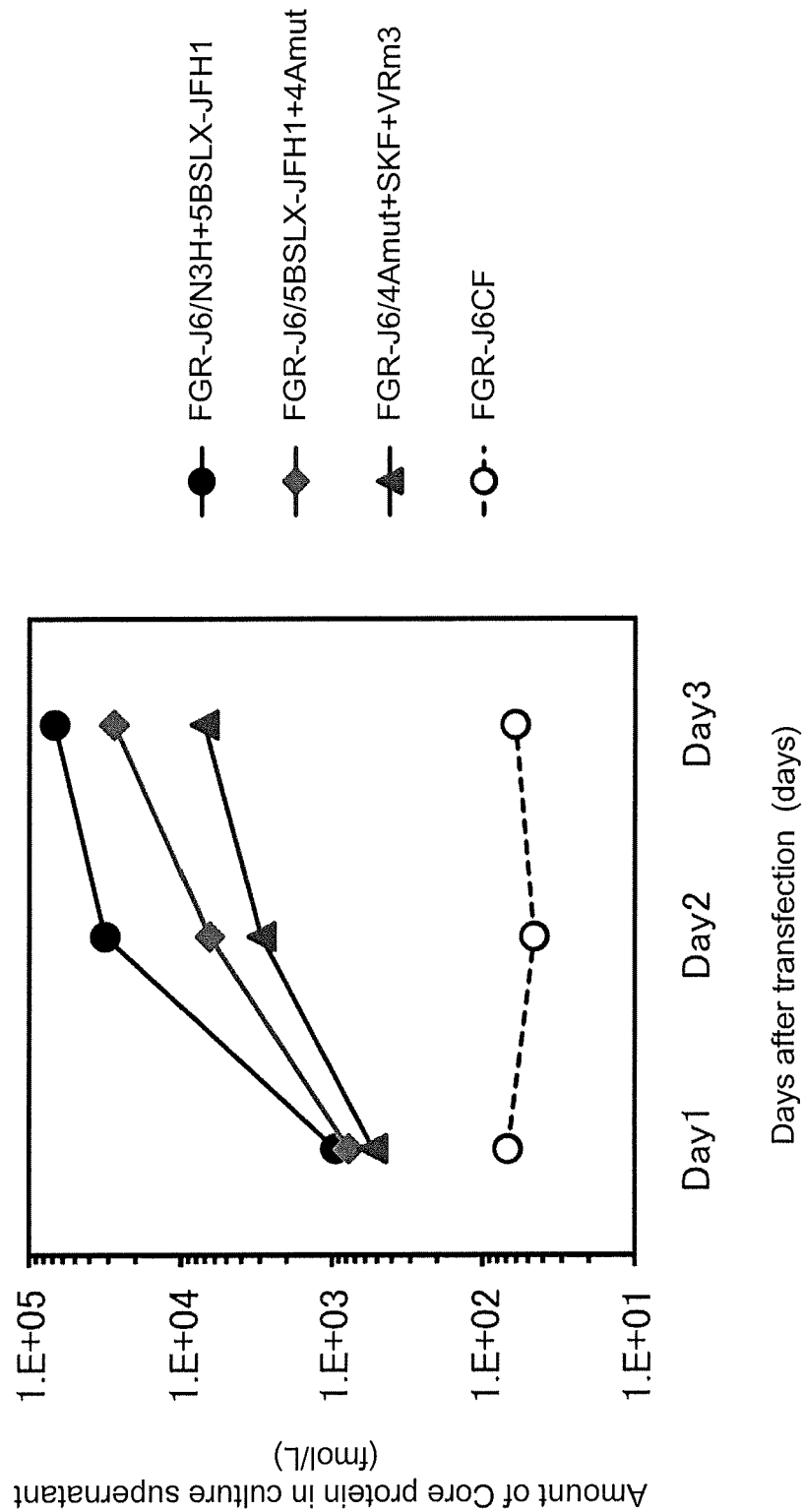
FIG. 10 shows the amount of the Core protein (the virus producing ability) in a culture supernatant of the Huh7.5.1 cell into which HCV full-genomic replicon RNA: FGR-J6/N3H+5BSLX-JFH1, FGR-J6/5BSLX-JFH1+4Amut, FGR-J6/4Amut+SKF+VRm3, or FGR-J6CF, had been introduced.

FIG. 10 shows the results thereof. In FIG. 10, the horizontal axis indicates days after transfection, and the vertical axis indicates the amount of Core protein in the culture supernatant (fmol/l). As shown in FIG. 10, the amount of Core protein in the culture supernatant of the cells into which FGR-J6/4Amut+SKF+VRm3 had been introduced was increased over time. Thus, the cells into which FGR-J6/4Amut+SKF+VRm3 had been introduced were found to produce viruses.

Example 13

Infectivity of Viruses (Virus Particles) Produced from Cells into which Mutant (Five-Site Mutagenized) HCV Full-Genomic Replicon RNA Derived from the J6CF Strain (Full-Length HCV Genomic RNA) Had been Introduced The culture supernatant of the cells into which the HCV full-genomic replicon RNA had been introduced, as obtained in Example 12 was considered to contain the viruses (the virus particles) produced. Thus, infectious titer of the culture supernatant was assayed. The assay of infectious titer was performed using the culture supernatant at 3 days after transfection. Fresh Huh7.5.1 cells were seeded in poly-D-lysine coated 96-well plate (BD) at $1 \times 10^4$ cells/well. On the following day, the diluted culture supernatant was added to the cells to infect the cells with the viruses. Three days after the infection treatment, the cells were fixed with methanol, and the infected cells were immunostained with anti-Core antibodies and AlexaFluor 488-conjugated anti-mouse IgG (Molecular Probes). The number of infection focuses was counted under a fluorescent microscope. The infectious titer of the culture supernatant is expressed in ffu/mL (the number of infection focus forming unit (ffu) per ml of a medium).

The results are shown in Table 1.

TABLE 1

| Replicon | Infectious titer 3 days later (FFU/ml) |
| --- | --- |
| FGR-J6/N3H + 5BSLX-JFH1 | $1.0 \times 10^5 \pm 7.0 \times 10^3$ |
| FGR-J6/5BSLX-JFH1 + 4Amut | $1.4 \times 10^4 \pm 2.2 \times 10^3$ |
| FGR-J6/4Amut + SKF + VRm3 | $1.7 \times 10^3 \pm 5.2 \times 10^2$ |
| FGR-J6CF | 0 |

As a result, high infectious titers were observed in the culture supernatants of the cells into which HCV full-genomic replicon RNAs: FGR-J6/N3H+5BSLX-JFH1, FGR-J6/5BSLX-JFH1+4Amut, or FGR-J6/4Amut+SKF+VRm3, had been introduced.

The results demonstrate that virus particles produced from the cells into which FGR-J6/4Amut+SKF+VRm3 that is a mutant (five-site mutagenized) HCV full-genomic replicon RNA derived from the J6CF strain had been introduced had also high infectivity.

In contrast, in the culture supernatant of the cells into which FGR-J6CF that is an HCV full-genomic replicon RNA of the J6CF strain had been introduced, the infectious titer was 0. That is, it was shown that the J6CF HCV full-genomic replicon RNA itself does not result in the production of infectious virus particles.

Example 14

Preparation of HCV Subgenomic Replicon RNA into which Mutations Had been Introduced in Different Combinations Five mutations introduced into the mutants in Example 10 were introduced into HCV subgenomic replicon RNAs in different combinations, and the effects thereof were examined. Specifically, HCV subgenomic replicon RNAs into which one or a combination of two of three types of mutations: A1680E mutation in the NS4A protein region (4Amut mutation), three substitutions of A2892S, R2959K, and Y3003F in the NS5B protein region (SKF mutation), and mutation nt9458(c→g) in the variable region of the 3' untranslated region (VRm3 mutation) had been introduced, were prepared.

Figure 8:
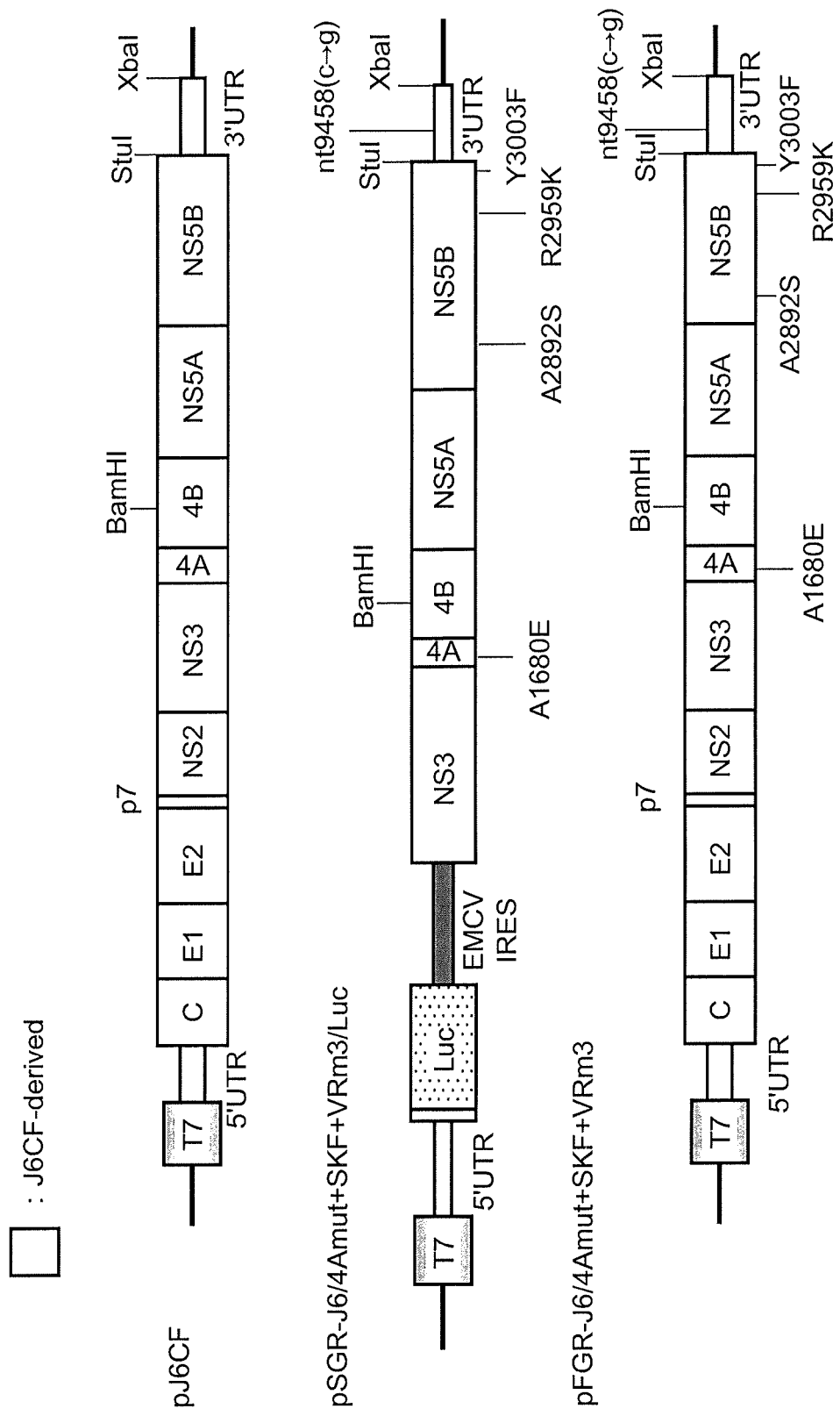
FIG. 8 shows the structures of the mutant (five-site mutagenized) HCV subgenomic replicon RNA expression vectors and mutant HCV full-genomic replicon RNA expression vectors derived from the J6CF strain.
Figure 11:
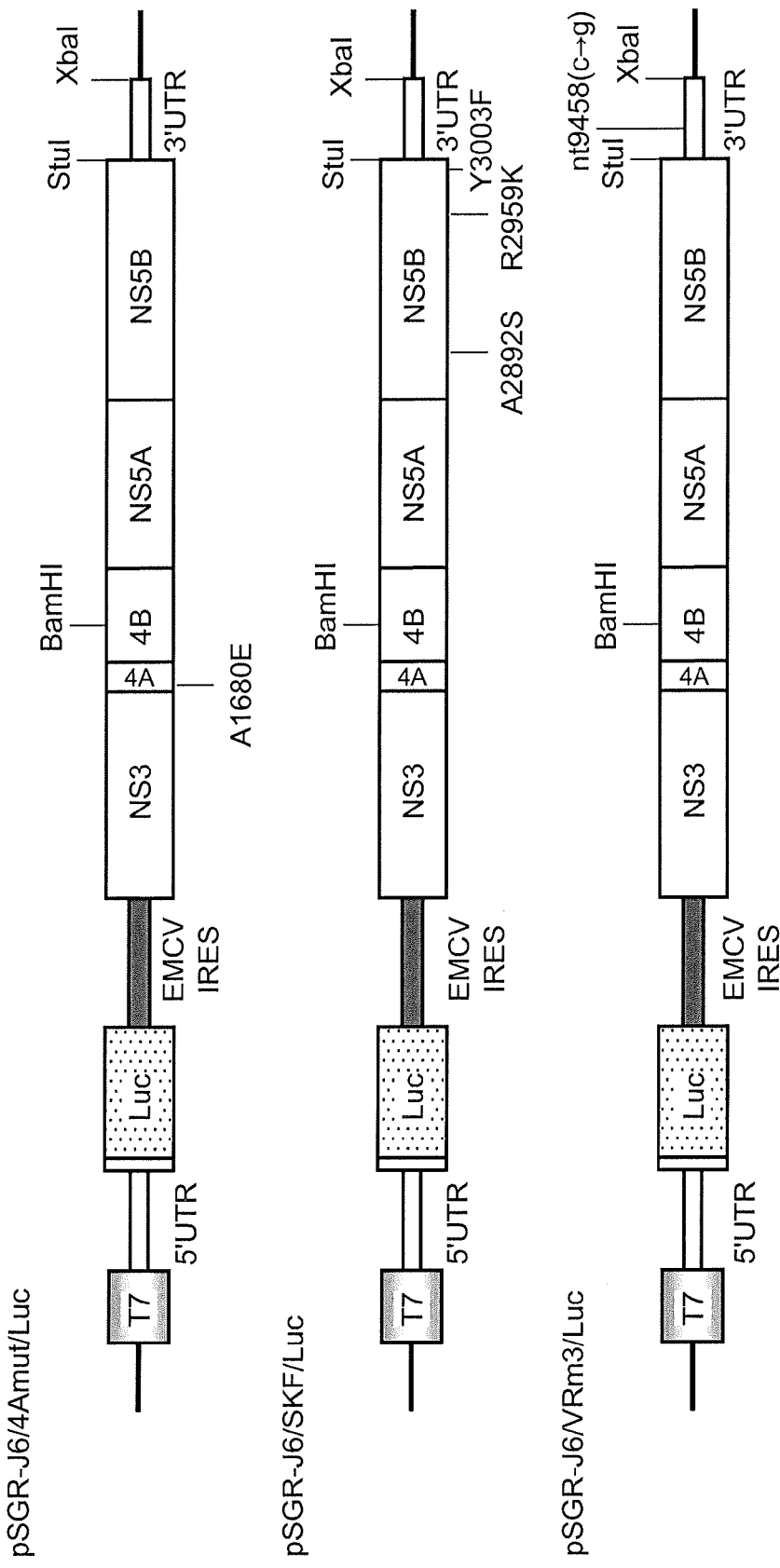
FIG. 11 shows the structure of an HCV subgenomic replicon RNA expression vector into which one of the mutations "4Amut," "SKF," or "VRm3" had been introduced.
Figure 12:
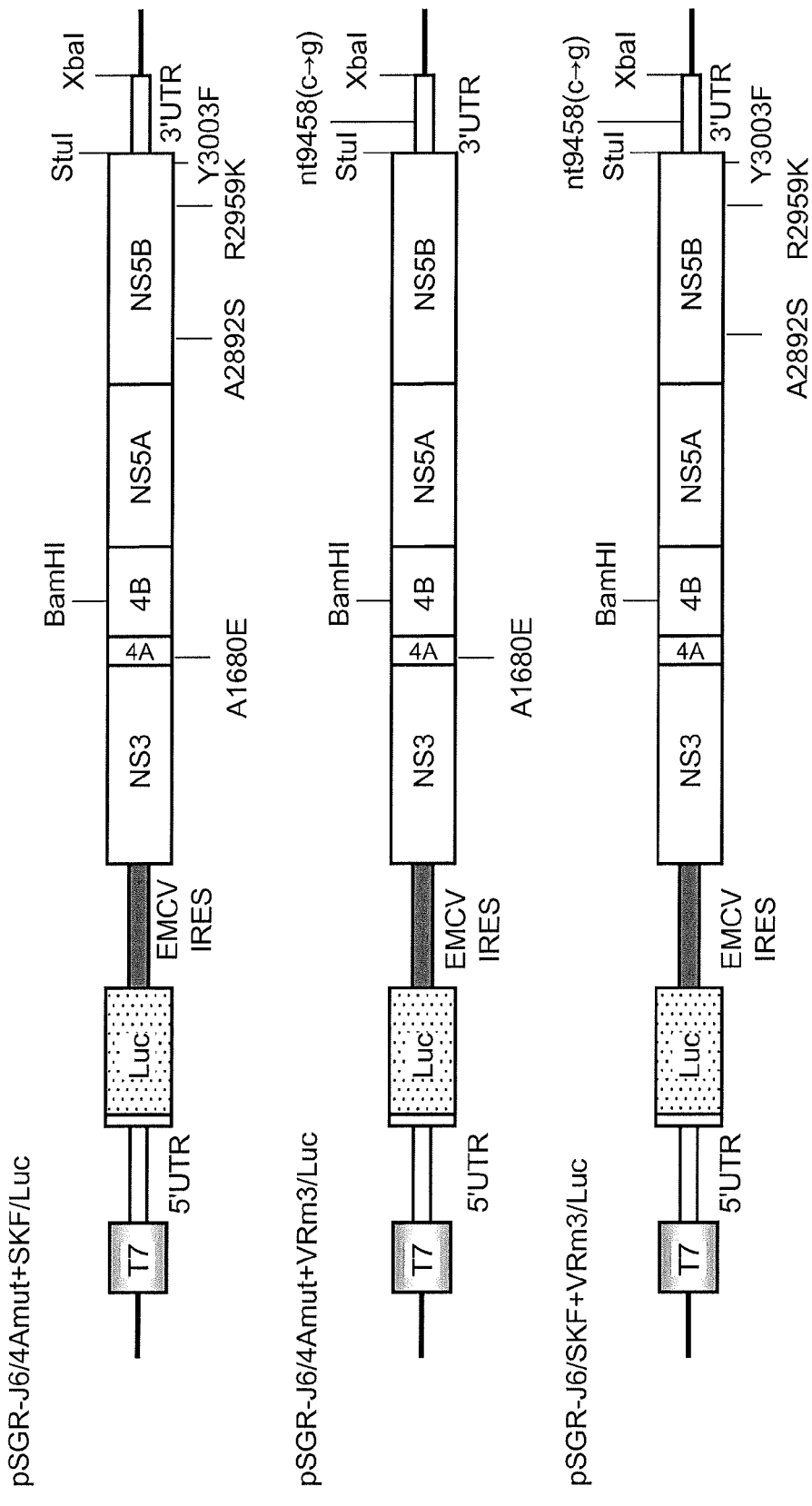
FIG. 12 shows the structure of an HCV subgenomic replicon RNA expression vector into which two of the mutations "4Amut," "SKF," or "VRm3" had been introduced.

Expression vectors to synthesize such HCV subgenomic replicon RNAs were prepared by introducing each mutation into the vector pSGR-J6CF/Luc in accordance with the method described in Example 10 (FIGS. 11 and 12). FIG. 11 shows the structures of expression vectors of the HCV subgenomic replicon RNAs into which a single type of mutation had been introduced, and FIG. 12 shows the structures of expression vectors of the HCV subgenomic replicon RNAs into which two types of mutations had been introduced. Notations in FIGS. 11 and 12 indicate the same objects as in FIGS. 1, 2, and 8.

Figure 13:
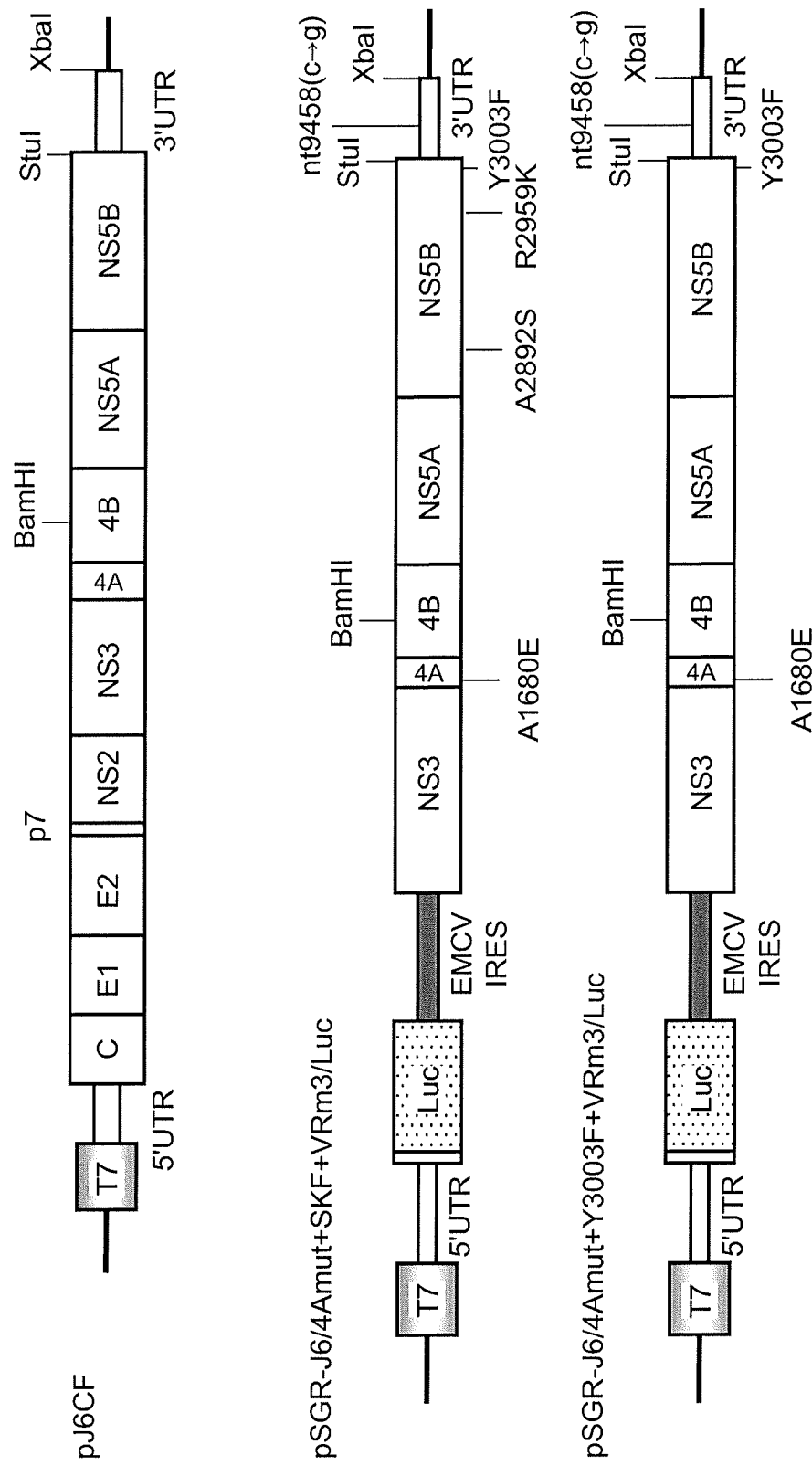
FIG. 13 shows the structures of the mutant HCV subgenomic replicon RNA expression vectors: the pSGR-J6/4Amut+SKF+VRm3/Luc expression vector or the pSGR-J6/4Amut+Y3003F+VRm3/Luc expression vector.

In addition, a nucleic acid construct was prepared by introducing Y3003F mutation alone as well as 4Amut mutation and VRm3 mutation into pSGR-J6CF/Luc in the same manner. The resulting expression vector is referred to as pSGR-J6/4Amut+Y3003F+VRm3/Luc. FIG. 13 shows the structure of the HCV subgenomic replicon RNA expression vector. Notations in the figure indicate the same objects as in FIGS. 1, 2, and 8.

Subsequently, HCV subgenomic replicon RNAs were prepared from the HCV subgenomic replicon RNA expression vectors in the same manner as in Example 2. The HCV subgenomic replicon RNA prepared from the HCV subgenomic replicon RNA expression vector pSGR-J6/4Amut/Luc is referred to as SGR-J6/4Amut/Luc, and other HCV subgenomic replicon RNAs were designated in the same manner.

Example 15

RNA Replication in Cells into which Various Mutant HCV Subgenomic Replicon RNAs Comprising Mutations in Different Combinations Had been Introduced 5 μg the mutant HCV subgenomic replicon RNA derived from the J6CF strain prepared in Example 10 or Example 14 was introduced (transfected) into the Huh7.5.1 cells as described in Example 3. The cells into which the HCV subgenomic replicon RNA had been introduced were seeded in 12-well plate and cultured, and the cells were collected 4, 24, and 48 hours after transfection. The collected cells were lysed in 250 μl of a lysis buffer (Passive Lysis reagent, Promega), centrifuged and the resulting culture supernatant was used as a sample. Luciferase activity of the sample was assayed using the luciferase assay system (Promega) and a luminometer (LB9507; EG&G Berthold). As a control, mutation-free HCV subgenomic replicon RNAs: SGR-JFH1/Luc and SGR-J6CF/Luc, were introduced into cells and cultured, and luciferase activity of the culture supernatant was assayed.

FIG. 14 shows the assay results. In FIG. 14, the horizontal axis indicates HCV subgenomic replicon RNA, and the vertical axis indicates luciferase activity levels at each time point (24 and 48 hours after transfection) relative to the luciferase activity assayed 4 hours after transfection as a reference. As shown in FIG. 14, luciferase activity levels were increased over time in the cells into which SGR-J6/4Amut+SKF+VRm3/Luc, which is a mutant (five-site mutagenized) HCV subgenomic replicon RNA derived from the J6CF strain, had been introduced, as with the positive control, SGR-JFH1/Luc. In contrast, luciferase activity levels were decreased over time in the cells into which the HCV subgenomic replicon RNAs comprising other combinations of the mutations had been introduced. Thus, only SGR-J6/4Amut+SKF+VRm3/Luc was found to be autonomously replicable. It was found that all the 5 mutations above are critical in efficiently replicating replicons derived from the genome of the J6CF strain in cells.

INDUSTRIAL APPLICABILITY

Full-genomic replicon RNAs, which are capable of autonomous amplification in cultured cells and producing infectious HCV particles of the J6CF strain of genotype 2a can be provided. For example, such RNA can be used advantageously in screening of anti-HCV drugs that inhibit the infection and replication of HCV of the J6CF strain of genotype 2a, research for elucidation of HCV replication mechanisms, development of HCV vaccines and the like. Further, a subgenomic replicon RNA derived from the J6CF strain having high replication ability in cultured cells can be also provided. This RNA can also be used in, for example, screening of anti-HCV drugs that inhibit the replication of HCV of the J6CF strain.

Infectious HCV particles can be prepared in a cultured cell system using full-genomic replicon RNA that has the J6CF genome as a backbone, and has autonomous replication ability and infectious HCV particle producing ability. This means that infectious HCV particles derived from a separate HCV strain are provided, in addition to existing infectious HCV particles only derived from the JFH-1 strain and chimeric strains using it. Such infectious HCV particles can be used for analysis of differences in efficacy of treatment with interferon or in how HCV mutates after infection, depending on different HCV strains. This, in turn, enables its use for elucidation of drug tolerance mechanisms. In addition, a screening for anti-HCV drugs using the HCV particles can be utilized for development of therapeutic agents having higher therapeutic effects.

All publications, patents, and patent applications cited herein are incorporated herein by reference in their entirety.

SEQUENCE LISTING FREE TEXT

SEQ ID NO: 1: cDNA sequence of SGR-J6/5BSLX-JFH1+4Amut/Luc, which is J6CF/JFH-1 chimeric mutant HCV subgenomic replicon RNA SEQ ID NO: 2: cDNA sequence of FGR-J6/5BSLX-JFH1+4Amut, which is J6CF/JFH-1 mutant HCV full-genomic replicon RNA SEQ ID NO: 3: precursor protein encoded by FGR-J6/5BSLX-JFH1+4Amut, which is J6CF/JFH-1 chimeric mutant HCV full-genomic replicon RNA SEQ ID NO: 4: cDNA sequence of SGR-J6/4Amut+SKF+VRm3/Luc, which is a mutant (five-site mutagenized) HCV subgenomic replicon RNA derived from the J6CF strain SEQ ID NO: 5: cDNA sequence of FGR-J6/4Amut+SKF+VRm3, which is a mutant (five-site mutagenized) HCV full-genomic replicon RNA derived from the J6CF strain SEQ ID NO: 6: precursor protein encoded by FGR-J6/4Amut+SKF+VRm3, which is a mutant (five-site mutagenized) HCV full-genomic replicon RNA derived from the J6CF strain;

SEQ ID NO: 7: sense primer 8680S-2a
SEQ ID NO: 8: antisense primer 9191R-2a
SEQ ID NO: 9: sense primer 9191S-2a
SEQ ID NO: 10: antisense primer 9440R-IH
SEQ ID NO: 11: sense primer 3471S-2a
SEQ ID NO: 12: antisense primer A1680Eas
SEQ ID NO: 13: sense primer A1680Es
SEQ ID NO: 14: antisense primer 6542R-IH
SEQ ID NO: 15: sense primer 7244S-RI
SEQ ID NO: 16: antisense primer J65BA450Sas
SEQ ID NO: 17: sense primer J65BA450Ss
SEQ ID NO: 18: antisense primer 9454R-IH
SEQ ID NO: 19: antisense primer J65BR517Kas
SEQ ID NO: 20: sense primer J65BR517Ks
SEQ ID NO: 21: antisense primer J65BY561Fas
SEQ ID NO: 22: sense primer J65BY561Fs
SEQ ID NO: 23: sense primer 92545-IH
SEQ ID NO: 24: antisense primer J6VRm3as
SEQ ID NO: 25: sense primer J6VRm3s
SEQ ID NO: 26: antisense primer M13R
SEQ ID NO: 27: NS5B protein of the hepatitis C virus J6CF strain
SEQ ID NO: 28: NS5B protein of the hepatitis C virus JFH-1 strain
SEQ ID NO: 29: cDNA sequence of the full-length genomic RNA of the hepatitis C virus J6CF strain
SEQ ID NO: 30: precursor protein encoded by the full-length genomic RNA of the hepatitis C virus J6CF strain
SEQ ID NO: 31: cDNA sequence of the 3' untranslated region (3' UTR) of the genomic RNA of the hepatitis C virus JFH-1 strain
SEQ ID NO: 32: DNA sequence encoding the chimeric NS5B protein comprising amino acid residues 1 to 515 of the NS5B protein of the J6CF strain and amino acid residues 516 to 591 of the NS5B protein of the JFH-1 strain SEQ ID NO: 33: chimeric NS5B protein comprising amino acid residues 1 to 515 of the NS5B protein of the J6CF strain and amino acid residues 516 to 591 of the NS5B protein of the JFH-1 strain

The invention claimed is:

1. A nucleic acid comprising a 5' untranslated region, a virus protein-coding region which contains an NS3 protein coding sequence, an NS4A protein coding sequence, an NS4B protein coding sequence, an NS5A protein coding sequence, and an NS5B protein coding sequence, and a 3' untranslated region of the genome of the hepatitis C virus J6CF strain in that order from the 5' to 3' direction, wherein the NS4A protein coding sequence comprises a mutation substituting alanine at position 1680 with glutamic acid, as determined on the basis of the amino acid sequence as shown in SEQ ID NO: 30 of the precursor protein of the J6CF strain.

2. The nucleic acid according to claim 1, wherein the NS5B protein coding sequence has mutations causing amino acid substitutions of (i) to (iii):
   (i) amino acid substitution of alanine at position 2892 with serine;
   (ii) amino acid substitution of arginine at position 2959 with lysine; and
   (iii) amino acid substitution of tyrosine at position 3003 with phenylalanine, as determined on the basis of the amino acid sequence as shown in SEQ ID NO: 30, and wherein the 3' untranslated region has a nucleotide substitution of cytosine at position 9458 with guanine, as determined on the basis of the nucleotide sequence as shown in SEQ ID NO: 29.

3. The nucleic acid according to claim 1, wherein the NS5B protein coding sequence is substituted with a nucleotide sequence encoding a protein comprising the amino acid sequence in which the sequence of amino acids 1 to 515 from the amino acid sequence as shown in SEQ ID NO: 27 and the sequence of amino acids 516 to 591 from the amino acid sequence as shown in SEQ ID NO: 28 are joined together in that order, and wherein the 3' untranslated region is substituted with the nucleotide sequence as shown in SEQ ID NO: 31.

4. The nucleic acid according to claim 1, comprising a foreign gene and an IRES sequence.

5. The nucleic acid according to claim 1, wherein the virus protein-coding region further comprises, on the 5' side of an NS3 protein coding sequence, a Core protein coding sequence, an E1 protein coding sequence, an E2 protein coding sequence, a p7 protein coding sequence, and an NS2 protein coding sequence of the hepatitis C virus genome in that order from the 5' to 3' direction.

6. A subgenomic replicon RNA of hepatitis C virus comprising the nucleic acid according to claim 1.

7. A full-genomic replicon RNA of hepatitis C virus comprising the nucleic acid according to claim 5.

8. A hepatitis C virus particle containing the nucleic acid according to claim 5 as a virus genome.

9. An expression vector comprising the nucleic acid according to claim 1.

10. A cell into which the nucleic acid according to claim 1 has been introduced.

11. A hepatitis C virus vaccine comprising the hepatitis C virus particle according to claim 8.

12. A method of screening for an anti-hepatitis C virus substance comprising:
   culturing the cell into which a nucleic acid comprising a 5' untranslated region, a virus protein-coding region which contains an NS3 protein coding sequence, an NS4A protein coding sequence, an NS4B protein coding sequence, an NS5A protein coding sequence, and an NS5B protein coding sequence, and a 3' untranslated region of the genome of the hepatitis C virus J6CF strain in that order from the 5' to 3' direction, wherein the NS4A protein coding sequence comprises a mutation substituting alanine at position 1680 with glutamic acid, as determined on the basis of the amino acid sequence as shown in SEQ ID NO: 30 of the precursor protein of the J6CF strain has been introduced or a mixture of the hepatitis C virus particle according to claim 8 and a hepatitis C virus-sensitive cell in the presence and in the absence of a test substance;

quantifying an amount of subgenomic replicon RNA, full-genomic replicon RNA, or hepatitis C virus particle in a culture obtained by the culturing; and evaluating a result of the quantifying, wherein the test substance is determined as a substance having an anti-hepatitis C virus activity if an amount of the subgenomic replicon RNA, the full-genomic replicon RNA, or the hepatitis C virus particle quantified in the presence of the test substance is lower than an amount of the subgenomic replicon RNA, the full-genomic replicon RNA, or the hepatitis C virus particle quantified in the absence of the test substance.

* * * * *